US011464867B2

(12) United States Patent
Mackay et al.

(10) Patent No.: US 11,464,867 B2
(45) Date of Patent: Oct. 11, 2022

(54) MULTIMERIC ELASTIN-LIKE POLYPEPTIDES

(71) Applicant: University of Southern California, Los Angeles, CA (US)

(72) Inventors: John Andrew Mackay, Los Angeles, CA (US); Mihir Shah, Los Angeles, CA (US); Sarah F. Hamm-Alvarez, Los Angeles, CA (US); Hao Guo, Los Angeles, CA (US); Santosh Peddi, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 96 days.

(21) Appl. No.: 16/274,192

(22) Filed: Feb. 12, 2019

(65) Prior Publication Data

US 2019/0282656 A1   Sep. 19, 2019

Related U.S. Application Data

(60) Provisional application No. 62/630,145, filed on Feb. 13, 2018.

(51) Int. Cl.
*A61K 47/68* (2017.01)
*C12N 15/62* (2006.01)
*C07K 16/28* (2006.01)
*A61K 38/13* (2006.01)

(52) U.S. Cl.
CPC ...... *A61K 47/6801* (2017.08); *A61K 47/6849* (2017.08); *A61K 38/13* (2013.01); *C07K 16/2887* (2013.01); *C12N 15/62* (2013.01)

(58) Field of Classification Search
CPC ............... C07K 16/2887; C07K 14/78; C07K 2317/622; A61K 47/6849; A61K 47/6801; A61K 38/13; A61K 31/203; A61K 31/436; A61K 38/00; A61K 47/6435; C12N 15/62
See application file for complete search history.

(56) References Cited

U.S. PATENT DOCUMENTS

| | | | |
|---|---|---|---|
| 6,852,834 B2 | 2/2005 | Chilkoti | |
| 8,252,740 B2 | 8/2012 | Raucher et al. | |
| 8,367,626 B2 | 2/2013 | Furgeson et al. | |
| 8,513,380 B2 | 8/2013 | Barker | |
| 8,841,414 B1 | 9/2014 | Raucher et al. | |
| 9,102,763 B2 | 8/2015 | Mackay et al. | |
| 2002/0013344 A1 | 1/2002 | Steiner et al. | |
| 2007/0265197 A1 | 11/2007 | Furgeson et al. | |
| 2008/0312156 A1 | 12/2008 | Setton et al. | |
| 2010/0048473 A1 | 2/2010 | Chaikof et al. | |
| 2010/0104554 A1 | 4/2010 | Scott et al. | |
| 2010/0119529 A1 | 5/2010 | Furgeson et al. | |
| 2010/0189643 A1 | 7/2010 | Chilkoti et al. | |
| 2011/0110866 A1 | 5/2011 | Chilkoti et al. | |
| 2011/0151006 A1 | 6/2011 | Weber et al. | |
| 2012/0213781 A1 | 8/2012 | Hilbert | |
| 2013/0196926 A1 | 8/2013 | Mackay et al. | |
| 2013/0210747 A1* | 8/2013 | Hamm-Alvarez | A61K 49/0043 514/21.2 |
| 2014/0294932 A1 | 10/2014 | Kim et al. | |
| 2015/0209335 A1 | 7/2015 | Mackay et al. | |
| 2015/0218280 A1 | 8/2015 | Epstein et al. | |
| 2015/0238431 A1 | 8/2015 | Hamm-Alvarez et al. | |
| 2016/0017004 A1 | 1/2016 | Hamm-Alvarez et al. | |
| 2019/0022190 A1 | 1/2019 | Despanie et al. | |
| 2019/0247317 A1 | 8/2019 | Hamm-Alvarez et al. | |
| 2019/0282656 A1 | 9/2019 | Mackay et al. | |
| 2019/0290726 A1 | 9/2019 | Mackay et al. | |
| 2020/0079868 A1 | 3/2020 | Epstein et al. | |

FOREIGN PATENT DOCUMENTS

| | | |
|---|---|---|
| CN | 101544694 A | 9/2009 |
| WO | WO-95/33052 A1 | 12/1995 |
| WO | WO-2010/144612 | 12/2010 |
| WO | WO-2011/006069 A1 | 1/2011 |
| WO | WO-2013/016578 A2 | 1/2013 |
| WO | WO-2014/059384 A2 | 4/2014 |
| WO | WO-2014/059385 A1 | 4/2014 |
| WO | WO-2014/161004 | 10/2014 |
| WO | WO-2017/020686 A1 | 2/2017 |

OTHER PUBLICATIONS

Bowie et al. (Science, 1990, 247:1306-1310) (Year: 1990).*
By Burgess et al. (J. Cell Biol. 111:2129-2138, 1990) (Year: 1990).*
Lazar et al. (Mol. Cell. Biol., 8:1247-1252, 1988) (Year: 1988).*
Bork (Genome Research, 2000,10:398-400) (Year: 2000).*
Esmaielbeiki etal (Brief Bioinform. Jan. 2016; 17(1): 117-131) (Year: 2016).*
Hamp etal (Bioinformatics, 31(10), 2015, 1521-1525) (Year: 2015).*
Fischman etal (Current Opinion in Structural Biology 2018, 51:156-162) (Year: 2018).*
Wagneretal (Structure 27, 1326-1335, Aug. 6, 2019) (Year: 2019).*
Oshima et al (J Chem Inf Model. Aug. 17, 2020) (Year: 2020).*
Bai et al (Proc Natl Acad Sci, Dec. 13, 2016;113(50):E8051-E8058. Epub Nov. 29, 2016) (Year: 2016).*
Roche et al (Int. J. Mol. Sci. 2015, 16, 29829-29842) (Year: 2015).*
Dhandhukia et al (Theranostics, 2017; 7(16): 3856-3872; published Aug. 29, 2017) (Year: 2017).*
Awasthi et al., "Biodistribution of Radioiodinated Adenovirus Fiber Protein Knob Domain after Intravenous Injection in Mice.," J. Virol., vol. 78, No. 12, Jun. 2004, pp. 6431-6438.

(Continued)

*Primary Examiner* — Brian Gangle
*Assistant Examiner* — Andrea K McCollum
(74) *Attorney, Agent, or Firm* — Foley & Lardner LLP

(57) ABSTRACT

This disclosure provides a novel compositions and methods to deliver cyclosporine A using genetically engineered protein polymers.

6 Claims, 32 Drawing Sheets

Specification includes a Sequence Listing.

(56) References Cited

OTHER PUBLICATIONS

Bowie et al., "Deciphering the Message in Protein Sequences: Tolerance to Amino Acid Substitutions", Science, vol. 247, No. 4948, Mar. 16, 1990, pp. 1306-1310.
Chilkoti et al., "Design of thermally responsive, recombinant polypeptide carriers for targeted drug delivery.," Advanced Drug Delivery Reviews, vol. 54, No. 8, Jul. 1, 2002, pp. 1093-1111.
Chilkoti et al., "Stimulus responsive elastin biopolymers: applications in medicine and biotechnology", Current Opinion in Chemical Biology, vol. 10, No. 6, Dec. 1, 2006, pp. 652-657.
Database Geneseq [Online] Jun. 19, 2014 (Jun. 19, 2014), "ELP component reference polypeptide construct S48I48, SEQ ID 4 #1.", retrieved from EBI accession No. GSP:BBF47655 Database accession No. BBF47655, 1 page.
Despanie et al. "Elastin-like polypeptides: Therapeutic applications for an emerging class of nanomedicines," J Control Release, vol. 240, Nov. 11, 2015, pp. 93-108.
Dhandhukia et al., "Switchable elastin-like polypeptides that respond to chemical inducers of dimerization.," Biomacromolecules, vol. 14, No. 4, Apr. 8, 2013, pp. 976-985.
DiJoseph et al., "CD20-Specific Antibody-Targeted Chemotherapy of Non-Hodgkins B-Cell Lymphoma Using Calicheamicin-Conjugated Rituximab.," Cancer Immunol. Immunother., vol. 56, No. 7, Dec. 12, 2006, pp. 1107-1117.
Dreher et al. Temperature triggered self-assembly of polypeptides into multivalent spherical micelles. J Am Chem Soc . Jan. 16, 2008;130(2):687-94. doi: 10.1021/ja0764862. Epub Dec. 18, 2007.
Dreher et al., "Temperature Triggered Self-Assembly of Polypeptides into Multivalent Spherical Micelles.," J Am Chem Soc., vol. 130, No. 2, Jan. 16, 2008, pp. 687-694.
Final Office Action for U.S. Appl. No. 13/764,476 dated Jun. 30, 2014, 15 pages.
Final Office Action on U.S. Appl. No. 14/420,308 dated Jul. 23, 2018, 19 pages.
Final Office Action on U.S. Appl. No. 14/683,033 dated May 22, 2018, 11 pages.
Final Office Action on U.S. Appl. No. 14/683,033 dated Dec. 6, 2019, 7 pages.
Final Office Action on U.S. Appl. No. 14/684,162 dated Mar. 9, 2017, 12 pages.
Final Office Action on U.S. Appl. No. 14/811,720 dated Jun. 28, 2018, 22 pages.
Floss et al., "Elastin-Like Polypeptides Revolutionize Recombinant Protein Expression and their Biomedical Application.," Trends in Biotechnology, vol. 28, No. 1, 2009, pp. 37-45.
Floss et al., "Expression and Immunogenicity of the Mycobacterial Ag85B/ESAT-6 Antigens Produced in Transgenic Plants by Elastin-Like Peptide Fusion Strategy", Journal of Biomedicine and Biotechnology, vol. 2010, Jan. 1, 2010, pp. 1-14.
Floss, et al., "Influence of Elastin-Like Peptide Fusions on the Quantity and Quality of a Tobacco-Derived Human Immunodeficiency Virus-Neutralizing Antibody", Plant Biotechnology Journal, vol. 7, No. 9, Aug. 7, 2009, pp. 899-913.
Guo et al., "Anti-CD20 Tetravalent Antibody and Preparation Method and Application Thereof"., Google.com/patents, 2009, pp. 1-19.
Hamm-Alvarez, "Design and Cellular Internalization of Genetically Engineered Polypeptide Nanoparticles Displaying Adenovirus Knob Domain." Utah Drug Delivery Conference, 15th International Symposium on Recent Advances in Drug Delivery Systems "Drug Delivery: New Directions In a New Decade". Salt Lake City, Utah, Feb. 13-16, 2011, 26 pages.
Hamm-Alvarez, "Design and Cellular Internalization of Genetically Engineered Polypeptide Nanoparticles Displaying Adenovirus Knob Domain." presented in Utah on Feb. 14, 2011, 34 pages.
Hassouneh et al., "Fusions of elastin-like polypeptides to pharmaceutical proteins", Methods in Enzymology, vol. 502, 2012, pp. 215-237, NIH Public Access Author Manuscript Version internal pp. 1-24.

Hassouneh et al., "Fusions of Elastin-Like Polypeptides to Pharmaceutical Proteins", Methods of Enzymology, vol. 502, 2012, pp. 215-237.
Holliger et al., "Engineered antibody fragments and the rise of single domains", Nature Biotechnology, vol. 23, No. 9, Sep. 7, 2005, pp. 1126-1136.
Hsueh et al., "Development of Novel Peptide Nanoparticles Targeted to Coxsackievirus-Adenovirus Receptor Expressing Cells." AAPS 2011, Washington, DC, Oct. 23-27, 2011, 1 page.
Joensuu et al., "Expression and purification of an anti-Foot-and-mouth disease virus single-chain variable antibody fragment in tobacco plants", Transgenic Res., vol. 18, Apr. 3, 2009, pp. 685-696.
Jubala et al., "CD20 Expression in Normal Canine B Cells and in Canine non-Hodgkin Lymphoma", Vet Pathol., vol. 24, 2005, pp. 468-476.
Jubala et al., "CD20 Expression in Normal Canine B Cells and in Canine non-Hodgkin Lymphoma", Vet Pathol., vol. 42, 2005, pp. 468-476.
MacCallum et al., "Antibody-antigen Interactions: Contact Analysis and Binding Site Topography", J. Mol. Biol., vol. 262, Jul. 30, 1996, pp. 732-745.
MacEwan et al., "Elastin-like polypeptides: biomedical applications of tunable biopolymers.," PeptideScience, vol. 94, No. 1, Oct. 8, 2009, pp. 60-77.
Mackay et al., "Genetically Engineered Polypeptide Nanoparticles." ACS Western Regional Meeting 2011, Pasadena, CA, Nov. 11, 2011, 31 pages.
Mackay et al., "Ocular Drug Delivery Using a Thermo-responsive Lacritin Fusion Protein," Abstract of presentation at ARVO 2012, Fort Lauderdale, FL (May 4-6, 2012), 2 pages.
Mackay, "Protein polymers—a platform for biopharmaceutical delivery and self-assembly." Keck Seminar, posted online Jun. 27, 2011, 53 pages.
McDaniel et al., "Drug delivery to solid tumors by elastin-like polypeptides.," Adv Drug Deliv Rev., vol. 62, No. 15, Dec. 30, 2010, pp. 1456-1467.
McDaniel et al., "Recursive Directional Ligation by Plasmid Reconstruction Allows Rapid and Seamless Cloning of Oligomeric Genes.," Biomacromolecules, vol. 11, No. 4, Apr. 12, 2010, pp. 944-952.
Meyer et al., "Purification of recombinant proteins by fusion with thermally-responsive polypeptides.," Nature Biotechnology, vol. 17, No. 11, Nov. 1999, pp. 1112-1115.
Non-Final Office Action for U.S. Appl. No. 13/764,476 dated Nov. 1, 2013, 18 pages.
Non-Final Office Action on U.S. Appl. No. 14/420,308 dated Mar. 31, 2017, 8 pages.
Non-Final Office Action on U.S. Appl. No. 14/683,033 dated Apr. 26, 2019, 10 pages.
Non-Final Office Action on U.S. Appl. No. 14/683,033 dated Jan. 4, 2018, 11 pages.
Non-Final Office Action on U.S. Appl. No. 14/684,162 dated Mar. 9, 2018, 14 pages.
Non-Final Office Action on U.S. Appl. No. 14/811,720 dated Oct. 4, 2017, 22 pages.
Non-final Office Action on U.S. Appl. No. 14/965,053 dated Jun. 1, 2018, 23 pages.
Non-Final Office Action on U.S. Appl. No. 16/206,896 dated May 22, 2020, 23 pages.
Non-Final Office Action on U.S. Appl. No. 16/254,531 dated Apr. 9, 2020, 30 pages.
Non-Final Office Action on U.S. Appl. No. 16/306,825 dated Apr. 16, 2020, 25 pages.
Non-Final Office Action on U.S. Appl. No. 16/038,051 dated Dec. 31, 2019, 22 pages.
Non-Final Office Action on U.S. Appl. No. 16/125,538 dated Dec. 2, 2019, 22 pages.
Putnam et al., "Primary structure of a human IgA1 immunoglobulin. IV. Streptococcal IgA1 protease, digestion, Fab and Fc fragments, and the complete amino acid sequence of the alpha 1 heavy chain." J. Biol. Chem., vol. 254, No. 8, Apr. 25, 1979, pp. 2865-2874.
Rudikoff et al., "Single amino acid substitution altering antigen-binding specificity", Proc. Natl. Acad. Sci. USA, vol. 27, Mar. 1982, pp. 1979-1983.

(56) References Cited

OTHER PUBLICATIONS

Scheller et al., "Forcing Single-Chain Variable Fragment Production in Tobacco Seeds by Fusion to Elastin-like Polypeptides", Plant Biotech. Journ., vol. 4, Oct. 27, 2005, pp. 243-249.
SHAH et al., "Biodegradation of elastin-like polypeptide nanoparticles.," Protein Sci., vol. 21, No. 6, Mar. 20, 2012, pp. 743-750.
Sheth et al., "Purification of monoclonal antibodies by affinity precipitation using thermally responsive elastin-like polypeptides(ELPs) fused to IgG binding domains: High-throughput analysis and scale up considerations.," Mar. 27, 2012, 1 page.
Shi et al., "Elastin-based protein polymer nanoparticles carrying drug at both corona and core suppress tumor growth in vivo.," J Control Release, vol. 171, No. 3, May 25, 2013, pp. 330-338.
SUN et al., "Design and cellular internalization of genetically engineered polypeptide nanoparticles displaying adenovirus knob domain" J Control Release., vol. 155, No. 2, Oct. 30, 2011, pp. 218-226.
Sun et al., "Genetically engineered polypeptide nanoparticles targeted to lacrimal gland acinar cells." Presented at ARVO 2011, Fort Lauderdale, FL, May 1-5, 2011, 1 page.
Supplement for Sun et al. "Design and cellular internalization of genetically engineered polypeptide nanoparticles displaying adenovirus knob domain" J Control Release., vol. 155, No. 2, Oct. 30, 2011, pp. 218-226.
Trabbic-Carlson et al., "Expression and purification of recombinant proteins from *Escherichia coli*: Comparison of an elastin-like polypeptide fusion with an oligohistidine fusion," Protein Science, vol. 13, No. 12, 2004, pp. 3274-3284.
UniProtKB/Swiss-Prot Direct Submission P62937.2. Locus PPIA_HUMAN. Oct. 3, 2012.[Retrieved from the Internet Jan. 17, 2014: <http://www.ncbi.nlm.nih.gov/protein/51702775?sat=16&satkey=10893480>], 10 pages.
UnitProt Accession No. P68871, accessed May 28, 2018 at URL . unitprot.org/unitprot/ P68871, 25 pages.
UnitProt Accession No. P69891, accessed May 28, 2018 at URL . unitprot.org/unitprot/ P69891, 5 pages.
UnitProt Accession No. P69905, accessed May 28, 2018 at URL . unitprot.org/unitprot/ P69905, 21 pages.
Urry. Physical Chemistry of Biological Free Energy Transduction as Demonstrated by Elastic Protein-Based Polymers. J. Phys. Chem. B 1997, 101, 51, 11007-11028. Publication Date:Dec. 18, 1997.
Vignot et al., "mTOR-targeted therapy of cancer with rapamycin derivatives.," Annals of Oncology, vol. 16, No. 4, Feb. 22, 2005, pp. 525-537.
Wang et al., "Control Of Ocular Drug Bioavailability Using Thermal-Responsive Polypeptides." Controlled Release Meeting, Aug. 3, 2011, 1 page.
Welply et al., "A peptide isolated by phage display binds to ICAM-1 and inhibits binding to LFA-1", Proteins: Structure, Function and Genetics, vol. 26, May 21, 1996, pp. 262-270.
White KD and Capra JD. Targeting mucosal sites by polymeric immunoglobulin receptor-directed peptides. J Exp Med. 2002;196(4):551-555. doi:10.1084/jem.20020581. Aug. 19, 2002.
Wu et al., "Fabrication of elastin-like polypeptide nanoparticles fordrug delivery by electrospraying," Biomacromolecules, vol. 10, No. 1, Jan. 12, 2009, pp. 19-24.
Wu et al., "Humanization of a Murine Monoclonal Antibody by Simultaneous Optimization of Framework and CDR Residues", J. Mol. Biol., vol. 294, 1999, pp. 151-162.
Wu et al., "Humanization of a Murine Monoclonal Antibody by Simultaneous Optimization of Framework and CDR Residues", J. Mol. Biol., vol. 294, Aug. 26, 1999, pp. 151-162.
Xie et al. Novel fiber-dependent entry mechanism for adenovirus serotype 5 in lacrimal acini.J Virol. Dec. 2006;80(23):11833-51. doi: 10.1128/JVI.00857-06. Epub Sep. 20, 2006.
Xie et al., "Novel Fiber-Dependent Entry Mechanism for Adenovirus Serotype 5 in Lacrimal Acini." J. Virol., vol. 80, No. 23, Dec. 2006, pp. 11833-11851.
Yampolsky et al., "The Exchangeability of Amino Acids in Proteins," Genetics, vol. 170, Aug. 2005, pp. 1459-1472.
Yeo et al., "Fabricated Elastin", Advanced Healthcare Materials, vol. 4, No. 16, Nov. 1, 2015, pp. 2530-2556.

* cited by examiner

MULTIMERIC ELASTIN-LIKE POLYPEPTIDES

CROSS-REFERENCE TO RELATED APPLICATION

This application claims priority under 35 U.S.C. § 119(e) to U.S. Provisional Application No. 62/630,145, filed Feb. 13, 2018, the contents of which are hereby incorporated by reference in their entirety.

SEQUENCE LISTING

The instant application contains a Sequence Listing which has been filed electronically in ASCII format and is hereby incorporated by reference in its entirety. Said ASCII copy, created on Jun. 3, 2018, is named 064189-9171_SL.txt and is 202,525 bytes in size.

BACKGROUND

Synthetic nanoparticles, such as dextran, PLGA, and liposomes have been designed as tissue and cell-specific targeting moieties. For example, bilayer phospholipid vesicles decorated with polyethylene glycol (PEG) or coated with charged polymers like poly (acrylic acid) and/or poly-allyl amine HCl (PAH) are currently used to encapsulate small molecule drugs. Other known methods include chemically synthesized block co-polymer nanoparticle poly(ethylene glycol)-b-poly((3-caprolactone) (PEG-PCL) to encapsulate small molecule drugs such as rapamycin by a co-solvent extraction technique. The nanoparticle performs a slow release with a half-life up to 39 hours. Immunosuppressive small molecule drugs have also been encapsulated in biodegradable polymers like acetylated dextran that forms microparticles following a single-emulsion production technique. The prior art compositions and therapies using the same suffer from dose-limiting toxicity, insufficient residence time in the body, and a lack of targeted delivery to intended tissues. This disclosure overcomes these limitations and provides related advantages as well.

SUMMARY

Derived from human tropoelastin, elastin-like polypeptides (ELPs) comprise, consist essentially of, or consist of pentameric repeats of (Val-Pro-Gly-Xaa-Gly)n (SEQ ID NO: 51) where Xaa is the guest residue and n is the length of the repetitive units. ELPs have a unique inverse transition behavior. Below their transition temperature (Tt), they are highly water soluble but once the temperature rises above their Tt, ELPs undergo a phase separation process and self-assemble into different kinds of coacervates including different size particles (Dhandhukia et al., 2013). This phase separation is a fully reversible process and can be used to effectively purify ELP-conjugated materials (Shah et al., 2013). Phase behavior can be precisely controlled by adjusting the hydrophobicity of guest residue "Xaa" and the number of pentapeptide repeats "n" (Urry, 1997). ELPs are biodegradable (Shah et al., 2012) and non-immunogenic (Shah, et al., 2013, Shi et al., 2013).

This disclosure provides an agent comprising, or consisting essentially of, or yet further consisting of a multimeric form of an elastin-like peptide (ELP) component that forms a drug binding domain stabilized by the ELP (also termed herein as an ELP agent or ELP fusion), a fragment or a biological equivalent thereof. The ELP is fused to two or more drug binding domains or drug carriers. In one aspect, at least one of the drug binding domains comprises cyclophilin A (SEQ ID NO: 22 or SEQ ID NO: 23), a fragment thereof, or a biological equivalent of cyclophilin A (SEQ ID NO: 22 or SEQ ID NO: 23).

The ELP fusion can further comprise, or consist essentially of, or yet further consist of, a therapeutic agent, e.g., cyclosporin A, prodrug or derivative thereof or a cathepsin S inhibitory peptide (CATSIP), which comprises, or alternatively consists essentially of, or yet further consists of the sequence NHLGDMTSEEVMSLTSS (SEQ ID NO: 30), or a biological equivalent of each thereof wherein a biological equivalent of cyclosporin A (also termed "reference peptide") or the cathepsin S inhibitory peptide (CATSIP) (also termed "reference peptide") is a peptide that has at least 80% sequence identity to the reference sequence or a peptide encoded by a polynucleotide that hybridizes under conditions of high stringency to a polynucleotide that encodes the reference peptide or its complement, wherein conditions of high stringency comprise hybridization reaction at about 60° C. in about 1×SSC, and binds cyclophilin A (SEQ ID NO: 22 or SEQ ID NO: 23).

In one aspect, the ELP component is of the group of: CA192 (SEQ ID NO: 3), CV96 (SEQ ID NO: 4), CAC (SEQ ID NO: 8), 3(CA)C (SEQ ID NO: 9) or a biological equivalent thereof, as well as dimers, trimers, tetramers and pentamers thereof.

These ELP fusions can be used to treat Sjorgren's syndrome, prevent immune system rejections, modulate inflammatory responses, treat autoimmune disorders, treat rheumatoid arthritis, and treats dry eye syndrome.

In another aspect, at least one of the two or more drug binding domains is the peptide prolyl isomerase protein (also known as reference peptide FK506 binding protein (FKBP) (an example of such is SEQ ID NO: 24)), a fragment or a biological equivalent thereof. A biological equivalent of the reference peptide is a peptide that has at least 80% sequence identity to the reference sequence or a peptide encoded by a polynucleotide that hybridizes under conditions of high stringency to a polynucleotide that encodes the reference peptide or its complement, wherein conditions of high stringency comprise hybridization reaction at about 60° C. in about 1×SSC and wherein the biological equivalent binds the ligand and/or the therapeutic agent. In one aspect, the ELP fusion further comprises a therapeutic agent such as rapamycin.

In addition to rapamycin, the therapeutic agent is of the group of everolimus, temsirolimus, ridaforolimus, tacrolimus, or cyclosporin A, and the drug binding domain for each comprises the reference peptide FK506 binding protein (FKBP or reference peptide), a fragment or a biological equivalent of each thereof, as defined herein, and wherein the biological equivalent binds the therapeutic agent of the group rapamycin, everolimus, temsirolimus, ridaforolimus, tacrolimus or cyclosporin A.

The ELP-FKBP fusion can further comprise a therapeutic agent, for example a small molecule drug. The FKPB specifically recognizes and binds the therapeutic agent, i.e., it comprises the cognate target of the therapeutic agent. In one aspect, fusion comprises the receptor for the therapeutic agent. Non-limiting examples of agent-ligand pairs include, without limitation rapamycin-FKBP, cyclosporinA-cyclophilin A, everolimus-FKBP, temsirolimus-FKBP, ridaforolimus-FKBP, tacrolimus-FKBP.

In one aspect, the ELP component is of the group of: CA192 (SEQ ID NO: 3), CV96 (SEQ ID NO: 4), 3(CA)C (SEQ ID NO: 9) or a biological equivalent thereof, as well as dimers, trimers, tetramers and pentamers thereof.

These ELP fusions can be used as immunosuppressant agents to suppress rejection after an organ transplant. Other uses include treatment of rheumatoid arthritis, psoriasis, Crohn's disease, nephrotic syndrome, keratoconjunctivitis sicca (dry eye). In another aspect, examples of additional disorders treatable can include, age-related macular degeneration, Sjögren's syndrome, autoimmune exocrinopathy, diabetic retinopathy, graft versus host disease (exocrinopathy associated with) retinal venous occlusions, retinal arterial occlusion, macular edema, postoperative inflammation, uveitis retinitis, proliferative vitreoretinopathy and glaucoma. In one embodiment, the disease is Sjögren's syndrome. In another embodiment, the disease is keratoconjunctivitis sicca (dry eye). In another embodiment the disease is scleritis. In another embodiment the disease is glaucoma.

In one aspect, these agents are useful to treat cancer, e.g., breast cancer. As is apparent to those of skill in the art, the cancer to be treated will vary with the therapeutic agent and the ELP fusion.

In another aspect, the at least one drug binding domain is a ligand that specifically targets and binds an ICAM-1 receptor. In certain embodiments, the ligand will target any cell or tissue that expresses an ICAM-1 receptor. Non-limiting examples of such cells include liver, heart, lacrimal gland, salivary gland, lung, brain, pancreatic acinar tissue, prostate or mucosal cells. In a related embodiment, the cell is a lacrimal acinar cell of the lacrimal gland. Non-limiting examples of ligands are human ICAM-1, murine ICAM-1, fragments or biological equivalents of each thereof. In one aspect, the ELP component is of the group of: CA192 (SEQ ID NO: 3), CV96 (SEQ ID NO: 4), 3(CA)C (SEQ ID NO: 9) or a biological equivalent thereof, as well as dimers, trimers, tetramers and pentamers thereof. These can also comprise a therapeutic agent such as peptidic protease inhibitors (e.g. cathepsin S inhibitory peptides), small molecules, or immunosuppressants for treating or ameliorating the symptoms of SjS. Thus, this disclosure also provides methods to treat or ameliorate the symptoms of SjS and associated disorders (e.g., autoimmune disorders) in a disease progression-oriented manner by targeting ICAM-1 receptors that are overexpressed on the surface of diseased lacrimal gland acinar cells. Since ICAM-1 receptor itself is internalized by endocytosis following ligand binding, this receptor is also an ideal target internalization of the targeted nanoparticles to the interior of the diseased acinar cells. The compositions also are useful to treat or ameliorate the symptoms of other autoimmune diseases, non-limiting examples of which include rheumatoid arthritis and systemic lupus erythematosus, or diseases eventually resulting in enhanced expression of ICAM-1 receptors.

In one embodiment, these agents can be used to treat a variety of autoimmune diseases, for example autoimmune diseases that include Coeliac disease, diabetes mellitus type 1 (IDDM), systemic lupus erythematosus (SLE), Sjögren's syndrome, Churg-Strauss Syndrome, Hasimoto's thyroiditis, Graves' disease, idiopathic thrombocytopenic purpura, and rheumatoid arthritis (RA).

In another aspect, the at least one drug binding domains is an antigen binding agent, such as an antibody fragment, e.g., a scFv reference peptide or an scFv peptide according to SEQ ID NO: 17 or SEQ ID NO: 18. In another aspect, the scFv is the single chain variable region of a reference anti-LGAC antibody, a reference anti-CD20 antibody or a biological equivalent of each thereof. A biological equivalent of the reference peptide is a peptide that has at least 80% sequence identity to the reference sequence or a peptide encoded by a polynucleotide that hybridizes under conditions of high stringency to a polynucleotide that encodes the reference peptide or its complement, wherein conditions of high stringency comprise hybridization reaction at about 60° C. in about 1×SSC and having similar activity as the reference peptide.

In one aspect, the ELP component is of the group of: CA192 (SEQ ID NO: 3), CV96 (SEQ ID NO: 4), 3(CA)C (SEQ ID NO: 9) or a biological equivalent thereof, as well as dimers, trimers, tetramers and pentamers thereof. These can be used to treat a disease or disorder that expresses the CD20 biomarker. In one aspect the disease is cancer such as lymphoma (non-Hodgkin's lymphoma) or CD20 expressing leukemia. In another aspect, the disease is an autoimmune disease such as Sjögren's syndrome, rheumatoid arthritis, coeliac disease, Crohn's disease and systemic lupus erythematosus. Tarella et al. (2013) Autoimmunity Reviews 12:802-813. In another aspect, a CD20-related disorder is any that has been treated by conventional CD20 antibody therapies such as rituximab.

In another aspect, the at least one of the drug binding domain is a ligand that specifically binds to a receptor selected from the group consisting of a reference CAR (GenBank acc.no. AF 200465.1) and a reference pIgR (NCBI Reference Sequence NM_002644.3), a fragment or a biological equivalent of each thereof. In another aspect, the drug binding domain is a ligand component selected from the group consisting of a reference knob ligand (SEQ ID NO: 26) and a reference mIgA ligand (SEQ ID NO: 27), a fragment or a biological equivalent thereof. A biological equivalent of the reference peptide is a peptide that has at least 80% sequence identity to the reference sequence or a peptide encoded by a polynucleotide that hybridizes under conditions of high stringency to a polynucleotide that encodes the reference peptide or its complement, wherein conditions of high stringency comprise hybridization reaction at about 60° C. in about 1×SSC and wherein the biological equivalent binds the at least one of the drug binding domains.

In one aspect, the ELP component is of the group of: CA192 (SEQ ID NO: 3), CV96 (SEQ ID NO: 4), 3(CA)C (SEQ ID NO: 9) or a biological equivalent thereof, as well as dimers, trimers, tetramers and pentamers thereof.

These fusions can be used to treat disorders of the eye and can optionally comprise, consist essentially of, or consist of a therapeutic agent and may be useful to encapsulate or attach drugs for treating disorders localized to the eye. By way of example, these disorders can include, age-related macular degeneration, Sjögren's syndrome, autoimmune exocrinopathy, diabetic retinopathy, graft versus host disease (exocrinopathy associated therewith) retinal venous occlusions, retinal arterial occlusion, macular edema, post-operative inflammation, uveitis retinitis, proliferative vitreoretinopathy and glaucoma. In one embodiment, the disease is Sjögren's syndrome. In another embodiment, the disease is keratoconjunctivitis sicca (dry eye). In another embodiment the disease is scleritis. In another embodiment the disease is glaucoma.

In one aspect, the ELP component is of the group of: 5FA (SEQ ID NO: 10), 5FV (SEQ ID NO: 11), FAF (SEQ ID NO: 25), or a biological equivalent thereof, as well as dimers, trimers, tetramers and pentamers thereof. In some embodiments, the drug binding domain comprises FKBP.

These ELP-FKBP fusions can be used to treat immune disorders and can optionally comprise, consist essentially of, or consist of a therapeutic agent and may be useful to encapsulate or attach drugs for treating disorders. These ELP fusions can be used as immunosuppressant agents to suppress rejection after an organ transplant. Other uses include treatment of rheumatoid arthritis, psoriasis, Crohn's disease, nephrotic syndrome, keratoconjunctivitis sicca (dry eye). In some embodiments, the disorder is any disorder known in the art to be treated with a rapalogue.

In addition to rapamycin, the therapeutic agent is of the group of everolimus, temsirolimus, ridaforolimus, or tacrolimus and the drug binding domain for each comprises the reference peptide FK506 binding protein (FKBP or reference peptide), a fragment or a biological equivalent of each thereof, as defined herein, and wherein the biological equivalent binds the therapeutic agent of the group rapamycin or an analog thereof, everolimus, temsirolimus, ridaforolimus, or tacrolimus.

The ELP-FKBP fusion can further comprise a therapeutic agent, for example a small molecule drug. The FKPB specifically recognizes and binds the therapeutic agent, i.e., it comprises the cognate target of the therapeutic agent. In one aspect, fusion comprises the receptor for the therapeutic agent. Non-limiting examples of agent-ligand pairs include, without limitation rapamycin-FKBP, cyclosporinA-cyclophilin A, everolimus-FKBP, temsirolimus-FKBP, ridaforolimus-FKBP, tacrolimus-FKBP.

In one aspect, the ELP component is 4PA (SEQ ID NO: 15) or a biological equivalent thereof, as well as dimers, trimers, tetramers and pentamers thereof.

In some embodiments, the drug binding domain comprises two or more, three or more, four or more, or five or more of a reference PIN1 peptide (SEQ ID NO: 31), a fragment, or an equivalent thereof. A biological equivalent of the reference peptide is a peptide that has at least 80% sequence identity to the reference sequence or a peptide encoded by a polynucleotide that hybridizes under conditions of high stringency to a polynucleotide that encodes the reference peptide or its complement, wherein conditions of high stringency comprise hybridization reaction at about 60° C. in about 1×SSC and wherein the biological equivalent retains similar biological activity.

These ELP-PIN1 fusions can be used to treat cancers and can optionally comprise, consist essentially of, or consist of a therapeutic agent and may be useful to encapsulate or attach drugs for treating acne or cancers. Non-limiting examples of these cancers include acute promyelocytic leukemia (APL), breast cancer, neuroblastoma, and myeloma. In some embodiments, the ELP further comprises a therapeutic agent of all-trans retinoic acid (ATRA). In some embodiments, the disorder treated is any disorder known in the art to be treated with all-trans retinoic acid (ATRA).

The two or more drug binding domains of the ELP fusions can be the same or different from each other.

In each of the above noted aspects, the agent may optionally comprise, or alternatively consist essentially of, or yet further consist of a detectable label.

In each of the above noted aspects, the agent may optionally comprise, or alternatively consist essentially of, or yet further consist of a linker that links the carrier drug binding domain to the therapeutic agent. Non-limiting examples of such include a thiol reactive linker, cleavable disulfide linker, a hydrophilic flexible linker comprised of amino acids (GGGGS (SEQ ID NO: 50)n or a rigid linker comprised of amino acids (EAAAK)n (SEQ ID NO: 33), wherein the subscript "n" denotes the number of repeats. In one aspect the peptide can be repeated from 2 to 10, or from 2 to 8, or from 3 to 8, or from 3 to 7, or 3 to 5, or 3 times.

Yet further provided are isolated polynucleotides encoding the ELP fusions. The isolated polynucleotide can optionally be operatively linked to regulatory or expression elements that facilitate recombinant expression of the polynucleotide, such as promoters, enhancers, etc. Also provided are isolated vectors and isolated host cells comprising, or alternatively consisting essentially of, or yet further consisting of the isolated polynucleotide. Also provided are methods for preparing an ELP fusion, the methods comprising, or alternatively consisting essentially of, or yet further consisting of expressing the isolated polynucleotide and optionally isolating the ELP fusion from the cell or cell supernatant.

In one embodiment, a substantially homogenous composition of the ELP fusion alone or in combination with the therapeutic agent is provided. These compositions can be combined with a carrier. In another embodiment, a substantially homogenous composition of the polynucleotides encoding an ELP fusion is provided.

The therapeutic agents and compositions such as substantially homogenous compositions of the multimers can be combined with carriers, such as pharmaceutically acceptable carriers, and the compositions can be further processed for ease of administration, e.g., by combining with stabilizer, preservatives or other active agents. In a further aspect, the compositions are processed for freezing or freeze-drying.

In one embodiment, this disclosure also provides a method for delivering a therapeutic agent in vitro or in vivo, the method comprising, or alternatively consisting essentially of, or yet further consisting of, contacting a tissue expressing a receptor for the ELP fusion (such as the receptor for cyclosporine A) with the ELP. Also provided are methods for delivering a drug in vivo, the methods comprising, or alternatively consisting essentially of, or yet further consisting of administering to a subject or patient an effective amount of the ELP fusion as disclosed herein. In one embodiment, also provided are methods for ameliorating the symptoms of a disease or condition or for treating a disease or condition, comprising, or alternatively consisting essentially of, or yet further consisting of, administering an effective amount of an ELP fusion disclosed herein to a subject or patient in need thereof.

In one embodiment, further provided is a kit for ameliorating the symptoms of a disease or condition or treating a disease, the kit comprising, consisting essentially of, or yet further consisting of an ELP fusion. The kit can optionally provide instructions for use of the ELP fusion.

BRIEF DESCRIPTION OF DRAWINGS

(FIG. 1A) Cartoon depicting a mono ELP fusion protein, CA192 (SEQ ID NO: 3) bound to CsA (FIG. 1B) SDS-PAGE of purified CA192 (SEQ ID NO: 3) (91.6 kDa) stained with copper chloride demonstrating a molecular weight shift upon fusing CypA to A192 (73.6 kDa).

(FIG. 2B) The concentration-temperature phase diagram was determined for both ELPs, and fit to the following equation: Tt=b−m $\log_{10}[C_{ELP}]$. The 95% CI around each best-fit line is indicated with dashed lines. The values of slope, m, and intercept, b, are shown in Table 1. (FIG. 2C) The phase transition behavior of CA192 (SEQ ID NO: 3) relative to A192 is shown. The data was obtained after size exclusion chromatography of CA192 (SEQ ID NO: 3) and the sample of CA192 (SEQ ID NO: 3) consists essentially of dimerized CA192 (SEQ ID NO: 3).

(FIG. 3B) and a half-life of 52 hr (95% CI: 44 to 61 hr) at 37° C. (FIG. 3C). As a comparison, the free CsA release profile follows a two-phase decay with a burst release due to precipitation along with buffer exchange. The terminal half-life during the second slower decay is 6.3 hr (95% CI: 2.7 to 99.0 hr) at 4° C. and 1.1 hr (95% CI: 0.8 to 1.6 hr) at 37° C.

(FIG. 4A) After loading with a 6× excess of free drug, the loading ratio of CsA to CA192 (SEQ ID NO: 3) (250 µM) or human Albumin (250 µM) was estimated. CA192 (SEQ ID NO: 3) entrapped significantly more drug than albumin (p<0.0001). Per molecule of protein, CA192 (SEQ ID NO: 3) binds 10× more drug than albumin. (FIG. 4B) Human albumin (1 mM) was unable to extract CsA from CA192 (SEQ ID NO: 3) the fusion over period of 48 h. The half-life was found to be 525.3 h, which was even higher than the release half-life estimated by dialysis. Briefly, human albumin was dissolved into a PBS solution of CsA-loaded CA192 (SEQ ID NO: 3), and the albumin concentration was adjusted to 1 mM, which is near the physiological concentration of albumin. The mixture was incubated at 37° C. and samples were collected at different time points up to 48 h. The ELP phase separation was induced to purify CA192 (SEQ ID NO: 3) from the mixture with Albumin, which was—followed by RP-HPLC analysis. (FIG. 4C) Instead of albumin, lipoproteins in the plasma, mainly high-(HDL) and low-(LDL) density lipoprotein, predominantly bind to cyclosporine in the plasma. Thus, CA192-CsA was also tested against mouse plasma over a period of 48 hr. Despite an initial drug loss due to incomplete isolation during the hot spin, more than 50% of CsA was maintained as CA192 (SEQ ID NO: 3) bound after 48 hr incubation at 37° C.

(FIG. 5A) Dynamic light scattering (DLS) intensity data reveals that unloaded CA192 (SEQ ID NO: 3) has a mean $R_h$ of 64.8±0.7 nm (p<0.05), significantly outsizing plain A192 with a $R_h$ 7.3±0.4 nm (p<0.05). Drug-loaded CA192 (SEQ ID NO: 3) has a mean $R_h$ of 64.5±0.5 nm (p<0.05). (FIG. 5B) The stability assay revealed that the $R_h$ of CA192 (SEQ ID NO: 3) is maintained throughout 48 h, suggesting good stability of this constructed fusion protein and stable aggregation at physiological temperature. (FIG. 5C) Size Exclusion Chromatography (SEC) was conducted to fractionate CA192 (SEQ ID NO: 3) depending on their particle size. Two fractions were observed. (FIG. 5D) 99.2% by mass of fraction 2 was found to have a $R_h$ of 6.5±0.1 nm (p<0.05), which is consistent with a monomer or dimer of CA192 (SEQ ID NO: 3). In contrast, the fraction 1 contains a mixture of larger aggregates.

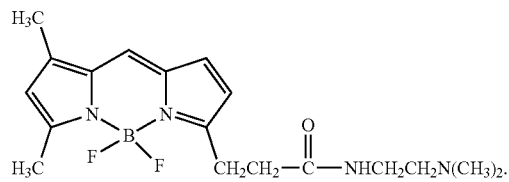

ELP constructs were labeled covalently with rhodamine. Cells were imaged by confocal laser scanning microscopy.

Figure 7A:
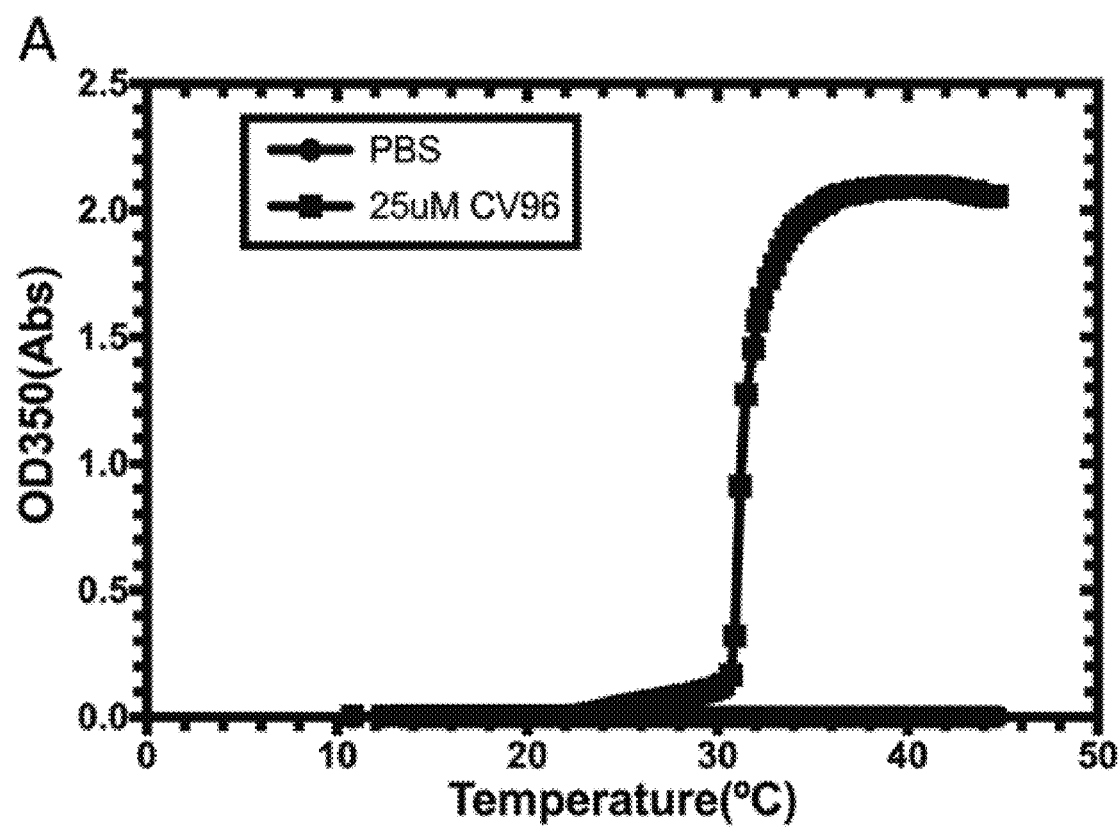
Figure 7B:
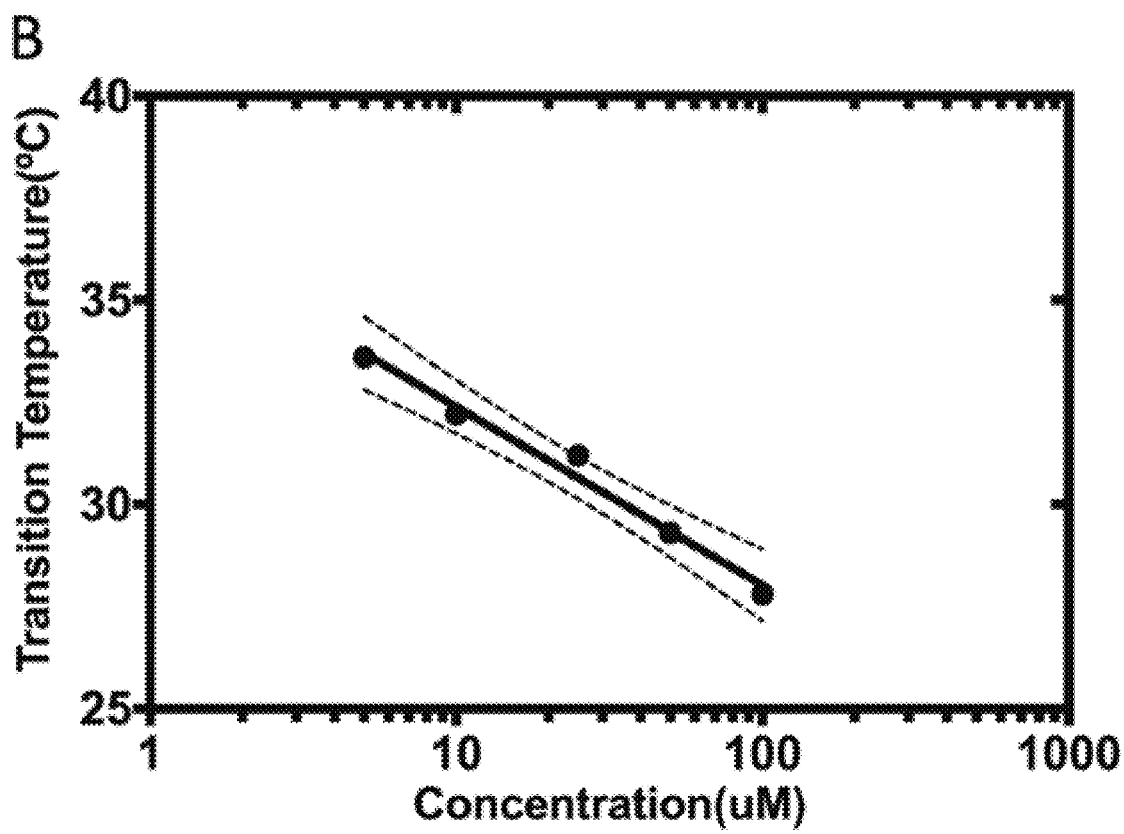

FIGS. 7A-7B: CA192 (SEQ ID NO: 3), CV96 (SEQ ID NO: 4) has a transition temperature (Tt) of 31.2° C. at 25 µM (FIG. 7A), which is well lower than physiological temperature, suggesting that CV96 (SEQ ID NO: 4) may form a depot after s.c. injection. The optical density profile representing the CV96 (SEQ ID NO: 4) phase separation behavior is shown in FIG. 7B.

Figure 8:
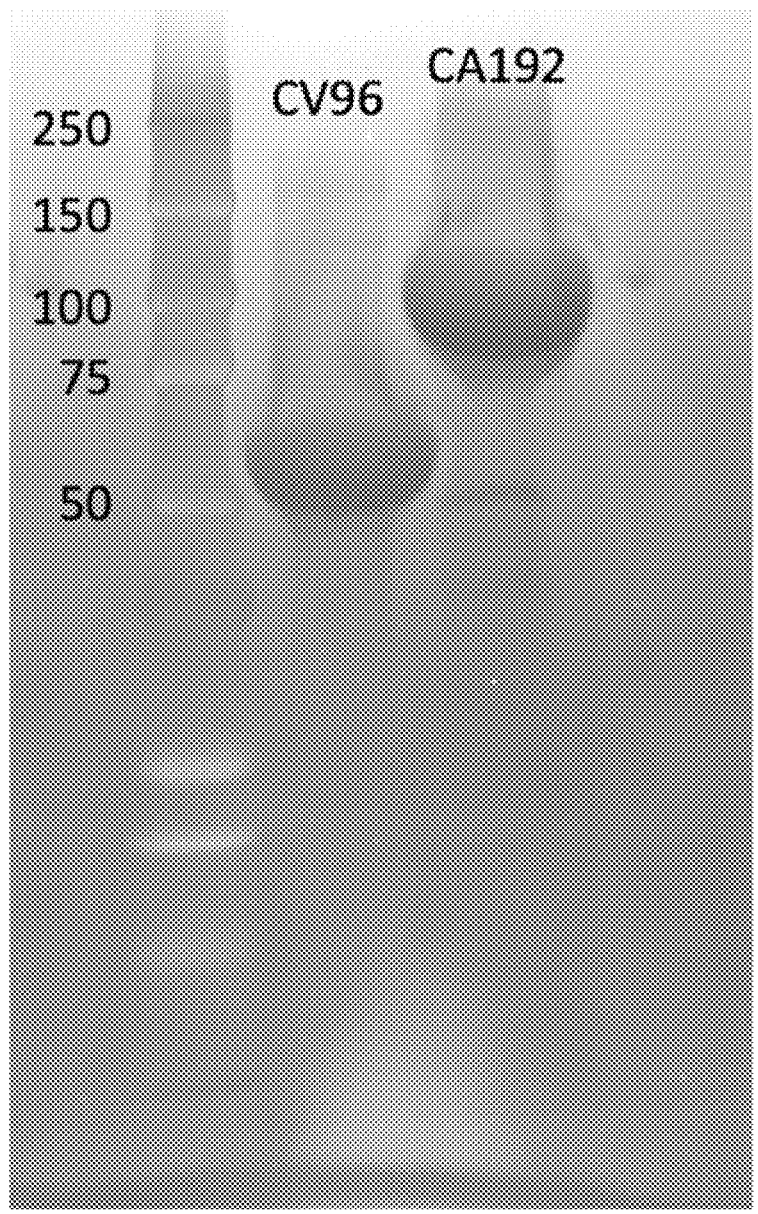

FIG. 8: The molecular weight of purified CV96 (SEQ ID NO: 4) was verified by SDS-PAGE stained with copper chloride ($CuCl_2$).

Figure 9:
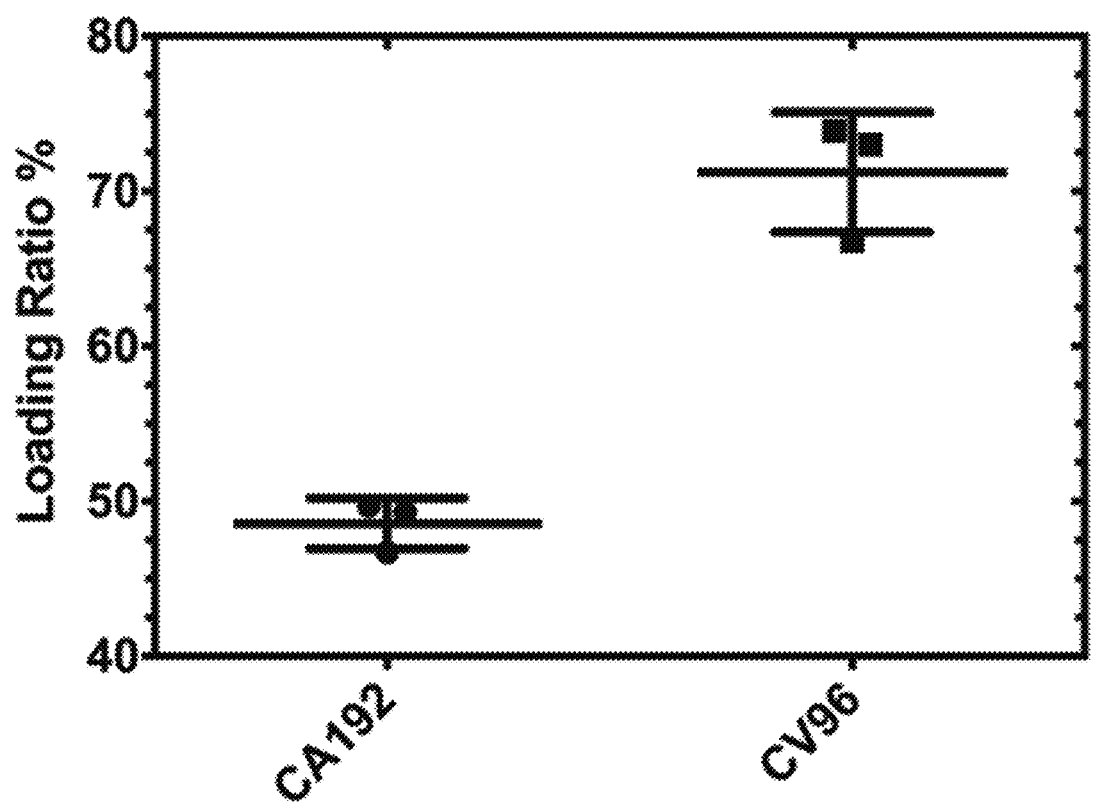

FIG. 9: Despite its lower phase transition temperature CV96 (SEQ ID NO: 4) has a similar capacity to load CsA in comparison with CA192 (SEQ ID NO: 3). ELP fusions that phase separate below physiological temperature can potentially contribute to reducing injection frequency.

Figure 10:
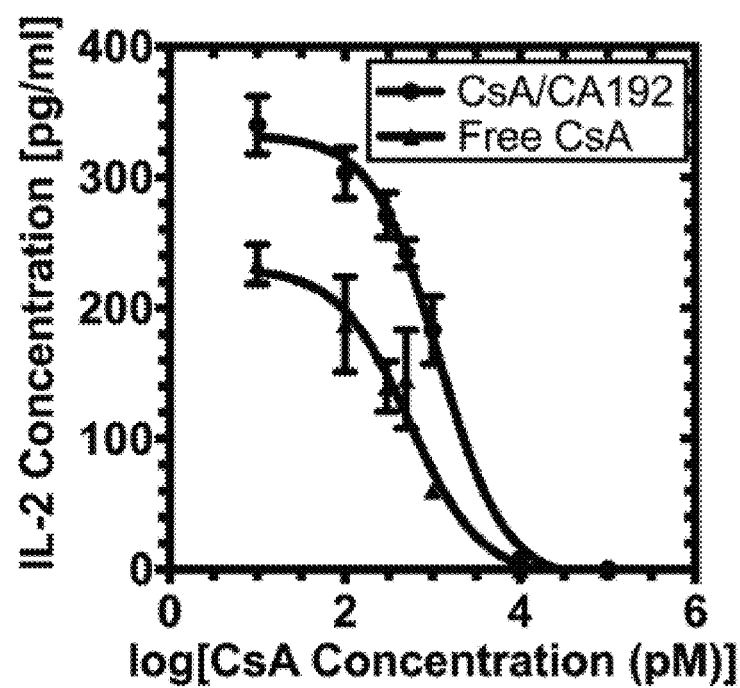

FIG. 10: CsA/CA192 exhibit comparable IL-2 inhibition efficacy. Upon stimulation, Jurkat cells produce IL-2. CsA, as an immunosuppressant, can effectively reduce IL-2 gene expression and secretion. The inhibitory concentration that blocks half of activation (IC50) of CsA/CA192 is 1239±391 pM, slightly higher than free CsA with an IC50 of 522±152 pM (n=3, mean±SD).

Figure 11A:
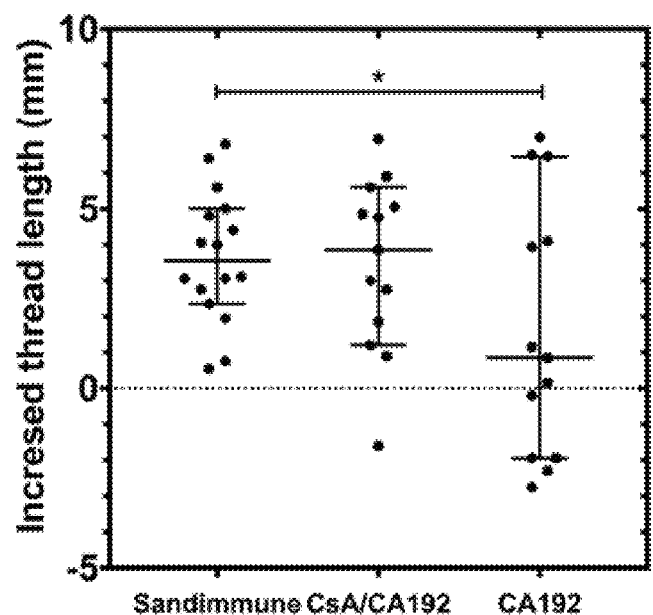
Figure 11B:
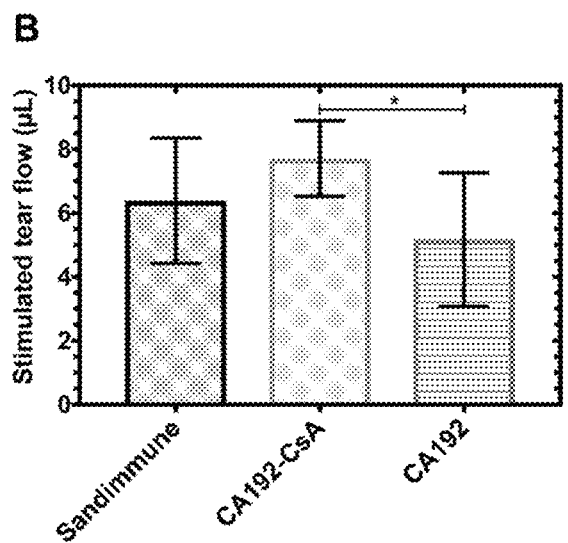

FIG. 11A-11B: (FIG. 11A) Treatment with Sandimmune and CsA/CA192 enhance tear production using a thread test. A t-test between Sandimmune and CA192 (SEQ ID NO: 3) shows a significant difference (p=0.016), while the difference between CsA/CA192 and CA192 (SEQ ID NO: 3) trends towards a significant value (p=0.055). (FIG. 11B) On the day of euthanasia, tears were collected after stimulating the LG topically with carbachol. CA192-CsA treated mice exhibited a significant increase in tear volume relative to CA192 (SEQ ID NO: 3) control (P=0.014). Error bars here represent mean±SD from n=15.

Figure 12:
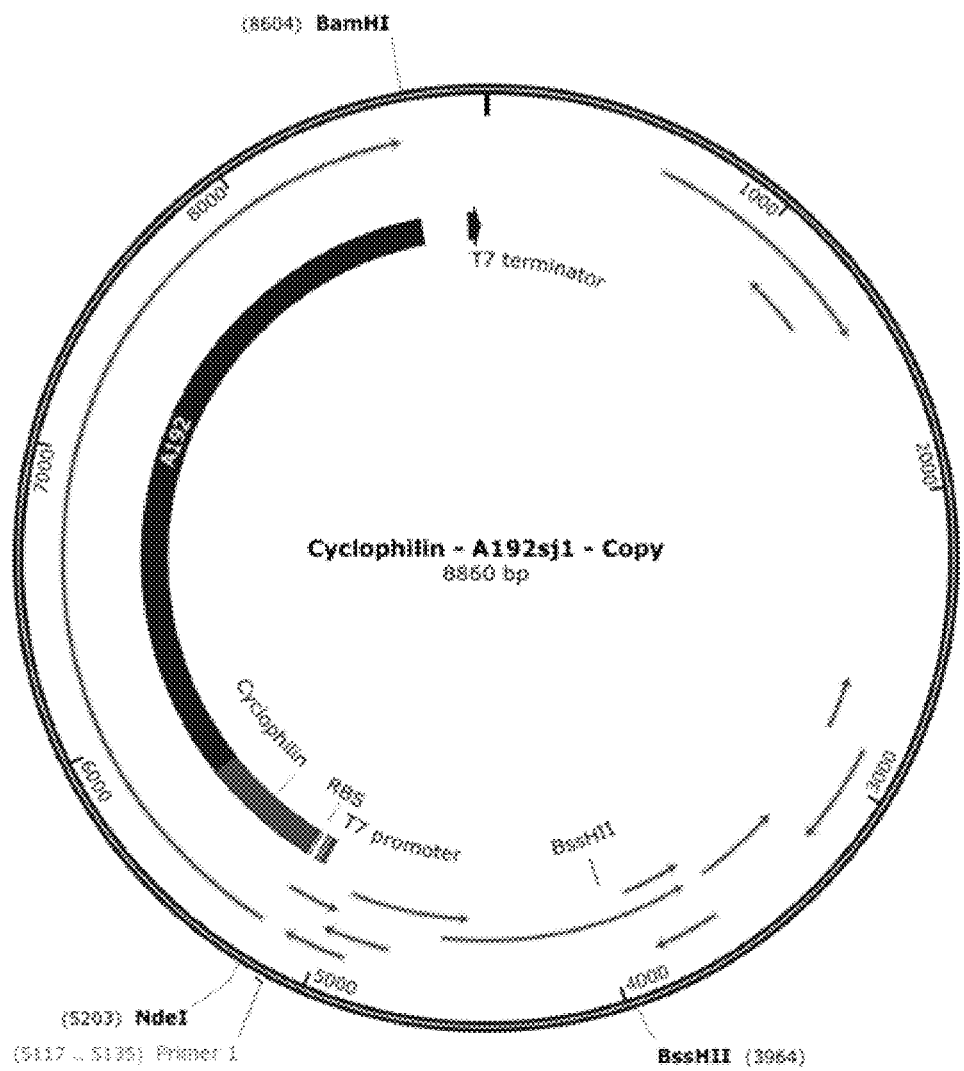

FIG. 12 is a map of the CA192 (SEQ ID NO: 3) plasmid.

Figure 13:
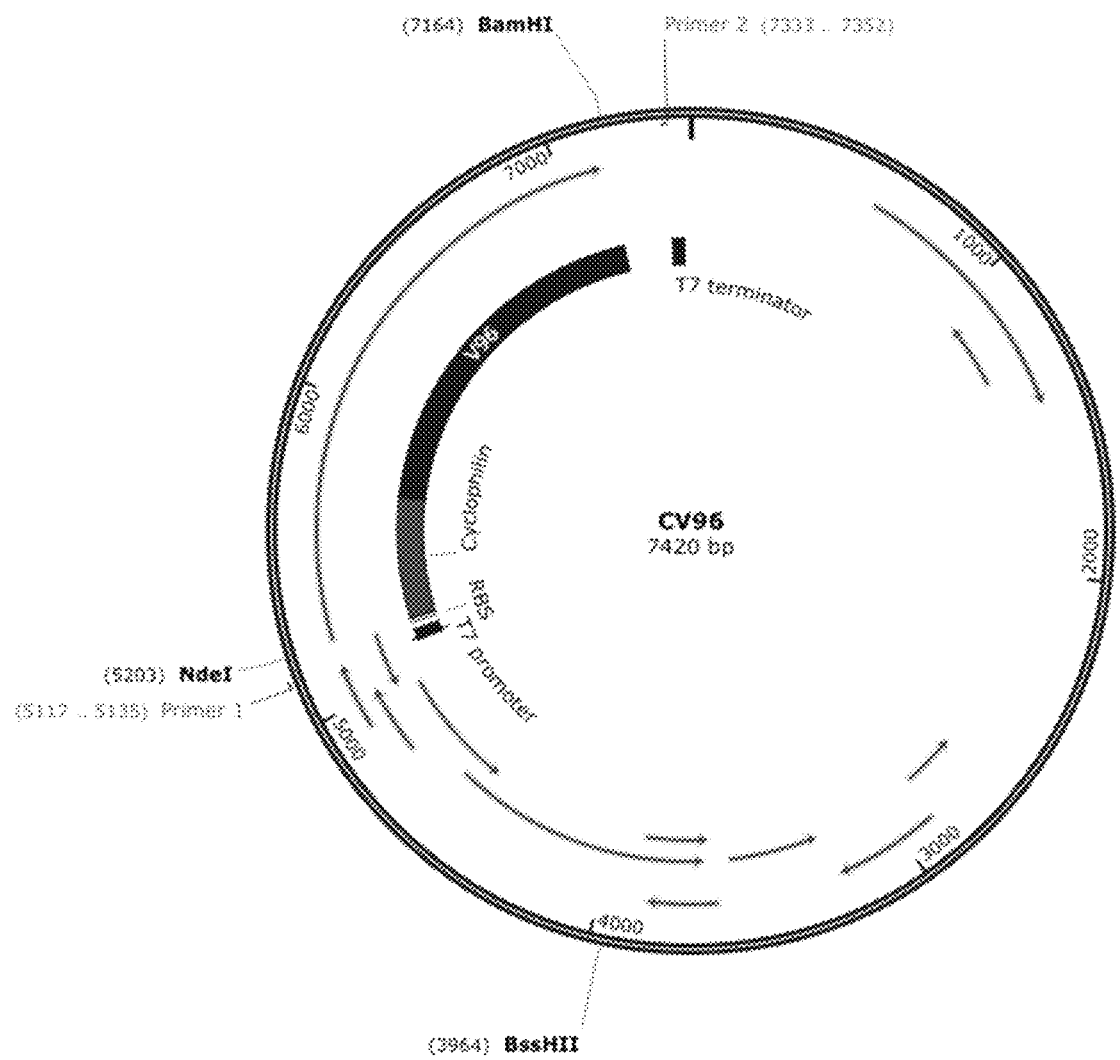

FIG. 13 is a map of the CV96 (SEQ ID NO: 4) plasmid.

Figure 14:
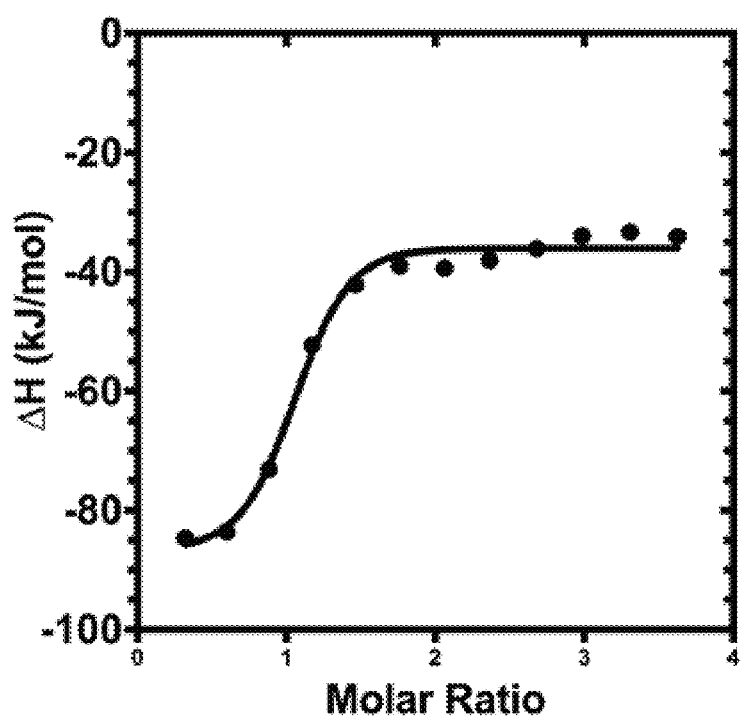

FIG. 14: Isothermal Titration calorimetry (ITC) demonstrated that dimerized CA192 (SEQ ID NO: 3) is the functional fraction to bind cyclosporine A (CsA) with a dissociation constant of 343±175 nM (n=3, mean±SD) at 25° C. Dimerized CA192 (SEQ ID NO: 3) was repeatedly titrated into the cell prefilled with CsA. The released heat from binding upon each injection was recorded, represented by each point in the figure. The binding affinity was then interpreted based on the inverse slope of the inflection. Similarly, the dissociation constant of CV96 (SEQ ID NO: 4) to CsA was also determined to be 230±57.8 nM.

Figure 15:
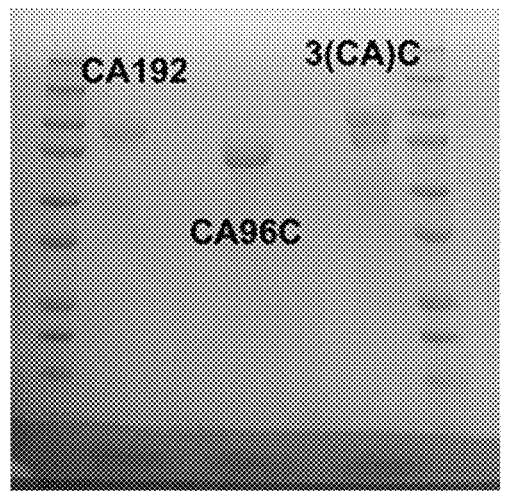

FIG. 15: SDS-PAGE demonstrating that three generations of ELP-based CsA carriers are successfully cloned, expressed and purified.

Figure 16:
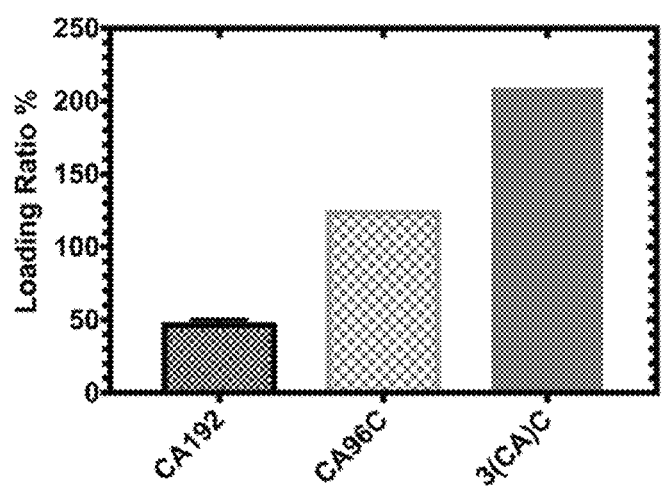

FIG. 16: The CsA loading ratio was significantly increased to 127.5% by $2^{nd}$ generation carrier, CA96C, and to 209.0% by 3rd gen carrier, 3(CA)C (SEQ ID NO: 9), from 48.6%±1.63% (mean±SD, n=3) of CA192 (SEQ ID NO: 3).

Figure 17:
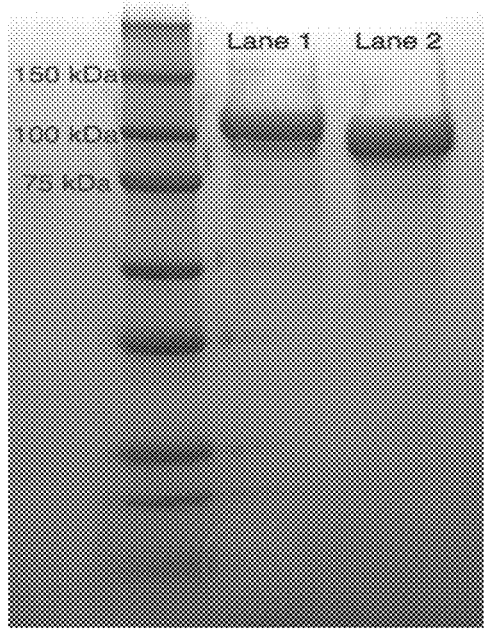

FIG. 17: SDS PAGE was used to estimate the purity and identity of high capacity FKBP-ELP fusions 5FA and WV.

Figure 18A:
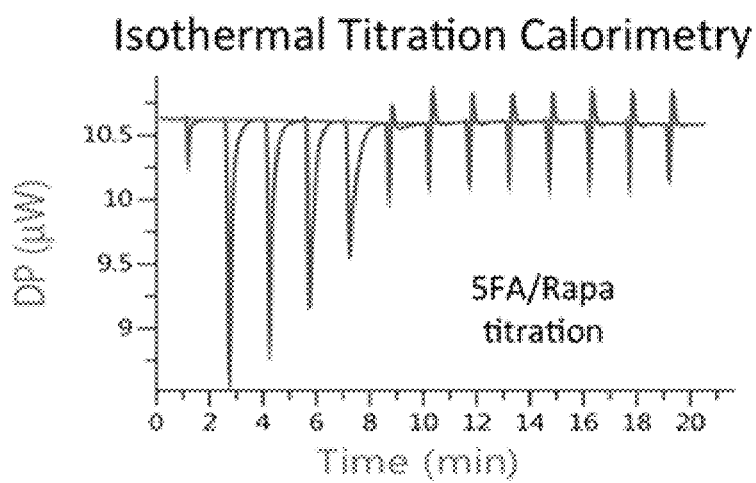
Figure 18B:
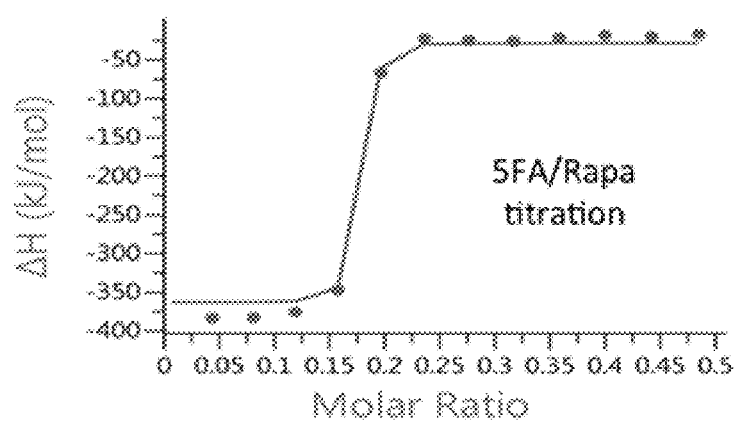

FIGS. 18A-18B: Results of Isothermal Titration calorimetry used to confirm that all five FKBP domains on 5FA bind rapamycin.

Figure 19A:
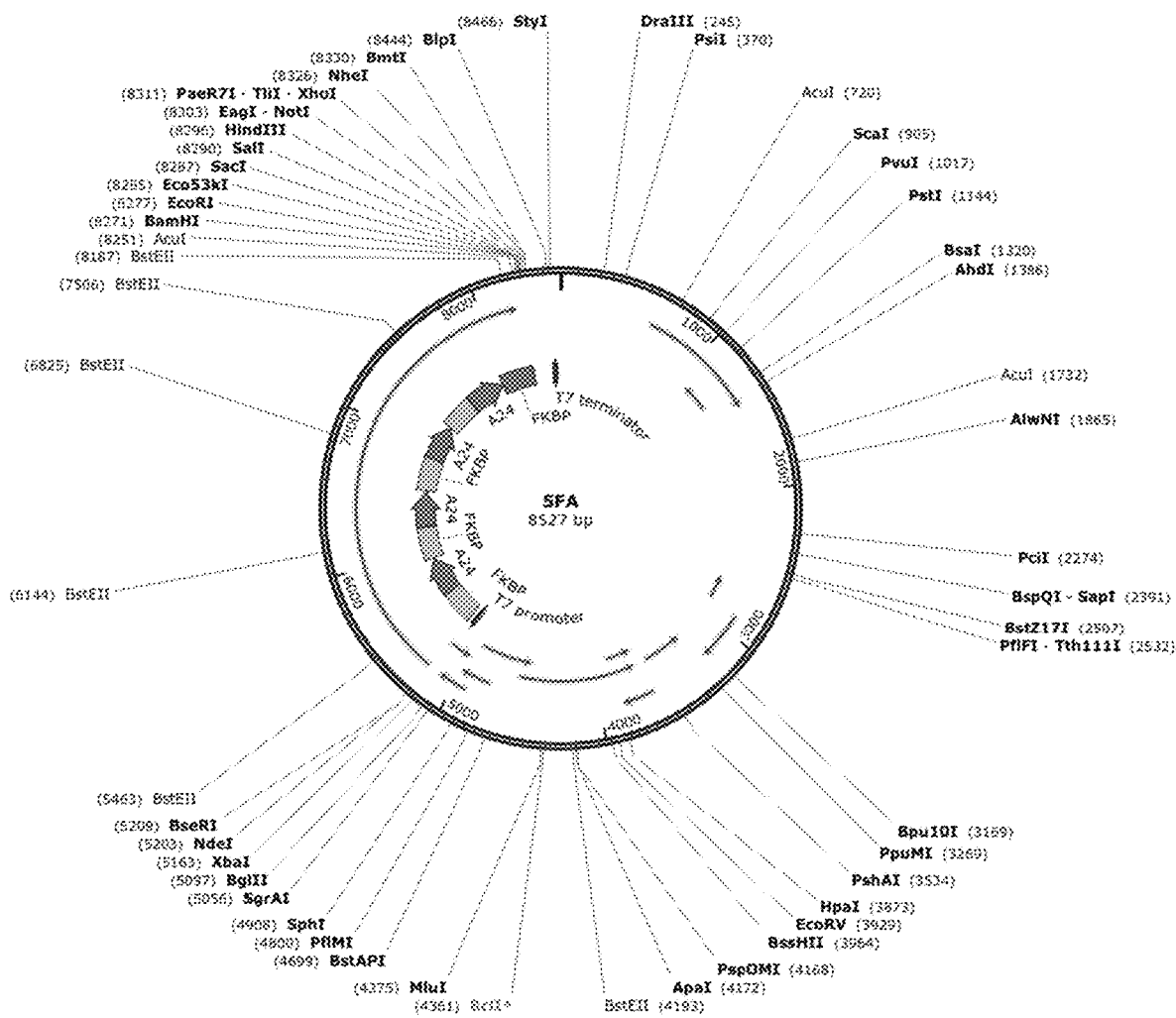
Figure 19B:
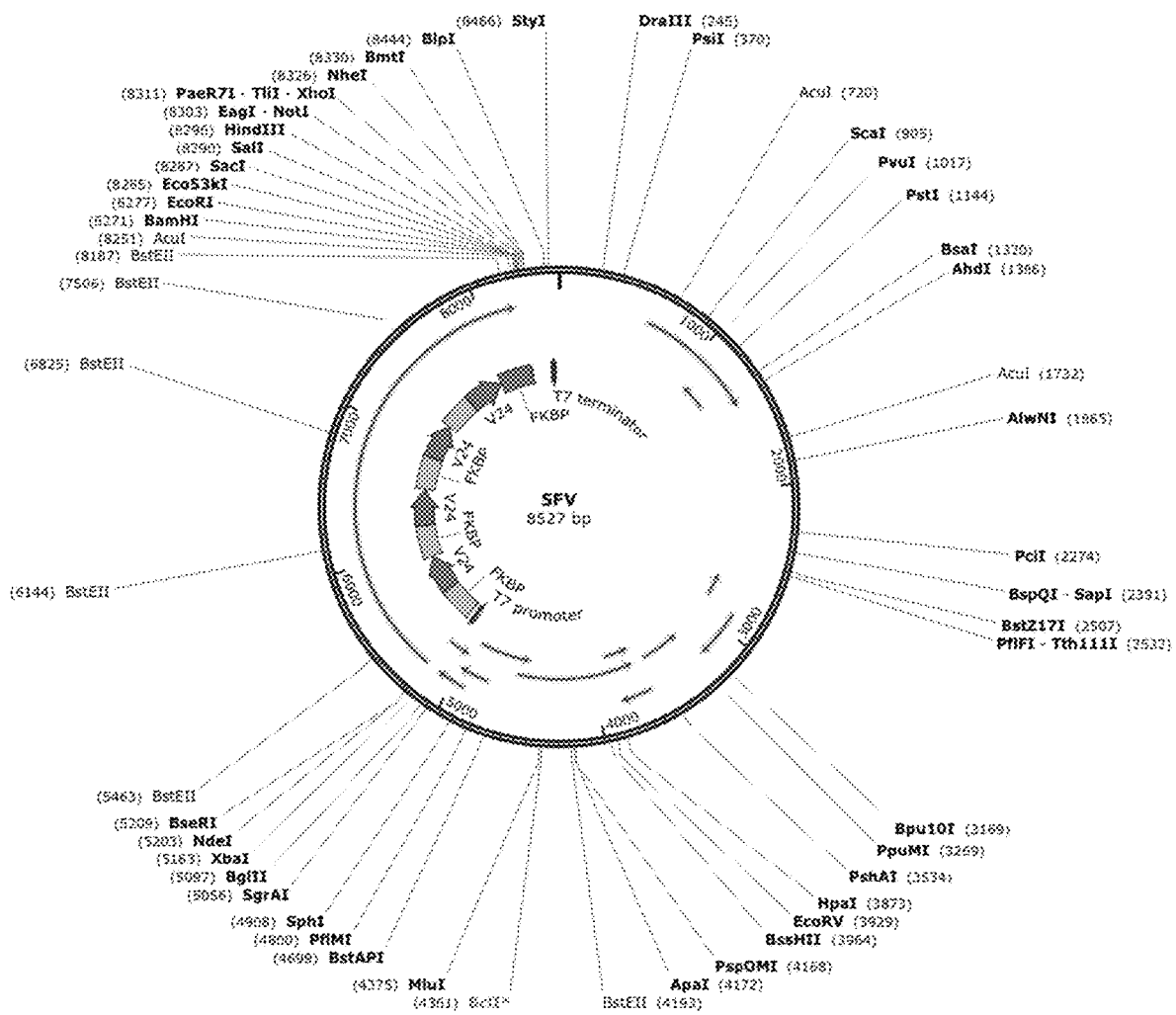

FIG. 19A-19B: Plasmid map depicting pET-25b (+) vector encoding high capacity ELP fusions, which each contain 5 FKBP domains that are linked by elastin-like polypeptide. FIG. 19A 5FA contains 5 FKBP domains linked by an ELP known as A24, which remains soluble at physiological temperatures, FIG. 19B 5FV contains 5 FKBP domains linked by an ELP known as V24, which is expected to phase separate at physiological temperatures.

Figure 20:
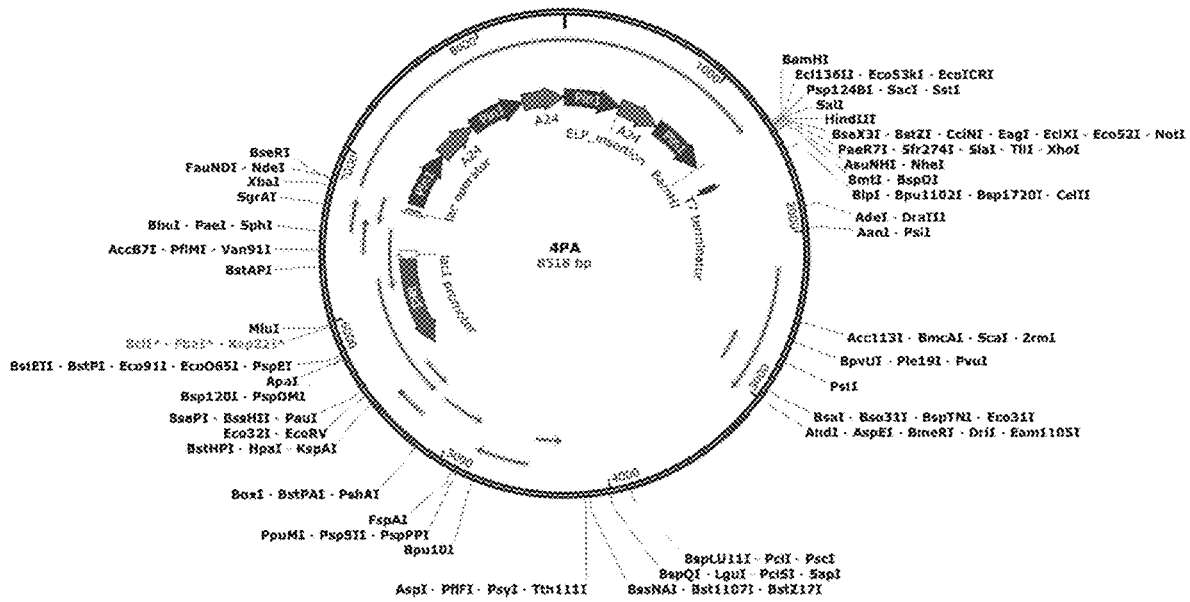

FIG. 20: Plasmid map depicting pET-25b (+) vector encoding 4PA24, which contains 4 Pin1 domains for every fusion protein, which are linked by elastin-like polypeptide known as A24.

Figure 21:
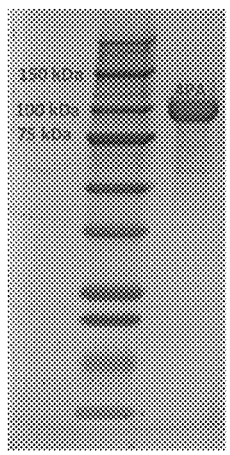

FIG. 21: SDS PAGE was used to resolve the purified 4PA fusion protein. To formulate ATRA-loaded 4PA, a two phase encapsulation method was adopted. After removing undissolved drug, HPLC was used to quantify 4PA and ATRA concentrations. Encapsulation ratio, defined as CATRA/C4PA was 2.7, theoretical maximum being 4. When encapsulation was performed using a control ELP A192, ATRA peak was not detectable on HPLC, thereby proving the solubilization process is mediated by Pin1-ATRA binding.

Figure 22A:
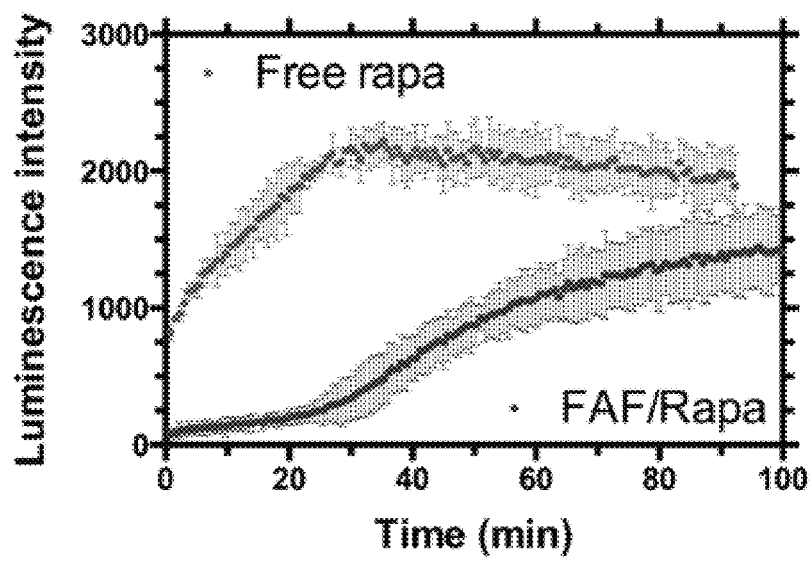
Figure 22B:
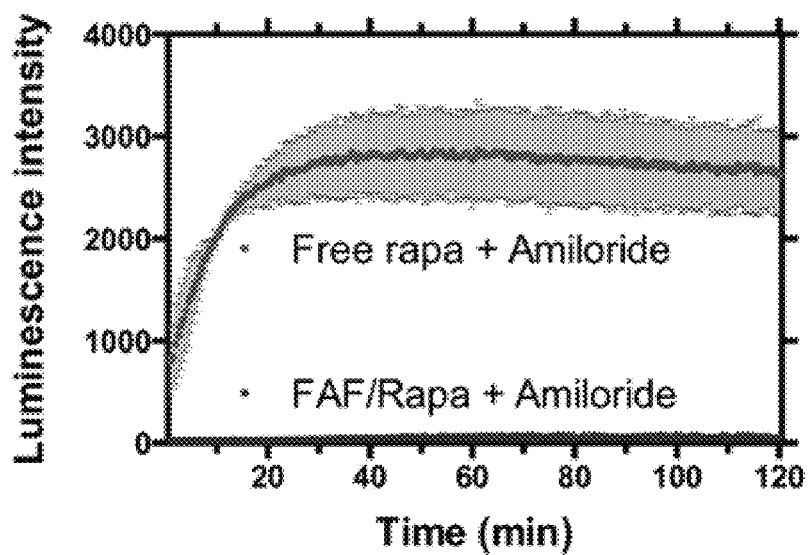

FIGS. 22A-22B: FAF delays the access of Rapa to the cytosol in a manner consistent with macropinocytosis. FIG. 22A: MDA-VB-468 cells were transfected with a split luciferase reporter that enables the specific detection of Rapa within the cytosol. When incubated with cells, free drug resulted in rapid luciferase activity consistent with diffusion across the plasma membrane as the mechanism of cellular entry. In contrast, FAF/Rapa produced luminescence only after 30-minutes, a period of time consistent with cellular uptake. FIG. 22B: Addition of the macropinocytosis inhibitor amiloride completely blocks cytosolic detection of Rapa from FAF/Rapa. Free Rapa luminescence kinetics were unaffected by amiloride. (Mean±95% CI, n=6).

Figure 23A:
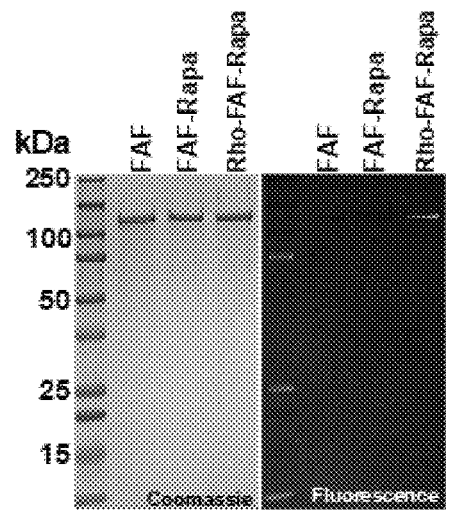
Figure 23B:
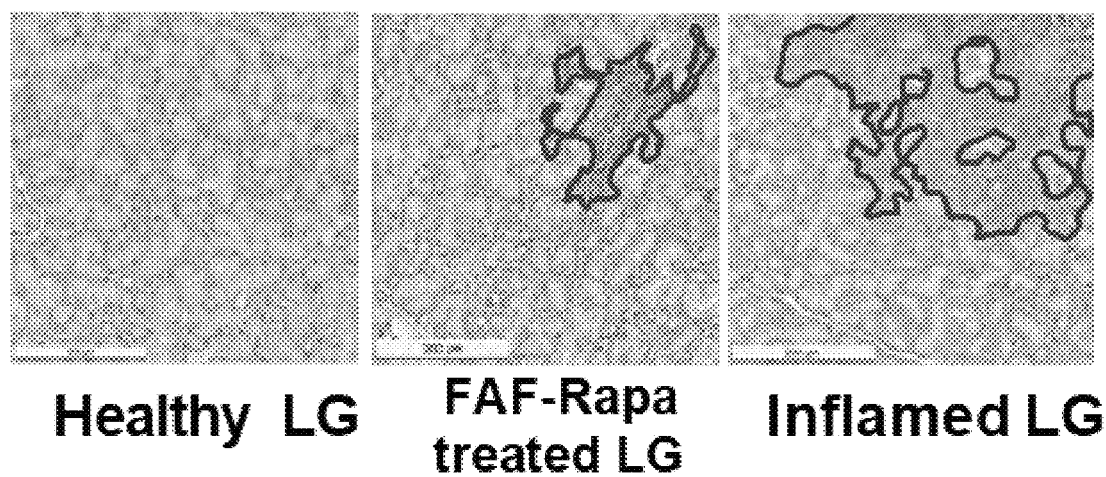
Figure 23C:
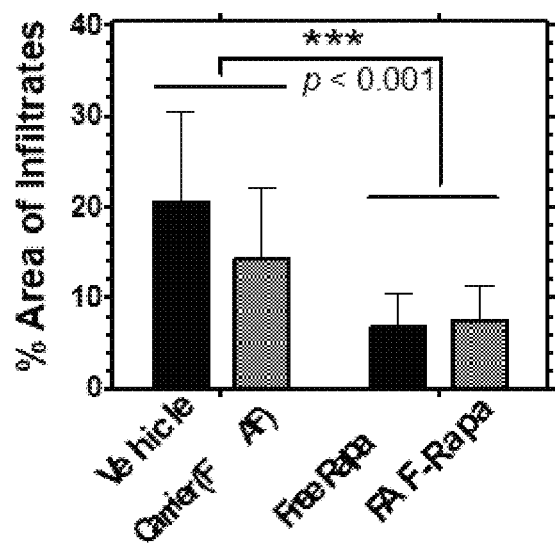

FIGS. 23A-23C: FAF-Rapa reduces lymphocytic infiltration in the LG of male NOD mice, FIG. 23A: identity, purity and fluorescence of FAF, FAF-Rapa and rhodamine-labeled FAF-Rapa (Rho-FAF-Rapa) were analyzed by Comassie blue staining and fluorescence imaging of SDS-PAGE. FIG. 23B: One LG from each mouse was collected at the conclusion of the study. Sections from $25^{th}$, $50^{th}$ and $75^{th}$ percentile sections from each LG were quantified by a blinded observer to determine the average percentage area of infiltrate per gland. Glands from 4 treatment groups (n=15) were compared. Inflamed LG show areas of purple nuclear staining, which indicate foci of infiltrating lymphocytes (outlined in blue). Severe lymphocytic infiltration was reduced by FAF-Rapa (middle panel). Scale bar represents 200 µm. FIG. 23C: The percent area of infiltration was calculated using ImageJ (mean±SD). A Kruskal-Wallis nonparametric test was used to compare groups.

Figure 24A:
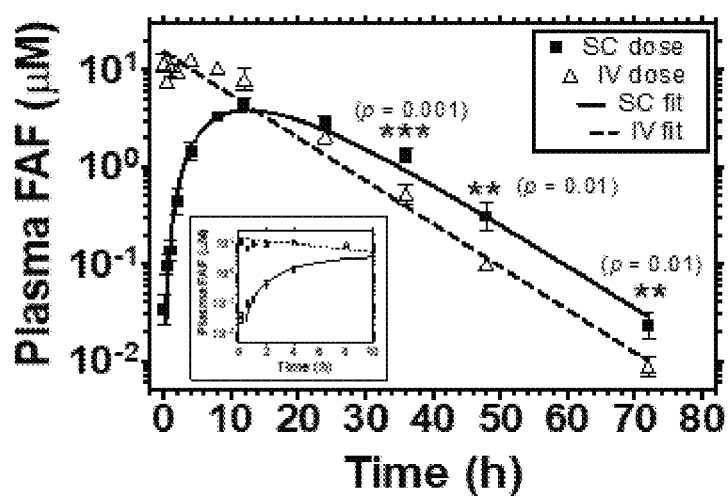
Figure 24B:
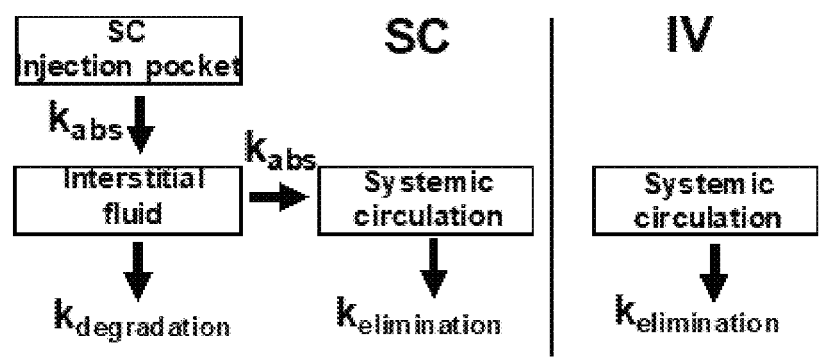

FIGS. 24A-24B: Compartmental modeling accurately fits Plasma. Conc. Vs. Time profiles of IV and SC administered FAF.1.0 mg Rapa/kg BW of Rho-FAF-Rapa was injected either IV (n=4) or SC (n=5) to male NOD mice. FIG. 24A shows data for the first ten hours are shown in the inset. SC administration yielded significantly higher Rho-FAF concentrations at 36, 48 and 72 hr (mean±SD). A student T-test was used to compare groups. FIG. 24B shows Data were well-fit by either a one-compartment (IV) or three-compartment (SC) pharmacokinetic model as indicated. $k_{abs} = k_{absorption}$.

Figure 25A:
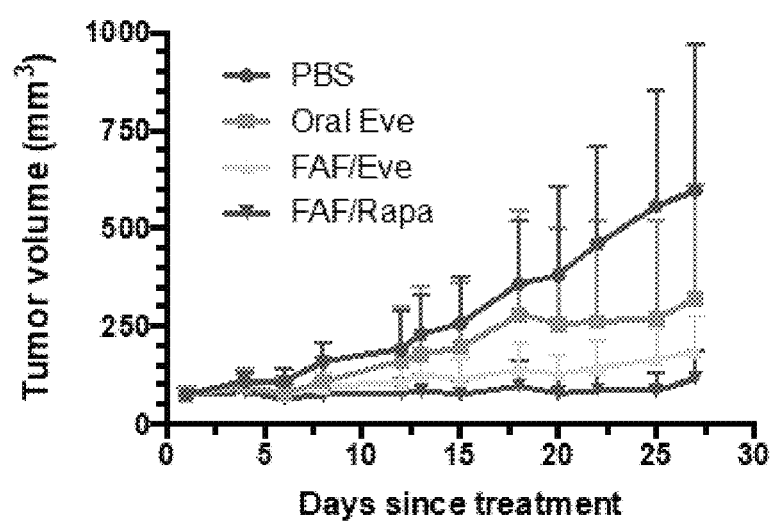
Figure 25B:
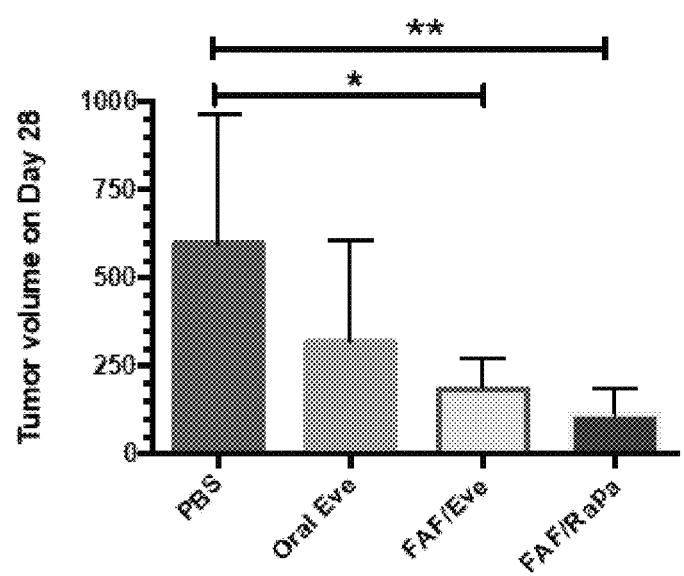

FIGS. 25A-25B: show results of administration of FAF formulations when tested for efficacy and safety in nude mice bearing orthotopic tumors of BT-474 cell line. Oral Eve at the same drug dose served as a clinically relevant control. Mice bearing tumors of average size 100 mm³ were randomized and treated with either oral Eve, FAF/Rapa or FAF/Eve at 1 mg/kg dose every other day for 4 weeks (FIG. 25A). Compared to PBS treated mice, only FAF/Eve and FAF/Rapamycin groups suppressed tumor growth significantly (FIG. 25B).

DETAILED DESCRIPTION

Definitions

The practice of the present disclosure will employ, unless otherwise indicated, conventional techniques of tissue culture, immunology, molecular biology, microbiology, cell biology and recombinant DNA, which are within the skill of the art. See, e.g., Sambrook et al., (1989) Molecular Cloning: A Laboratory Manual, 2nd edition; Ausubel et al., eds. (1987) Current Protocols In Molecular Biology; MacPherson, B. D. Hames and G. R. Taylor eds., (1995) PCR 2: A Practical Approach; Harlow and Lane, eds. (1988) Antibodies, A Laboratory Manual; Harlow and Lane, eds. (1999) Using Antibodies, a Laboratory Manual; and R. I. Freshney, ed. (1987) Animal Cell Culture.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a," "an" and "the" include plural references unless the context clearly dictates otherwise.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Embodiments defined by each of these transition terms are within the scope of this disclosure.

A "composition" is also intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. In the context of this application, the active agent is the ELP-containing a ligand and therapeutic agent as described herein. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising, or alternatively consisting essentially of, or yet further consisting of alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this disclosure, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

A "pharmaceutical composition" is intended to include the combination of an active agent with a carrier, inert or active, making the composition suitable for diagnostic or therapeutic use in vitro, in vivo or ex vivo.

The term "pharmaceutically acceptable carrier" (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present disclosure include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodible). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

As used herein, the term "patient" or "subject" intends an animal, a mammal or yet further a human patient. For the purpose of illustration only, a mammal includes but is not limited to a human, a feline, a canine, a simian, a murine, a bovine, an equine, a porcine or an ovine.

The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

The term "therapeutic" refers to an agent or component capable of inducing a biological effect in vivo and/or in vitro. The biological effect may be useful for treating and/or preventing a condition, disorder, or disease in a subject or patient. A therapeutic may include, without limitation, a small molecule, a nucleic acid, or a polypeptide. Non-limiting examples of such include rapamycin and cyclosporin A, prodrugs and pharmaceutically acceptable salts thereof.

As used herein, the term "elastin-like peptide (ELP) component" intends a polypeptide that forms stable drug binding domain (which is in some embodiments a nanoparticle or a micelle). In one aspect, the ELP component comprises, or alternatively consists essentially of, or yet further consists of the polypeptide as noted above, either (VPGXG)n (SEQ ID NO: 51) or G(Val-Pro-Gly-Xaa-Gaa)n (SEQ ID NO: 52), or, wherein Xaa is any amino acid, or alternatively Gly, Ala, Ser, Ile or Val, and wherein n is an integer that denotes the number of repeats, and can be from about between 2 and 400, alternatively between about 2 and about 300, or alternatively from about 2 to about 200, or from about 2 to 125, or from about 2 to 100, or from about 5 and about 300, or alternatively from about 5 to about 200, or from about 5 to 125, or from about 5 to 100, or from about 10 to 200, or from about 10 to 125, or from about 10 to 100, or alternatively between about 25 and about 250, or alternatively between about 180 to about 250, or from about 195 to about 225, or from about 190 to about 195, or from about 75 to 125, or from about 85 to 115, or from about 90 to about 100, or from about 92 to about 98, or from about 5 to about 150, or from about 6 to about 200, or alternatively from about 15 to 195, or alternatively from 40 to about 195, from 60 to 195, or alternatively from 70 to 195, or alternatively from 80 to 195, or alternatively from 90 to 195, or alternatively from 92 to 195, or alternatively from 92 to 192, or alternatively from 100 to 195, or alternatively from 105 to 192, or alternatively from 110 to 195, or alternatively from 120 to 195, or alternatively from 150 to 195, or alternatively about 24, or alternatively about 48, or alternatively about 96, or alternatively about 192. In one aspect, the ELP is A192 (SEQ ID NO: 1): (VPGAG)192 (SEQ ID NO: 34) (FIG. 1A, Table 1) or A96: (VPGAG)96 (SEQ ID NO: 35), or V96 (SEQ ID NO: 2): (VPGVG)96, or an equivalent of each thereof. In another aspect the ELP has the sequence selected from the group of: (VPGAG)n(VPGIG)n (SEQ ID NO: 53), (VPGAG)n (SEQ ID NO: 54), or (VPGVG)n (SEQ ID NO: 55) (wherein n is an integer that denotes the number of repeats, and can be from about 2 and 400, alternatively between 2 and 300, or alternatively from about 2 to about 200, or from about 2 to 125, or from about 2 to 100, or from about 5 and 400, alternatively between 5 and 300, or alternatively from about 5 to about 200, or from about t to 125, or from about 5 to 100, or from about 10 to 200, or from about 10 to 125, or from about 10 to 100, or alternatively between 25 and 250, or alternatively between 25 and 150, or from about 6 to about 200, or alternatively from about 15 to 195, or alternatively from 40 to about 195, from 60 to 195, or alternatively from 70 to 195, or alternatively from 80 to 195, or alternatively from 90 to 195, or alternatively from 92 to 195, or alternatively from 92 to 192, or alternatively from 100 to 195, or alternatively from 105 to 192, or alternatively from 110 to 195, or alternatively from 120 to 195, or alternatively from 150 to 195, or alternatively about 24, or alternatively about 48, or alternatively about 96, or alternatively about 192. In one aspect, the ELP comprises, or alternatively consists essentially of, or yet further consists of A96I96: (VPGAG)96(VPGIG)96 (SEQ ID NO: 36), A192: (VPGAG)192 (SEQ ID NO: 1), A96: (VPGAG)96 (SEQ ID NO: 35), A24: (VPGAG)24 (SEQ ID NO: 37), V96: (VPGVG)96 (SEQ ID NO: 2), V24: G(VPGVG)24 (SEQ ID NO: 38) or a biological equivalent of each thereof. A biological equivalent of an ELP polypeptide is a peptide that has at least 80% sequence identity to the ELP or a peptide encoded by a polynucleotide that hybridizes under conditions of high stringency to a polynucleotide that encodes the ELP or its complement, wherein conditions of high stringency comprise hybridization reaction at about 60° C. in about 1×SSC.

As used herein, the term "biological equivalent thereof" is used synonymously with "equivalent" unless otherwise specifically intended. When referring to a reference protein, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 60%, or 65%, or 70%, or 75%, or 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid. Alternatively, a biological equivalent is a peptide encoded by a nucleic acid that hybridizes under stringent conditions to a nucleic acid or complement that encodes the peptide or with respect to polynucleotides, those hybridize under stringent conditions to the reference polynucleotide or its complement. Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide or polynucleotide region (or a polypeptide or polypeptide region) having a certain percentage (for example, about 60%, 65%, 70%, 75%, 80%, 85%, 90%, 95% or 97%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is basic local alignment search tool BLAST, using default parameters. In particular, preferred programs are BLASTN (BLAST-nucleotide) and BLASTP(BLAST-protein), using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+ EMBL+DDBJ+PDB+GenBank CDS translations+ SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

An "equivalent" of a polynucleotide or polypeptide refers to a polynucleotide or a polypeptide having a substantial homology or identity to the reference polynucleotide or polypeptide. In one aspect, a "substantial homology" is greater than about 60%, 65%, 70%, 75%, 80%, 85%, 90%, 95% or 98% homology.

"Substantially homogenous" when referring to a composition intends greater than about 50%, or about 60%, or about 65%, or about 70%, or about 75%, or about 80%, or about 85%, or about 90%, or about 95% or about 98%, or about 100% homogenous.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

"Regulatory polynucleotide sequences" intends any one or more of promoters, operons, enhancers, as known to those skilled in the art to facilitate and enhance expression of polynucleotides.

An "expression vehicle" is a vehicle or a vector, non-limiting examples of which include viral vectors or plasmids, that assist with or facilitate expression of a gene or polynucleotide that has been inserted into the vehicle or vector.

A "delivery vehicle" is a vehicle or a vector that assists with the delivery of an exogenous polynucleotide into a target cell. The delivery vehicle may assist with expression or it may not, such as traditional calcium phosphate transfection compositions.

"An effective amount" refers to the amount of an active agent or a pharmaceutical composition sufficient to induce a desired biological and/or therapeutic result. That result can be alleviation of the signs, symptoms, or causes of a disease, or any other desired alteration of a biological system. The effective amount will vary depending upon the health condition or disease stage of the subject being treated, timing of administration, the manner of administration and the like, all of which can be determined readily by one of ordinary skill in the art.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder. In one aspect, the terms "treating" and "treatment" excludes prevention or prophylaxis.

As used herein, to "treat" further includes systemic amelioration of the symptoms associated with the pathology and/or a delay in onset of symptoms. Clinical and sub-clinical evidence of "treatment" will vary with the pathology, the subject and the treatment.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, topical application, intraperitoneal, intravenous and by inhalation. An agent of the present disclosure can be administered for therapy by any suitable route of administration. It will also be appreciated that the preferred route will vary with the condition and age of the recipient, and the disease being treated.

The agents and compositions of the present disclosure can be used in the manufacture of medicaments and for the treatment of humans and other animals by administration in accordance with conventional procedures, such as an active ingredient in pharmaceutical compositions.

As used herein, the term "patient" or "subject" intends an animal, a mammal or yet further a human patient. For the purpose of illustration only, a mammal includes but is not limited to a human, a feline, a canine, a simian, a murine, a bovine, an equine, a porcine or an ovine. In terms of cells, the term "mammalian cells" includes, but is not limited to cells of the following origin: a human, a feline, a canine, a simian, a murine, a bovine, an equine, a porcine or an ovine.

As used herein, the term "detectable label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn, and $^{119}$Sn, a non-radioactive isotope such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition that is detectable. The labels can be suitable for small-scale detection or more suitable for high-throughput screening. As such, suitable labels include, but are not limited to magnetically active isotopes, non-radioactive isotopes, radioisotopes, fluorochromes, luminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescent labeling assay components are known in the art and described for example in Haugland, Richard P. (1996) Handbook of Fluorescent Probes and Research Chemicals (6$^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite Green™ having the structure of:

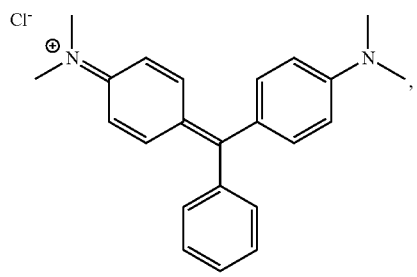

stilbene, Lucifer Yellow™ having the structure of:

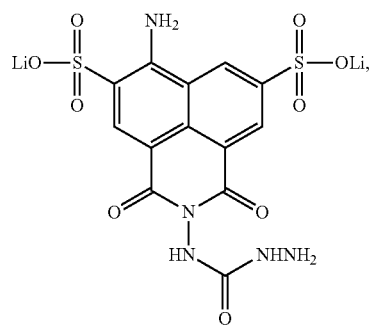

Cascade Blue™ having the structure of:

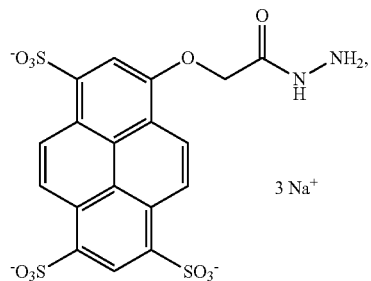

and Texas Red™ having the structure of:

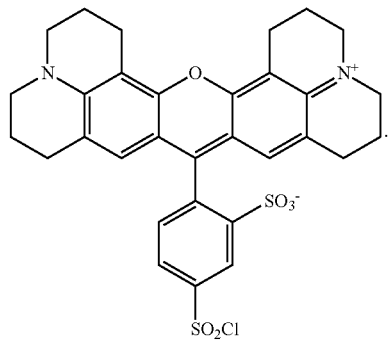

Other suitable optical dyes are described in the Haugland, Richard P. (1996) Handbook of Fluorescent Probes and Research Chemicals (6$^{th}$ ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

The term "scFv" refers to a single-chain variable fragment. scFv is a fusion protein of the variable regions of the heavy (VH) and light chains (VL) of immunoglobulins, connected with a linker peptide. The linker peptide can be from about 5 to 40 amino acids or from about 10 to 30 amino acids or about 5, 10, 15, 20, 25, 30, 35, or 40 amino acids in length. Single-chain variable fragments lack the constant Fc region found in complete antibody molecules, and, thus, the common binding sites (e.g., Protein G) used to purify antibodies. These fragments can often be purified or immobilized using Protein L, since Protein L interacts with the variable region of kappa light chains. More commonly, scientists incorporate a six histidine tag (SEQ ID NO: 56) on the c-terminus of the scFv molecule and purify them using immobilized metal affinity chromatography (IMAC). For unknown reasons, some scFv can also be captured by Protein A.

As used herein, the term CD20$^+$ or CD20-related disorder intends a disease or condition marked by the expression of the CD20 receptor on the diseased or cell or tissue. In one aspect the disease is cancer such as lymphoma (non-Hodgkin's lymphoma) or CD20 expressing leukemia. In another aspect, the disease is an autoimmune disease such as Sjögren's syndrome, rheumatoid arthritis, coeliac disease, Crohn's disease and systemic lupus erythematosus. Tarella et al. (2013) Autoimmunity Reviews 12:802-813. In another aspect, a CD20-related disorder is any that has been treated by conventional CD20 antibody therapies such as rituximab. ELP fusions comprising an anti-CD20 antibody fragment are useful to treat these disorders.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention. The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. It also includes in some aspects, antibody variants, polyclonal antibodies, human antibodies, humanized antibodies, chimeric antibodies, antibody derivatives, a bispecific molecule, a multispecific molecule, a heterospecific molecule, heteroantibodies and human monoclonal antibodies.

Examples of binding fragments encompassed within the term "antigen binding portion" of an antibody include a Fab fragment, a monovalent fragment consisting of the $V_L$, $V_H$, $C_L$ and CH, domains; a F(ab')2 fragment, a bivalent fragment comprising two Fab fragments linked by a disulfide bridge at the hinge region; a Fd fragment consisting of the $V_H$ and $C_H$, domains; a Fv fragment consisting of the $V_L$ and $V_H$ domains of a single arm of an antibody, a dAb fragment (Ward et al. (1989) Nature 341:544-546), which consists of a $V_H$ domain; and an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). Bird et al. (1988) Science 242:423-426 and Huston et al. (1988) Proc. Natl. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

Cyclosporin A is a cyclic undecapeptide from an extract of soil fungi. It is a powerful immunosuppressant with a specific action on T-lymphocytes. It is used for the prophylaxis of graft rejection in organ and tissue transplantation. (From Martindale, The Extra Pharmacopoeia, 30th ed). The IUPAC name is cyclo[((2S)-2-aminobutyryl)-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl-N-methyl-(4R)-4-[(E)-but-2-enyl]-4-methyl-L-threonyl] (SEQ ID NO: 39) or (3 S,6S,9S,12R,15S,18S,21S, 24S,30S,33S)-30-ethyl-33-[(E,1R,2R)-1-hydroxy-2-methylhex-4-enyl]-1,4,7,10,12,15,19,25,28-nonamethyl-6,9,18,24-tetrakis(2-methylpropyl)-3,21-di(propan-2-yl)-1,4,7,10,13,16,19,22,25,28,31-undecazacyclotritriacontane-2,5,8,11,14,17,20,23,26,29,32-undecone. The undecapeptide has the structure:

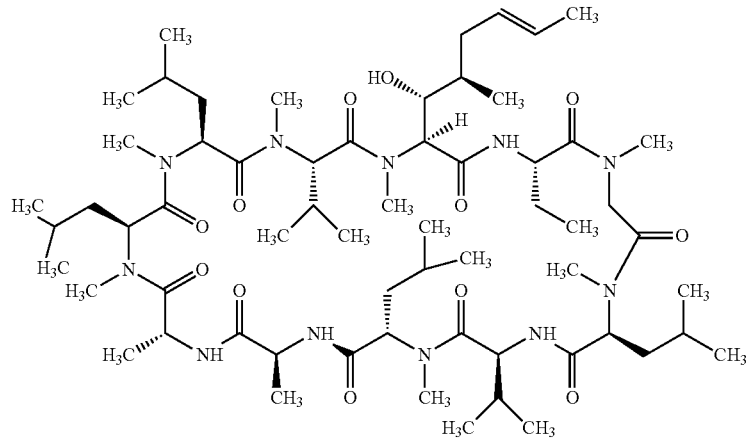

Cyclosporin A has the amino acid sequence: 0 D-Ala 1 Leu 2 Leu 3 Val 4 Thr 5 Abu 6 Sar 7 Leu 8 Val 9 Leu 10 Ala (Cyclization: 0-10) (SEQ ID NO: 39).

All trans retinoic acid (ALTA), as used herein, is a medication used for the treatment of acne, acute promyelocytic leukemia and other cancers as described herein. ALTA has the structure:

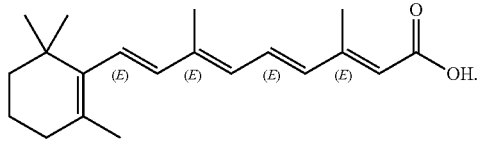 [SMILES: CC1=C(/C=C/C(C)=C/C=C/C(C)=C/C(=O)O)C(C)(C)CCC1]

Cyclophilin A (SEQ ID NO: 22 or SEQ ID NO: 23) is also known as peptidylprolyl isomerase A. It is found in the cytosol. The sequence of the human protein and polynucleotide encoding the protein is disclosed under GenBank Accession No.: NP_066953 (last accessed on Oct. 7, 2013).

As used herein "CA96C" refers to a polynucleotide encoding the ELP fusion protein of amino acid sequence SEQ ID NO: 8, or to the protein itself.

As used herein "3(CA24)C" refers to a polynucleotide encoding the ELP fusion protein of amino acid sequence SEQ ID NO: 9, or to the protein itself.

As used herein "5FA" refers to a polynucleotide encoding the ELP fusion protein of amino acid sequence SEQ ID NO: 10, or to the protein itself.

As used herein "5FV" refers to a polynucleotide encoding the ELP fusion protein of amino acid sequence SEQ ID NO: 11, or to the protein itself.

As used herein "4PA" refers to a polynucleotide encoding the ELP fusion protein of amino acid sequence SEQ ID NO: 15, or to the protein itself.

As used herein "FAF" refers to a polynucleotide encoding the ELP fusion protein of amino acid sequence SEQ ID NO: 25, or to the protein itself.

FK506 Binding protein 12 (FKBP (SEQ ID NO: 24)) is a protein that has prolylisomerase activity and is related to the cyclophilins in function. Along with cyclophilin, FKBP belongs to the immunophilin family. The gene that encodes for FKBP is FRAP1, having GenBank Accession No.: K17584057.1. A published amino acid sequence comprises, or alternatively consists essentially of, or yet further consists of that according to SEQ ID NO: 24.

"PIN1" or peptidyl-prolyl cis/trans isomerase (PPIase), isomerizes only phospho-Serine/Threonine-Proline motifs. The enzyme binds to a subset of proteins and thus plays a role as a post phosphorylation control in regulating protein function. The amino acid sequence of PIN1 is: ADEEKLPPGWEKRMSRSSGRVYYTNHITNASQWE-RPSGNSSSGGKNGQGEPARVRCSH LLVKHSQSRR-PSSWRQEKITRTKHEALELINGYIQKIKSGEEDFE-SLASQFSDCSSAKARG DLGAFSRGQMQKPFEDAS-FALRTGEMSGPVFTDSGIHIILRTEG (SEQ ID NO: 31). The sequence of the polynucleotide encoding this protein can be found under Gen Bank Accession Nos. NM_006221, NM_023371, and NM_001364495.

In some embodiments, therapeutic agents for use in the ELP fusions are cathepsin S inhibitory peptides (CATSIP) that comprise, or alternatively consist essentially of, or yet further consist of the sequence NHLGDMTSEEVMSLTSS (SEQ ID NO: 30) or a biological equivalent thereof. The polynucleotide encoding the therapeutic agent (and therefore the polypeptide upon expression of the polynucleotide) can be fused to the N-terminal or C-terminal end of the ELP fusion or within it. In one embodiment, the therapeutic agent is trapped within a stable nanoparticle formed by the ELP when the environmental temperature is above the transition temperature of the ELP.

ICAM-1 also is known as intercellular adhesion molecule 1 and major group rhinovirus receptor, CD54 antigen. ICAMs are members of the Ig superfamily of calcium-independent transmembrane glycoproteins. ICAM-1 is a ligand for lymphocyte function-associated (LFA) and Mac-1 integrins and the major human rhinovirus receptor. The primary function of ICAM-1 is to provide adhesion between endothelial cells and leukocytes after stress or injury. The human ICAM-1 gene codes for a 505 amino acid transmembrane glycoprotein containing a 29 amino acid cytoplasmic domain, a 23 amino acid transmembrane domain, and a 453 amino acid extracellular domain. Recombinant human ICAM-1 is a 49.5 kDa glycoprotein comprising the extracellular domain (453 amino acid residues) of ICAM-1. Monomeric glycosylated ICAM-1 migrates at an apparent molecular weight of approximately 72.0-80.0 kDa by SDS-PAGE analysis under reducing conditions. The protein is available commercially from PeproTech (Cat. #150-05). A published amino acid sequence is: QTSVSPSKVI LPRGGSVLVT CSTSCDQPKL LGIETPLPKK ELLLPGNNRK VYELSNVQED SQPMCYSNCP DGQSTAKTFL TVYWTPERVE LAPLPSWQPV GKNLTLRCQV EGGAPRANLT VVLLRGEKEL KREPAVGEPA EVTTTVLVRR DHHGANFSCR TELD-LRPQGL ELFENTSAPY QLQTFVLPAT PPQLVSPRVL EVDTQGTVVC SLDGLFPVSE AQVHLALGDQ RLNPTVTYGN DSFSAKASVS VTAEDEGTQR LTCAV-ILGNQ SQETLQTVTI YSFPAPNVIL TKPEVSEGTE VTVKCEAHPR AKVTLNGVPA QPLGPRAQLL LKAT-PEDNGR SFSCSATLEV AGQLIHKNQT RELRVLYGPR LDERDCPGNW TWPENSQQTP MCQAWGNPLP ELKCLKDGTF PLPIGESVTV TRDLEGTYLC RARSTQ-GEVT RKVTVNVLSP RYE (SEQ ID NO: 32).

ICAM-1 has been shown to bind to CD11a, EZR and CD18. CD11a is Integrin, alpha L (antigen CD11A (p180), lymphocyte function-associated antigen 1; alpha polypeptide), also known as ITGAL, is a human gene that functions in the immune system. It is involved in cellular adhesion and costimulatory signaling. It is the target of the drug Efalizumab. Efalizumba (trade name Raptiva, marketed by Genentech, Merck Serono) is used to treat autoimmune diseases such as psoriasis. It is a recombinant humanized monoclonal antibody which acts by inhibiting lymphocyte activation and cell migration out of blood vessels into tissues. ITGAL encodes the integrin alpha L chain. EZR or Ezrin also known as cytovillin or villin-2 is a protein that in humans is encoded by the EZR gene. The cytoplasmic peripheral membrane protein encoded by this gene functions as a protein-tyrosine kinase substrate in microvilli. As a member of the ERM protein family, this protein serves as an intermediate between the plasma membrane and the actin cytoskeleton. It plays a key role in cell surface structure adhesion, migration, and organization. CD18 is also known as integrin beta-2. It is encoded by the ITGB2 gene. It is reported as the beta subunit of four different structures: LFA-1 (paired with CD11a); Macrophage-1 antigen (paired with CD11b); Integrin alphaXbeta2 (paired with CD11c); and Integrin alphaDbeta2 (paired with CD11d). The ITGB2 protein product is the integrin beta chain beta 2. Integrins are integral cell-surface proteins composed of an alpha chain and a beta chain. A given chain may combine with multiple partners resulting in different integrins. For example, beta 2 combines with the alpha L chain to form the integrin LFA-1, and combines with the alpha M chain to form the integrin Mac-1. Integrins are known to participate in cell adhesion as well as cell-surface mediated signaling. In humans lack of CD18 causes Leukocyte Adhesion Deficiency, a disease defined by a lack of leukocyte extravasation from blood into tissues.

In one aspect, the ELP comprises a carrier agent that binds the ICAM-1 receptor, an example of such that comprises, or alternatively consists essentially of, or consists of the amino acid sequence FEGFSFLAFEDFVSSI (SEQ ID NO: 28) or a biological equivalent thereof. A biological equivalent of this ELP fusion is a peptide that has at least 80% sequence identity to FEGFSFLAFEDFVSSI (SEQ ID NO: 28) or a peptide encoded by a polynucleotide that hybridizes under conditions of high stringency to a polynucleotide that encodes FEGFSFLAFEDFVSSI (SEQ ID NO: 28) or its complement, wherein conditions of high stringency comprise hybridization reaction at about 60° C. in about 1×SSC. The biological equivalent will retain the characteristic or function of binding to the receptor.

In another aspect, the ELP comprises a carrier agent that binds the ICAM-1 receptor, an example of such as the agent that comprises, or alternatively consists essentially of, or yet further consists of, the amino acid sequence EWCEYLG-GYLRCYA (SEQ ID NO: 29) or a biological equivalent thereof. A biological equivalent of EWCEYLGGYLRCYA (SEQ ID NO: 29) is a peptide that has at least 80% sequence identity to EWCEYLGGYLRCYA (SEQ ID NO: 29) or a peptide encoded by a polynucleotide that hybridizes under conditions of high stringency to a polynucleotide that encodes EWCEYLGGYLRCYA (SEQ ID NO: 29) or its complement, wherein conditions of high stringency comprise hybridization reaction at about 60° C. in about 1×SSC. The biological equivalent will retain the characteristic or function of binding to the receptor.

Rapamycin is a small molecule drug with the IUPAC name (3S,6R,7E,9R,10R,12R,14S,15E,17E,19E,21S,23S, 26R,27R,34aS)-9,10,12,13,14,21,22,23,24,25,26,27,32,33, 34,34a-hexadecahydro-9,27-dihydroxy-3-[(1R)-2-[(1S,3R, 4R)-4-hydroxy-3-methoxycyclohexyl]-1-methylethyl]-10, 21-dimethoxy-6,8,12,14,20,26-hexamethyl-23,27-epoxy-3H-pyrido[2,1-c][1,4]-oxaazacyclohentriacontine-1,5,11, 28,29 (4H,6H,31H)-pentoneis). It is an immunosuppressant drug used to prevent rejection in organ transplantation and has been used in the treatment of cancers. It is marketed under the trade name Rapamune™ by Pfizer.

The mammalian target of rapamycin is known as mTOR or FK506 binding protein 12-rapamycin associated protein 1 (FRAP1, referenced herein is FK506 Binding Protein or "FKBP"), is a protein that in humans is encoded by the FRAP1 gene. The protein and gene sequence encoding the protein are disclosed under GenBank Accession No. NG_033239 (last accessed on Sep. 6, 2013). mTOR is a serine/threonine protein kinase that regulates cell growth, proliferation, cell survival, protein synthesis among other functions.

Everolimus is the 40-O-(2-hydroxyethyl) derivative of sirolimus and works similarly to sirolimus as an inhibitor of the mammalian target of rapamycin. It is marketed under the tradenames Zortress (USA) and Certican (Europe and other countries) in transplantation medicine, and Afinitor in oncology. Everolimus also is available with Biocon with the brand name of Evertor. It is used as an immunosuppressant to prevent rejection of organ transplants and the treatment of tumors such as renal cell cancer. The compound also is known as dihydroxy-12-[(2R)-1-[(1S,3R,4R)-4-(2-hydroxy-ethoxy)-3-methoxycyclohexyl]propan-2-yl]-19,30-dime-thoxy-15,17,21,23,29,35-hexamethyl-11,36-dioxa-4-azatri-cyclo[30.3.1.0 hexatriaconta-16,24,26,28-tetraene-2,3,10, 14,20-pentone.

Temsirolimus is (CCI-779) is a derivative of sirolimus and is sold as Torisel. It is an intravenous drug for the treatment of renal cell carcinoma, developed by Wyeth Pharmaceuticals. It also is approved by the European Medicines Agency (EMEA) on November 2007. The compound also is known as (1R,2R,4S)-4-{(2R)-2-[(3S,6R,7E,9R,10R, 12R,14S,15E,17E,19E,21S,23S,26R,27R,34aS)-9,27-dihy-droxy-10,21-dimethoxy-6,8,12,14,20,26-hexamethyl-1,5, 11,28,29-pentaoxo-1,4,5,6,9,10,11,12,13,14,21,22,23,24, 25,26,27,28,29,31,32,33,34,34a-tetracosahydro-3H-23,27-epoxypyrido[2,1-c][1,4]oxazacyclohentriacontin-3-yl] propyl}-2-methoxycyclohexyl 3-hydroxy-2-(hydroxy-methyl)-2-methylpropanoate.

Ridaforolimus (also known as AP23573 and MK-8669; formerly known as Deforolimus) is an investigational targeted and small-molecule inhibitor of the protein mTOR. The compound also is known as (1R,2R,4S)-4-[(2R)-2-[(1R, 9S,12S,15R,16E,18R,19R,21R,23S,24E,26E,28Z,30S,32S, 35R)-1,18-dihydroxy-19,30-dimethoxy-15,17,21,23,29,35-hexamethyl-2,3,10,14,20-pentaoxo-11,36-dioxa-4-azatricyclo[30.3.1.0⁴,⁹]hexatriaconta-16,24,26,28-tetraen-12-yl]propyl]-2-methoxycyclohexyl dimethylphosphinate.

Tacrolimus (also FK-506 or fujimycin, trade names Prograf, Advagraf, Protopic) is an immunosuppressive drug that is mainly used after allogeneic organ transplant to reduce patient rejection. The drug also is known as 3 S[3R*[E (1S*,3 S*,4S*)],4S*,5R*,8S*,9E,12R*,14R*,15S*,16R*, 18S*,19S*,26aR*5,6,8,11,12,13,14,15,16,17,18,19,24,25, 26,26 a-hexadecahydro-5,19-dihydroxy-3-[2-(4-hydroxy-3 methoxycyclohexyl)-1-methylethenyl]-14,16-dimethoxy-4, 10,12,18-tetramethyl-8-(2-propenyl)-15,19-epoxy-3H-pyrido[2,1-c][1,4]oxaazacyclotricosine-1,7,20,21(4H,23H)-tetrone, monohydrate.

The term "coxsackievirus and adenovirus receptor" or "CAR" refers to a high affinity receptor that is present in many human tissues, including liver, heart, lacrimal gland, salivary gland, lung, and brain, pancreas and prostate. In humans CAR exists in various isoforms as follows:

Isoform 1:
(SEQ ID NO: 40)
MALLLCFVLL CGVVDFARSL SITTPEEMIE KAKGETAYLP

CKFTLSPEDQ GPLDIEWLIS PADNQKVDQV IILYSGDKIY

DDYYPDLKGR VHFTSNDLKS GDASINVTNL QLSDIGTYQC

KVKKAPGVAN KKIHLVVLVK PSGARCYVDG SEEIGSDFKI

KCEPKEGSLP LQYEWQKLSD SQKMPTSWLA EMTSSVISVK

NASSEYSGTY SCTVRNRVGS DQCLLRLNVV PPSNKAGLIA

GAIIGTLLAL ALIGLIIFCC RKKRREEKYE KEVHHDIRED

VPPPKSRTST ARSYIGSNHS SLGSMSPSNM EGYSKTQYNQ

VPSEDFERTP QSPTLPPAKV AAPNLSRMGA IPVMIPAQSK DGSIV

Isoform 2:
(SEQ ID NO: 41)
MALLLCFVLL CGVVDFARSL SITTPEEMIE KAKGETAYLP

CKFTLSPEDQ GPLDIEWLIS PADNQKVDQV IILYSGDKIY

DDYYPDLKGR VHFTSNDLKS GDASINVTNL QLSDIGTYQC

KVKKAPGVAN KKIHLVVLVK PSGARCYVDG SEEIGSDFKI

KCEPKEGSLP LQYEWQKLSD SQKMPTSWLA EMTSSVISVK

NASSEYSGTY SCTVRNRVGS DQCLLRLNVV PPSNKAGLIA

GAIIGTLLAL ALIGLIIFCC RKKRREEKYE KEVHHDIRED

VPPPKSRTST ARSYIGSNHS SLGSMSPSNM EGYSKTQYNQ

VPSEDFERTP QSPTLPPAKF KYPY

Isoform 3:
(SEQ ID NO: 42)
MALLLCFVLL CGVVDFARSL SITTPEEMIE KAKGETAYLP

CKFTLSPEDQ GPLDIEWLIS PADNQKVDQV GRCATSKEPY

VHCQKLHRQ

Isoform 4:
(SEQ ID NO: 43)
MALLLCFVLL CGVVDFARSL SITTPEEMIE KAKGETAYLP

CKFTLSPEDQ GPLDIEWLIS PADNQKVDQV IILYSGDKIY

DDYYPDLKGR VHFTSNDLKS GDASINVTNL QLSDIGTYQC

KVKKAPGVAN KKIHLVVLGK MCHLQRAVRP LPEATSAVII

HPWGPCLLPT WKDIPRLSIT KYQVKTLNAL LRVRLSHLLR

Isoform 5:
(SEQ ID NO: 44)
MALLLCFVLL CGVVDFARSL SITTPEEMIE KAKGETAYLP

CKFTLSPEDQ GPLDIEWLIS PADNQKVDQV IILYSGDKIY

DDYYPDLKGR VHFTSNDLKS GDASINVTNL QLSDIGTYQC

KVKKAPGVAN KKIHLVVLVK PSGARCYVDG SEEIGSDFKI

KCEPKEGSLP LQYEWQKLSD SQKNIPTSWLA GKMCHLQRAV

RPLPEATSAV IIHPWGPCLL PTWKDIPRLS ITKYQVKTLN

ALLRVRLSHL

Isoform 6:
(SEQ ID NO: 45)
MALLLCFVLL CGVVDFARSL SITTPEEMIE KAKGETAYLP

CKFTLSPEDQ GPLDIEWLIS PADNQKVDQV IILYSGDKIY

DDYYPDLKGR VHFTSNDLKS GDASINVTNL QLSDIGTYQC

KVKKAPGVAN KKIHLVVLVK PSGARCYVDG SEEIGSDFKI

KCEPKEGSLP LQYEWQKLSD SQKMPTSWLA EMTSSVISVK

NASSEYSGTY SCTVRNRVGS DQCLLRLNVV PPSNKAGLIA

GAIIGTLLAL ALIGLIIFCC RKKRREEKYE KEVHHDIRED

VPPPKSRTST ARSYIGSNHS SLGSMSPSNM EGYSKTQYNQ

VPSEDFERTP QSPTLPPAKF KYPYKTDGIT

Isoform 7:
(SEQ ID NO: 46)
MALLLCFVLL CGVVDFARSL SITTPEEMIE KAKGETAYLP

CKFTLSPEDQ GPLDIEWLIS PADNQKVDQV IILYSGDKIY

DDYYPDLKGR VHFTSNDLKS GDASINVTNL QLSDIGTYQC

KVKKAPGVAN KKIHLVVLVK PSGARCYVDG SEEIGSDFKI

KCEPKEGSLP LQYEWQKLSD SQKMPTSWLA ASNKAGLIAG

AIIGTLLALA LIGLIIFCCR KKRREEKYEK EVHHDIREDV

PPPKSRTSTA RSYIGSNHSS LGSMSPSNME GYSKTQYNQV

PSEDFERTPQ SPTLPPAKVA APNLSRMGAI PVMIPAQSKD GSIV

The term "Polymeric Immunoglobulin Receptor" or "pIgR" refers to a high affinity receptor that is expressed by human mucosal cells. pIgR has the sequence of: MLLFVLT-CLL (SEQ ID NO: 47)
AVFPAISTKS PIFGPEEVNS VEGNSVSITC YYPPTSVNRH

TRKYWCRQGA RGGCITLISS EGYVSSKYAG RANLTNFPEN

GTFVVNIAQL SQDDSGRYKC GLGINSRGLS FDVSLEVSQG

```
PGLLNDTKVY TVDLGRTVTI NCPFKTENAQ KRKSLYKQIG

LYPVLVIDSS GYVNPNYTGR IRLDIQGTGQ LLFSVVINQL

RLSDAGQYLC QAGDDSNSNK KNADLQVLKP EPELVYEDLR

GSVTFHCALG PEVANVAKFL CRQSSGENCD VVVNTLGKRA

PAFEGRILLN PQDKDGSFSV VITGLRKEDA GRYLCGAHSD

GQLQEGSPIQ AWQLFVNEES TIPRSPTVVK GVAGGSVAVL

CPYNRKESKS IKYWCLWEGA QNGRCPLLVD SEGWVKAQYE

GRLSLLEEPG NGTFTVILNQ LTSRDAGFYW CLTNGDTLWR

TTVEIKIIEG EPNLKVPGNV TAVLGETLKV PCHFPCKFSS

YEKYWCKWNN TGCQALPSQD EGPSKAFVNC DENSRLVSLT

LNLVTRADEG WYWCGVKQGH FYGETAAVYV AVEERKAAGS

RDVSLAKADA APDEKVLDSG FREIENKAIQ DPRLFAEEKA

VADTRDQADG SRASVDSGSS EEQGGSSRAL VSTLVPLGLV

LAVGAVAVGV ARARHRKNVD RVSIRSYRTD ISMSDFENSR

EFGANDNMGA SSITQETSLG GKEEFVATTE STTETKEPKK

AKRSSKEEAE MAYKDFLLQS STVAAEAQDG PQEA
```

"LGAC" or "lacrimal gland acinar cell" is a specific cell type of the lacrimal gland that expresses CAR and pIgR on the cell surface. These cells are also sometimes referred to as lacrimal acinar epithelial cells.

"Knob" as used herein refers to the knob domain of Human adenovirus C serotype 5 (HAdV-5) (Human adenovirus 5) having the sequence:

```
                                              (SEQ ID NO: 26)
GAITVGNKNNDKLTLWTTPAPSPNCRLNAEKDAKLTLVLTKCGSQILATV

SVLAVKGSLAPISGTVQSAHLIIRFDENGVLLNNSFLDPEYWNFRNGDLT

EGTAYTNAVGFMPNLSAYPKSHGKTAKSNIVSQVYLNGDKTKPVTLTITL

NGTQETGDTTPSAYSMSFSWDWSGHNYINEIFATSSYTFSYIAQE.
```

The term "mIgA" refers to the pIgR-binding site in the Cα3 domain of dimeric human IgA. The Cα3 domain is represented by the protein sequence: RP EVHLLPPPSE ELALNELVTL TCLARGFSPK DVLVRWLQGS QELPREKYLT WASRQEPSQG TTTFAVTSIL RVAAEDWKKG DTFSCMVGHE ALPLAFTQKT ID (SEQ ID. NO: 27) (See for e.g. Frank W. Putnam, et al. J. Biol. Chem. 254, 2865-2874).

In further embodiments, the ELP comprises a mIgA ligand or double mIgA ligand. This ligand is represented by the amino acid sequence TWASRQEPSQGTTTFAVTS (SEQ ID. NO: 48) or a biological equivalent thereof. In one embodiment, the mIgA ligand comprises a polypeptide having the sequence of TWASRQEPSQGTTTFAVTS (SEQ ID NO: 49) or a biological equivalent thereof. The term "biological equivalent" is defined above. In one aspect, a biological equivalent is a peptide encoded by a nucleic acid that hybridizes to a nucleic acid that encodes the mIgA ligand or double mIgA ligand or its complement under conditions of a high stringency hybridization reaction, that is performed at about 60° C. in about 1×SSC that has substantial identical biological activity to the above-noted sequence. In certain embodiments, the ELP comprises the mIgA ligand or a polypeptide with at least 80% identity to mIgA. Alternatively, the polypeptide has about at least 85% or about at least 90% or about at least 95%, or about at least 99% identity to mIgA.

"Rapalogue" as used herein, refers to analogues of rapamycin. Analogues may include substitution of one or more positions of rapamycin with alternate functional groups. In general, "substitution" refers to substitution of a rapamycin-like compound (e.g., Rapamycin, Everolimus, Temsirolimus, Ridaforolimus, Tacrolimus) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted rapamycin-like compound will be substituted with one or more substituents, unless otherwise specified. In some embodiments, a substituted compound is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitre groups; nitrites (i.e., CN); and the like. In one embodiment the rapalogue is Rapamycin, Everolimus, Temsirolimus, Ridaforolimus or, Tacrolimus.

ELP Compositions

This disclosure provides an isolated agent comprising, or alternatively consisting essentially of, or yet further consisting of a multimeric elastin-like peptide (ELP) component that forms a drug binding domain stabilized by the ELP fused to a drug binding domain such as cyclophilin A (SEQ ID NO: 22 or SEQ ID NO: 23) or a fragment thereof, or an equivalent of each thereof, and optionally, a therapeutic agent. Therapeutic agents would include small molecule drugs capable of binding to the ELP fusion. For example, if the ELP contained cyclophilin, then it can be used to carry cyclosporine A. Alternatively, if the ELP fusion contains the FKBP (SEQ ID NO: 24) protein, it could carry a member of the drug family known as the rapalogues. Alternatively, if the ELP fusion contains the PIN1 protein, it could carry all-trans retinoic acid.

In contrast to prior ELP compositions, the agents of this disclosure exists in a dimeric, trimeric or other multimeric form, wherein the ELP components are conjugated to each other in solution. The molecular weight of the dimeric form of the agent is from about 170 kD to about 200 kD, or from about 180 kD to about 190 kD, or about 185 kD, or about 180 kD, or about 181 kD, or about 182 kD, or about 183 kD, or about 184 kD (+/−4.133%). In one aspect the polymeric form of the ELP is a dimer, a trimer, or a tetramer, or a pentamer of the ELP-cyclophilin A construct.

The molecular weight of the trimeric form of the agent is from about 270 kD (+/−4.133%).

The molecular weight of the quaternary form of the agent is from about 360 kD (+/−4.133%).

In some embodiments, the agent comprises 1 ELP. In some embodiments, the agent comprises 2 ELPs. In some embodiments, the agent comprises 3 ELPs. In some embodiments, the agent comprises 4 ELPs. In some embodiments, the agent comprises 5 ELPs.

In some embodiments, the agent comprises 1 drug binding domain. In some embodiments, the agent comprises 2 drug binding domains. In some embodiments, the agent comprises 3 drug binding domains. In some embodiments, the agent comprises 4 drug binding domains. In some embodiments, the agent comprises 5 or more drug binding domains.

Also provided is a substantially homogenous composition of ELP fusion agents.

Applicants have found that the multimeric agent has superior drug solubility, absorption, bioavailability, and reduce clearance once in the blood. Therefore, this polymeric form enables intermuscular, intraperitoneal, and subcutaneous administration. Thus, the use of the polymeric form also reduces dose frequency.

Drug Binding Domains
Cyclophilin A

In one aspect, the at least one of the two or more drug binding domains is cyclophilin A (SEQ ID NO: 22 or SEQ ID NO: 23), a fragment or an equivalent of each thereof. In one aspect, two, three, four or all of the two or more drug binding domains in the ELP fusion are cyclophilin A (SEQ ID NO: 22 or SEQ ID NO: 23), a fragment or an equivalent of each thereof. Cyclophilin A (SEQ ID NO: 22 or SEQ ID NO: 23) binds to cyclosporine, its cognate receptor. Cyclophilin A (SEQ ID NO: 22 or SEQ ID NO: 23) also binds to cell surface receptor, CD147. In one aspect, an equivalent of cyclophilin A (SEQ ID NO: 22 or SEQ ID NO: 23) or its fragment binds to cyclosporine or CD147. In one aspect, a therapeutic agent is bound to or trapped within the ELP or coacervate formed by the ELP, which in one aspect, is when the ELP is above the transition temperature. The cyclophilin-ELP fusion can be noncovalently complexed with the therapeutic agent, such that it promotes drug solubility, absorption, and bioavailability following administration. In another aspect, the ELP is selected for its ability to form a nanoparticle or coacervate at body temperature, such that duration of drug efficacy is extended, thus reducing the frequency of administration, such as parenteral administration.

In another aspect, the ELP fusion further comprises a therapeutic agent that binds to cyclophilin A (SEQ ID NO: 22 or SEQ ID NO: 23) and is selected to treat one or more of organ rejection in patients receiving liver, kidney, or heart transplant; Graft-versus-host disease, particularly in bone-marrow transplantation; Rheumatoid arthritis, and related diseases, Psoriasis, Persistent nummular keratitis, Atopic dermatitis, Kimura disease, Pyoderma gangrenosum, chronic autoimmune urticaria, Acute systemic mastocytosis, and, Dry eyes, Sjögren's syndrome, autoimmune disorders such as acute severe ulcerative colitis, systemic lupus erythematosus, and autoimmune urticaria that do not respond to treatment with steroids; posterior or intermediate uveitis with noninfective cause; and atopic dermatitis (veterinary use), neuronal cellular damage and reperfusion injury in traumatic brain injury, and cardiac hypertrophy.

In a yet further aspect, the therapeutic agent is cyclosporin A, a prodrug or a pharmaceutically acceptable salt thereof, and wherein biological equivalent of cyclosporin A or the fragment thereof is a peptide that has at least 80% sequence identity to cyclosporin A or the fragment, or a peptide encoded by a polynucleotide that hybridizes under conditions of high stringency to a polynucleotide that encodes cyclophilin A (SEQ ID NO: 22 or SEQ ID NO: 23), the fragment or their complements, wherein conditions of high stringency comprise hybridization reaction at about 60° C. in about 1×SSC and binds cyclophilin A. Examples of the peptide sequence of cyclosporin A are provided herein.

Cyclosporin A (CsA) is a well-known lipophilic cyclic immunosuppressant peptide containing 11 amino acids and works by blocking T-cell proliferation and inhibiting the release of inflammatory cytokines, such as IL-2 and IFN-γ (Stevenson et al., 2012). It has been widely used in prevention of rejection after organ transplantation and in modulation of inflammatory responses in several autoimmune disorders, such as rheumatoid arthritis and psoriasis (Colombo and Ammirati, 2011).

When administered topically, CsA has been broadly used to treat dry eye syndrome (DES), a multifactorial disease of the ocular surface caused by decreased tear production which affects an estimated 5-30% of the population (Cornec et al., 2015, Janine, 2007), by suppressing ocular surface inflammation. Because of its hydrophobic property, the only commercially available topical administration form of CsA is as an oil-in-water emulsion eye drop, which leads to poor ocular tolerance, low bioavailability, and instability (Gupta and Chauhan, 2011). In addition, when administered through intravenous injection, CsA can potentially lead to a number of serious adverse drug reactions (ADRs) because of its narrow therapeutic window (Mahalati et al., 2001). Below the therapeutic window, CsA cannot effectively inhibit T cell proliferation and the release of related cytokines, its major therapeutic actions, while above the therapeutic window, it is known to elicit severe side effects including nephrotoxicity and neurotoxicity (Survase et al., 2011). Thus, the disclosed ELP fusions comprising CsA can be used for treatment of the same diseases or disorders as CsA.

In one embodiment, the therapeutic agent is selected from Rapamycin, Everolimus, Temsirolimus, Ridaforolimus, or Tacrolimus. In one embodiment, the therapeutic agent is a rapamycin analog or rapalogue.

In a further aspect, the therapeutic agent is an agent that is selected from the group of: an agent that treats Sjögren's Syndrome, an agent that prevents immune rejection, an agent that modulates inflammatory responses, an agent that treats autoimmune disorders, an agent that treats rheumatoid arthritis, an agent that treats psoriasis, an agent to treat dry eye syndrome (DES). In another aspect, the therapeutic agent is a peptide that treats or ameliorates the symptoms of Sjögren's Syndrome ("SjS") and comprises a cathepsin S inhibitory peptide (CATSIP), which comprises, or alternatively consists essentially of, or yet further consists of the sequence NHLGDMTSEEVMSLTSS (SEQ ID NO: 30), a fragment or a biological equivalent of each thereof. In one aspect, a therapeutic agent is bound to or trapped within the ELP or coacervate formed by the ELP, which in one aspect, is when the ELP is above the transition temperature. The cyclophilin-ELP fusion can be noncovalently complexed with the therapeutic agent, such that it promotes drug solubility, absorption, and bioavailability following administration. In another aspect, the ELP is selected for its ability to form a nanoparticle or coacervate at body temperature, such that duration of drug efficacy is extended, thus reducing the frequency of administration, such as parenteral administration.

In one aspect, the ELP fusions are useful for delivering a therapeutic agent in vitro by contacting a tissue expressing the receptor the drug binding domain with the agent. In one aspect, a method for delivering a drug in vivo is provided comprising administering an effective amount of the ELP fusion to a subject. In one aspect, a method for ameliorating the symptoms of a disease or condition or for treating a disease or condition is provided, comprising administering an effective amount of the ELP fusion to a subject suffering from the disease or condition or susceptible to the disease or condition.

In one aspect, the disease or condition is of the group of organ transplant rejection, rheumatoid arthritis, psoriasis, Crohn's disease, nephrotic syndrome, or keratoconjunctivitis sicca (thy eye).

Antigen Binding Peptides

In another aspect, the at least one, or alternatively at least two, three, four or all of the two or more drug binding domains at least one of the two or more drug binding domains are polypeptides comprising, or alternatively consisting essentially of, or yet further consisting of an antigen binding peptide, e.g., a scFv, or a biological equivalent of the scFv. The scFv is a polypeptide that recognizes, has affinity, and/or binds to a specific antigen. In one aspect, all of the two or more drug binding domains in the ELP fusion antigen binding peptides, fragments or equivalents thereof.

In one embodiment, the scFv comprises, or alternatively consists essentially of or yet further consists of the single chain variable region from the anti-CD20 antibody or an antibody that bind LGAC. Examples of the single chain variable region from the scFv include the polypeptides of SEQ ID NOS: 17 and 18. In certain embodiments, the scFv comprises, or alternatively consists essentially of or yet further consists of the sequence of SEQ ID NO: 17 or SEQ ID NO: 18 or a biological equivalent thereof. In further embodiments, the scFv-ELP polypeptide corresponds to a sequence selected from the group consisting of SEQ ID NOS: 19, 20, and 21 or a biological equivalent thereof.

The scFv can have a peptide linker between the heavy and light chains. The linker is variable in length and, in certain embodiments, comprise amino acid residues such as glycine or serine. It is also within the scope of this disclosure to have scFvs with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Consequently, diabody drugs could be dosed much lower than other therapeutic antibodies and are capable of highly specific targeting of tumors in vivo. Still shorter linkers (one or two amino acids) lead to the formation of trimers, so-called triabodies or tribodies. Tetrabodies have also been produced. They exhibit an even higher affinity to their targets than diabodies. All of these formats can be composed from variable fragments with specificity for two different antigens, in which case they are types of bispecific antibodies.

The ELP fusions can further comprise a therapeutic agent. In one aspect, a therapeutic agent is bound to or trapped within the ELP or coacervate formed by the ELP, which in one aspect, is when the ELP is above the transition temperature. The ELP fusion can be noncovalently complexed with the therapeutic agent, such that it promotes drug solubility, absorption, and bioavailability following administration. In another aspect, the ELP is selected for its ability to form a nanoparticle or coacervate at body temperature, such that duration of drug efficacy is extended, thus reducing the frequency of administration, such as parenteral administration.

The scFv polypeptides described herein are useful for the specific targeting of scFv-ELPs to cells. One aspect relates to a method for targeting a scFv-ELP to a cell comprising, or alternatively consisting essentially of, or yet further consisting of: contacting the cell with an effective amount of the scFv-ELP polypeptide, wherein the scFv component of the scFv-ELP binds to a cellular component of the cell. The contacting can be to a cell in vitro or in vivo. In one embodiment, the scFv component binds to a cell surface receptor of the cell. In a further embodiment, the scFv component binds to a intercellular receptor or a cellular component found on the surface or inside of the cell. These polypeptides may be used to target cell populations with a specific component by using a scFv that recognizes the specific component. The targeting can facilitate drug delivery by conjugating a drug to the scFv-ELP or facilitate cellular signaling by agonizing or antagonizing a cellular receptor. The cellular signaling may induce a specific cellular response. In the case of CD20, multivalent biding of the anti-CD20 to the cell-surface receptor induces apoptosis of the cell. Accordingly, one aspect relates to a method for inducing apoptosis of a CD20+ cell comprising contacting the cell with an effective amount of the scFv-ELP polypeptide wherein the scFv component comprises, or alternatively consists essentially of or yet further consists of the single chain variable region from the anti-CD20 antibody. In a related embodiment, the cell is a malignant B-cell. In another aspect, the compositions are useful to treat a CD20-related disease or disorder, e.g., a CD20-expressing cancer, by administering to a patient in need of such treatment the polypeptide of any one of the compositions of this disclosure. In one aspect, the CD2-expressing cancer is non-Hodgkin lymphoma.

In some embodiments of the disclosure, the entire anti-CD20 antibody is linked to the ELP. Linking the entire antibody to the ELP may provide additional benefits to therapeutic applications utilizing the anti-CD20 antibody alone. For example, the ELP-conjugated CD20 antibody may provide a more efficient mechanism for crosslinking the antibody. Since activation of apoptosis in CD20+ cells requires multivalent binding of the CD20 cell surface antigen, the ELP-conjugated anti-CD20 antibody may provide more efficient activation of apoptosis. In one aspect, a portion of the anti-CD20 antibody is used, such as the scFV fragment.

A further aspect relates to a method for treating a CD20 expressing cancer, comprising administering to a patient in need of such treatment the scFv-ELP fusion wherein the scFv component comprises, or alternatively consists essentially of or yet further consists of the single chain variable region from the anti-CD20 antibody or a polynucleotide encoding such polypeptide. One example of a CD20 expressing cancer is non-Hodgkin lymphoma. Another example is CD20-expressing leukemia.

LGAC-Targeting Ligands

In certain embodiments of the invention, the drug binding domain is at least one of LGAC-targeted ligands. A LGAC-targeted ligand is a peptide, polypeptide, or molecule that targets the ELP to the LGAC. In one embodiment, the at least one, or alternatively at least two, three, four or all of the two or more drug binding domains of the ELP fusion is the adenovirus knob domain (Knob), which is a LGAC-targeted ligand. This domain is represented by the protein sequence: GAITVGNKNNDKLTLWTTPAPSPNCRLNAEKDAK-LTLVLTKCGSQILATVSVLAVKGSL APISGTVQSAHL-IIRFDENGVLLNNSFLDPEYWNFRNGDLTEGTAYT-NAVGFMPNLSAY PKSHGKTAKSNIVSQVYLNG-DKTKPVTLTITLNGTQETGDTTPSAYSMSFSWDW-SGHN YINEIFATSSYTFSYIAQE (SEQ ID NO: 26), a fragment or a biological equivalent thereof. The term "biological equivalent" is defined above. In one aspect, a biological equivalent is a peptide encoded by a nucleic acid that hybridizes to a nucleic acid that encodes the LGAC-targeted ligand 2 or its complement under conditions of a high stringency hybridization reaction, that is performed at about 60° C. in about 1×SSC that has substantial identical biological activity to the above-noted sequence. In a further aspect, the ELP fusion further comprise a therapeutic agent.

In further embodiments, the at least one, or alternatively at least two, three, four or all of the two or more drug binding domains comprise a mIgA ligand or double mIgA ligand or a fragment or a biological equivalent of each thereof. These drug binding domains can be represented by the amino acid sequence: TWASRQEPSQGTTTFAVTS (SEQ ID. NO: 48) and TWASRQEPSQGTTTFAVTS (SEQ ID NO: 49), respectively, or a fragment or a biological equivalent thereof.

The term "biological equivalent" is defined above. In one aspect, a biological equivalent is a peptide encoded by a nucleic acid that hybridizes to a nucleic acid that encodes the mIgA ligand or double mIgA ligand or its complement under conditions of a high stringency hybridization reaction, that is performed at about 60° C. in about 1×SSC that has substantial identical biological activity to the above-noted sequence. In certain embodiments, the ELP fusion comprises the mIgA ligand or a polypeptide with at least 80% identity to mIgA or the fragment thereof. Alternatively, the polypeptide has about at least 85% or about at least 90% or about at least 95%, or about at least 99% identity to mIgA or the fragment.

Still further, there is provided a method for delivering a therapeutic agent comprising an ELP fusion to a cell, the method comprising, or alternatively consisting essentially of, or yet further consisting of, administering an (ELP) component and a ligand component to the cell; wherein the drug binding domain is the knob ligand or mIgA ligand.

The contacting can be in vitro or in vivo. In one embodiment, the drug is in contact with the ocular surface of the eye. Transcytosis allows the drug to have access to the ocular surface of the eye. The transcytosis property enables treatment of the surface of the eye for a variety of conditions like dry eye, scleritis, and the like.

In yet another aspect, provided is a method for treating a disease of the lacrimal gland, comprising, or alternatively consisting essentially of, or yet further consisting of, administering to a patient in need of such treatment one or more of the ELP fusion comprising a ligand component that specifically binds to knob, thereby treating the patient. In one aspect, the disease is cancer.

In certain embodiments, the cell is any cell that expresses a CAR or pIGR receptor. Non-limiting examples include liver, heart, lacrimal gland, salivary gland, lung, brain, pancreatic acinar tissue, prostate or mucosal cells. In a related embodiment, the cell is the lacrimal acinar cell of the lacrimal gland (LGAC). CAR is detected in liver and lacrimal gland as well as in human umbilical vein endothelial cells and pancreatic acinar tissue (acinar cells and islets), as well as in prostate. Most mucosal epithelial cells display pIgR including the cells lining the gut, pulmonary epithelial cells, acinar cells (salivary, lacrimal gland) and other barrier epithelial tissues responsible for maintaining mucosal immunity. Accordingly, in one embodiment, the drug is released from interstitial to luminal surfaces on a mucosal epithelial cell.

In a yet further aspect, the ELP fusions further comprise a therapeutic agent, e.g., cyclosporin A, rapamycin or an analog thereof, a prodrug or a pharmaceutically acceptable salt thereof.

These ELP fusions are useful ameliorating the symptoms of disease for treating disease. Non-limiting examples of such include cancer, an autoimmune disease, age-related macular degeneration, Sjögren's syndrome, autoimmune exocrinopathy, diabetic retinopathy, graft versus host disease, exocrinopathy, retinal venous occlusions, retinal arterial occlusion, macular edema, postoperative inflammation, uveitis retinitis, proliferative vitreoretinopathy, glaucoma, keratoconjunctivitis sicca (dry eye), scleritis or glaucoma.

In one aspect, the ELP fusion treats or ameliorates symptoms of diseases or disorders of the eye. The lacrimal gland acinar cell targeted ELPs provide a site-specific target therapeutic. Accordingly, these ELP nanoparticles may be useful to encapsulate or attach drugs for treating disorders localized to the eye. By way of example, these disorders can include, age-related macular degeneration, Sjögren's syndrome, autoimmune exocrinopathy, diabetic retinopathy, graft versus host disease (exocrinopathy associated with) retinal venous occlusions, retinal arterial occlusion, macular edema, postoperative inflammation, uveitis retinitis, proliferative vitreoretinopathy and glaucoma. In one embodiment, the disease is Sjögren's syndrome. In another embodiment, the disease is keratoconjunctivitis sicca (dry eye). In another embodiment the disease is scleritis. In another embodiment the disease is glaucoma.

ICAM-1

In one aspect, the at least one, or alternatively at least two, three, four or all of the two or more drug binding domains are ligands are selected for targeting the mammalian ICAM-1 receptor. In another aspect, all drug binding domains of the ELP fusion are ligands are selected for targeting the mammalian ICAM-1 receptor. In certain aspects, either mouse ICAM-1 targeting peptides, FEGFSFLAFEDFVSSI (SEQ ID NO: 28), or human ICAM-1 targeting peptides, EWCEYLGGYLRCYA (SEQ ID NO: 29), fragments or biological equivalents of each thereof are the drug binding domains. Examples of biological equivalents include peptides having at least at least 80% identity to knob. Alternatively, the polypeptide has about at least 85% or about at least 90% or about at least 95%, or about at least 99% identity to the ligands or a peptides encoded by polynucleotides that hybridize under conditions of high stringency to a reference polypeptide that encodes FEGFSFLAFEDFVSSI (SEQ ID NO: 28) or EWCEYLGGYLRCYA (SEQ ID NO: 29) or their complements and retain the ability to selectively bind a ICAM-1 receptor. Conditions of high stringency and methods to determine sequence identity are disclosed herein and known in the art.

In one aspect, the therapeutic agent comprises a cathepsin S inhibitory peptide (CATSIP) of the reference sequence NHLGDMTSEEVMSLTSS (SEQ ID NO: 30), a fragment or a biological equivalent of each thereof, wherein a biological equivalent of the reference peptide is a peptide that has at least 80% sequence identity to the reference sequence or a peptide encoded by a polynucleotide that hybridizes under conditions of high stringency to a polynucleotide that encodes the reference peptide or its complement, wherein conditions of high stringency comprise hybridization reaction at about 60° C. in about 1×SSC.

In another aspect, these ELP fusions are useful in a method for delivering a drug or therapeutic agent to the luminal area of LGACs by transcytosis, the methods comprising, or alternatively consisting of, or yet further consisting of, contacting the LGAC with the ELP fusion. In one aspect, the ELP fusion is in contact with the ocular surface of the eye. In another aspect, the ELP fusion is releases the therapeutic agent from interstitial to luminal surfaces on a mucosal epithelial cell. In another aspect, the cell is one or more of a mucosal cell, an epithelial cell or a hepatocyte and/or contained within a lacrimal gland or tissue. The contacting can be in vitro or in vivo.

In a further aspect, the ELP fusions are useful to treat a disease of the lacrimal gland, comprising, or alternatively consisting essentially of, or yet further consisting of, administering to a patient in need of such treatment an ELP fusion. In one aspect, the disease is cancer or Sjorgren's Syndrome. In another aspect, the administration is by inhalation or via injection.

In another aspect, the ELP fusions are useful to treat of rheumatoid arthritis, psoriasis, Crohn's disease, nephrotic syndrome, keratoconjunctivitis sicca (dry eye). In another aspect the ELP fusions are useful to treat acne, acute promyelocytic leukemia (APL), breast cancer, neuroblastoma, and myeloma.

ELPs

The ELP fusions contain an elastin-like-polypeptide (ELP) component. ELPS are a genetically engineered polypeptide with unique phase behavior (see for e.g. S.R. MacEwan, et al., Biopolymers 94(1) (2010) 60-77), which promotes recombinant expression, protein purification, and self-assembly of nanostructures (see for e.g. A. Chilkoti, et al., Advanced Drug Delivery Reviews 54 (2002) 1093-1111). ELPs are artificial polypeptides composed of repeated pentapeptide sequences, (Val-Pro-Gly-Xaa-Gly)n (SEQ ID NO: 51) derived from human tropoelastin, where Xaa is the "guest residue" which is any amino acid, an amino acid analog or amino acid derivative thereof. In one embodiment, Xaa is any amino acid except proline. In another aspect, the guest residue is Ile, Val, Ala or Ser. This peptide motif displays rapid and reversible de-mixing from aqueous solutions above a transition temperature, $T_t$. Below $T_t$, ELPs adopt a highly water soluble random coil conformation; however, above $T_t$, they separate from solution, coalescing into a second aqueous phase. The $T_t$ of ELPs can be tuned by choosing the guest residue and ELP chain length as well as fusion peptides at the design level (see for e.g. MacEwan SR, et al., Biopolymers 94(1):60-77). The ELP phase is both biocompatible and highly specific for ELPs or ELP fusion proteins, even in complex biological mixtures. Genetically engineered ELPs are monodisperse, biodegradable, nontoxic. Throughout this description, ELPs are identified by the single letter amino acid code of the guest residue followed by the number of repeat units, n.

In one aspect, the ELP component comprises, or alternatively consists essentially of, or yet further consists of the polypeptide as noted above, more specifically (VPGXG)n (SEQ ID NO: 51), or G(VPGXG)n (SEQ ID NO: 58), or G(VPGXG)nY (SEQ ID NO: 59), wherein X is any amino acid, or alternatively Ala, Ser, Ile or Val, and wherein n is an integer that denotes the number of repeats, and can be from about between 5 and 400, alternatively between about 2 and about 300, or alternatively between about 25 and about 250, or alternatively between about 180 to about 250, or from about 195 to about 225, or from about 190 to about 195, or from about 75 to 125, or from about 85 to 115, or from about 90 to about 100, or from about 92 to about 98, or from about 5 to about 150, or from about 6 to about 200, or alternatively from about 15 to 195, or alternatively from 40 to about 195, from 60 to 195, or alternatively from 70 to 195, or alternatively from 80 to 195, or alternatively from 90 to 195, or alternatively from 92 to 195, or alternatively from 92 to 192, or alternatively from 100 to 195, or alternatively from 105 to 192, or alternatively from 110 to 195, or alternatively from 120 to 195, or alternatively from 150 to 195, or alternatively about 24, or alternatively about 48, or alternatively about 96, or alternatively about 192. In another aspect, the ELP is CV192: (VPGAG)192 (SEQ ID NO: 34) (FIG. 1A, Table 1) or A96: (VPGAG)96 (SEQ ID NO: 35), or V96 (VPGVG)96 (SEQ ID NO: 2), or an equivalent of each thereof, (wherein n is an integer that denotes the number of repeats, and can be from about 2 and 400, alternatively between 2 and 300, or alternatively between 25 and 250, or alternatively between 25 and 150, or from about 6 to about 200, or alternatively from about 15 to 195, or alternatively from 40 to about 195, from 60 to 195, or alternatively from 70 to 195, or alternatively from 80 to 195, or alternatively from 90 to 195, or alternatively from 92 to 195, or alternatively from 92 to 192, or alternatively from 100 to 195, or alternatively from 105 to 192, or alternatively from 110 to 195, or alternatively from 120 to 195, or alternatively from 150 to 195, or alternatively about 24, or alternatively about 48, or alternatively about 96, or alternatively about 192. In another aspect the ELP has the sequence selected from the group of: (VPGAG)n(VPGIG)n (SEQ ID NO: 53), (VPGAG)n (SEQ ID NO: 54), or (VPGVG)96 (SEQ ID NO: 2) (wherein n is an integer that denotes the number of repeats, and can be from about 2 and 400, alternatively between 2 and 300, or alternatively between 25 and 250, or alternatively between 25 and 150, or from about 6 to about 200, or alternatively from about 15 to 195, or alternatively from 40 to about 195, from 60 to 195, or alternatively from 70 to 195, or alternatively from 80 to 195, or alternatively from 90 to 195, or alternatively from 92 to 195, or alternatively from 92 to 192, or alternatively from 100 to 195, or alternatively from 105 to 192, or alternatively from 110 to 195, or alternatively from 120 to 195, or alternatively from 150 to 195, or alternatively about 24, or alternatively about 48, or alternatively about 96, or alternatively about 192. In one aspect, the ELP comprises, or alternatively consists essentially of, or yet further consists of A96I96: (VPGAG)96 (VPGIG)96 (SEQ ID NO: 36), A96: (VPGAG)96 (SEQ ID NO: 35), or V96 (VPGVG)96 (SEQ ID NO: 2) or a biological equivalent of each thereof. A biological equivalent of an ELP polypeptide is a peptide that has at least 80% sequence identity to the reference polypeptide or a peptide encoded by a polynucleotide that hybridizes under conditions of high stringency to a polynucleotide that encodes ELP polypeptide or its complement, wherein conditions of high stringency comprise hybridization reaction at about 60° C. in about 1×SSC.

The guest residue X may be a non-classical (non-genetically encoded) amino acid. Examples of non-classical amino acids include: D-isomers of the common amino acids, 2,4-diaminobutyric acid, α-amino isobutyric acid, A-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, C α-methyl amino acids, N α-methyl amino acids, and amino acid analogs in general.

Selection of X is independent in each ELP structural unit (e.g., for each structural unit defined herein having a guest residue X). For example, X may be independently selected for each structural unit as an amino acid having a positively charged side chain, an amino acid having a negatively charged side chain, or an amino acid having a neutral side chain, including in some embodiments, a hydrophobic side chain.

In each embodiment, the structural units, or in some cases polymeric or oligomeric repeats, of the ELP sequences may be separated by one or more amino acid residues that do not eliminate the overall effect of the molecule, that is, in imparting certain improvements to the therapeutic component as described. In certain embodiments, such one or more amino acids also do not eliminate or substantially affect the phase transition properties of the ELP component (relative to the deletion of such one or more amino acids).

The ELP component in some embodiments is selected or designed to provide a Tt ranging from about 10 to about 80° C., such as from about 35 to about 60° C., or from about 38 to about 45° C. In some embodiments, the $T_t$ is greater than about 40° C. or greater than about 42° C., or greater than about 45° C., or greater than about 50° C. The transition temperature, in some embodiments, is above the body temperature of the subject or patient (e.g., >37° C.) thereby remaining soluble in vivo, or in other embodiments, the $T_t$ is below the body temperature (e.g., <37° C.) to provide alternative advantages, such as in vivo formation of a drug depot for sustained release of the therapeutic agent.

The $T_t$ of the ELP component can be modified by varying ELP chain length, as the Tt generally increases with decreasing MW. For polypeptides having a molecular weight >100,000, the hydrophobicity scale developed by Urry et al. (PCT/US96/05186, which is hereby incorporated by reference in its entirety) is preferred for predicting the approximate $T_t$ of a specific ELP sequence. However, in some embodiments, ELP component length can be kept relatively small, while maintaining a target $T_t$, by incorporating a larger fraction of hydrophobic guest residues (e.g., amino acid residues having hydrophobic side chains) in the ELP sequence. For polypeptides having a molecular weight <100,000, the $T_t$ may be predicted or determined by the following function:

$$T_t = T_c + m\ln(C) + n\frac{1}{l} + k\frac{1}{l}\ln(C)$$

where $T_c$ is a critical transition temperature, m is the dependence on the natural logarithm of concentration, n is the dependence on the inverse of the ELP length l, and k is an interaction term between length and concentration. A summary of values for Tc, m, n, and k for Xaa=Val, Ile, Ser, and Ala are presented in Table 1.

TABLE 1

Multivariate fit parameters describing the phase diagram of ELP monoblock copolymers

| Monoblock Library | $T_c$ [° C.] | m [° C./ln(µM)] | n [° C. pentamers] | K [° C. pentamers/ ln(µM)] |
|---|---|---|---|---|
| (Val-Pro-Gly-Ser-Gly) (SEQ ID NO: 60) | 63.6 ± 1.1 | −1.86 ± 0.31 | 0 | 0 |
| (Val-Pro-Gly-Ala-Gly) (SEQ ID NO: 61) | 40.5 ± 1.6 | 0 | 7009 ± 345 | −850.1 ± 51.5 |
| (Val-Pro-Gly-Val-Gly) (SEQ ID NO: 62) | 21.2 ± 0.9 | 0 | 1607 ± 90 | −163.1 ± 23.3 |
| (Val-Pro-Gly-Ile-Gly) (SEQ ID NO: 63) | 13.0 ± 0.6 | 0 | 760 ± 30 | −81.2 ± 7.9 |

While the $T_t$ of the ELP component, and therefore of the ELP component coupled to a therapeutic component, is affected by the identity and hydrophobicity of the guest residue, X, additional properties of the molecule may also be affected. Such properties include, but are not limited to solubility, bioavailability, persistence, and half-life of the molecule.

In another aspect, the ELP comprises, or alternatively consists essentially of, or yet further consists of reference sequence G(VPGXG)n (SEQ ID NO: 58) or G(VPGXG)nY (SEQ ID NO: 59 (wherein n is an integer that denotes the number of repeats and X is an amino acid, such as for example A, I, S or V, or a biological equivalent thereof, wherein a biological equivalent of the reference is a peptide that has at least 80% sequence identity to reference peptide or a peptide encoded by a polynucleotide that hybridizes under conditions of high stringency to a polynucleotide that encodes the reference or its complement, wherein conditions of high stringency comprise hybridization reaction at about 60° C. in about 1×SSC. In one aspect, n is from about 180 to about 250, or from about 175 to about 225, or from about 190 to about 195, or about 192, or from about 75 to about 125, or from about 85 to about 115, or from about 90 to about 100, or from about 92 to about 98, or about 96. In one aspect, X is A and n is from about 180 to about 250, or from about 175 to about 225, or from about 190 to about 195, or about 192. In another aspect, X is V and n is from about 75 to about 125, or from about 85 to about 115, or from about 90 to about 100, or from about 92 to about 98, or about 96.

In a yet further aspect, the ELP-cyclophilin A fusion is CA192 (SEQ ID NO: 3), CV96 (SEQ ID NO: 4) (SEQ ID NO: 4), 3(CA)C (SEQ ID NO: 9) or a biological equivalent thereof, as well as dimers, trimers, tetramers and pentamers of them, as well as substantially purified compositions containing same. The hydrodynamic radius of the dimers range from about 5 nm to about 10 nm, or about 6 nm to about 9 nm, or about 6 nm, or about 7 nm, or about 8 nm. In a further aspect, the ELP fusion is a dimer and has a hydrodynamic radius of from about 5 nm to about 10 nm, or about 6 nm to about 9 nm, or about 6 nm, about 7 nm, or about 8 nm.

In a further aspect, the ELP-FKBP fusion is 5FA (SEQ ID NO: 10), 5FV (SEQ ID NO: 11), FAF (SEQ ID NO: 25), or a biological equivalent thereof, as well as dimers, trimers, tetramers and pentamers thereof. The hydrodynamic radius of the the ELP-FKBP fusion, or dimer, trimer, tetramer, or pentamer thereof ranges from about 5 nm to about 10 nm, or about 6 nm to about 9 nm, or about 6 nm, or about 7 nm, or about 8 nm. In a further aspect, the ELP fusion is a dimer and has a hydrodynamic radius of from about 5 nm to about 10 nm, or about 6 nm to about 9 nm, or about 6 nm, about 7 nm, or about 8 nm.

In a further aspect, the ELP-PIN1 fusion is 4PA (SEQ ID NO: 15) or a biological equivalent thereof, as well as dimers, trimers, tetramers and pentamers thereof. The hydrodynamic radius of the ELP-PIN1 fusion, or dimer, trimer, tetramer, or pentamer thereof ranges from about 5 nm to about 10 nm, or about 6 nm to about 9 nm, or about 6 nm, or about 7 nm, or about 8 nm. In a further aspect, the ELP fusion is a dimer and has a hydrodynamic radius of from about 5 nm to about 10 nm, or about 6 nm to about 9 nm, or about 6 nm, about 7 nm, or about 8 nm.

In one aspect, Applicants have prepared the substantially homogenous compositions by use of a gel filtration column to isolate dimerized CA192 (SEQ ID NO: 3) from aggregated CA192 (SEQ ID NO: 3). Before isolation, gel filtration column is conditioned with 2 column volumes of phosphate buffered saline (PBS). The loading of CA192 (SEQ ID NO: 3) into the column is followed by an isocratic flow of one column volume of PBS. The elution is detected by a UV detector at 210 nm. Fractions with an UV absorption above 10 mAU are collected by an automatic fraction collector. As is apparent to the skilled artisan, this method is useful to isolate and purify compositions of other multimer fusions.

ELPs have potential advantages over chemically synthesized polymers as drug delivery agents. First, because they are biosynthesized from a genetically encoded template, ELPs can be made with precise molecular weight. Chemical synthesis of long linear polymers does not typically produce an exact length, but instead a range of lengths. Consequently, fractions containing both small and large polymers yield mixed pharmacokinetics and bio-distribution. Second, ELP biosynthesis produces very complex amino acid sequences with nearly perfect reproducibility. This enables very precise selection of the location of drug attachment. Thus drug can be selectively placed on the outside, buried in the core, or dispersed equally throughout any complexes. Third, ELPs can modulate the self-assembly of fusion proteins into multivalent nanostructures (dimers, trimers, tetramers, and micelles with higher aggregation numbers) that can have excellent site-specific accumulation and drug carrying properties. Fourth, because ELPs can be designed from directly using native amino acid sequences found extensively in the human body they are biodegradable, biocompatible, and tolerated by the immune system. Fifth, ELPs undergo an inverse phase transition temperature, Tt, above which they phase separate into large aggregates. Upon introduction into the body, optimized ELPs can thus be tuned to assemble a depot, which can release active drug for significantly extended durations.

In some embodiments the ELP comprises 5-100 kDa and connects multiple drug binding domains. In some embodiments, the ELP imparts aqueous solubility to the agent. In some embodiments, the ELP is charge neutral. The mass of the ELP(s) may be selected so that the agent has a mass of 60-200 kDa. In some embodiments, the ELP has a critical solution temperature that is low to facilitate extended release of a therapeutic agent.

In addition to therapeutics, the ELPs may also be associated with a detectable label that allows for the visual detection of in vivo uptake of the ELPs. Suitable labels include, for example, fluorescein, rhodamine, tetramethylrhodamine, eosin, erythrosin, coumarin, methyl-coumarins, pyrene, Malacite green, Alexa-Fluor® (i.e., any one of Alexa-Fluors 350, 405, 488, 532, 546, 555, 561, 568, 594, 647, 660, 680, 700, and 750), stilbene, Lucifer Yellow, Cascade Blue™, and Texas Red. Other suitable optical dyes are described in Haugland, Richard P. (1996) Molecular Probes Handbook.

Expression of Recombinant Proteins

This disclosure also provides a polynucleotide expressing ELP fusions as described herein. The ELP fusions and other recombinant proteins described herein can be prepared by expressing polynucleotides encoding the ELP fusion (the ELP and the drug binding domain, e.g., cyclophilin A (SEQ ID NO: 22 or SEQ ID NO: 23) polypeptide sequences of this disclosure) in an appropriate host cell, i.e., a prokaryotic or eukaryotic host cell. This can be accomplished by methods of recombinant DNA technology known to those skilled in the art. It is known to those skilled in the art that modifications can be made to any peptide to provide it with altered properties. Polypeptides of the disclosure can be modified to include unnatural amino acids. Thus, the peptides may comprise D-amino acids, a combination of D- and L-amino acids, and various "designer" amino acids (e.g., β-methyl amino acids, C-α-methyl amino acids, and N-α-methyl amino acids, etc.) to convey special properties to peptides. Additionally, by assigning specific amino acids at specific coupling steps, peptides with α-helices, β turns, β sheets, α-turns, and cyclic peptides can be generated. Generally, it is believed that beta-turn spiral secondary structure or random secondary structure is preferred. The complements and equivalents of these polynucleotides are further provided herein.

Thus, in one aspect, provided herein is an isolated polynucleotide encoding the ELP fusion, e.g., comprising a polynucleotide encoding cyclophilin A (SEQ ID NO: 22 or SEQ ID NO: 23), a fragment thereof or an equivalent thereof, and the ELP, a fragment or an equivalent of each thereof. In a yet further aspect, the polynucleotide further comprises, or alternatively consists essentially of, or yet further consists of a detectable label. In a yet further aspect, the polynucleotide further comprises, or alternatively consists essentially of, or yet further consists of an expression vector and regulatory sequences for expression in the appropriate host cell system. The vector can be a plasmid. As is understood by those of skill in the art, the regulatory sequences are positioned to drive expression of the polynucleotide encoding the ligand and ELP. The polynucleotides and expression vectors can be incorporated into a host cell. Plasmid, viral vectors and other expression vectors are known in the art.

The ELPs can be expressed and purified from a suitable host cell system. Suitable host cells include prokaryotic and eukaryotic cells, which include, but are not limited to bacterial cells, yeast cells, insect cells, animal cells, mammalian cells, murine cells, rat cells, sheep cells, simian cells and human cells. Examples of bacterial cells include *Escherichia coli, Salmonella enterica* and *Streptococcus gordonii*. In one embodiment, the host cell is *E. coli*. The cells can be purchased from a commercial vendor such as the American Type Culture Collection (ATCC, Rockville Md., USA) or cultured from an isolate using methods known in the art.

Examples of suitable eukaryotic cells include, but are not limited to 293T HEK cells, as well as the hamster cell line BHK-21; the murine cell lines designated NIH3T3, NS0, C127, the simian cell lines COS, Vero; and the human cell lines HeLa, PER.C6 (commercially available from Crucell) U-937 and Hep G2. A non-limiting example of an insect cell includes *Spodoptera frugiperda*. Examples of yeast useful for expression include, but are not limited to *Saccharomyces, Schizosaccharomyces, Hansenula, Candida, Torulopsis, Yarrowia*, or *Pichia*. See e.g., U.S. Pat. Nos. 4,812,405; 4,818,700; 4,929,555; 5,736,383; 5,955,349; 5,888,768 and 6,258,559.

Yet further provided are methods to prepare the ELP fusions, e.g., CA192 (SEQ ID NO: 3), CV96 (SEQ ID NO: 4), 3(CA)C (SEQ ID NO: 9), 5FA (SEQ ID NO: 10), 5FV (SEQ ID NO: 11), FAF (SEQ ID NO: 25), 4PA (SEQ ID NO: 15) or a fragment thereof, as well as dimers, trimers, tetramers and pentamers thereof or an equivalent thereof through genetic recombination by expressing a polynucleotide encoding such in a suitable host cell. The polynucleotide is inserted into the host cell and the cell is grown under conditions that favor expression of the polynucleotide. In a further aspect, the ELP fusion is purified from the host cell system. Dimers, trimers, tetramers and pentamers of the fusion proteins may be formed through said expression of the monomeric form of the ELP fusion protein from the polynucleotide encoding the same, followed by subjecting the expressed monomer to conditions readily determined by the skilled artisan or described in the Examples herein to promote dimerization, trimerization, tetramerization, or pentamerization.

Protein Purification

The phase transition behavior of the ELPs allows for easy purification. The ELPs may also be purified from host cells using methods known to those skilled in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide or polypeptide are filtration, ion-exchange chromatography, exclusion chromatography, polyacrylamide gel electrophoresis, affinity chromatography, or isoelectric focusing. A particularly efficient method of purifying peptides is fast protein liquid chromatography or even HPLC. In the case of ELP compositions protein purification may also be aided by the thermal transition properties of the ELP domain as described in U.S. Pat. No. 6,852,834.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, about 98%, or 100% or more of the fusions in the composition.

Various methods for quantifying the degree of purification of the fusion protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "[n]-fold purification number" wherein "n" is an integer. The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxyapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

To purify ELP fusions, e.g., with cyclophilin, such as CA192 (SEQ ID NO: 3), it is necessary to remove nanoaggregates (50-100 nm in hydrodynamic radius) from the major fraction that contains the dimeric CA192 (SEQ ID NO: 3). This is achieved using size exclusion liquid chromatography with packing media (such as a HiLoad™ 26/600 Superdex® 200 pg) capable of retaining the monomer, dimer, trimeric, and tetrameric assemblies of CA192 (SEQ ID NO: 3), which have expected molecular weights up to about 400 kD. Prior to loading a sample, a size exclusion chromatography column (60 cm by 26 mm) is washed with two columns of phosphate buffered saline. A sample containing CA192 (SEQ ID NO: 3) (100 mg) is injected into the column (5 mL) peaks are eluted by an isocratic flow (2.6 mL/min) of one column volume of PBS. The elution can be followed using UV spectrophotometry at 214 nm. Fractions with an UV absorption above a baseline threshold (such as 10 mAU) can be collected by an automatic fraction collector. Due to their larger hydrodynamic radius, CA192 (SEQ ID NO: 3) nanoaggregates are not retained by the resin, and they flow through in the void volume as a first fraction. Upon further elution, the purified dimeric CA192 (SEQ ID NO: 3) peak fraction can be obtained and loaded with CsA.

Pharmaceutical Compositions

Pharmaceutical compositions are further provided. The compositions comprise a carrier the ELP fusion or a polynucleotide encoding the ELP fusion, as described herein or other compositions (e.g., polynucleotide, vector system, host cell) as described herein. The carriers can be one or more of a solid support or a pharmaceutically acceptable carrier. In one aspect, the compositions are formulated with one or more pharmaceutically acceptable excipients, diluents, carriers and/or adjuvants. In addition, embodiments of the compositions include ELPs, formulated with one or more pharmaceutically acceptable auxiliary substances.

The disclosure provides pharmaceutical formulations in which the one or more of an agent, ELP-fusion with a therapeutic agent, or a polynucleotide, vector or host cells can be formulated into preparations for injection or other appropriate route of administration in accordance with the disclosure by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives or other antimicrobial agents.

Aerosol formulations provided by the disclosure can be administered via inhalation. For example, embodiments of the pharmaceutical formulations of the disclosure comprise a compound of the disclosure formulated into pressurized acceptable propellants such as dichlorodifluoromethane, propane, nitrogen and the like.

Embodiments of the pharmaceutical formulations of the disclosure include those in which the composition is formulated in an injectable composition. Injectable pharmaceutical formulations of the disclosure are prepared as liquid solutions or suspensions; or as solid forms suitable for solution in, or suspension in, liquid vehicles prior to injection. The preparation may also be emulsified or the active ingredient encapsulated in liposome vehicles in accordance with other embodiments of the pharmaceutical formulations of the disclosure.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Routes of administration applicable to the methods and compositions described herein include intranasal, intraperitoneal, intramuscular, subcutaneous, intradermal, topical application, intravenous, nasal, oral, inhalation, intralacrimal, retrolacrimal perfusion along the duct, intralacrimal, and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery, include systemic or localized routes. In one embodiment, the composition comprising, or alternatively consisting essentially of, or yet further consisting of the ELP and agent is administered intralacrimally through injection. In further embodiments, the composition is administered systemically, topically on top of the eye, by retrolacrimal perfusion, or intranasally.

Encapsulation and Release of Therapeutic Agents

This disclosure also provides a method to encapsulate therapeutic agents within the nanoparticles. A two phase method can be used. An aqueous phase PBS containing the ELP is mixed with an organic phase hexane/EtOH containing the therapeutic agent in a small glass vial. A nitrogen flow is applied to facilitate the evaporation of the hexane/EtOH phase. Centrifugation is performed to remove any insoluble drug after the organic phase evaporated out. 100 µL of the sample is filtered and injected into a C-18 reverse phase HPLC column to analyze the amount of the drug that is initially encapsulated. RP-HPLC can be used to determine the amount of drug that is retained inside the ELP fusion protein.

Alternatively, an aqueous phase phosphate-buffered saline (PBS) containing the ELP is s mixed with an organic phase 90% hexane/10% EtOH containing the therapeutic agent or drug. Under a nitrogen environment and constant stirring, along with the evaporation of organic solvent, the drug is gradually released into the aqueous phase and encapsulated by the fusion protein. This is followed by high-speed centrifugation and filtration to remove the excess insoluble drug. To determine the encapsulation efficiency and characterize the release profile, Applicants use a reversed-phase high-performance liquid chromatography (RP-HPLC) analysis method to measure the CsA concentration in the ELP, as described in the experimental section below.

Treatment of Disease

This disclosure also provides a method for delivering a therapeutic agent in vitro comprising, or alternatively consisting essentially of, or yet further consisting of contacting a tissue expressing the receptor for the drug binding domain, e.g., for CSA with an ELP-cyclophilin containing agent as described herein. The cells can be eukaryotic or prokaryotic. Non-limiting examples of eukaryotic cells include animal cells, mammalian cells and human cells. Further provided is a method for delivering a therapeutic agent in vivo comprising, or alternatively consisting essentially of, or yet further consisting of administering an effective amount of the agent as described herein to a subject. In one aspect, the subject is an animal, such as a mammal or human subject.

Further provided is a method for ameliorating the symptoms of a disease or condition or for treating a disease or condition, comprising, or alternatively consisting essentially of, or yet further consisting of administering an effective amount of the agent ELP-containing agent as described herein to a subject suffering from the disease or condition or susceptible to the disease or condition. In one aspect, the subject is an animal, such as a mammal or human subject. Non-limiting examples of such diseases or conditions include, for example, cancer, organ rejection, e.g., in patients receiving liver, kidney, or heart transplant; Graft-versus-host disease, particularly in bone-marrow transplantation; Rheumatoid arthritis, and related diseases, Psoriasis, Persistent nummular keratitis, Atopic dermatitis, Kimura disease, Pyoderma gangrenosum, chronic autoimmune urticaria, Acute systemic mastocytosis, and, Dry eyes, Sjögren's syndrome, autoimmune disorders such as systemic lupus erythematosus (SLE), acute severe ulcerative colitis and autoimmune urticaria that do not respond to treatment with steroids; posterior or intermediate uveitis with noninfective cause; and atopic dermatitis (veterinary use), neuronal cellular damage and reperfusion injury in traumatic brain injury, and cardiac hypertrophy.

Administration can be by any acceptable route, and can be local or systemic. The route of administration, the dose and dosing schedule can be determined by the treating veterinarian or physician.

The agents can be co-administered with other agents known for the treatment of disease, e.g., a steroid composition, or immunotherapy or chemotherapy for the treatment of cancer. Administration can be concurrent or sequential and multiple doses can be administered.

Use of Compounds for Preparing Medicaments

The ELPs of the present disclosure are also useful in the preparation of medicaments to treat a variety of pathologies as described herein. The methods and techniques for preparing medicaments of a composition are known in the art. For the purpose of illustration only, pharmaceutical formulations and routes of delivery are detailed herein. In one aspect when the ELP is combined with another therapy or therapeutic agent, provided herein the compositions are useful in the preparation of combination compositions that can be simultaneously or concurrently administered.

Thus, one of skill in the art would readily appreciate that any one or more of the compositions described above, including the many specific embodiments, can be used by applying standard pharmaceutical manufacturing procedures to prepare medicaments to treat the many disorders described herein. Such medicaments can be delivered to the subject by using delivery methods known in the pharmaceutical arts.

Kits

The ELPs as described herein, can be provided in kits. The kits can further contain additional therapeutics and optionally, instructions for making or using the ELPs. In a further aspect, the kit contains reagents and instructions to perform a screen as detailed herein.

Screening Assays

This disclosure also provides screening assays to identify potential therapeutic agents of known and new compounds and combinations. For example, one of skill in the art can also determine if the ELP provides a therapeutic benefit in vitro by contacting the ELP or combination comprising, or alternatively consisting essentially of, or yet further consisting of the ELP with a sample cell or tissue to be treated. The cell or tissue can be from any species, e.g., simian, canine, bovine, ovine, rat, mouse or human.

The contacting can also be performed in vivo in an appropriate animal model or human patient. When performed in vitro, the ELPs can be directly added to the cell culture medium. When practiced in vitro, the method can be used to screen for novel combination therapies, formulations or treatment regimens, prior to administration to an animal or a human patient.

In another aspect, the assay requires contacting a first sample comprising, or alternatively consisting essentially of, or yet further consisting of suitable cells or tissue ("control sample") with an effective amount of an ELP as disclosed herein and contacting a second sample of the suitable cells or tissue ("test sample") with the ELP, agent or combination to be assayed. In one aspect in the case of cancer, the inhibition of growth of the first and second cell samples are determined. If the inhibition of growth of the second sample is substantially the same or greater than the first sample, then the agent is a potential drug for therapy. In one aspect, substantially the same or greater inhibition of growth of the cells is a difference of less than about 1%, or alternatively less than about 5% or alternatively less than about 10%, or alternatively greater than about 10%, or alternatively greater than about 20%, or alternatively greater than about 50%, or alternatively greater than about 90%. The contacting can be in vitro or in vivo. Means for determining the inhibition of growth of the cells are well known in the art.

In a further aspect, the test agent is contacted with a third sample of cells or tissue comprising, or alternatively consisting essentially of, or yet further consisting of normal counterpart cells or tissue to the control and test samples and selecting agents that treat the second sample of cells or tissue but does not adversely affect the third sample. For the purpose of the assays described herein, a suitable cell or tissue is described herein such as cancer or other diseases as described herein. Examples of such include, but are not limited to cancer cell or tissue obtained by biopsy, blood, breast cells, colon cells.

Efficacy of the test composition is determined using methods known in the art which include, but are not limited to cell viability assays or apoptosis evaluation.

In yet a further aspect, the assay requires at least two cell types, the first being a suitable control cell.

The assays also are useful to predict whether a subject will be suitably treated by this disclosure by delivering an ELP to a sample containing the cell to be treated and assaying for treatment, which will vary with the pathology, or for screening for new drugs and combinations. In one aspect, the cell or tissue is obtained from the subject or patient by biopsy. This disclosure also provides kits for determining whether a pathological cell or a patient will be suitably treated by this therapy by providing at least one composition of this disclosure and instructions for use.

The test cells can be grown in small multi-well plates and is used to detect the biological activity of test compounds. For the purposes of this disclosure, the successful ELP or other agent will block the growth or kill the cancer cell but leave the control cell type unharmed.

Combination Treatments

Administration of the therapeutic agent or substance of the present disclosure to a patient will follow general protocols for the administration of that particular secondary therapy, taking into account the toxicity, if any, of the treatment. It is expected that the treatment cycles would be repeated as necessary. It also is contemplated that various standard therapies, as well as surgical intervention, may be applied in combination with the described therapy.

As is apparent to those skilled in the art, the combination therapy can take the form of a combined therapy for concurrent or sequential administration.

The following examples are included to demonstrate some embodiments of the disclosure. However, those of skill in the art should, in light of the present disclosure, appreciate that many changes can be made in the specific embodiments which are disclosed and still obtain a like or similar result without departing from the spirit and scope of the disclosure.

EXPERIMENTAL METHODS

Example 1

The following methods are merely exemplary. Applicants designed the encoding sequence of cyclosporin A (CypA) using *Escherichia coli* biased codons. As indicated as follows, the custom encoding sequence flanked by restriction recognition sites of NdeI and BamHI at the 5' and 3' ends was ordered from Integrated DNA Technologies (IDT) as follows:

```
(SEQ ID NO: 64)
5'-CATATGGTTAACCCGACCGTTTTCTTCGACATCGCTGTTGACGGTGA

ACCGCTGGGTCGTGTTTCTTTCGAACTGTTCGCTGACAAAGTTCCGAAAA

CCGCTGAAAACTTCCGTGCTCTGTCTACCGGTGAAAAAGGTTTCGGTTAC

AAAGGTTCTTGCTTCCACCGTATCATCCCGGGTTTCATGTGCCAGGGTGG

TGACTTCACCCGTCACAACGGTACCGGTGGTAAATCTATCTACGGTGAAA

AATTCGAAGACGAAAACTTCATCCTGAAACACACCGGTCCGGGTATCCTG

TCTATGGCTAACGCTGGTCCGAACACCAACGGTTCTCAGTTCTTCATCTG

CACCGCTAAAACCGAATGGCTGGACGGTAAACACGTTGTTTTCGGTAAAG

TTAAAGAAGGTATGAACATCGTTGAAGCTATGGAACGTTTCGGTTCTCGT

AACGGTAAAACCTCTAAAAAAATCACCATCGCTGACTGCGGTCAGCTGGA

AGGTTACTGATCTCCTCGGATCC-3'
```

The NdeI and BamHI restriction sites enabled the insertion of the sequence into the pET-25b(+) vector. Besides these two sites, BseRI restriction site was placed right ahead of the BamHI restriction site, enabling the ligation of the A192 encoding sequence, which was synthesized by recursive directional ligation in a modified pET-25b(+) vector (Janib et al., 2014). After verifying the correct sequence through DNA sequencing, the resulted plasmid with the fusion protein sequence was first amplified in TOP10 competent cells and then transfected into BLR competent cells for expression. After expression, centrifugation and lysis, the CA192 fusion protein was further purified by inverse transition cycling (ITC) (Sun et al., 2011) using the unique thermal responsiveness of ELPs.

The molecular weight of purified fusion protein was verified by SDS-PAGE stained with copper chloride ($CuCl_2$). The parent ELP, A192, served as a control. CypA has a molecular weight of 18 kDa. Combined with the 73.6 kDa molecular weight of A192, the molecular weight of CA192 (SEQ ID NO: 3) should be around 91.6 kDa. This shift for the CA192 (SEQ ID NO: 3) is seen on SDS-PAGE (FIG. 1B).

Figure 2A:
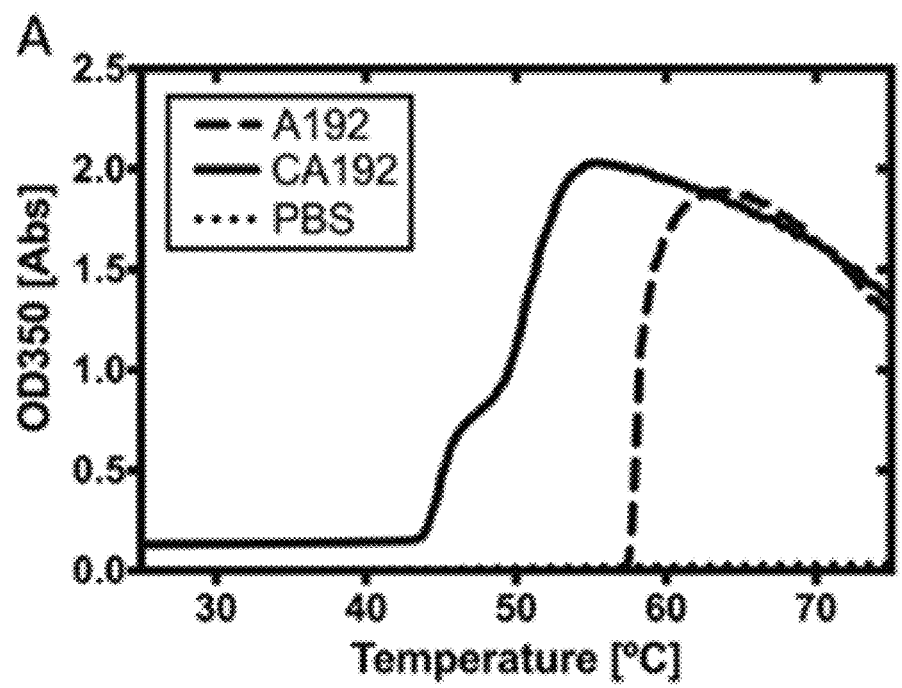
FIGS. 2A-2C: A192 Fusion to CypA reduces the phase transition temperature relative to the free ELP and the phase transition behavior of A192 relative to CA192 (SEQ ID NO: 3) is shown, this data was obtained on CA192 (SEQ ID NO: 3) before size exclusion chromatography (SEC) (FIG. 2A). Optical density was determined as a function of temperature (1° C./min) for 25 µM CA192 (SEQ ID NO: 3), free A192, and a PBS control. The temperature with the maximum positive slope was defined as the phase transition temperature for each condition.
Figure 2B:
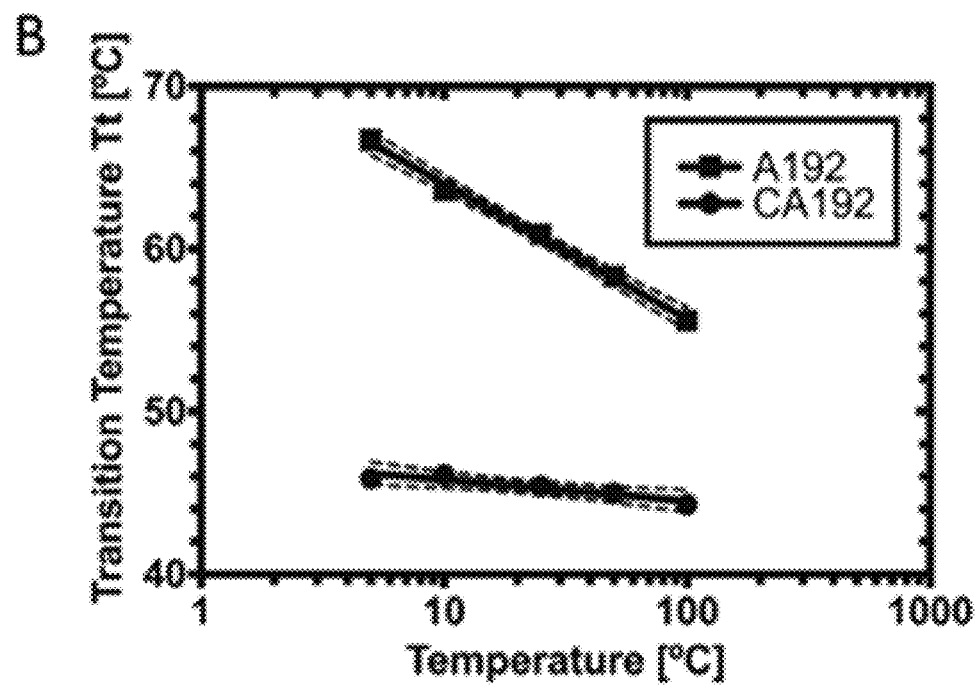
Figure 2C:
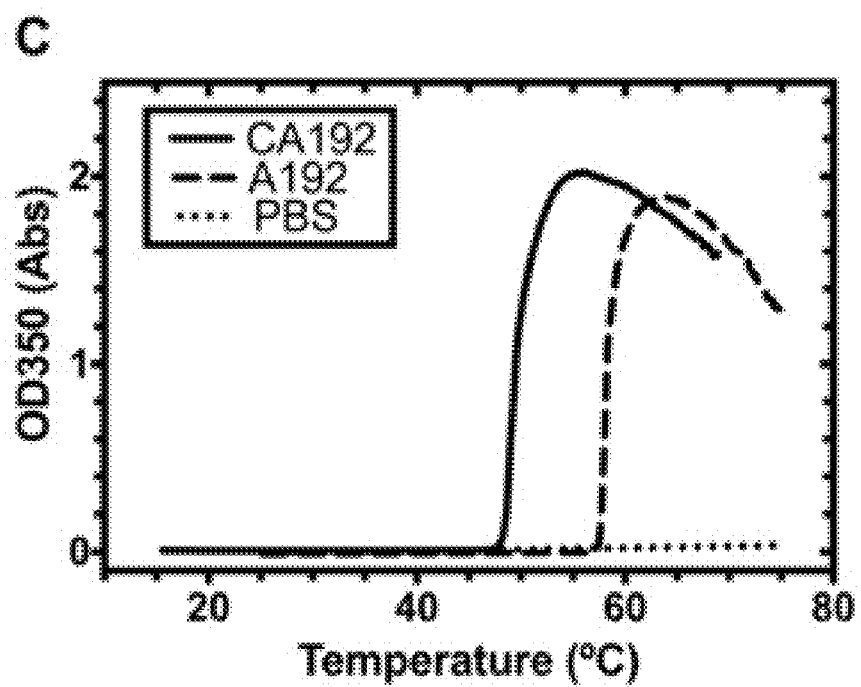

The thermal responsiveness property of CA192 (SEQ ID NO: 3), along with the parent A192, was characterized using UV-Vis by measuring their optical density of these constructs at 350 nm, where neither fusion protein nor plain A192 contributes significant absorption. The CA192 (SEQ ID NO: 3) used had not been subjected to size exclusion chromatography. Both ELPs at different concentrations (5 µM to 100 µM) were subject to a precisely controlled temperature increase from 25 to 75° C. at a rate of 1° C./min. The optical density profile representing the ELP phase separation behavior is shown in FIG. 2A. The Tt of ELPs is defined as the temperature at which the first derivative of the optical density with respect to the temperature reaches a maximum. At 25 µM concentration, the Tt of CA192 (SEQ ID NO: 3) was found to be 45.4° C. Consistent with our previous finding (Wang et al., 2015), the Tt of CA192 (SEQ ID NO: 3) was also found to be a function of concentration: $Tt=b-mLog_{10}[C_{ELP}]$, where the intercept "b" is equal to 47.1, the slope "m" equals to 1.3 and $[C_{ELP}]$ represents the fusion protein concentration (FIG. 2B, Table 1). Finally, CA192 (SEQ ID NO: 3) exhibited a two-phase transition, distinct from A192. Thus, CA192 (SEQ ID NO: 3) subjected to size exclusion chromatography (SEC) and dimerized CA192 (SEQ ID NO: 3) isolated as one of two fractions. The dimerized CA192 (SEQ ID NO: 3) and A192 ELPs at different concentrations (5 µM to 100 µM) were subject to a precisely controlled temperature increase from 25 to 75° C. at a rate of 1° C./min. The optical density profile representing the ELP phase separation behavior is shown in FIG. 2C. At 25 µM concentration, the Tt of dimerized CA192 was found to be 49.3° C., notably shifted from that of CA192 of 45.4° C. These findings suggest that the CypA moiety was interacting to modulate the properties of A192 to change the properties of this nanoparticle.

(RP-HPLC) analysis method to measure the CsA concentration in CA192. Briefly, CsA separation and detection was achieved on a C4 reverse-phase HPLC column (150×4.6 mm, particle size 5 µm) at 210 nm. The mobile phase flow rate was set to 1.0 ml/min. The linear gradient from 20% to 95% of methanol was applied from 0 to 5 min. Then the mobile phase was changed to 95% methanol isocratic flow for 10 min. The elution time is 9.5 min.

Figure 3A:
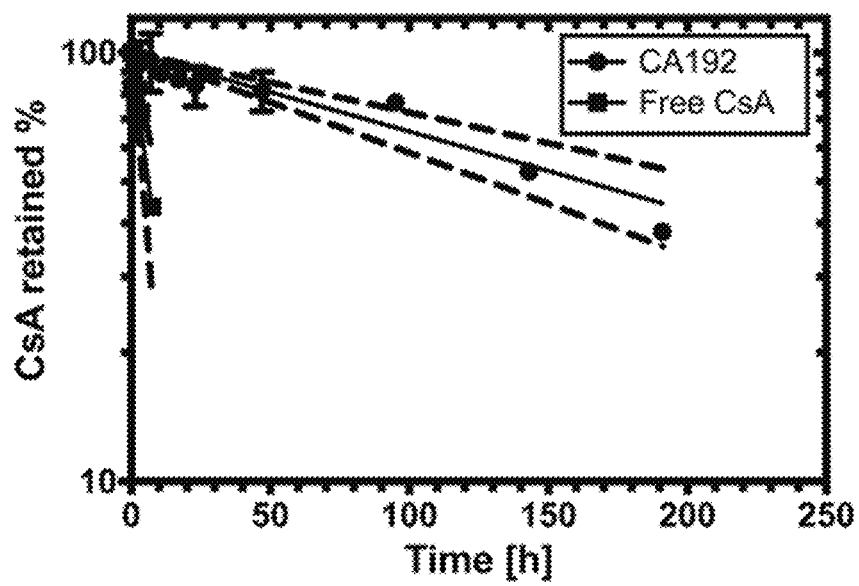
FIGS. 3A-3C: CA192 (SEQ ID NO: 3) solubilizes CsA and reduces its release under dialysis compared to free drug. CsA-bound CA192 (SEQ ID NO: 3) (150 µM) solutions were loaded into a 10,000 MWCO dialysis cassette, dialyzed under sink-conditions against PBS at 4° C., sampled over a period of one week (n=3), and quantified using a calibrated RP-HPLC assay. As a control, free drug release was also conducted. Methanol was used to solubilize CsA in a solution of PBS. For each condition, drug concentration decreased according to a one-phase exponential decay. A best-fit line for each is indicated along with a 95% CI in dashed lines is shown in FIG. 3A. The release half-life for CsA from CA192 (SEQ ID NO: 3) was 163.6 (CI: 128.8 to 214.3) h, which was much slower than for free drug loaded in Methanol/PBS, 6.1 (CI: 4.1 to 9.9) h. This data was obtained with CA192 (SEQ ID NO: 3) not yet subjected to SEC. Dimerized CA192 (SEQ ID NO: 3) was isolated and tested. The drug release from dimerized CA192 (SEQ ID NO: 3) fits a one-phase decay model with a half-life of 954 hr (95% CI: 553 to 3219 hr), of roughly 40 days, at 4° C.
Figure 3B:
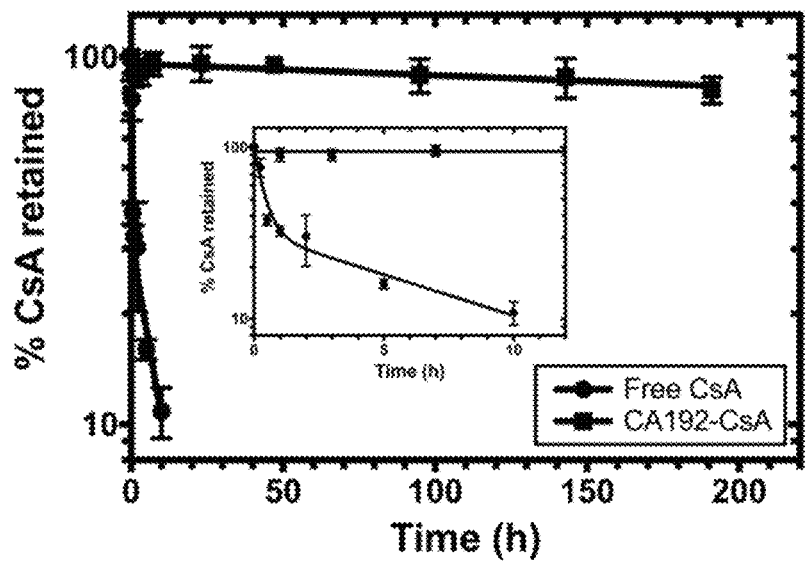
Figure 3C:
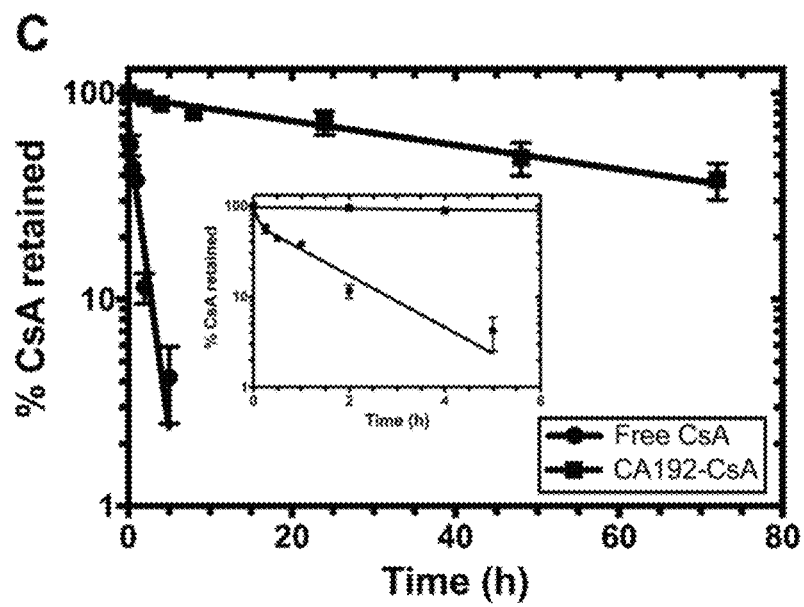
Figure 4A:
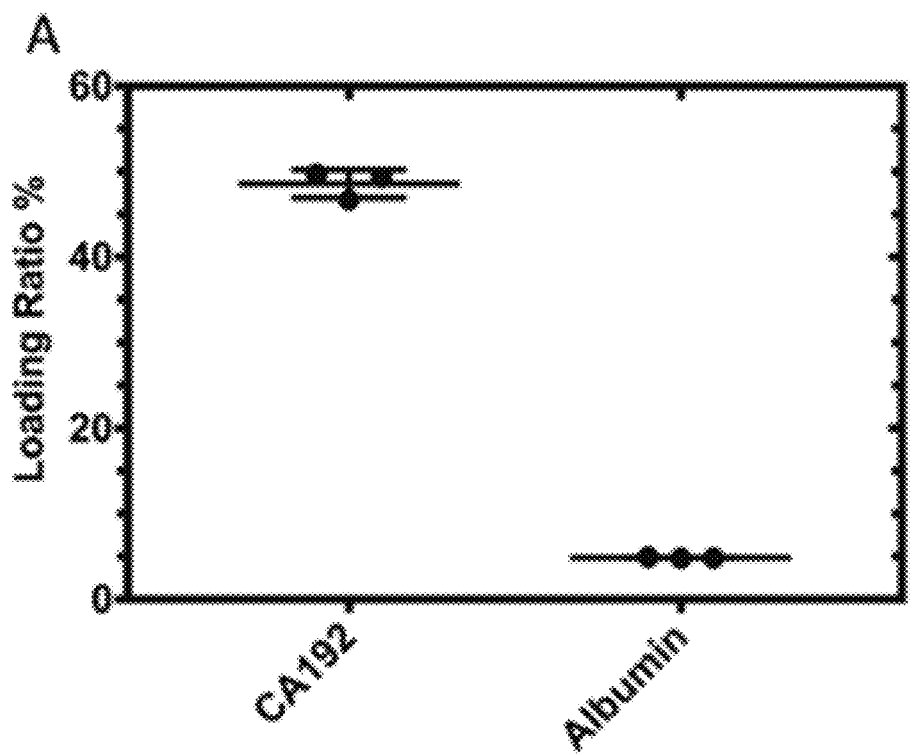
FIGS. 4A-4C: CA192 (SEQ ID NO: 3) resists transfer of CsA to albumin.
Figure 4B:
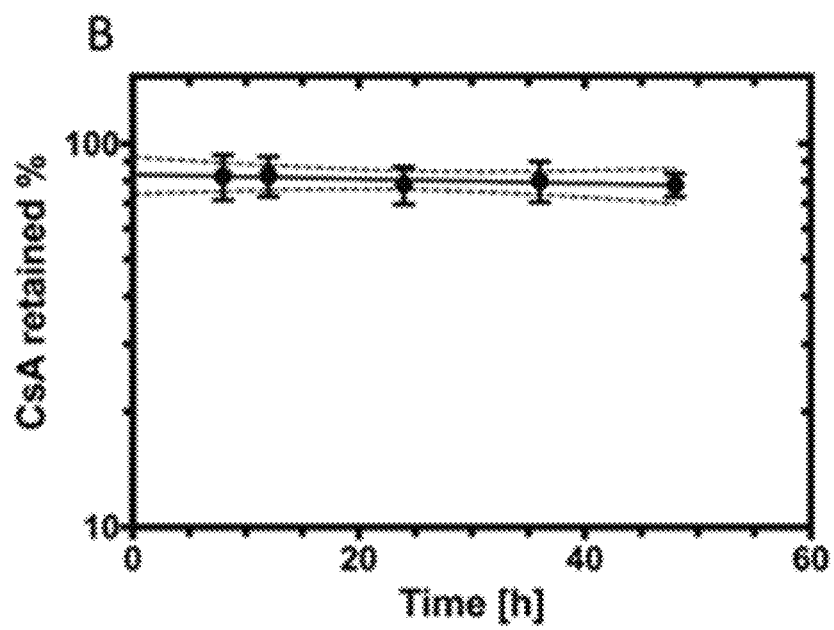

To evaluate the characteristics of CsA released from CA192 (not yet subjected to SEC) in vitro, its release profile from the fusion protein was characterized by performing dialysis against PBS at 4° C. Samples were collected from the dialysis cassette at different time points between 0 and 192 h and analyzed by RP-HPLC. The release profile fits a one-phase decay model with a half-life of 163.6 h (FIG. 3A). The same drug release experiment was performed using CA192 dimer obtained via SEC. Dialysis was performed against PBS at 37° C. (FIG. 3B) and 4° C. (FIG. 3C). To further validate the release profile, as a control group, with the same encapsulation method, human albumin was explored to load CsA. The entrapment efficiency was determined to be 4.8%, significantly lower than CA192 (FIG. 4A). In order to mimic the physiological situation where fusion-loaded drug could be displaced by albumin, Applicants dissolved human albumin into a PBS solution of CsA-loaded CA192 and adjusted the albumin concentration to 1 mM, the physiological concentration of albumin. The mixture was incubated at 37° C. and samples were collected at different time points up to 48 h. Another round of ITC was performed to purify CA192 from the mixture, followed by RP-HPLC analysis. No significant drug loss from fusion carrier to albumin was observed within 2 days (FIG. 4B). Albumin cannot deplete CsA from CA192 carrier effectively within a 48 h period, suggesting the high binding affinity

TABLE 2

Protein-polymers evaluated in this Example

| Label | Amino Acid Sequence | Exp. M.W. [kDa] | [a]Slope, m [° C./Log$_{10}$ (µM)] | [b]Intercept, b [° C.] | [c]Purity [%] |
|---|---|---|---|---|---|
| A192 | (VPGAG)$_{192}$ (SEQ ID NO: 1) | 73.6 | 8.3 ± 0.28 | 72.3 ± 0.41 | 98.1 |
| CA192 | MVNPTVFFDIAVDGEPLGRVSFELEADKVP KTAENFRALSTGEKGFGYKGSCFHRIIPGFM CQGGDFTRHNGTGGKSIYGEKFEDENFILK HTGPGILSMANAGPNTNGSQFFICTAKTEW LDGKHVVFGKVKEGMNIVEAMERFGSRNG KTSKKITIADCGQLEG(VPGAG)$_{192}$Y (SEQ ID NO: 3) | 91.6 | 1.3 ± 0.27 | 47.1 ± 0.39 | 98.8 |

[a,b]The ELP phase diagram as a function of temperature, $T_t$, and concentration, $C_{ELP}$, was fit to the following relationship: $T_t = b - m\ Log_{10}[C_{ELP}]$ where b is the intercept at 1 µM and m are ° C. change for a 10-fold change in concentration. mean ± 95% CI.
[c]Polypeptide purity was assessed using SDS-PAGE and subsequent densitometry of copper chloride stained gel.

Figure 4C:
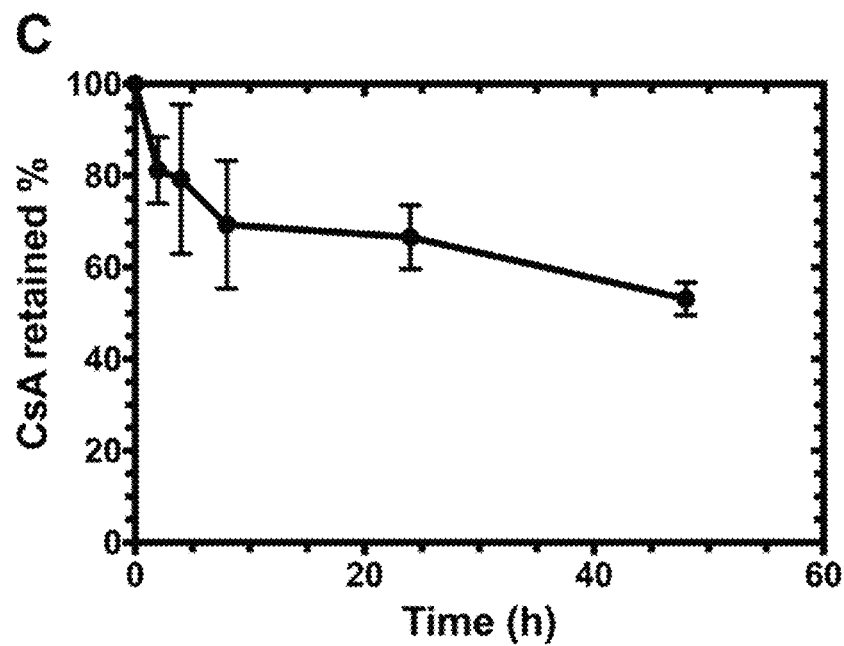

CsA was encapsulated in the fusion protein based on a previously reported two-phase solvent evaporation method (Shi, et al., 2013). Briefly, an aqueous phase phosphate-buffered saline (PBS) containing 300 µM CA192 was mixed with an organic phase 90% hexane/10% EtOH containing 900 µM CsA. Under a nitrogen environment and constant stirring, along with the evaporation of organic solvent, CsA was gradually released into the aqueous phase and encapsulated by the fusion protein. This was followed by high-speed centrifugation and filtration to remove the excess insoluble drug. To determine the encapsulation efficiency and characterize the release profile, Applicants established a reversed-phase high-performance liquid chromatography between CsA and CA192 is likely to be maintained when administrated systemically. Similar to this competition method against albumin, 300 µM CA192-CsA in PBS was diluted 1:1 in mouse plasma to achieve a final concentration of 150 µM. Similarly, the mixture was incubated at 37° C. and sampled from 8 to 48 h (FIG. 4C). The phase separation of CA192 was induced with 1 M NaCl at 37° C. and the ELP was isolated by centrifugation. The pellet following centrifugation was resuspended for RP-HPLC analysis to measure the remaining CsA bound to CA192.

Figure 5A:
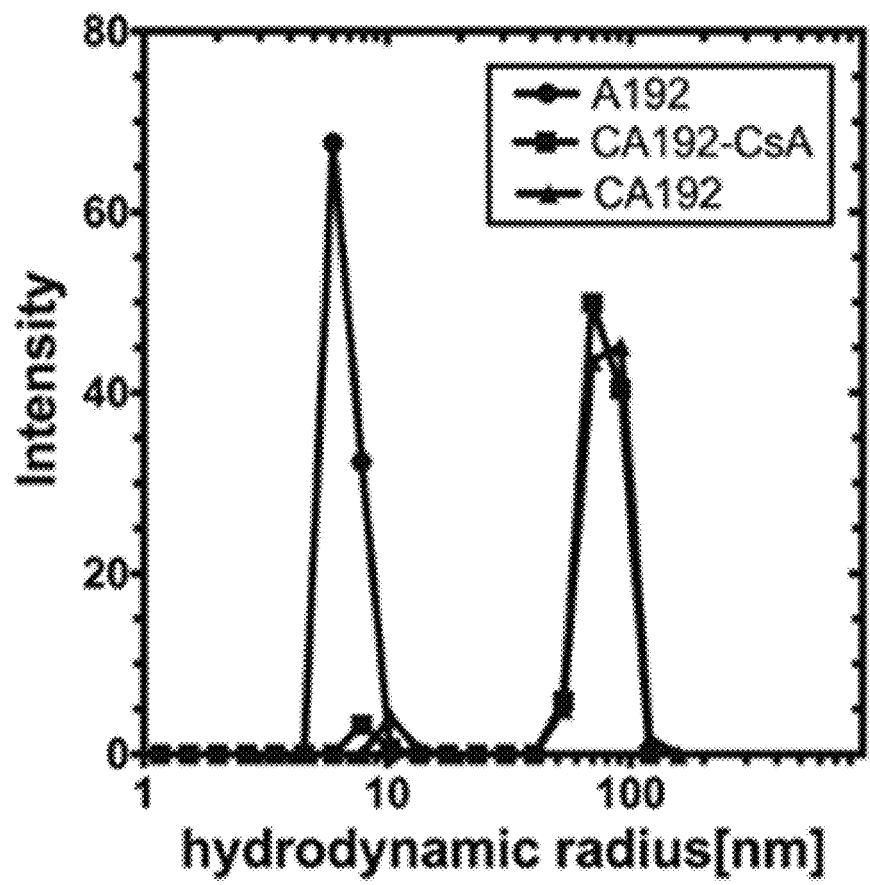
FIGS. 5A-5D: CA192 (SEQ ID NO: 3) has a good stability in terms of hydrodynamic radius. There are two fractions present in the CA192 (SEQ ID NO: 3) solution: an aggregated form and dimeric form. A dimerized form has similar hydrodynamic radius, $R_h$, as A192.
Figure 5B:
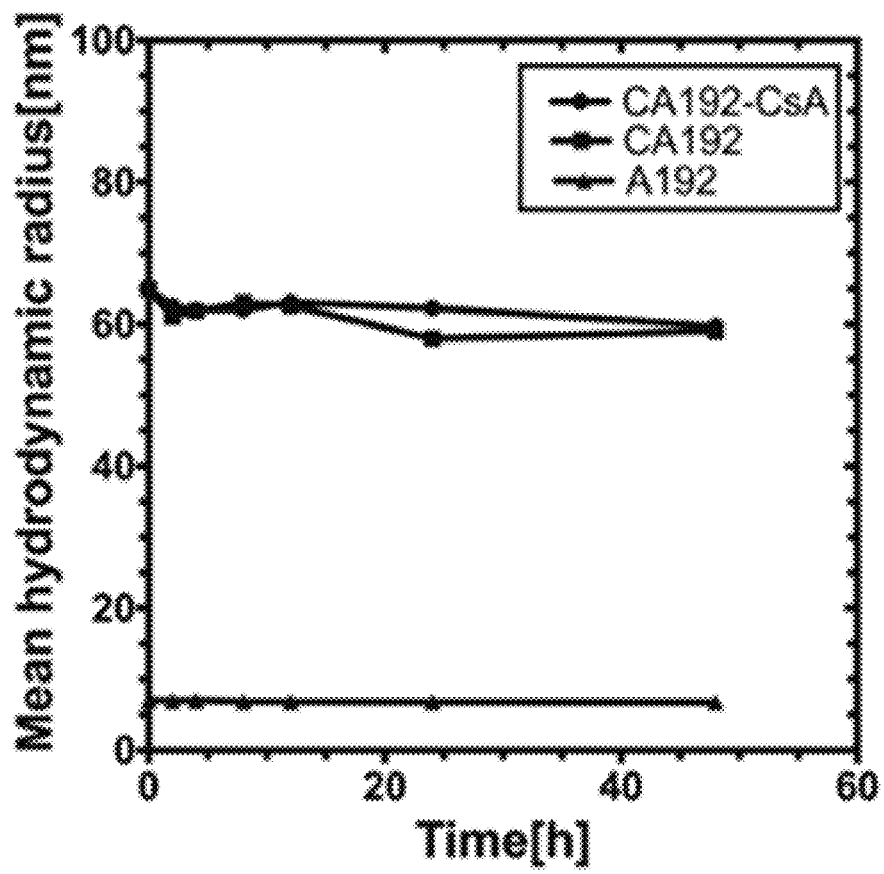
Figure 5C:
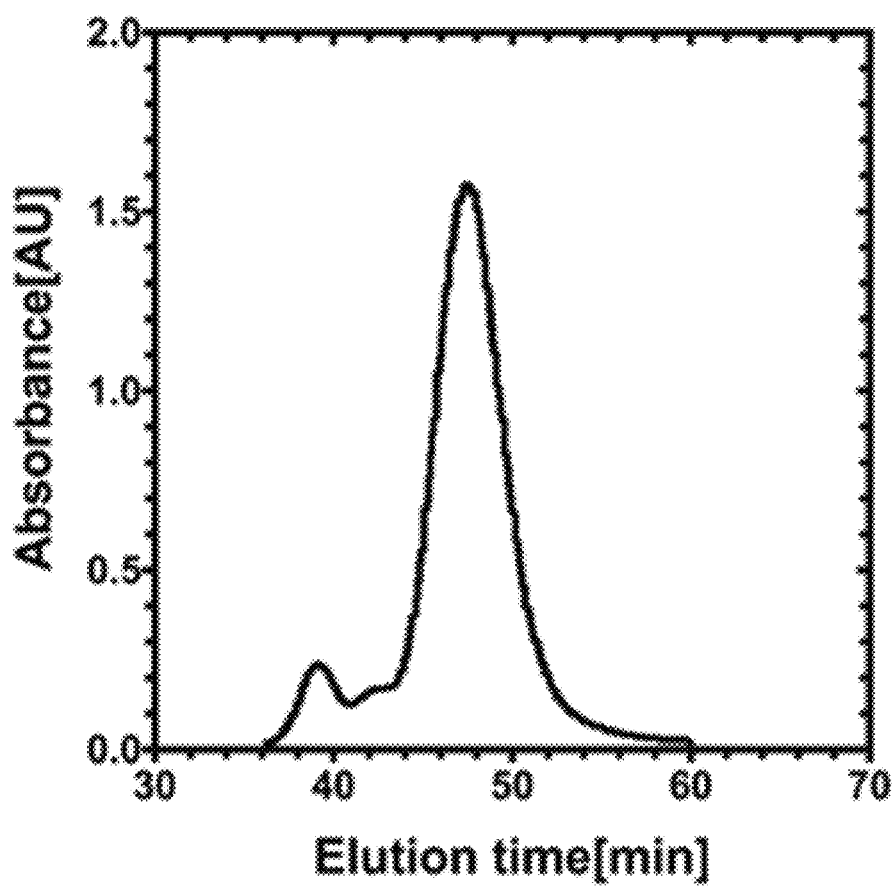
Figure 5D:
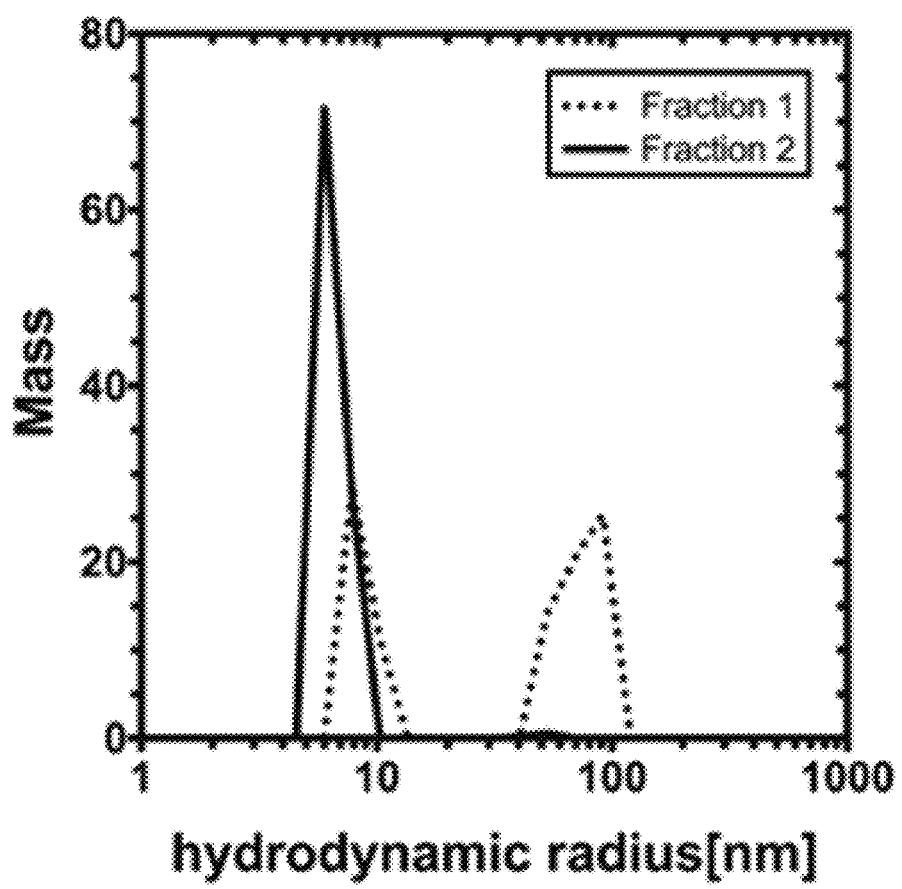

The hydrodynamic radius (Rh) of both the loaded and unloaded fusion protein, along with plain A192, was measured via dynamic light scattering (DLS) using a DynaPro Plate Reader II from Wyatt Technology. Before the DLS measurement, solutions were filtered through 0.2 µM pore size filters. The concentration of each solution was then adjusted to 20 µM. 60 µL from each sample was pipetted into three different wells on the plate reader and covered by 15 µL mineral oil each to avoid solvent evaporation. Centrifugation was then performed to remove air bubbles. DLS intensity revealed that unloaded CA192 has a mean $R_h$ of around 64.8±0.7 nm (p<0.05), significantly outsizing that of the plain A192 of 7.3±0.6 nm (p<0.05) (FIG. 5A). Based on this DLS method, Applicants performed a stability assay to explore the stability of the fusion protein by measuring the mean $R_h$ shift during incubation at physiological temperature. Briefly, the fusion solution was incubated at 37° C. for different periods of time up to 48 h and the mean $R_h$ of CA192 at these different time points was measured with DLS. This assay demonstrated that the mean $R_h$ of CA192 is well maintained throughout 48 h, suggesting good stability and stable aggregation status at physiological temperature (FIG. 5B). There might be some slight aggregation occurring in the CA192 protein solution. Through contributing most of the intensity, this aggregated form could lead to the significantly bigger mean size of CA192 than plain A192. To determine if this was the case, further separation was conducted with size exclusion chromatography (SEC). This process was performed at 4° C. using a Hiload 26/600 column (26×600 mm, particle size 24-44 µM). Elution was achieved with an isocratic flow rate of 2.6 mL/min and the detection wavelength of 214 nm. Fragments with absorption above 10 mAu were collected and concentrated with a Spin-X concentrator (pore size 10 kDa). Two fractions were observed after SEC separation (FIG. 5C). Both species were reanalyzed through DLS, demonstrating that 99.2% by mass of fraction 2 exhibited a $R_h$ of 6.5±0.1 nm (p<0.05) and seemed fairly monodisperse. Fraction 1, on the other hand, exhibited significantly higher heterogeneity. (FIG. 5D) Through measuring the CA192 concentration of both fractions, Applicants determined that 20.8% by mass in solution is represented by the multimerized particles. Multi-Angle static Light Scattering (MALS) was then applied to evaluate the aggregation and oligomeric state of CA192. The molecular weight of fraction 2 was determined to be 181.0±5.6 kDa (p<0.05), suggesting that a dimerization process was occurring in the solution. Thus, it was concluded that the CA192 fusion protein is mostly maintained as dimerized nanoparticles with a 6.5 nm hydrodynamic radius.

As shown in FIG. 5C, Size Exclusion Chromatography (SEC) has identified the presence of two fractions of CA192 in solution (FIG. 5C). To further evaluate the aggregation and oligomeric state of each fraction, Multi-Angle Static Light Scattering (MALS) was then used to measure the molecular weight of both peaks. The molecular weight of fraction 2 was determined to be 181.0±5.6 kDa (±4.133%), which roughly doubles that of CA192 monomer, suggesting that fraction 2 is actually dimerized CA192. Similarly, fraction 1 was identified as aggregated form. There is no monomeric form of CA192 existing in solution.

Figure 6:
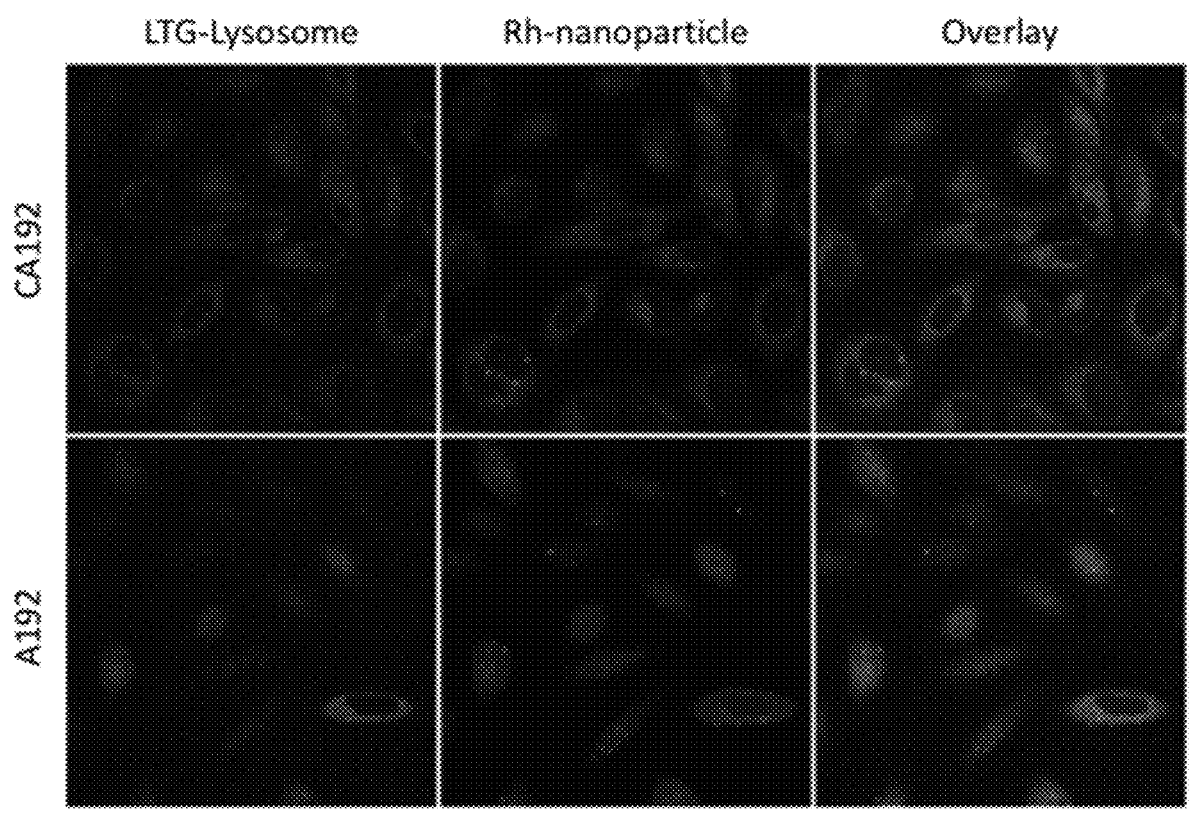
FIG. 6: Both A192 and CA192 (SEQ ID NO: 3) co-localizing with lysosomes in HeLa cells. Lysosomes were labeled by LysoTracker Green® having the structure.

In order to further validate the potential efficacy of CA192 working as a potent drug binding domain, an in vitro cell uptake study was performed. Briefly, CA192 and A192 was labeled with rhodamine and HeLa cell lysosome with LysoTracker Green (LTG)® having the structure as described herein. For the treatment group, HeLa cells were incubated with 30 µM of rhodamine-labeled (rh)-CA192 and 70 nM of LTG for 120 min. For the control group, HeLa cells were incubated with 30 µM of rhodamine-labeled (rh)-A192 and 70 nM of LTG for 120 min. Cells were then rinsed with warm HBSS three times, maintained in the fresh culture medium, and imaged by confocal microscopy. Images were acquired using a Zeiss laser scanning microscope 510 Meta NLO confocal imaging system equipped with Argon, red HeNe, green HeNe laser, and a Coherent Chameleon Ti-Sapphire laser (LSM) mounted on a vibration-free table (Carl Zeiss, Thornwood, N.Y.). All images were acquired using a Plan-Apochromat 63× Oil immersion lens with a working distance of 0.19 mm. As shown in FIG. 6, both CA192 and A192 shown obvious co-localization with lysosome, suggesting efficient cell uptake when administrated.

In summary, using molecular cloning, Applicants successfully constructed an ELP-based CsA carrier, CA192. It maintains both the phase transition property characteristic of ELPs and the CsA binding affinity of CypA. In comparison with its parent ELP, A192, the constructed CA192 has a lower transition temperature that, however, is still well above physiological temperature. CsA encapsulation efficiency of CA192 was determined to be 48.6±4.0%, significantly higher than that of albumin. The half-life of CsA drug release from CA192 was determined to be 128.3 h. DLS-based stability assay demonstrated that throughout 48 h at 37° C., no significant hydrodynamic radius shift was occurring in the solution, implying good stability of the construct. In addition, like A192, CA192 co-localized with lysosomes in HeLa cells, which implies that both constructs are endocytosed.

Figure 1A:
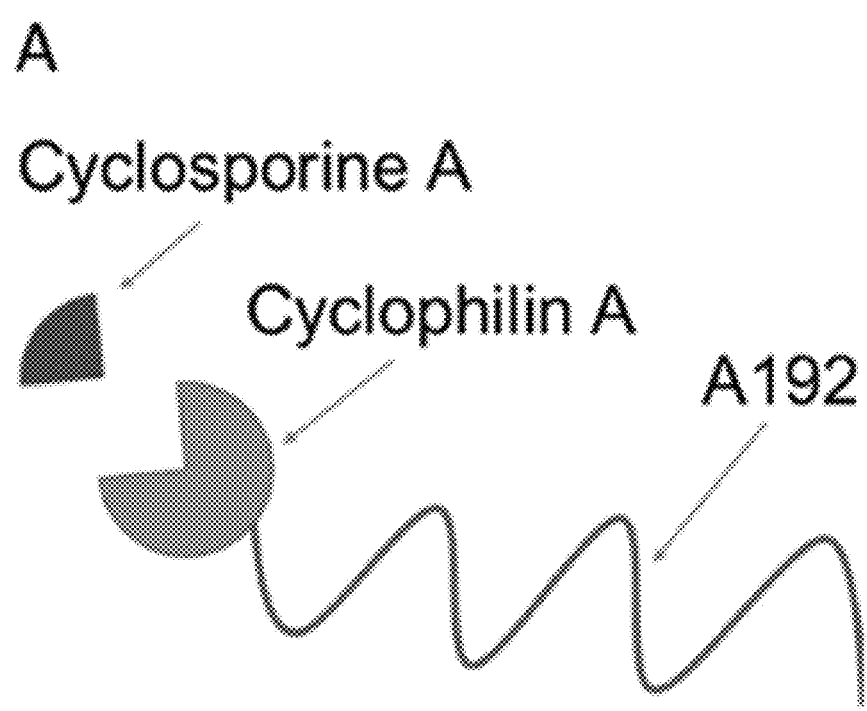
FIGS. 1A-1B: Construction of a mono cyclophilin-ELP fusion to solubilize cyclosporin A.
Figure 1B:
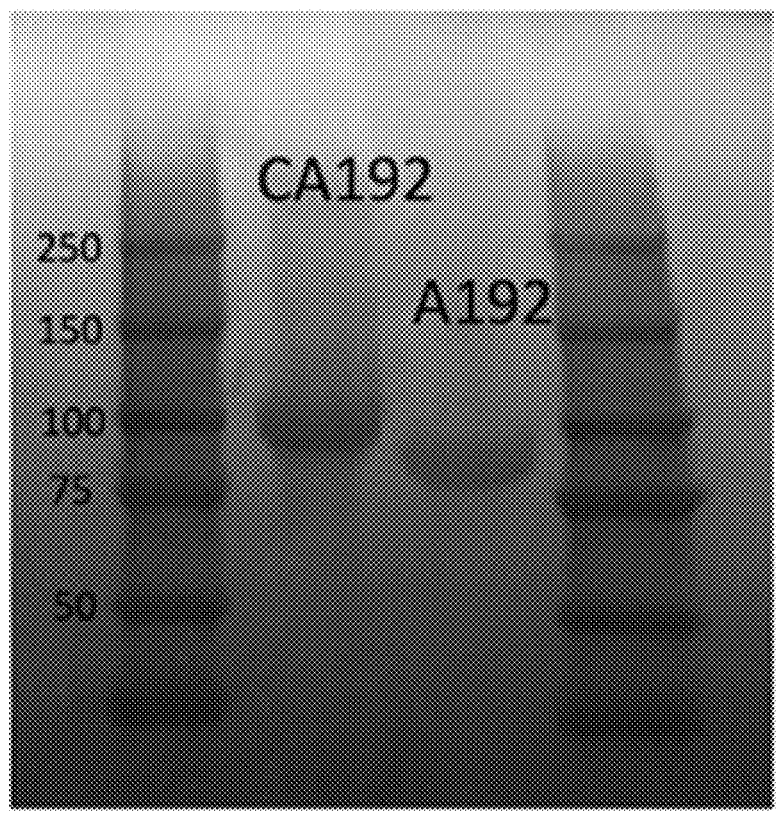

Through molecular cloning, Applicants successfully fused the cytosolic sequence of the human receptor of CsA, cyclophilin A (SEQ ID NO: 22 or SEQ ID NO: 23) (CypA), to a particular ELP, A192, which has the amino acid sequence of G(VPGAG)192Y (SEQ ID NO: 65) (FIG. 1A, Table 2). The CypA-A192 (CA192) fusion protein is designed to help in solubilizing the poorly soluble CsA and to function as a drug binding domain to improve the CsA safety profile when administered systemically. Unlike free CsA, as the molecular weight of CA192 well exceeds the renal filtration cutoff, fusion-bound drug should have significantly reduced renal clearance. The results reported herein describe the physical properties of the resulting carrier as well as the release characteristics of CsA bound to CA192.

As a potent macrolide immunosuppressant, cyclosporin A (CsA) is used to treat multiple autoimmune diseases, including autoimmune-mediated dry eye disease, rheumatoid arthritis and psoriasis. Despite its potency, CsA has poor solubility, poor bioavailability, and induces serious adverse drug reactions, including nephrotoxicity and neurotoxicity. To overcome these limitations, CsA has been formulated for systemic and topical delivery using advanced drug binding domains including emulsions and liposomes. Applicants disclose a new strategy to carry CsA that utilizes its human target, a protein called cyclophilin, to which CsA binds with a Kd of 36.8 nM. Due to its low MW (1.2 kD), cyclophilin is below the renal filtration cutoff (<40 kD) and would be rapidly filtered from the blood by the kidneys. To overcome this limitation, Applicants used recombinant protein-engineering to increase the molecular weight of cyclophilin through recombinant fusion with a 73 kD elastin-like polypeptide (ELP). Surprisingly, this fusion protein (CA192) promoted assembly of nanoparticles with stability over 2 days. Most importantly, these fusion proteins efficiently solubilize CsA, which they released with a half-life of 163.6 h under dialysis and in incubation with an excess concentration of albumin.

In terms of patient compliance, Applicants built another injectable prolonged release elastin-like polypeptide (ELP)-based Cyclosporin A (CsA) carrier, which requires less injection frequency. This Cyclophilin A (CypA)-ELP fusion made through molecular cloning, has a transition temperature lower than physiological temperature. Once it is injected into the body subcutaneously, this ELP will trigger a thermal phase transition and thereby forming a stable drug depot. Active CsA will be released into circulation system over time, providing a prolonged drug release.

Following this hypothesis, another ELP from Applicants' ELP library named as V96, which has the amino acid sequence of G(VPGVG)96Y (SEQ ID NO: 66), was successfully fused to Cyclophilin A (SEQ ID NO: 22 or SEQ ID NO: 23). The new construct was named as CypA-V96 (CV96 (SEQ ID NO: 4)). Unlike CA192, CV96 has a transition temperature (Tt) of 31.2° C. at 25 μM (FIG. 8A), which is well lower than physiological temperature, suggesting that CV96 will form a depot after s.c. injection. The optical density profile representing the CV96 phase separation behavior is shown in FIG. 8B. The $T_t$ of CV96 was also found to be a function of concentration: $Tt=b-mLog_{10}[C_{ELP}]$, where the intercept "b" is equal to 36.8, the slope "m" equals to 4.4 and $[C_{ELP}]$ represents the CV96 concentration.

The molecular weight of purified CV96 was verified by SDS-PAGE stained with copper chloride ($CuCl_2$) (FIG. 9). CA192, with a molecular weight of 91.6 kDa, served as a control. The expected molecular weight of CV96 is 57.7 kDa.

Consistent with the characterization of CA192, a two-phase solvent evaporation method was used to find out the CsA loading ratio of CV96. Briefly, an aqueous phase phosphate-buffered saline (PBS) containing 300 μM CV96 was mixed with an organic phase 90% hexane/10% EtOH containing 900 μM CsA. Under a nitrogen environment and constant stirring, along with the evaporation of organic solvent, CsA was gradually released into the aqueous phase and encapsulated by the fusion protein. This was followed by high-speed centrifugation and filtration to remove the excess insoluble drug. The loading ratio was then determined by reversed-phase high-performance liquid chromatography (RP-HPLC) analysis method. As shown in FIG. 10, CV96 has a higher loading ratio in comparison with CA192, which can potentially contribute to reducing injection frequency.

Isothermal titration calorimetry (ITC) was also used to determine the binding affinity between CV96 and CsA. The basic idea behind this instrument is to measure the amount of heat that is released upon drug binding. The Kd was found to be 230±57.8 nM, reasonably higher than their native Kd of 36.8 nM, demonstrating that the CsA binding affinity of CypA is well maintained after fusing to V96.

Immunosuppressive Efficacy of CA192/CsA on Jurkat Cell.

CsA, upon binding to endogenous intracellular CypA, is known to inhibit IL-2 gene expression and excretion from activated T cells (Andersson, J. et al. (1992). The nuclear translocation of NFAT is initiated upon dephosphorylation by calcineurin (CN) (Tanaka, Y. et al. (2013) Viruses, 5(5):1250-1260). CsA-CypA works by blocking the dephosphorylation activity of calcineurin through direct binding (Huai, Q. et al. (2002) PNAS 99(19):12037-12042). As a result, CsA treatment significantly reduces IL-2 secretion. Thus, IL-2 secretion assay will be utilized to quantify the efficacy of CsA/CA192. Jurkat cells are activated by the combined stimulation of Phorbol 12-myristate 13-acetate (PMA) and Ionomycin, immediately followed by treatment of free CsA, CsA/CA192 or CA192 control for 6 h. IL-2 concentration in culture media is then assessed using ELISA assay. The IC50 of CsA/CA192 has been demonstrated by IL-2 secretion assay to be 1239±391 μM, slightly higher than free CsA with an IC50 of 522±152 μM (n=3, mean±SD) (FIG. 10).

TABLE 3

Protein-polymers evaluated in this Example

| Label | Amino Acid Sequence | Exp. M.W. [kDa] | $^a$Slope, m [° C./$Log_{10}$ (μm)] | $^b$Intercept, b [° C.] | $^c$Purity [%] |
|---|---|---|---|---|---|
| CV96 | MVNPTVFFDIAVDGEPLGRVSFELFAD KVPKTAENFRALSTGEKGFGYKGSCF HRIIPGFMCQGGDFTRHNGTGGKSIYG EKFEDENFILKHTGPGILSMANAGPNT NGSQFFICTAKTEWLDGKHVVFGKVK EGMNIVEAMERFGSRNGKTSKKITIAD CGQLEG(VPGVG)$_{96}$Y (SEQ ID NO: 4) | 57.7 | 4.4 | 36.8 | 95.9 |

$^{ab}$The ELP phase diagram as a function of temperature, $T_t$, and concentration, $C_{ELP}$, was fit to the following relationship: $T_t = b - m \: Log_{10}[C_{ELP}]$, where b is the intercept at 1 μM and m are ° C. change for a 10-fold change in concentration.
$^c$Polypeptide purity was assessed using SDS-PAGE and subsequent densitometry of copper chloride stained gel.

Tear Stimulation effect of CA192/CsA on NOD mice model.

As a preliminary therapeutic study, 2.5 mg/kg CsA/CA192 was given s.c. to 14-week-old male NOD mice every other day for 2 weeks. The basal tear production was measured before and after treatment. Sandimmune (CsA formulated for IV injection) was introduced as a positive control, while CA192 without drug binding was used as a negative vehicle control. CsA treatments (Sandimmune and CsA/CA192) benefited more mice than CA192 vehicle control in terms of tear production (FIG. 11). The increased wet lengths in Sandimmune group is significantly higher than CA192 group (p=0.016). CsA/CA192 nearly approached significance relative to CA192 group (p=0.055); furthermore, a higher powered study may be capable of detecting this effect. Stimulated tear collection was conducted under full anesthesia as a terminal procedure. After intraperitoneal injection with a mixture of ketamine/xylazine at concentrations of 100 mg/kg and 10 mg/kg, respectively, mice were subjected to a small bilateral incision on the axis between the outer junction of the eyelid and the ear to expose the LG on both sides. Then 3 μL of 50 μM carbachol (CCh) was applied directly onto the LG to stimulate tear secretion, followed by tear collection from both eyes using 2 µL micro-capillary tubes, which were placed at the tear meniscus in the medial canthus for 5 min. This stimulation and collection procedure was repeated two more times and the volume of collected tears was recorded.

Synthesis and Drug Release Testing of $2^{nd}$ and $3^{rd}$ Generation ELP Fusion Proteins.

Progressing from CypA-ELPs, such as CA192 and CV96, where only one receptor was fused to one ELP backbone, the feasibility to clone and express ELP-based CsA carriers with significantly higher drug loading ratio was also accomplished. These $2^{nd}$ generation carriers have one CypA on the N-terminus and another on the C-terminus of the ELP backbone, sequenced as CypA-ELPs-CypA. As the design suggested, these carriers are able to deliver 2× CsA than $1^{st}$ generation CypA-ELPs described above. When using shorter ELPs as the backbones, the drug loading ratio can be further improved by stitching multiple $1^{st}$ and $2^{nd}$ generation carriers together through molecular cloning, evolving into a $3^{rd}$ generation of constructs, for example, CypA-ELPs-CypA-ELPs-CypA-ELPs-CypA.

CypA-A96-CypA (CA96C) and CypA-A24-CypA-A24-CypA-A24-CypA (3(CA)C) were made as representatives of $2^{nd}$ and $3^{rd}$ generation carriers, respectively. These two carriers have been successfully cloned, expressed and purified (FIG. 15). The cloning methods are detailed below. Then they can be expressed and purified using the same method of Sun et al., 2011 and Janib et al., 2014 discussed above and as used for CA192.

The drug loading capability of $2^{nd}$ and $3^{rd}$ generation carriers were also tested using the same encapsulation method detailed above employing the method of Shi, et al., 2013. This data was compared with that of CA192. As shown in FIG. 16, $2^{nd}$ generation carriers are able to increase the loading ratio by 1-fold, and $3^{rd}$ generation carriers by 3-fold.

To make CA96C, another CypA needs to be fused to the C-terminus of CA96, which requires a slightly modified CypA, "CypA_C-term," sequenced as below:

5'-TCTAGAAATAATTTTGTTTAACTTTAAGAAG-GAGGAGTACATATGGGTATGGTTAA CCCGACCG-TTTTCTTCGACATCGCTGTTGACGGTGAACCGC-TGGGTCGTGTTTCTTT CGAACTGTTCGCTGACAA-AGTTCCGAAAACCGCTGAAAACTTCCGTGCTCTG-TCTA CCGGTGAAAAAGGTTTCGGTTACAAAGGT-TCTTGCTTCCACCGTATCATCCCGGGT TTCATGTG-CCAGGGTGGTGACTTCACCCGTCACAACGGTA-CCGGTGGTAAATCTAT CTACGGTGAAAAATTCGAA-GACGAAAACTTCATCCTGAAACACACCGGTCCGG-GT ATCCTGTCTATGGCTAACGCTGGTCCGAACAC-CAACGGTTCTCAGTTCTTCATCTGC ACCGCT-AAAACCGAATGGCTGGACGGTAAACACGTTGTTT-TCGGTAAAGTTAAAG AAGGTATGAACATCGTT-GAAGCTATGGAACGTTTCGGTTCTCGTAACGG-TAAAACC TCTAAAAAAATCACCATCGCTGACTGC-GGTCAGCTGGAAGGTTGATAATGATCTTC AGGATCC-3' (SEQ ID NO: 5). Flanked by restriction sites of XbaI and BamHI at the 5' and 3' ends enabling the insertion to intact pET-25b(+) vector, CypA_C-term (SEQ ID NO: 5) has a BserI recognition site whose restriction site locates right after the start codon, ATG, of the encoding sequence, to enable the C-terminus insertion.

CypA_C-term (SEQ ID NO: 5) was first inserted to intact pET-25b(+) vector using XbaI and BamHI. The resultant CypA_C-term on intact pET-25b(+) vector and the pET-25b (+) vector with the encoding sequence of CA96 were digested differently by BssHII and BserI, and, BssHII and AcuI, respectively. After verifying the correct sequence through DNA sequencing, the resultant plasmid with CA96C protein sequence was amplified and expressed using the same method of Sun et al., 2011 and Janib et al., 2014.

To make 3(CA)C of sequence:
(SEQ ID NO: 9)
MGMVNPTVFFDIAVDGEPLGRVSFELFADKVPKTAENFRALSTGEKGFGY

KGSCFHRIIPGFMCQGGDFTRHNGTGGKSIYGEKFEDENFILKHTGPGIL

SMANAGPNTNGSQFFICTAKTEWLDGKHVVFGKVKEGMNIVEAMERFGSR

NGKTSKKITIADCGQLEG-(VPGAG)$_{24}$-MVNPTVFFDIAVDGEPLGRVS

FELFADKVPKTAENFRALSTGEKGFGYKGSCFHRIIPGFMCQGGDFTRHN

GTGGKSIYGEKFEDENFILKHTGPGILSMANAGPNTNGSQFFICTAKTEW

LDGKHVVFGKVKEGMNIVEAMERFGSRNGKTSKKITIADCGQLEG- (VPGAG)$_{24}$-MVNPTVFFDIAVDGEPLGRVSFELFADKVPKTAENFRALS

TGEKGFGYKGSCFHRIIPGFMCQGGDFTRHNGTGGKSIYGEKFEDENFIL

KHTGPGILSMANAGPNTNGSQFFICTAKTEWLDGKHVVFGKVKEGMNIVE

AMERFGSRNGKTSKKITIADCGQLEG-(VPGAG)$_{24}$-MVNPTVFFDIAVD

GEPLGRVSFELFADKVPKTAENFRALSTGEKGFGYKGSCFHRIIPGFMCQ

GGDFTRHNGTGGKSIYGEKFEDENFILKHTGPGILSMANAGPNTNGSQFF

ICTAKTEWLDGKHVVFGKVKEGMNIVEAMERFGSRNGKTSKKITIADCGQ

LEG,

CA24CA24CA24 of sequence:
MG-[MVNPTVFFDIAVDGEPLGRVSFELFADKVPKTAENFRALSTGEKGF

GYKGSCFHRIIPGFMCQGGDFTRHNGTGGKSIYGEKFEDENFILKHTGPG

ILSMANAGPNTNGSQFFICTAKTEWLKHVVFGKVKEGMNIVEAMERFGSR

NGKTSKKITIADCGQLEG-(VPGAG)$_{24}$]$_3$, (SEQ ID NO: 57)

needs to be first synthesized by recursive directional ligation in a modified pET-25b(+) vector (Janib, et al., 2014; Meyer, et al., 2002) from CA24, which requires another modified CypA, "CypA_extra glycine." As sequenced below, CypA_extra glycine has three more base pairs, GGT, encoding an extra glycine, right after start codon, ATG. Using CypA_extra glycine, CA24 was first cloned using the same method employing methods of Sun et al., 2011 and Janib et al., 2014, which was further synthesized into CA24CA24CA24 by recursive directional ligation in a modified pET-25b(+) vector (Janib, et al., 2014; Meyer, et al., 2002). Lastly, another CypA_C-term (SEQ ID NO: 5) was inserted to the C-terminus of CA24CA24CA24 to make CA24CA24CA24C (3(CA)C), using the same method described above for fusing CypA to the C-terminus of CA96.

TABLE 4

Multi-Angle Static Light Scattering (MALS) demonstrated that the dimeric form of CA192 accounts for approximately 90% of the total mass of CA192 in solution.

|  | Fraction 1 (Nano-aggregated form) | Fraction 2 (Dimeric form) |
| --- | --- | --- |
| Molar mass moments (g/mol) | $8.511 \times 10^7$ (±2.539%) | $1.810 \times 10^5$ (±4.133%) |
| Calculated Mass (µg) | 31.67 | 282.73 |
| Mass Fraction (%) | 10.1 | 89.9 |

Example 2: High Capacity, 3<sup>rd</sup> Generation FKBP-ELP Carriers to Facilitate Delivery of Rapalogues Rapalogues bind the cytosolic protein called FKBP12 and modulate mTOR (rapamycin, everolimus, temsirolimus or calcineurin (tacrolimus) signaling. FDA-approved rapalogues have indications from transplant surgery, to autoimmune disease, to cancer. Despite clinical successes, these drugs are limited by low solubility, poor oral bioavailability (~15%), and variability in pharmacokinetics. Additionally, major clinical studies show consistent adverse events of rapalogues, including stomatitis, pulmonary toxicity, fatigue, anemia, infection, hyperlipidemia, hypercholesterolemia, and acute kidney injury. Strategies to mitigate these side-effects could have a major impact in breast cancer and prevention of transplant rejection. The incidence of breast cancer remains significant with nearly a quarter of a million new cases of invasive breast cancer diagnosed annually. While the survival rates of early stage breast cancer are relatively high, advanced disease kills nearly 40,000 women per year in the USA. The rapalogue everolimus (Eve) was approved in combination with exemestane for hormone (estrogen/progesterone) receptor positive HR+/HER2− breast cancer patients. Despite tripling progression free survival, the pivotal BOLERO-2 clinical trial reported adverse events necessitating dose reduction, discontinuation of treatment for 75%, 10% of patients respectively. Better delivery strategies could significantly improve compliance and efficacy within this clinically-validated population. Another rapalogue tacrolimus (Tac) is used as an immunosuppressive in nearly 90% of transplant recipients. Of organ transplants (~32,000) per year in the USA, the majority (~18,000) are kidney transplants. While all rapalogues bind FKBP, only tacrolimus acts through the calcineurin pathway. The toxicity profile of tacrolimus thus includes other side effects (nephrotoxicity, hypertension, heart failure, arrhythmia, neurotoxicity, pure red cell aplasia), which suggest that it too may benefit from carrier-assisted delivery. Moreover, the ADMIRAD study identified low adherence to tacrolimus with a 20% discontinuation rate 6 months' post-transplant, thereby resulting in an 8-fold increase in chance of rejection.

To improve the current status of rapalogue therapy, we propose an intelligent drug-carrier system that leverages human FKBP protein using elastin-like polypeptides (ELPs). ELPs are high molecular weight polypeptides derived from human tropoelastin and consist of a pentameric sequence, [Val-Pro-Gly-Xaa-Gly]n (SEQ ID NO: 51), where Xaa can be any amino acid and n specifies the number of repeats. As a function of Xaa and n, ELP fusion proteins display a characteristic inverse phase transition temperature (Tt) above which they transform into a reversible gel-like coacervate. As polypeptides, they can be recombinantly expressed as fusion proteins, including FKBP-ELP drug binding domains. While FKBP mediates high affinity binding and solubilization of rapalogues, ELP's heat-responsive property can be tuned to assemble a drug depot at body temperature. Such depots are retained for weeks at injection sites and elute with near zero-order kinetics that may enable patient compliant low frequency self-administration. Moreover, FKBP-ELPs are designed to efficiently sequester, slowly release and retarget free rapalogues to disease sites, each of which is aimed towards improving their toxicity profile. Recently, Applicant has characterized new high-capacity FKBP-ELP formulations, 5FA and 5FV, which remain soluble or assemble into a depot at body temperature. These high capacity carriers solubilize rapalogues up to 5% by mass.

Molecular Cloning, Bacterial Expression and Purification.

Both 5FA and 5FV were successfully cloned by Recursive Directional Ligation by plasmid reconstruction (RDL), a strategy developed to facilitate cloning of oligomeric genes. The proteins were expressed in *E. coli* and purified by inverse transition cycling, a non-chromatographic purification strategy utilizing unique biophysical properties of ELPs, specifically their responsiveness to heat and ionic strength. ELPs appended to FKBP retained their stimulus sensing properties and three rounds of purification resulted in >90% pure protein, as visualized by copper stained SDS-PAGE gel (FIG. 17). The proteins demonstrate high production yields (180 mg/L and 90 mg/L of bacterial culture in case of 5FA and 5FV respectively), and their molecular weights agree with molecular weights predicted based on amino acid sequence (99.5 kDa and 102 kDa for 5FA and 5FV respectively).

Drug Binding to a Model Rapalogue Rapamycin.

Using Isothermal Titration calorimetry (ITC), the binding stoichiometry of 5FA/Rapa interaction was estimated to be 5. This suggests all the FKBPs in 5FA are properly folded and retain their ability to bind to rapamycin. Though the equilibrium dissociation constant ($K_D$) was estimated to be 1.5 nM (FIG. 18), the true $K_D$ is likely much lower and beyond the limit of detection of ITC (low nM range). In terms of binding thermodynamics, a negative binding enthalpy (FIG. 18B) (−58 kJ/mol interactions) suggests an exothermic binding, and a negative TAS (−48 kJ/mol interactions) suggests an entropic cost associated with binding, which can be explained by rapamycin transitioning from a free, unbound state in solution to a more ordered FKBP bound state. An overall negative Gibbs free energy (−10 kJ/mol interactions) indicates FKBP/Rapa binding is thermodynamically favorable.

Drug Encapsulation.

A working formulation of rapamycin encapsulated in 5FA or 5FV was prepared by a two phase encapsulation method. To 10 mL 300 µM 5FA or 5FV in buffer, 3× molar excess Rapa (LC Laboratories, Woburn, Mass.) in hexane/EtOH mixture (7:3 v/v) was added. After evaporation of the organic phase at 4° C. using a rotary evaporator, the aqueous suspension was centrifuged at 13,000 g to pellet unbound Rapa precipitate. The supernatant was subjected to additional rounds of centrifugation until no pellet was observed. The formulation was added to a 10 kDa MWCO dialysis bag (Thermo Fischer Scientific, Waltham, Mass.) and dialyzed against PBS (1:750 sample: dialysate) for 12 hours to remove free Rapa and residual solvent. After removal of un-encapsulated drug, HPLC was used to simultaneously determine 5FA or 5FV and Rapa concentrations, and the encapsulation ratio (ER) was calculated as $C_{Rapa}/C_{carrier}$. Following a large scale encapsulation, an ER of 4.4 was achieved, the theoretical maximum being 5.

Example 3: High Capacity 3<sup>rd</sup> Generation Pin1-ELP Carriers (4PA) to Facilitate Delivery of all-Trans Retinoic Acid (ATRA)

ATRA is an FDA approved treatment for acute promyelocytic leukemia (APL). Apart from APL, ATRA is under clinical trials for breast, melanoma, neuroblastoma, myeloma and few other cancers as a stand-alone or combination therapy. Though being actively pursued, ATRA's poor drug like properties limit its clinical efficacy, especially i) extremely short 45-minute half-life ii) water insolubility iii) variable bioavailability and PK, and most importantly iv) induction of its own metabolism causing decreased drug exposure with repeated administration. With daily treatment, ATRA plasma concentrations decline rapidly, with AUC on $28^{th}$ day of administration only 10% of AUC on day 1 of treatment. This results in progressively low plasma concentrations and development of drug resistance and disease relapse. Pin1, a human protein belonging to the prolyl-isomerases family binds to ATRA with a sun-micromolar affinity and hence can be used to bind and deliver ATRA. Pin1-ELPs can potentially improve the current status of ATRA treatment by solubilizing and enabling non-oral administration, improving half-life by reducing drug accessibility to metabolizing enzymes and allowing on-target effect.

Purification.

The high capacity Pin1 carrier 4PA was successfully cloned by Recursive Directional Ligation by plasmid reconstruction (RDL), a strategy developed to facilitate cloning of oligomeric genes. The protein was expressed in *E. Coli* Shuffle T7 Express cells and purified by inverse transition cycling (ITC), a non-chromatographic purification strategy utilizing unique biophysical properties of ELPs, specifically their responsiveness to heat and ionic strength. Three rounds of ITC purification resulted in >90% pure protein, as visualized by copper stained SDS-PAGE gel (FIG. 21) with a production yield of 85 mg/L of bacterial culture.

concentrations up to 100 µM, suggesting a role for fluid phase endocytosis. Rho-FAF did colocalize with dextran, a marker of fluid phase endocytosis. To understand drug release, cells were engineered to express a luciferase reporter for cytosolic Rapamycin. In this assay, FAF delayed the cytosolic access of Rapa in comparison to free drug by about a half-hour (FIG. 22A). A specific macropinocytosis inhibitor, amiloride, completely suppressed the cytosolic delivery of Rapamycin from FAF (FIG. 22B). Each of these results are consistent with macropinocytosis as the mechanism of cellular uptake necessary for the hand-off of Rapamycin from FAF to endogenous FKBP12 in the cytosol. This is evidence that FAF dominates the intracellular delivery of rapalogues.

Breast Cancer Efficacy.

Accounting for nearly 40,000 deaths per year, breast cancer is the second deadliest cancer affecting American women. Everolimus (Eve), an analog of Rapamycin is approved to treat HR+/HER2− subtype in combination with exemestane. Currently administered as an oral formulation, Eve suffers from poor physico-chemical properties and toxicity issues like Rapamycin. Novel FAF formulations were tested for efficacy and safety in nude mice bearing orthotopic tumors of BT-474 cell line. Being a HR+ cell line, BT-474 represents nearly 80% of clinically diagnosed breast cancer. Oral Eve at the same drug dose served as a clinically relevant control. Mice bearing tumors of average size 100 mm³ were randomized and treated with either oral Eve,

TABLE 5

$2^{nd}$ and $3^{rd}$ generation drug-carriers with multiple drug-binding domains per polypeptide

| Title | *Amino acid sequence | **Expected M.W. [kDa] | drug-binding domains per molecule | Transition temperature at 25 µM [° C.] |
|---|---|---|---|---|
| 3(CA24)C | MG-[CypA-(VPGAG)$_{24}$(SEQ ID NO: 37)]$_3$-CypA | 99.9 | 4 | expected >50 |
| CA96C | M-CypA-(VPGAG)$_{96}$(SEQ ID NO: 35)-CypA | 72.9 | 2 | expected >50 |
| FAF | MG-FKBP-(VPGAG)$_{192}$(SEQ ID NO: 1)-FKBP (SEQ ID NO: 25) | 97.0 | 2 | 55.1 |
| 5FA | MG-[FKBP-(VPGAG)$_{24}$(SEQ ID NO: 37)]$_4$-FKBP (SEQ ID NO: 10) | 99.5 | 5 | 53.2 |
| 5FV | MG-[FKBP-(VPGVG)$_{24}$(SEQ ID NO: 67)]$_4$-FKBP (SEQ ID NO: 11) | 102.0 | 5 | 27.7 |
| 4PA | MG-[Pin1-(VPGAG)$_{24}$(SEQ ID NO: 37)]$_3$-Pin1 (SEQ ID NO: 15) | 100.4 | 4 | 52.8 |

**Expected molecular weight based on the open reading frame for the expressed protein.

Example 4: FKBP Elastin-Like Polypeptide Fusions for Sustained Delivery of mTOR Inhibitors By fusing FKBP12, the cognate receptor for Rapamycin (*Rapa*) to each termini of the ELP A192 [(VPGAG)192 (SEQ ID NO: 1)], FAF was generated. While FKBP mediates high affinity drug binding and solubilization, the high molecular weight A192 is designed to reduce carrier renal clearance and improve plasma half-life. FAF also sequesters free circulating Rapamycin, thereby arresting drug accumulation in non-target organs and reducing toxicity.

Using the MDA-MB-468 cell line as the model system, Applicant studied mechanisms of cellular uptake and drug release from high-affinity FAF/Rapa complexes. Cellular uptake of FAF showed no dose-dependent saturation at FAF/Rapa or FAF/Eve at 1 mg/kg dose every other day for 4 weeks (FIG. 25A). Compared to PBS treated mice, only FAF/Eve and FAF/Rapamycin groups suppressed tumor growth significantly (FIG. 25B). While the mean tumor volume of oral Eve group was lower than PBS group, the difference was not statistically significant. This is presumably a result of Eve's poor oral bioavailability. Additionally, no significant weight loss was observed across groups, suggesting all 3 formulations were reasonably tolerated. This study demonstrates that everolimus and rapamycin have similar efficacy, that SC FAF does a better job than oral administration, and shows in an HR+ cell line it remains effective. Everolimus is currently approved in HR+ populations, so this suggests FAF delivery could be effective in the same patient population already approved.

Efficacy in the Non-Obese Diabetic (NOD) Mouse of Dacryoadenitis, a Model relevant to Sjögren's Syndrome (SS).

One symptom of this systemic autoimmune disease model is lymphocyte infiltration into the tear-producing lacrimal gland, which is associated with severe dry eyes. To confirm that subcutaneous FAF-Rapa depots can treat this model, this aim will compare treated and untreated male NOD mice for inflammation of the lacrimal gland with respect to lymphocytic infiltration, a Cathepsin-S biomarker for SS, corneal staining that identifies defects consistent with dry eye disease, and the volume of basal tear production using a thread test.

Efficacy in a Mouse Model of Sjögren's Syndrome (SS).

SS is a chronic autoimmune disease that affects about 4 million people in the US. Lymphocytic infiltration and inflammation in the exocrine glands, mainly lacrimal gland (LG) and salivary gland causes severe forms of dry eyes and dry mouth. Current treatment strategies provide short-term symptomatic relief and are not generally efficacious in severe forms of dry eye. To assess immunosuppressive efficacy of FAF/Rapa in SS, we used male Non-obese diabetic (NOD) mice, a well-established model of dry eye disease. Four groups of mice received either vehicle, free Rapa, carrier (FAF only) or FAF/Rapa subcutaneously at a dose of 1.0 mg Rapa/kg every other day for 2 weeks. Following this, the LG from all mice were sectioned, stained and lymphocytic infiltration was quantified. Both free Rapa and FAF-Rapa significantly suppressed lymphocytic infiltration compared to vehicle only controls (2.7 and 1.9 fold respectively), with no difference in inhibition between free Rapa and FAF/Rapa (FIG. 23). Histopathological analysis of excised organs and serum chemistry panels suggested FAF/Rapa is free from acute toxicities.

Pharmacokinetics (PK).

An in-depth PK analysis of FAF was carried out in NOD mice using rhodamine labeled FAF. Concentration vs. time profiles were plotted for IV and SC administered FAF by measuring plasma fluorescence of rhodamine probe at various time points. For compartmental modeling, a one- and three-compartment model depicted in FIG. 24B could fit the observed data well. IV FAF demonstrated an elimination half-life of about 7 hrs. Additionally, SC FAF resulted in statistically significantly higher plasma concentration compared to IV FAF during the elimination phase (36 hr~72 hr, FIG. 24A) suggesting a sustained release capability for FAF when administered subcutaneously. SC FAF reached $C_{max}$ 12 hrs after injection, followed by a mono-exponential decay thereafter (FIG. 24B). The mean absorption time and mean residence time were calculated as 9.6 hrs and 20.3 hrs respectively (Table 6). The bioavailability of SC FAF-Rapa was 52.7~65.5%. This study shows clearly how FAF maintains very excellent absorption from an SC site, maintain drug levels above those for free Rapa alone.

TABLE 6

Pharmacokinetic parameters of intravenously- or subcutaneously-delivered FAF-Rapa analyzed using compartmental analysis and non-compartmental analysis.

| Parameter (Unit) | Route of Administration | | | |
|---|---|---|---|---|
| | Intravenous (IV) | Subcutaneous (SC) | Intravenous (IV) | Subcutaneous (SC) |
| | Preferred Model | | | |
| | 1 Compartment | 3 Compartments | Non-compartment | |
| AUC (µM · hr) | 141.1 ± 15.5 | 92.4 ± 18.7 | 206.5 ± 33.4 | 108.8 ± 13.9 |
| AUMC (µM · hr$^2$) | nd* | nd* | 2,207 ± 344 | 2,214 ± 328 |
| F (%) | 100 | 65.5 ± 13.2 | 100 | 52.7 ± 6.7 |
| CL (mL/hr) | 0.15 ± 0.01 | 0.15** | 0.10 ± 0.01 | 0.09 ± 0.01 |
| CL/F (mL/hr) | 0.15 ± 0.01 | 0.23 ± 0.04 | 0.10 ± 0.01 | 0.18 ± 0.03 |
| $V_d$ (mL)** | 1.46 ± 0.2 | 1.46*** | 0.88 ± 0.1 | 0.85 ± 0.1 |
| $C_{max}$ (µM) | 13.4 ± 2.4 | 3.3 ± 0.1 | 11.7 ± 2.9 | 4.4 ± 0.7 |
| $T_{max}$ (hr) | 0.0 | 12.4 ± 0.7 | 0.0 | 12.0 |
| MRT (hr) | nd* | nd* | 10.7 ± 0.3 | 20.3 ± 1.1 |
| MAT (hr) | — | nd* | — | 9.6 ± 1.1 |
| $T_{1/2, Absorption}$ (hr) | — | 4.2 ± 0.4 | — | — |
| $T_{1/2, Elimination}$ (hr) | 6.9 ± 0.5 | 6.9*** | 6.2 ± 0.4 | 6.4 ± 0.7 |
| $k_{absorption}$ (hr$^{-1}$) | — | 0.16**** | — | — |
| $k_{elimination}$ (hr$^{-1}$) | 0.10 ± 0.008 | 0.10*** | 0.11 ± 0.01 | 0.11 ± 0.01 |
| $k_{degradation}$ (hr$^{-1}$) | — | 0.09 ± 0.05 | — | N/A |

*not determined
**The volume of distribution indicates the volume of the plasma compartment, $V_1$, for the Compartmental fits and the $V_{area}$ for the noncompartmental analysis.
***compartmental values from IV analysis are adopted to estimate SC parameters
****to fit the observed time to peak concentration, the assumption was required that $k_{absorption} = k_{Injection\ site \to Interstitial\ fluid} = k_{Interstitial\ fluid \to Systemic\ circulation}$.

EQUIVALENTS

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

```
                        SEQUENCE LISTING

A192: (VPGAG)192 (SEQ ID NO: 1)

V96: (VPGVG)96 (SEQ ID NO: 2)

Cyclophilin-A192
MVNPTVFFDIAVDGEPLGRVSFELFADKVPKTAENFRALSTGEKGFGYKGSCFHRIIPGF
MCQGGDFTRHNGTGGKSIYGEKFEDENFILKHTGPGILSMANAGPNTNGSQFFICTAKTE
WLDGKHVVFGKVKEGMNIVEAMERFGSRNGKTSKKITIADCGQLE - G(VPGAG)192Y
(SEQ ID NO: 3)

Cyclophlin-V96
MMVNPTVFFDIAVDGEPLGRVSFELFADKVPKTAENFRALSTGEKGFGYKGSCFHRIIPG
FMCQGGDFTRHNGTGGKSIYGEKFEDENFILKHTGPGILSMANAGPNTNGSQFFICTAKT
EWLDGKHVVFGKVKEGMNIVEAMERFGSRNGKTSKKITIADCGQLE - (VPGVG)96Y (SEQ
ID NO: 4)

CypA_C-term nucleotide
5' -
TCTAGAAATAATTTTGTTTAACTTTAAGAAGGAGGAGTACATATGGGTATGGTTAAC
CCGACCGTTTTCTTCGACATCGCTGTTGACGGTGAACCGCTGGGTCGTGTTTCTTTCG
AACTGTTCGCTGACAAAGTTCCGAAAACCGCTGAAAACTTCCGTGCTCTGTCTACCG
GTGAAAAAGGTTTCGGTTACAAAGGTTCTTGCTTCCACCGTATCATCCCGGGTTTCA
TGTGCCAGGGTGGTGACTTCACCCGTCACAACGGTACCGGTGGTAAATCTATCTACG
GTGAAAAATTCGAAGACGAAAACTTCATCCTGAAACACACCGGTCCGGGTATCCTG
TCTATGGCTAACGCTGGTCCGAACACCAACGGTTCTCAGTTCTTCATCTGCACCGCT
AAAACCGAATGGCTGGACGGTAAACACGTTGTTTTCGGTAAAGTTAAAGAAGGTAT
GAACATCGTTGAAGCTATGGAACGTTTCGGTTCTCGTAACGGTAAAACCTCTAAAAA
AATCACCATCGCTGACTGCGGTCAGCTGGAAGGTTGATAATGATCTTCAGGATCC-3'
(SEQ ID NO: 5)

CypA_extra glycine
5' -
TATGGGTATGGTTAACCCGACCGTTTTCTTCGACATCGCTGTTGACGGTGAACCGCT
GGGTCGTGTTTCTTTCGAACTGTTCGCTGACAAAGTTCCGAAAACCGCTGAAAACTT
CCGTGCTCTGTCTACCGGTGAAAAAGGTTTCGGTTACAAAGGTTCTTGCTTCCACCG
TATCATCCCGGGTTTCATGTGCCAGGGTGGTGACTTCACCCGTCACAACGGTACCGG
TGGTAAATCTATCTACGGTGAAAAATTCGAAGACGAAAACTTCATCCTGAAACACA
CCGGTCCGGGTATCCTGTCTATGGCTAACGCTGGTCCGAACACCAACGGTTCTCAGT
TCTTCATCTGCACCGCTAAAACCGAATGGCTGGACGGTAAACACGTTGTTTTCGGTA
AAGTTAAAGAAGGTATGAACATCGTTGAAGCTATGGAACGTTTCGGTTCTCGTAACG
GTAAAACCTCTAAAAAAATCACCATCGCTGACTGCGGTCAGCTGGAAGGTTACTGAT
CTCCTCGGATC-3' (SEQ ID NO: 6)

Custom encoding sequence flanked by restriction recognition sites of NdeI and BamHI at the 5'
and 3' ends was ordered from Integrated DNA Technologies (IDT)
5' -
CATATGGTTAACCCGACCGTTTTCTTCGACATCGCTGTTGACGGTGAACCGCTGGGT
CGTGTTTCTTTCGAACTGTTCGCTGACAAAGTTCCGAAAACCGCTGAAAACTTCCGT
GCTCTGTCTACCGGTGAAAAAGGTTTCGGTTACAAAGGTTCTTGCTTCCACCGTATC
ATCCCGGGTTTCATGTGCCAGGGTGGTGACTTCACCCGTCACAACGGTACCGGTGGT
AAATCTATCTACGGTGAAAAATTCGAAGACGAAAACTTCATCCTGAAACACACCGG
TCCGGGTATCCTGTCTATGGCTAACGCTGGTCCGAACACCAACGGTTCTCAGTTCTTC
ATCTGCACCGCTAAAACCGAATGGCTGGACGGTAAACACGTTGTTTTCGGTAAAGTT
AAAGAAGGTATGAACATCGTTGAAGCTATGGAACGTTTCGGTTCTCGTAACGGTAA
AACCTCTAAAAAAATCACCATCGCTGACTGCGGTCAGCTGGAAGGTTACTGATCTCC
TCGGATCC-3' (SEQ ID NO: 7)

Amino acid sequence encoded by 2$^{nd}$ generation CA96C
MMVNPTVFFDIAVDGEPLGRVSFELFADKVPKTAENFRALSTGEKGFGYKGSCFHRIIPG
FMCQGGDFTRHNGTGGKSIYGEKFEDENFILKHTGPGILSMANAGPNTNGSQFFICTAKT
EWLDGKHVVFGKVKEGMNIVEAMERFGSRNGKTSKKITIADCGQLEG-(VPGAG)96-
MVNPTVFFDIAVDGEPLGRVSFELFADKVPKTAENFRALSTGEKGFGYKGSCFHRIIPGF
MCQGGDFTRHNGTGGKSIYGEKFEDENFILKHTGPGILSMANAGPNTNGSQFFICTAKTE
WLDGKHVVFGKVKEGMNIVEAMERFGSRNGKTSKKITIADCGQLEG (SEQ ID NO: 8)

Amino acid sequence encoded by 3$^{rd}$ generation 3(CA24)C:
MGMVNPTVFFDIAVDGEPLGRVSFELFADKVPKTAENFRALSTGEKGFGYKGSCFHRIIP
GFMCQGGDFTRHNGTGGKSIYGEKFEDENFILKHTGPGILSMANAGPNTNGSQFFICTA
KTEWLDGKHVVFGKVKEGMNIVEAMERFGSRNGKTSKKITIADCGQLEG-(VPGAG)24-
MVNPTVFFDIAVDGEPLGRVSFELFADKVPKTAENFRALSTGEKGFGYKGSCFHRIIPGF
MCQGGDFTRHNGTGGKSIYGEKFEDENFILKHTGPGILSMANAGPNTNGSQFFICTAKTE
WLDGKHVVFGKVKEGMNIVEAMERFGSRNGKTSKKITIADCGQLEG-(VPGAG)24-
```

SEQUENCE LISTING

```
MVNPTVFFDIAVDGEPLGRVSFELFADKVPKTAENFRALSTGEKGFGYKGSCFHRIIPGF
MCQGGDFTRHNGTGGKSIYGEKFEDENFILKHTGPGILSMANAGPNTNGSQFFICTAKTE
WLDGKHVVFGKVKEGMNIVEAMERFGSRNGKTSKKITIADCGQLEG-(VPGAG)24-
MVNPTVFFDIAVDGEPLGRVSFELFADKVPKTAENFRALSTGEKGFGYKGSCFHRIIPGF
MCQGGDFTRHNGTGGKSIYGEKFEDENFILKHTGPGILSMANAGPNTNGSQFFICTAKTE
WLDGKHVVFGKVKEGMNIVEAMERFGSRNGKTSKKITIADCGQLEG (SEQ ID NO: 9)

Amino acid sequence encoded by 5FA:
MGVQVETISPGDGRTFPKRGQTCVVHYTGMLEDGKKFDSSRDRNKPFKFMLGKQEVIR
GWEEGVAQMSVGQRAKLTISPDYAYGATGHPGIIPPHATLVFDVELLKLE-(VPGAG)24
GVQVETISPGDGRTFPKRGQTCVVHYTGMLEDGKKFDSSRDRNKPFKFMLGKQEVIRG
WEEGVAQMSVGQRAKLTISPDYAYGATGHPGIIPPHATLVFDVELLKLE-(VPGAG)24
GVQVETISPGDGRTFPKRGQTCVVHYTGMLEDGKKFDSSRDRNKPFKFMLGKQEVIRG
WEEGVAQMSVGQRAKLTISPDYAYGATGHPGIIPPHATLVFDVELLKLE-(VPGAG)24
GVQVETISPGDGRTFPKRGQTCVVHYTGMLEDGKKFDSSRDRNKPFKFMLGKQEVIRG
WEEGVAQMSVGQRAKLTISPDYAYGATGHPGIIPPHATLVFDVELLKLE-(VPGAG)24
GVQVETISPGDGRTFPKRGQTCVVHYTGMLEDGKKFDSSRDRNKPFKFMLGKQEVIRG
WEEGVAQMSVGQRAKLTISPDYAYGATGHPGIIPPHATLVFDVELLKLE (SEQ ID NO:
10)

Amino acid sequence encoded by 5FV:
MGVQVETISPGDGRTFPKRGQTCVVHYTGMLEDGKKFDSSRDRNKPFKFMLGKQEVIR
GWEEGVAQMSVGQRAKLTISPDYAYGATGHPGIIPPHATLVFDVELLKLE-(VPGVG)24
GVQVETISPGDGRTFPKRGQTCVVHYTGMLEDGKKFDSSRDRNKPFKFMLGKQEVIRG
WEEGVAQMSVGQRAKLTISPDYAYGATGHPGIIPPHATLVFDVELLKLE-(VPGVG)24
GVQVETISPGDGRTFPKRGQTCVVHYTGMLEDGKKFDSSRDRNKPFKFMLGKQEVIRG
WEEGVAQMSVGQRAKLTISPDYAYGATGHPGIIPPHATLVFDVELLKLE-(VPGVG)24
GVQVETISPGDGRTFPKRGQTCVVHYTGMLEDGKKFDSSRDRNKPFKFMLGKQEVIRG
WEEGVAQMSVGQRAKLTISPDYAYGATGHPGIIPPHATLVFDVELLKLE-(VPGVG)24
GVQVETISPGDGRTFPKRGQTCVVHYTGMLEDGKKFDSSRDRNKPFKFMLGKQEVIRG
WEEGVAQMSVGQRAKLTISPDYAYGATGHPGIIPPHATLVFDVELLKLE (SEQ ID NO:
11)

Exemplary DNA sequence encoding for FKBP:
5'-
ATGGGTGTTCAGGTTGAAACCATCTCTCCGGGTGACGGTCGTACCTTCCCGAAACGT
GGTCAGACCTGCGTTGTTCACTACACCGGTATGCTGGAAGACGGTAAAAAATTCGAC
CGTGGTTGGGAAGAAGGTGTTGCTCAGATGTCTGTTGGTCAGCGTGCTAAACTGACC
ATCTCTCCGGACTACGCTTACGGTGCTACCGGTCACCCGGGTATCATCCCGCCGCAC
GCTACCCTGGTTTTCGACGTTGAACTGCTGAAACTGGAAGGTTAC-3' (SEQ ID NO:
12)

DNA sequence encoding for (VPGAG)24(SEQ ID NO: 37):
5'-
GTTCCGGGCGCTGGTGTACCAGGTGCAGGTGTACCGGGTGCCGGCGTACCTGGCGC
AGGTGTCCCGGGTGCCGGTGTTCCGGGTGCTGGTGTTCCGGGCGCTGGTGTACCAGG
TGCAGGTGTACCGGGTGCCGGCGTACCTGGCGCAGGTGTCCCGGGTGCCGGTGTTCC
GGGTGCTGGTGTTCCGGGCGCTGGTGTACCAGGTGCAGGTGTACCGGGTGCCGGCGT
ACCTGGCGCAGGTGTCCCGGGTGCCGGTGTTCCGGGTGCTGGTGTTCCGGGCGCTGG
TGTACCAGGTGCAGGTGTACCGGGTGCCGGCGTACCTGGCGCAGGTGTCCCGGGTG
CCGGTGTTCCGGGTGCTGGT-3' (SEQ ID NO: 13)

DNA sequence encoding for (VPGVG)24(SEQ ID NO: 67):
5'-
GTTCCGGGCGTGGGTGTACCAGGTGTCGGTGTACCGGGTGTCGGCGTACCTGGCGTC
GGTGTCCCGGGTGTTGGTGTTCCGGGTGTAGGTGTTCCGGGCGTGGGTGTACCAGGT
GTCGGTGTACCGGGTGTCGGCGTACCTGGCGTCGGTGTCCCGGGTGTTGGTGTTCCG
GGTGTAGGTGTTCCGGGCGTGGGTGTACCAGGTGTCGGTGTACCGGGTGTCGGCGTA
CCTGGCGTCGGTGTCCCGGGTGTTGGTGTTCCGGGTGTAGGTGTTCCGGGCGTGGGT
GTACCAGGTGTCGGTGTACCGGGTGTCGGCGTACCTGGCGTCGGTGTCCCGGGTGTT
GGTGTTCCGGGTGTAGGT-3' (SEQ ID NO: 14)

4PA encoded amino acid sequence:
MADEEKLPPGWEKRMSRSSGRVYYFNHITNASQWERPSGNSSSGGKNGQGEPARVRCS
HLLVKHSQSRRPSSWRQEKITRTKEEALELINGYIQKIKSGEEDFESLASQFSDCSSAKAR
GDLGAFSRGQMKPFEDASFALRTGEMSGPVFTDSGIHIILRTE-(VPGAG)24-
ADEEKLPPGWEKRMSRSSGRVYYFNHITNASQWERPSGNSSSGGKNGQGEPARVRCSH
LLVKHSQSRRPSSWRQEKITRTKEEALELINGYIQKIKSGEEDFESLASQFSDCSSAKARG
DLGAFSRGQMQKPFEDASFALRTGEMSGPVFTDSGIHIILRTE-(VPGAG)24-
ADEEKLPPGWEKRMSRSSGRVYYFNHITNASQWERPSGNSSSGGKNGQGEPARVRCSH
LLVKHSQSRRPSSWRQEKITRTKEEALELINGYIQKIKSGEEDFESLASQFSDCSSAKARG
DLGAFSRGQMQKPFEDASFALRTGEMSGPVFTDSGIHIILRTE-(VPGAG)24-
ADEEKLPPGWEKRMSRSSGRVYYFNHITNASQWERPSGNSSSGGKNGQGEPARVRCSH
LLVKHSQSRRPSSWRQEKITRTKEEALELINGYIQKIKSGEEDFESLASQFSDCSSAKARG
DLGAFSRGQMQKPFEDASFALRTGEMSGPVFTDSGIHIILRTE (SEQ ID NO: 15)
```

SEQUENCE LISTING

DNA sequence encoding for Pin1:
5'-
ATGGGTGCTGACGAAGAGAAGTTACCTCCAGGCTGGGAAAAACGTATGTCTCGTTC
GAGCGGCAGAGTCTATTACTTCAACCACATTACCAACGCATCCCAGTGGGAGCGGC
CCTCCGGGAATTCTTCTAGCGGTGGCAAAAACGGTCAGGGTGAACCAGCCAGAGTG
CGCTGTTCCCACTTGTTAGTTAAACACTCTCAAAGCGTCGCCCCTCATCTTGGAGA
CAGGAGAAAATTACTCGGACCAAGGAAGAGGCCCTTGAACTTATCAATGGCTACAT
TCAGAAGATTAAGAGCGGGGAAGAGGATTTCGAATCCCTGGCGAGTCAATTCTCGG
ATTGTTCGAGTGCTAAAGCGCGGGGAGATCTTGGAGCATTCAGTCGTGGGCAAATG
CAAAAACCTTTTGAGGACGCTTCCTTTGCCTTGAGAACTGGGGAAATGTCCGGTCCA
GTTTTCACAGACTCTGGCATCCACATCATCCTGCGTACTGAG-3' (SEQ ID NO: 16)

scFv synthetic polypeptide
Gln Val Gln Leu Gln Gln Pro Gly Ala Glu Leu Val Lys Pro Gly Ala Ser Val Lys Met Ser Cys
Lys Ala Ser Gly Tyr Thr Phe Thr Ser Tyr Asn Met His Trp Val Lys Gln Thr Pro Gly Arg Gly
Leu Glu Trp Ile Gly Ala Ile Tyr Pro Gly Asn Gly Asp Thr Ser Tyr Asn Gln Lys Phe Lys Gly Lys
Ala Thr Leu Thr Ala Asp Lys Ser Ser Ser Thr Ala Tyr Met Gln Leu Ser Ser Leu Thr Ser Glu
Asp Ser Ala Val Tyr Tyr Cys Ala Arg Ser Thr Tyr Tyr Gly Gly Asp Trp Tyr Phe Asn Val Trp
Gly Ala Gly Thr Thr Val Thr Val Ser Ala Gly Gly Gly Gly Ser Gly Gly
Gly Gly Ser Gln Ile Val Leu Ser Gln Ser Pro Ala Ile Leu Ser Ala Ser Pro Gly Glu Lys Val Thr
Met Thr Cys Arg Ala Ser Ser Ser Val Ser Tyr Ile His Trp Phe Gln Gln Lys Pro Gly Ser Ser Pro
Lys Pro Trp Ile Tyr Ala Thr Ser Asn Leu Ala Ser Gly Val Pro Val Arg Phe Ser Gly Ser Gly Ser
Gly Thr Ser Tyr Ser Leu Thr Ile Ser Arg Val Glu Ala Glu Asp Ala Ala Thr Tyr Tyr Cys Gln Gln
Trp Thr Ser Asn Pro Pro Thr Phe Gly Gly Gly Thr Lys Leu Glu Ile Lys Arg Thr Gly (SEQ ID
NO: 17)

scFv synthetic polypeptide
Gln Val Gln Leu Gln Gln Pro Gly Ala Glu Leu Val Lys Pro Gly Ala Ser Val Lys Met Ser Cys
Lys Ala Ser Gly Tyr Thr Phe Thr Ser Tyr Asn Met His Trp Val Lys Gln Thr Pro Gly Arg Gly
Leu Glu Trp Ile Gly Ala Ile Tyr Pro Gly Asn Gly Asp Thr Ser Tyr Asn Gln Lys Phe Lys Gly Lys
Ala Thr Leu Thr Ala Asp Lys Ser Ser Ser Thr Ala Tyr Met Gln Leu Ser Ser Leu Thr Ser Glu
Asp Ser Ala Val Tyr Tyr Cys Ala Arg Ser Thr Tyr Tyr Gly Gly Asp Trp Tyr Phe Asn Val Trp
Gly Ala Gly Thr Thr Val Thr Val Ser Ala Gly Gly Gly Gly Ser Gly Gly Gly Gly Ser Gly Gly
Gly Gly Ser Gly Gly Gly Gly Ser Gln Ile Val Leu Ser Gln Ser Pro Ala Ile Leu Ser Ala Ser Pro
Gly Glu Lys Val Thr Met Thr Cys Arg Ala Ser Ser Ser Val Ser Tyr Ile His Trp Phe Gln Gln Lys
Pro Gly Ser Ser Pro Lys Pro Trp Ile Tyr Ala Thr Ser Asn Leu Ala Ser Gly Val Pro Val Arg Phe
Ser Gly Ser Gly Ser Gly Thr Ser Tyr Ser Leu Thr Ile Ser Arg Val Glu Ala Glu Asp Ala Ala Thr
Tyr Tyr Cys Gln Gln Trp Thr Ser Asn Pro Pro Thr Phe Gly Gly Gly Thr Lys Leu Glu Ile Gly
Arg Thr Gly (SEQ ID NO: 18)

scFv-ELP fusion polypeptide
Met Gly Gln Val Gln Leu Gln Gln Pro Gly Ala Glu Leu Val Lys Pro
Gly Ala Ser Val Lys Met Ser Cys Lys Ala Ser Gly Tyr Thr Phe Thr
Ser Tyr Asn Met His Trp Val Lys Gln Thr Pro Gly Arg Gly Leu Glu
Trp Ile Gly Ala Ile Tyr Pro Gly Asn Gly Asp Thr Ser Tyr Asn Gln
Lys Phe Lys Gly Lys Ala Thr Leu Thr Ala Asp Lys Ser Ser Ser Thr
Ala Tyr Met Gln Leu Ser Ser Leu Thr Ser Glu Asp Ser Ala Val Tyr
Tyr Cys Ala Arg Ser Thr Tyr Tyr Gly Gly Asp Trp Tyr Phe Asn Val
Trp Gly Ala Gly Thr Thr Val Thr Val Ser Ala Gly Gly Gly Gly Ser
Gly Gly Gly Gly Ser Gly Gly Gly Gly Ser Gln Ile Val Leu Ser Gln
Ser Pro Ala Ile Leu Ser Ala Ser Pro Gly Glu Lys Val Thr Met Thr
Cys Arg Ala Ser Ser Ser Val Ser Tyr Ile His Trp Phe Gln Gln Lys
Pro Gly Ser Ser Pro Lys Pro Trp Ile Tyr Ala Thr Ser Asn Leu Ala
Ser Gly Val Pro Val Arg Phe Ser Gly Ser Gly Ser Gly Thr Ser Tyr
Ser Leu Thr Ile Ser Arg Val Glu Ala Glu Asp Ala Ala Thr Tyr Tyr
Cys Gln Gln Trp Thr Ser Asn Pro Pro Thr Phe Gly Gly Gly Thr Lys
Leu Glu Ile Lys Arg Thr Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly
Ala Gly Val Pro Gly Ala Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly
Ala Gly Val Pro Gly Ala Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly
Ala Gly Val Pro Gly Ala Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly

SEQUENCE LISTING

Ala Gly Val Pro Gly Ala Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly
Ala Gly Val Pro Gly Ala Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly
Ala Gly Val Pro Gly Ala Gly Val Pro Gly Ile Gly Val Pro Gly Ile
Gly Val Pro Gly Ile Gly Val Pro Gly Ile Gly Val Pro Gly Ile Gly
Val Pro Gly Ile Gly Val Pro Gly Ile Gly Val Pro Gly Ile Gly Val
Pro Gly Ile Gly Val Pro Gly Ile Gly Val Pro Gly Ile Gly Val Pro
Gly Ile Gly Val Pro Gly Ile Gly Val Pro Gly Ile Gly Val Pro Gly
Ile Gly Val Pro Gly Ile Gly Val Pro Gly Ile Gly Val Pro Gly Ile
Gly Val Pro Gly Ile Gly Val Pro Gly Ile Gly Val Pro Gly Ile Gly
Val Pro Gly Ile Gly Val Pro Gly Ile Gly Val Pro Gly Ile Gly Val
Pro Gly Ile Gly Val Pro Gly Ile Gly Val Pro Gly Ile Gly Val Pro
Gly Ile Gly Val Pro Gly Ile Gly Val Pro Gly Ile Gly Val Pro Gly
Ile Gly Val Pro Gly Ile Gly Val Pro Gly Ile Gly Val Pro Gly Ile
Gly Val Pro Gly Ile Gly Val Pro Gly Ile Gly Val Pro Gly Ile Gly
Val Pro Gly Ile Gly Val Pro Gly Ile Gly Val Pro Gly Ile Gly Val
Pro Gly Ile Gly Val Pro Gly Ile Gly Val Pro Gly Ile Gly Val Pro
Gly Ile Gly Val Pro Gly Ile Gly Val Pro Gly Ile Gly Val Pro Gly
Ile Gly Val Pro Gly Ile Gly Val Pro Gly Ile Gly Val Pro Gly Ile
Gly Val Pro Gly Ile Gly Val Pro Gly Ile Gly Val Pro Gly Ile Gly
Val Pro Gly Ile Gly Val Pro Gly Ile Gly Val Pro Gly Ile Gly Val
Pro Gly Ile Gly Val Pro Gly Ile Gly Val Pro Gly Ile Gly Val
Pro Gly Ile Gly Val Pro Gly Ile Gly Val Pro Gly Ile Gly Val
Pro Gly Ile Gly Val Pro Gly Ile Gly Val Pro Gly Ile Gly Val
Pro Gly Ile Gly Val Pro Gly Ile Gly Val Pro Gly Ile Gly Val
Pro Gly Ile Gly Val Pro Gly Ile Gly Val Pro Gly Ile Gly Val
Pro Gly Ile Gly Val Pro Gly Ile Gly Val Pro Gly Ile Gly Val
Pro Gly Ile Gly Val Pro Gly Ile Gly Val Pro Gly Ile Gly Val
Pro Gly Ile Gly Val Pro Gly Ile Gly Val Pro Gly Ile Gly Val
Pro Gly Ile Gly Val Pro Gly Ile Gly Val Pro Gly Ile Gly Val
Pro Gly Ile Gly Val Pro Gly Ile Gly Val Pro Gly Ile Gly Val
Pro Gly Ile Gly Val Pro Gly Ile Gly Val Pro Gly Ile Gly Val
Pro Gly Ile Gly Tyr (SEQ ID NO: 19)

scFv-ELP fusion synthetic polypeptide
Met Gly Gln Val Gln Leu Gln Gln Pro Gly Ala Glu Leu Val Lys Pro
Gly Ala Ser Val Lys Met Ser Cys Lys Ala Ser Gly Tyr Thr Phe Thr
Ser Tyr Asn Met His Trp Val Lys Gln Thr Pro Gly Arg Gly Leu Glu
Trp Ile Gly Ala Ile Tyr Pro Gly Asn Gly Asp Thr Ser Tyr Asn Gln
Lys Phe Lys Gly Lys Ala Thr Leu Thr Ala Asp Lys Ser Ser Ser Thr
Ala Tyr Met Gln Leu Ser Ser Leu Thr Ser Glu Asp Ser Ala Val Tyr
Tyr Cys Ala Arg Ser Thr Tyr Tyr Gly Gly Asp Trp Tyr Phe Asn Val
Trp Gly Ala Gly Thr Thr Val Thr Val Ser Ala Gly Gly Gly Gly Ser
Gly Gly Gly Gly Ser Gly Gly Gly Gly Ser Gln Ile Val Leu Ser Gln
Ser Pro Ala Ile Leu Ser Ala Ser Pro Gly Glu Lys Val Thr Met Thr
Cys Arg Ala Ser Ser Ser Val Ser Tyr Ile His Trp Phe Gln Gln Lys
Pro Gly Ser Ser Pro Lys Pro Trp Ile Tyr Ala Thr Ser Asn Leu Ala
Ser Gly Val Pro Val Arg Phe Ser Gly Ser Gly Ser Gly Thr Ser Tyr
Ser Leu Thr Ile Ser Arg Val Glu Ala Glu Asp Ala Ala Thr Tyr Tyr
Cys Gln Gln Trp Thr Ser Asn Pro Pro Thr Phe Gly Gly Gly Thr Lys
Leu Glu Ile Lys Arg Thr Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly
Ala Gly Val Pro Gly Ala Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly
Ala Gly Val Pro Gly Ala Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly
Ala Gly Val Pro Gly Ala Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val -continued

SEQUENCE LISTING

Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly
Ala Gly Val Pro Gly Ala Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly
Ala Gly Val Pro Gly Ala Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly
Ala Gly Val Pro Gly Ala Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly
Ala Gly Val Pro Gly Ala Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val Pro
Gly Ala Gly Val Pro Gly Ala Gly Val Pro Gly Ala Gly Val Pro Gly
Ala Gly Val Pro Gly Ala Gly Val Pro Gly Ala Gly Val Pro Gly Ala
Gly Val Pro Gly Ala Gly Val Pro Gly Ala Gly Val Pro Gly Ala Gly
Val Pro Gly Ala Gly Val Pro Gly Ala Gly Val Pro Gly Ala Gly Val
Pro Gly Ala Gly Val Pro Gly Ala Gly Val Pro Gly Ala Gly Val
Pro Gly Ala Gly Val Pro Gly Ala Gly Val Pro Gly Ala Gly Val
Pro Gly Ala Gly Val Pro Gly Ala Gly Val Pro Gly Ala Gly Val
Pro Gly Ala Gly Val Pro Gly Ala Gly Val Pro Gly Ala Gly Val
Pro Gly Ala Gly Val Pro Gly Ala Gly Val Pro Gly Ala Gly Val
Pro Gly Ala Gly Val Pro Gly Ala Gly Val Pro Gly Ala Gly Val
Pro Gly Ala Gly Val Pro Gly Ala Gly Val Pro Gly Ala Gly Val
Pro Gly Ala Gly Val Pro Gly Ala Gly Val Pro Gly Ala Gly Val
Pro Gly Ala Gly Val Pro Gly Ala Gly Val Pro Gly Ala Gly Val
Pro Gly Ala Gly Val Pro Gly Ala Gly Val Pro Gly Ala Gly Val
Pro Gly Ala Gly Val Pro Gly Ala Gly Val Pro Gly Ala Gly Val (SEQ ID NO: 20)

scFv-ELP fusion synthetic polypeptide
Met Gly Gln Val Gln Leu Gln Gln Pro Gly Ala Glu Leu Val Lys Pro
Gly Ala Ser Val Lys Met Ser Cys Lys Ala Ser Gly Tyr Thr Phe Thr
Ser Tyr Asn Met His Trp Val Lys Gln Thr Pro Gly Arg Gly Leu Glu
Trp Ile Gly Ala Ile Tyr Pro Gly Asn Gly Asp Thr Ser Tyr Asn Gln
Lys Phe Lys Gly Lys Ala Thr Leu Thr Ala Asp Lys Ser Ser Ser Thr
Ala Tyr Met Gln Leu Ser Ser Leu Thr Ser Glu Asp Ser Ala Val Tyr
Tyr Cys Ala Arg Ser Thr Tyr Tyr Gly Gly Asp Trp Tyr Phe Asn Val
Trp Gly Ala Gly Thr Thr Val Thr Val Ser Ala Gly Gly Gly Gly Ser
Gly Gly Gly Gly Ser Gly Gly Gly Gly Ser Gln Ile Val Leu Ser Gln
Ser Pro Ala Ile Leu Ser Ala Ser Pro Gly Glu Lys Val Thr Met Thr
Cys Arg Ala Ser Ser Ser Val Ser Tyr Ile His Trp Phe Gln Gln Lys
Pro Gly Ser Ser Pro Lys Pro Trp Ile Tyr Ala Thr Ser Asn Leu Ala
Ser Gly Val Pro Val Arg Phe Ser Gly Ser Gly Ser Gly Thr Ser Tyr
Ser Leu Thr Ile Ser Arg Val Glu Ala Glu Asp Ala Ala Thr Tyr Tyr
Cys Gln Gln Trp Thr Ser Asn Pro Pro Thr Phe Gly Gly Gly Thr Lys
Leu Glu Ile Lys Arg Thr Gly Val Pro Gly Ser Gly Val Pro Gly Ser
Gly Val Pro Gly Ser Gly Val Pro Gly Ser Gly Val Pro Gly Ser Gly
Val Pro Gly Ser Gly Val Pro Gly Ser Gly Val Pro Gly Ser Gly Val
Pro Gly Ser Gly Val Pro Gly Ser Gly Val Pro Gly Ser Gly Val Pro
Gly Ser Gly Val Pro Gly Ser Gly Val Pro Gly Ser Gly Val Pro Gly
Ser Gly Val Pro Gly Ser Gly Val Pro Gly Ser Gly Val Pro Gly Ser
Gly Val Pro Gly Ser Gly Val Pro Gly Ser Gly Val Pro Gly Ser Gly
Val Pro Gly Ser Gly Val Pro Gly Ser Gly Val Pro Gly Ser Gly Val
Pro Gly Ser Gly Val Pro Gly Ser Gly Val Pro Gly Ser Gly Val Pro
Gly Ser Gly Val Pro Gly Ser Gly Val Pro Gly Ser Gly Val Pro Gly
Ser Gly Val Pro Gly Ser Gly Val Pro Gly Ser Gly Val Pro Gly Ser
Gly Val Pro Gly Ser Gly Val Pro Gly Ser Gly Val Pro Gly Ser Gly
Val Pro Gly Ser Gly Val Pro Gly Ser Gly Val Pro Gly Ser Gly Val
Pro Gly Ser Gly Val Pro Gly Ser Gly Val Pro Gly Ser Gly Val Pro
Gly Ser Gly Val Pro Gly Ser Gly Val Pro Gly Ser Gly Val Pro Gly
Phe Gly Val Pro Gly Ser Gly Val Pro Gly Ile Gly Val Pro Gly Ile
Gly Val Pro Gly Ile Gly Val Pro Gly Ile Gly Val Pro Gly Ile Gly

SEQUENCE LISTING

```
Val Pro Gly Ile Gly Val Pro Gly Ile Gly Val Pro Gly Ile Gly Val
Pro Gly Ile Gly Val Pro Gly Ile Gly Val Pro Gly Ile Gly Val Pro
Gly Ile Gly Val Pro Gly Ile Gly Val Pro Gly Ile Gly Val Pro Gly
Ile Gly Val Pro Gly Ile Gly Val Pro Gly Ile Gly Val Pro Gly Ile
Gly Val Pro Gly Ile Gly Val Pro Gly Ile Gly Val Pro Gly Ile Gly
Val Pro Gly Ile Gly Val Pro Gly Ile Gly Val Pro Gly Ile Gly Val
Pro Gly Ile Gly Val Pro Gly Ile Gly Val Pro Gly Ile Gly Val Pro
Gly Ile Gly Val Pro Gly Ile Gly Val Pro Gly Ile Gly Val Pro Gly
Ile Gly Val Pro Gly Ile Gly Val Pro Gly Ile Gly Val Pro Gly Ile
Gly Val Pro Gly Ile Gly Val Pro Gly Ile Gly Val Pro Gly Ile Gly
Val Pro Gly Ile Gly Val Pro Gly Ile Gly Val Pro Gly Ile Gly Val
Pro Gly Ile Gly Val Pro Gly Ile Gly Val Pro Gly Ile Gly Val Pro
Gly Ile Gly Val Pro Gly Ile Gly Val Pro Gly Ile Gly Val Pro Gly
Ile Gly Val Pro Gly Ile Gly Tyr (SEQ ID NO: 21)
```

Exemplary Cyclophilin Polynucleotide Sequences and Comparison of WT Cyclophilin to Optimized Sequence

```
Opt.Seq    1 CATATGGTTAACCCGACCGTTTTCTTCGACATCGCTGTTGACGGTGAACC  50
             ||||| |||||  |||||  |||||||||||  ||  || ||||| || ||
PPIA_WT    1 ---atggtcaacccc accatgttcttcgacattgccgtcaacggcgagcc  47

Opt.Seq   51 GCTGGGTCGTGTTTCTTTCGAACTGTTCGCTGACAAAGTTCCGAAAACCG 100
             ·· ||||·||·||·||·||·||·|||||·||·||||||·||·||·||·||·|
PPIA_WT   48 cttgggccgcgtctcctttgagctgtttgcagacaaggtcccaaagacag  97

Opt.Seq  101 CTGAAAACTTCCGTGCTCTGTCTACCGGTGAAAAGGTTTCGGTTACAAA 150
             |·||||||·||·|||||||||·····||·||·||·||||||·||·||||||·||·
PPIA_WT   98 cagaaaatttcgtgctctgagcactggagagaaaggatttggttataag 147

Opt.Seq  151 GGTTCTTGCTTCCACCGTATCA-TCCCGGGTTTCATGTGCCAGGGTGGTG 199
             |||||·|||||·|||·|·||·| |||·||||||| |||||·|||||||||
PPIA_WT  148 ggttcctgctttcacagaattattccagggttt-atgtgtcagggtggtg 196

Opt.Seq  200 ACTTCACCCGTCACAACGGTACCGGTGGTAAATCTATCTACGGTGAAAAA 249
             ||||||·||·||·||·||·||·||·|||||·||·|||||·||·||·||·||
PPIA_WT  197 acttcacacgccataatggcactggtggcaagtccatctatggggagaaa 246

Opt.Seq  250 TTCGAAGACGAAAACTTCATCCTGAAACACACCGGTCCGGGTATCCTGTC 299
             ||·|||||·||·||||||||||||·||·||·||·|||||·||·|||·||||
PPIA_WT  247 tttgaagatgagaacttcatcctaaagcatacgggtcctggcatcttgtc 296

Opt.Seq  300 TATGGCTAACGCTGGTCCGAACACCAACGGTTCTCAGTTCTTCATCTGCA 349
             ·|||||·||·|||||·||·||||||·||·||||||·||||||·||||||||
PPIA_WT  297 catggcaaatgctggacccaacacaaatggttcccagttttcatctgca 346

Opt.Seq  350 CCGCTAAAACCGAATGGCTGGACGGTAAACACGTTGTTTTCGGTAAAGTT 399
             |·||·||·||·||·|||·||||·||·||·||·||·||·||·||·||||||·
PPIA_WT  347 ctgccaagactgagtggttggatggcaagcatgtggtgtttggcaaagtg 396

Opt.Seq  400 AAAGAAGGTATGAACATCGTTGAAGCTATGGAACGTTTCGGTTCTCGTAA 449
             ||||||||·|||||·||·||·||·||·||·||||||·||·||·||·|·||
PPIA_WT  397 aaagaagacatgaatattgtggaagccatggagcgctttaggtccaggaa 446

Opt.Seq  450 CGGTAAAACCTCTAAAAAAATCACCATCGCTGACTGCGGTCAGCTGGAAG 499
             ·||·||·|||···||·||·|||||||||·|||||||·||·||·||·|||
PPIA_WT  447 tggcaagaccagcaagaagatcaccattgctgactgtggacaactcgaa- 495

Opt.Seq  500 GTTACTGATCTCCTCGGATCC                        520 (SEQ ID NO: 22)
             |·|
PPIA_WT  496 -taa-----------------                        498 (SEQ ID NO: 23)
```

Exemplary FKBP Protein Sequence:

(SEQ ID NO: 24)
VQVETISPGDGRTFPKRGQTCVVHYTGMLEDGKKFDSSRDRNKPFKFMLG
KQEVIRGWEEGVAQMSVGQRAKLTISPDYAYGATGHPGIIPPHATLVFDV
ELLKLEG

REFERENCES

1. Colombo D. and Ammirati E. (2011) Cyclosporin in transplantation—a history of converging timelines. *Journal of biological regulators and homeostatic agents*, 25, 493.
2. Cornec D., Saraux A., Jousse-Joulin S., Pers J.-O., Boisramé-Gastrin S., Renaudineau Y., Gauvin Y., Roguedas-Contios A.-M., Genestet S. and Chastaing M. (2015) The differential diagnosis of dry eyes, dry mouth, and parotidomegaly: a comprehensive review. *Clinical reviews in allergy &immunology,* 49, 278-287.
3. Dhandhukia J., Weitzhandler I., Wang W. and MacKay J. A. (2013) Switchable elastin-like polypeptides that respond to chemical inducers of dimerization. *Biomacromolecules,* 14, 976-985.
4. Gupta C. and Chauhan A. (2011) Ophthalmic delivery of cyclosporin A by punctal plugs. *J Control Release,* 150, 70-76.
5. Janib S. M., Pastuszka M., Aluri S., Folchman-Wagner Z., Hsueh P. Y., Shi P., Yi A., Cui H. and Mackay J. A. (2014) A quantitative recipe for engineering protein polymer nanoparticles. *Polym Chem,* 5, 1614-1625.
6. Janine A. (2007) The epidemiology of dry eye disease: report of the epidemiological subcommittee of the international dry eye workshop. *Ocul Surf* 5, 93-107.
7. Mahalati K., Belitsky P., West K., Kiberd B., Fraser A., Sketris I., Macdonald A. S., McAlister V. and Lawen J. (2001) Approaching the therapeutic window for cyclosporin in kidney transplantation: a prospective study. *Journal of the American Society of Nephrology,* 12, 828-833.
8. Shah M., Edman M. C., Janga S. R., Shi P., Dhandhukia J., Liu S., Louie S. G., Rodgers K., MacKay J. A. and Hamm-Alvarez S. F. (2013) A rapamycin-binding protein polymer nanoparticle shows potent therapeutic activity in suppressing autoimmune dacryoadenitis in a mouse model of Sjögren's syndrome. *Journal of Controlled Release,* 171, 269-279.
9. Shah M., Hsueh P. Y., Sun G., Chang H. Y., Janib S. M. and MacKay J. A. (2012) Biodegradation of elastin-like polypeptide nanoparticles. *Protein Science,* 21, 743-750.
10. Shi P., Aluri S., Lin Y. A., Shah M., Edman M., Dhandhukia J., Cui H. and MacKay J. A. (2013) Elastin-based protein polymer nanoparticles carrying drug at both corona and core suppress tumor growth in vivo. *J Control Release,* 171, 330-338.
11. Stevenson W., Chauhan S. K. and Dana R. (2012) Dry eye disease: an immune-mediated ocular surface disorder. *Archives of Ophthalmology,* 130, 90-100.
12. Sun G., Hsueh P.-Y., Janib S. M., Hamm-Alvarez S. and MacKay J. A. (2011) Design and cellular internalization of genetically engineered polypeptide nanoparticles displaying adenovirus knob domain. *Journal of controlled release,* 155, 218-226.
13. Survase S. A., Kagliwal L. D., Annapure U.S. and Singhal R. S. (2011) Cyclosporin A—A review on fermentative production, downstream processing and pharmacological applications. *Biotechnology advances,* 29, 418-435.
14. Urry D. W. (1997) Physical chemistry of biological free energy transduction as demonstrated by elastic protein-based polymers. *The Journal of Physical Chemistry B,* 101, 11007-11028.
15. Wang W., Jashnani A., Aluri S. R., Gustafson J. A., Hsueh P.-Y., Yarber F., McKown R. L., Laurie G. W., Hamm-Alvarez S. F. and MacKay J. A. (2015) A thermo-responsive protein treatment for dry eyes. *Journal of Controlled Release,* 199, 156-167.
16. Andersson, J., et al., Effects of FK506 and cyclosporin A on cytokine production studied in vitro at a single-cell level. *Immunology,* 1992. 75(1): p. 136.
17. Tanaka, Y., Y. Sato, and T. Sasaki, Suppression of coronavirus replication by cyclophilin inhibitors. *Viruses,* 2013. 5(5): p. 1250-1260.
18. Huai, Q., et al., Crystal structure of calcineurin-cyclophilin-cyclosporin shows common but distinct recognition of immunophilin-drug complexes. *Proceedings of the National Academy of Sciences,* 2002. 99(19): p. 12037-12042.
19. D. E. Meyer, A. Chilkoti, Genetically encoded synthesis of protein-based polymers with precisely specified molecular weight and sequence by recursive directional ligation: examples from the elastin-like polypeptide system, *Biomacromolecules,* 3 (2002) 357-367.

What is claimed is:

1. An agent comprising a multimeric form of an elastin-like peptide (ELP) component that forms a drug binding domain stabilized by the ELP and two or more FKBP drug binding domains, wherein the agent is SEQ ID NO: 10 (5FA) or SEQ ID NO: 11 (5FV), or dimers, trimers, tetramers or pentamers thereof.

2. The agent of claim 1, further comprising a therapeutic agent.

3. The agent of claim 2, wherein the therapeutic agent is bound or trapped by the ELP or coacervate formed by the ELP.

4. The agent of claim 1, further comprising a detectable label.

5. An agent comprising a polypeptide selected from SEQ ID NO: 3 (CA192), SEQ ID NO: 4 (CV96), SEQ ID NO: 8 (CAC), SEQ ID NO: 9 (3(CA)C), SEQ ID NO: 15 (4PA), or dimers, trimers, tetramers or pentamers thereof.

6. A method for delivering a therapeutic agent in vitro comprising contacting a tissue or cell with an effective amount of the agent of claim 2.

* * * * *

SEQUENCE LISTING

```
<160> NUMBER OF SEQ ID NOS: 67

<210> SEQ ID NO 1
<211> LENGTH: 960
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Val Pro Gly Ala Gly Val Pro Gly Ala Gly Val Pro Gly Ala Gly Val
1               5                   10                  15

Pro Gly Ala Gly Val Pro Gly Ala Gly Val Pro Gly Ala Gly Val Pro
            20                  25                  30

Gly Ala Gly Val Pro Gly Ala Gly Val Pro Gly Ala Gly Val Pro Gly
        35                  40                  45

Ala Gly Val Pro Gly Ala Gly Val Pro Gly Ala Gly Val Pro Gly Ala
    50                  55                  60

Gly Val Pro Gly Ala Gly Val Pro Gly Ala Gly Val Pro Gly Ala Gly
65                  70                  75                  80

Val Pro Gly Ala Gly Val Pro Gly Ala Gly Val Pro Gly Ala Gly Val
                85                  90                  95
```

```
Pro Gly Ala Gly Val Pro Gly Ala Gly Val Pro Gly Ala Gly Val Pro
            100                 105                 110

Gly Ala Gly Val Pro Gly Ala Gly Val Pro Gly Ala Gly Val Pro Gly
        115                 120                 125

Ala Gly Val Pro Gly Ala Gly Val Pro Gly Ala Gly Val Pro Gly Ala
    130                 135                 140

Gly Val Pro Gly Ala Gly Val Pro Gly Ala Gly Val Pro Gly Ala Gly
145                 150                 155                 160

Val Pro Gly Ala Gly Val Pro Gly Ala Gly Val Pro Gly Ala Gly Val
                165                 170                 175

Pro Gly Ala Gly Val Pro Gly Ala Gly Val Pro Gly Ala Gly Val Pro
            180                 185                 190

Gly Ala Gly Val Pro Gly Ala Gly Val Pro Gly Ala Gly Val Pro Gly
        195                 200                 205

Ala Gly Val Pro Gly Ala Gly Val Pro Gly Ala Gly Val Pro Gly Ala
    210                 215                 220

Gly Val Pro Gly Ala Gly Val Pro Gly Ala Gly Val Pro Gly Ala Gly
225                 230                 235                 240

Val Pro Gly Ala Gly Val Pro Gly Ala Gly Val Pro Gly Ala Gly Val
                245                 250                 255

Pro Gly Ala Gly Val Pro Gly Ala Gly Val Pro Gly Ala Gly Val Pro
            260                 265                 270

Gly Ala Gly Val Pro Gly Ala Gly Val Pro Gly Ala Gly Val Pro Gly
        275                 280                 285

Ala Gly Val Pro Gly Ala Gly Val Pro Gly Ala Gly Val Pro Gly Ala
    290                 295                 300

Gly Val Pro Gly Ala Gly Val Pro Gly Ala Gly Val Pro Gly Ala Gly
305                 310                 315                 320

Val Pro Gly Ala Gly Val Pro Gly Ala Gly Val Pro Gly Ala Gly Val
                325                 330                 335

Pro Gly Ala Gly Val Pro Gly Ala Gly Val Pro Gly Ala Gly Val Pro
            340                 345                 350

Gly Ala Gly Val Pro Gly Ala Gly Val Pro Gly Ala Gly Val Pro Gly
        355                 360                 365

Ala Gly Val Pro Gly Ala Gly Val Pro Gly Ala Gly Val Pro Gly Ala
    370                 375                 380

Gly Val Pro Gly Ala Gly Val Pro Gly Ala Gly Val Pro Gly Ala Gly
385                 390                 395                 400

Val Pro Gly Ala Gly Val Pro Gly Ala Gly Val Pro Gly Ala Gly Val
                405                 410                 415

Pro Gly Ala Gly Val Pro Gly Ala Gly Val Pro Gly Ala Gly Val Pro
            420                 425                 430

Gly Ala Gly Val Pro Gly Ala Gly Val Pro Gly Ala Gly Val Pro Gly
        435                 440                 445

Ala Gly Val Pro Gly Ala Gly Val Pro Gly Ala Gly Val Pro Gly Ala
    450                 455                 460

Gly Val Pro Gly Ala Gly Val Pro Gly Ala Gly Val Pro Gly Ala Gly
465                 470                 475                 480

Val Pro Gly Ala Gly Val Pro Gly Ala Gly Val Pro Gly Ala Gly Val
                485                 490                 495

Pro Gly Ala Gly Val Pro Gly Ala Gly Val Pro Gly Ala Gly Val Pro
            500                 505                 510

Gly Ala Gly Val Pro Gly Ala Gly Val Pro Gly Ala Gly Val Pro Gly
```

```
                515                 520                 525
Ala Gly Val Pro Gly Ala Gly Val Pro Gly Ala Gly Val Pro Gly Ala
    530                 535                 540
Gly Val Pro Gly Ala Gly Val Pro Gly Ala Gly Val Pro Gly Ala Gly
545                 550                 555                 560
Val Pro Gly Ala Gly Val Pro Gly Ala Gly Val Pro Gly Ala Gly Val
                565                 570                 575
Pro Gly Ala Gly Val Pro Gly Ala Gly Val Pro Gly Ala Gly Val Pro
            580                 585                 590
Gly Ala Gly Val Pro Gly Ala Gly Val Pro Gly Ala Gly Val Pro Gly
        595                 600                 605
Ala Gly Val Pro Gly Ala Gly Val Pro Gly Ala Gly Val Pro Gly Ala
    610                 615                 620
Gly Val Pro Gly Ala Gly Val Pro Gly Ala Gly Val Pro Gly Ala Gly
625                 630                 635                 640
Val Pro Gly Ala Gly Val Pro Gly Ala Gly Val Pro Gly Ala Gly Val
                645                 650                 655
Pro Gly Ala Gly Val Pro Gly Ala Gly Val Pro Gly Ala Gly Val Pro
            660                 665                 670
Gly Ala Gly Val Pro Gly Ala Gly Val Pro Gly Ala Gly Val Pro Gly
        675                 680                 685
Ala Gly Val Pro Gly Ala Gly Val Pro Gly Ala Gly Val Pro Gly Ala
    690                 695                 700
Gly Val Pro Gly Ala Gly Val Pro Gly Ala Gly Val Pro Gly Ala Gly
705                 710                 715                 720
Val Pro Gly Ala Gly Val Pro Gly Ala Gly Val Pro Gly Ala Gly Val
                725                 730                 735
Pro Gly Ala Gly Val Pro Gly Ala Gly Val Pro Gly Ala Gly Val Pro
            740                 745                 750
Gly Ala Gly Val Pro Gly Ala Gly Val Pro Gly Ala Gly Val Pro Gly
        755                 760                 765
Ala Gly Val Pro Gly Ala Gly Val Pro Gly Ala Gly Val Pro Gly Ala
    770                 775                 780
Gly Val Pro Gly Ala Gly Val Pro Gly Ala Gly Val Pro Gly Ala Gly
785                 790                 795                 800
Val Pro Gly Ala Gly Val Pro Gly Ala Gly Val Pro Gly Ala Gly Val
                805                 810                 815
Pro Gly Ala Gly Val Pro Gly Ala Gly Val Pro Gly Ala Gly Val Pro
            820                 825                 830
Gly Ala Gly Val Pro Gly Ala Gly Val Pro Gly Ala Gly Val Pro Gly
        835                 840                 845
Ala Gly Val Pro Gly Ala Gly Val Pro Gly Ala Gly Val Pro Gly Ala
    850                 855                 860
Gly Val Pro Gly Ala Gly Val Pro Gly Ala Gly Val Pro Gly Ala Gly
865                 870                 875                 880
Val Pro Gly Ala Gly Val Pro Gly Ala Gly Val Pro Gly Ala Gly Val
                885                 890                 895
Pro Gly Ala Gly Val Pro Gly Ala Gly Val Pro Gly Ala Gly Val Pro
            900                 905                 910
Gly Ala Gly Val Pro Gly Ala Gly Val Pro Gly Ala Gly Val Pro Gly
        915                 920                 925
Ala Gly Val Pro Gly Ala Gly Val Pro Gly Ala Gly Val Pro Gly Ala
    930                 935                 940
```

Gly Val Pro Gly Ala Gly Val Pro Gly Ala Gly Val Pro Gly Ala Gly
945                 950                 955                 960

<210> SEQ ID NO 2
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
                20                  25                  30

Gly Val Gly Val Pro Gly Val Gly Val Pro Gly Val Gly Val Pro Gly
            35                  40                  45

Val Gly Val Pro Gly Val Gly Val Pro Gly Val Gly Val Pro Gly Val
        50                  55                  60

Gly Val Pro Gly Val Gly Val Pro Gly Val Gly Val Pro Gly Val Gly
65                  70                  75                  80

Val Pro Gly Val Gly Val Pro Gly Val Gly Val Pro Gly Val Gly Val
                85                  90                  95

Pro Gly Val Gly Val Pro Gly Val Gly Val Pro Gly Val Gly Val Pro
                100                 105                 110

Gly Val Gly Val Pro Gly Val Gly Val Pro Gly Val Gly Val Pro Gly
            115                 120                 125

Val Gly Val Pro Gly Val Gly Val Pro Gly Val Gly Val Pro Gly Val
        130                 135                 140

Gly Val Pro Gly Val Gly Val Pro Gly Val Gly Val Pro Gly Val Gly
145                 150                 155                 160

Val Pro Gly Val Gly Val Pro Gly Val Gly Val Pro Gly Val Gly Val
                165                 170                 175

Pro Gly Val Gly Val Pro Gly Val Gly Val Pro Gly Val Gly Val Pro
                180                 185                 190

Gly Val Gly Val Pro Gly Val Gly Val Pro Gly Val Gly Val Pro Gly
            195                 200                 205

Val Gly Val Pro Gly Val Gly Val Pro Gly Val Gly Val Pro Gly Val
        210                 215                 220

Gly Val Pro Gly Val Gly Val Pro Gly Val Gly Val Pro Gly Val Gly
225                 230                 235                 240

Val Pro Gly Val Gly Val Pro Gly Val Gly Val Pro Gly Val Gly Val
                245                 250                 255

Pro Gly Val Gly Val Pro Gly Val Gly Val Pro Gly Val Gly Val Pro
                260                 265                 270

Gly Val Gly Val Pro Gly Val Gly Val Pro Gly Val Gly Val Pro Gly
            275                 280                 285

Val Gly Val Pro Gly Val Gly Val Pro Gly Val Gly Val Pro Gly Val
        290                 295                 300

Gly Val Pro Gly Val Gly Val Pro Gly Val Gly Val Pro Gly Val Gly
305                 310                 315                 320

Val Pro Gly Val Gly Val Pro Gly Val Gly Val Pro Gly Val Gly Val
                325                 330                 335

Pro Gly Val Gly Val Pro Gly Val Gly Val Pro Gly Val Gly Val Pro

```
            340                 345                 350
Gly Val Gly Val Pro Gly Val Gly Val Pro Gly Val Gly Val Pro Gly
            355                 360                 365

Val Gly Val Pro Gly Val Gly Val Pro Gly Val Gly Val Pro Gly Val
            370                 375                 380

Gly Val Pro Gly Val Gly Val Pro Gly Val Gly Val Pro Gly Val Gly
385                 390                 395                 400

Val Pro Gly Val Gly Val Pro Gly Val Gly Val Pro Gly Val Gly Val
            405                 410                 415

Pro Gly Val Gly Val Pro Gly Val Gly Val Pro Gly Val Gly Val Pro
            420                 425                 430

Gly Val Gly Val Pro Gly Val Gly Val Pro Gly Val Gly Val Pro Gly
            435                 440                 445

Val Gly Val Pro Gly Val Gly Val Pro Gly Val Gly Val Pro Gly Val
            450                 455                 460

Gly Val Pro Gly Val Gly Val Pro Gly Val Gly Val Pro Gly Val Gly
465                 470                 475                 480

<210> SEQ ID NO 3
<211> LENGTH: 1127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Arg Ile Ile Pro Gly Phe Met Cys Gln Gly
    50                  55                  60

Gly Asp Phe Thr Arg His Asn Gly Thr Gly Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu Gly Val Pro Gly Ala Gly Val Pro Gly Ala Gly
                165                 170                 175

Val Pro Gly Ala Gly Val Pro Gly Ala Gly Val Pro Gly Ala Gly Val
            180                 185                 190

Pro Gly Ala Gly Val Pro Gly Ala Gly Val Pro Gly Ala Gly Val Pro
        195                 200                 205

Gly Ala Gly Val Pro Gly Ala Gly Val Pro Gly Ala Gly Val Pro Gly
    210                 215                 220
```

-continued

```
Ala Gly Val Pro Gly Ala Gly Val Pro Gly Ala Gly Val Pro Gly Ala
225                 230                 235                 240
Gly Val Pro Gly Ala Gly Val Pro Gly Ala Gly Val Pro Gly Ala Gly
                245                 250                 255
Val Pro Gly Ala Gly Val Pro Gly Ala Gly Val Pro Gly Ala Gly Val
            260                 265                 270
Pro Gly Ala Gly Val Pro Gly Ala Gly Val Pro Gly Ala Gly Val Pro
        275                 280                 285
Gly Ala Gly Val Pro Gly Ala Gly Val Pro Gly Ala Gly Val Pro Gly
    290                 295                 300
Ala Gly Val Pro Gly Ala Gly Val Pro Gly Ala Gly Val Pro Gly Ala
305                 310                 315                 320
Gly Val Pro Gly Ala Gly Val Pro Gly Ala Gly Val Pro Gly Ala Gly
                325                 330                 335
Val Pro Gly Ala Gly Val Pro Gly Ala Gly Val Pro Gly Ala Gly Val
            340                 345                 350
Pro Gly Ala Gly Val Pro Gly Ala Gly Val Pro Gly Ala Gly Val Pro
        355                 360                 365
Gly Ala Gly Val Pro Gly Ala Gly Val Pro Gly Ala Gly Val Pro Gly
    370                 375                 380
Ala Gly Val Pro Gly Ala Gly Val Pro Gly Ala Gly Val Pro Gly Ala
385                 390                 395                 400
Gly Val Pro Gly Ala Gly Val Pro Gly Ala Gly Val Pro Gly Ala Gly
                405                 410                 415
Val Pro Gly Ala Gly Val Pro Gly Ala Gly Val Pro Gly Ala Gly Val
            420                 425                 430
Pro Gly Ala Gly Val Pro Gly Ala Gly Val Pro Gly Ala Gly Val Pro
        435                 440                 445
Gly Ala Gly Val Pro Gly Ala Gly Val Pro Gly Ala Gly Val Pro Gly
    450                 455                 460
Ala Gly Val Pro Gly Ala Gly Val Pro Gly Ala Gly Val Pro Gly Ala
465                 470                 475                 480
Gly Val Pro Gly Ala Gly Val Pro Gly Ala Gly Val Pro Gly Ala Gly
                485                 490                 495
Val Pro Gly Ala Gly Val Pro Gly Ala Gly Val Pro Gly Ala Gly Val
            500                 505                 510
Pro Gly Ala Gly Val Pro Gly Ala Gly Val Pro Gly Ala Gly Val Pro
        515                 520                 525
Gly Ala Gly Val Pro Gly Ala Gly Val Pro Gly Ala Gly Val Pro Gly
    530                 535                 540
Ala Gly Val Pro Gly Ala Gly Val Pro Gly Ala Gly Val Pro Gly Ala
545                 550                 555                 560
Gly Val Pro Gly Ala Gly Val Pro Gly Ala Gly Val Pro Gly Ala Gly
                565                 570                 575
Val Pro Gly Ala Gly Val Pro Gly Ala Gly Val Pro Gly Ala Gly Val
            580                 585                 590
Pro Gly Ala Gly Val Pro Gly Ala Gly Val Pro Gly Ala Gly Val Pro
        595                 600                 605
Gly Ala Gly Val Pro Gly Ala Gly Val Pro Gly Ala Gly Val Pro Gly
    610                 615                 620
Ala Gly Val Pro Gly Ala Gly Val Pro Gly Ala Gly Val Pro Gly Ala
625                 630                 635                 640
Gly Val Pro Gly Ala Gly Val Pro Gly Ala Gly Val Pro Gly Ala Gly
```

-continued

```
                645                 650                 655
Val Pro Gly Ala Gly Val Pro Gly Ala Gly Val Pro Gly Ala Gly Val
                660                 665                 670

Pro Gly Ala Gly Val Pro Gly Ala Gly Val Pro Gly Ala Gly Val Pro
                675                 680                 685

Gly Ala Gly Val Pro Gly Ala Gly Val Pro Gly Ala Gly Val Pro Gly
                690                 695                 700

Ala Gly Val Pro Gly Ala Gly Val Pro Gly Ala Gly Val Pro Gly Ala
705                 710                 715                 720

Gly Val Pro Gly Ala Gly Val Pro Gly Ala Gly Val Pro Gly Ala Gly
                725                 730                 735

Val Pro Gly Ala Gly Val Pro Gly Ala Gly Val Pro Gly Ala Gly Val
                740                 745                 750

Pro Gly Ala Gly Val Pro Gly Ala Gly Val Pro Gly Ala Gly Val Pro
                755                 760                 765

Gly Ala Gly Val Pro Gly Ala Gly Val Pro Gly Ala Gly Val Pro Gly
                770                 775                 780

Ala Gly Val Pro Gly Ala Gly Val Pro Gly Ala Gly Val Pro Gly Ala
785                 790                 795                 800

Gly Val Pro Gly Ala Gly Val Pro Gly Ala Gly Val Pro Gly Ala Gly
                805                 810                 815

Val Pro Gly Ala Gly Val Pro Gly Ala Gly Val Pro Gly Ala Gly Val
                820                 825                 830

Pro Gly Ala Gly Val Pro Gly Ala Gly Val Pro Gly Ala Gly Val Pro
                835                 840                 845

Gly Ala Gly Val Pro Gly Ala Gly Val Pro Gly Ala Gly Val Pro Gly
                850                 855                 860

Ala Gly Val Pro Gly Ala Gly Val Pro Gly Ala Gly Val Pro Gly Ala
865                 870                 875                 880

Gly Val Pro Gly Ala Gly Val Pro Gly Ala Gly Val Pro Gly Ala Gly
                885                 890                 895

Val Pro Gly Ala Gly Val Pro Gly Ala Gly Val Pro Gly Ala Gly Val
                900                 905                 910

Pro Gly Ala Gly Val Pro Gly Ala Gly Val Pro Gly Ala Gly Val Pro
                915                 920                 925

Gly Ala Gly Val Pro Gly Ala Gly Val Pro Gly Ala Gly Val Pro Gly
                930                 935                 940

Ala Gly Val Pro Gly Ala Gly Val Pro Gly Ala Gly Val Pro Gly Ala
945                 950                 955                 960

Gly Val Pro Gly Ala Gly Val Pro Gly Ala Gly Val Pro Gly Ala Gly
                965                 970                 975

Val Pro Gly Ala Gly Val Pro Gly Ala Gly Val Pro Gly Ala Gly Val
                980                 985                 990

Pro Gly Ala Gly Val Pro Gly Ala  Gly Val Pro Gly Ala  Gly Val Pro
                995                1000                1005

Gly Ala  Gly Val Pro Gly Ala  Gly Val Pro Gly Ala  Gly Val Pro
               1010                1015                1020

Gly Ala  Gly Val Pro Gly Ala  Gly Val Pro Gly Ala  Gly Val Pro
               1025                1030                1035

Gly Ala  Gly Val Pro Gly Ala  Gly Val Pro Gly Ala  Gly Val Pro
               1040                1045                1050

Gly Ala  Gly Val Pro Gly Ala  Gly Val Pro Gly Ala  Gly Val Pro
               1055                1060                1065
```

```
Gly Ala Gly Val Pro Gly Ala Gly Val Pro Gly Ala Gly Val Pro
        1070                1075                1080

Gly Ala Gly Val Pro Gly Ala Gly Val Pro Gly Ala Gly Val Pro
        1085                1090                1095

Gly Ala Gly Val Pro Gly Ala Gly Val Pro Gly Ala Gly Val Pro
        1100                1105                1110

Gly Ala Gly Val Pro Gly Ala Gly Val Pro Gly Ala Gly Tyr
        1115                1120                1125

<210> SEQ ID NO 4
<211> LENGTH: 647
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Arg Ile Ile Pro Gly Phe Met Cys Gln Gly
    50                  55                  60

Gly Asp Phe Thr Arg His Asn Gly Thr Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu Gly Val Pro Gly Val Gly Val Pro Gly Val Gly
                165                 170                 175

Val Pro Gly Val Gly Val Pro Gly Val Gly Val Pro Gly Val Gly Val
            180                 185                 190

Pro Gly Val Gly Val Pro Gly Val Gly Val Pro Gly Val Gly Val Pro
        195                 200                 205

Gly Val Gly Val Pro Gly Val Gly Val Pro Gly Val Gly Val Pro Gly
    210                 215                 220

Val Gly Val Pro Gly Val Gly Val Pro Gly Val Gly Val Pro Gly Val
225                 230                 235                 240

Gly Val Pro Gly Val Gly Val Pro Gly Val Gly Val Pro Gly Val Gly
                245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Val Pro
        275                 280                 285

Gly Val Gly Val Pro Gly Val Gly Val Pro Gly Val Gly Val Pro Gly
```

```
            290                 295                 300
Val Gly Val Pro Gly Val Gly Val Pro Gly Val Gly Val Pro Gly Val
305                 310                 315                 320

Gly Val Pro Gly Val Gly Val Pro Gly Val Gly Val Pro Gly Val Gly
                325                 330                 335

Val Pro Gly Val Gly Val Pro Gly Val Gly Val Pro Gly Val Gly Val
                340                 345                 350

Pro Gly Val Gly Val Pro Gly Val Gly Val Pro Gly Val Gly Val Pro
                355                 360                 365

Gly Val Gly Val Pro Gly Val Gly Val Pro Gly Val Gly Val Pro Gly
        370                 375                 380

Val Gly Val Pro Gly Val Gly Val Pro Gly Val Gly Val Pro Gly Val
385                 390                 395                 400

Gly Val Pro Gly Val Gly Val Pro Gly Val Gly Val Pro Gly Val Gly
                405                 410                 415

Val Pro Gly Val Gly Val Pro Gly Val Gly Val Pro Gly Val Gly Val
                420                 425                 430

Pro Gly Val Gly Val Pro Gly Val Gly Val Pro Gly Val Gly Val Pro
                435                 440                 445

Gly Val Gly Val Pro Gly Val Gly Val Pro Gly Val Gly Val Pro Gly
        450                 455                 460

Val Gly Val Pro Gly Val Gly Val Pro Gly Val Gly Val Pro Gly Val
465                 470                 475                 480

Gly Val Pro Gly Val Gly Val Pro Gly Val Gly Val Pro Gly Val Gly
                485                 490                 495

Val Pro Gly Val Gly Val Pro Gly Val Gly Val Pro Gly Val Gly Val
                500                 505                 510

Pro Gly Val Gly Val Pro Gly Val Gly Val Pro Gly Val Gly Val Pro
                515                 520                 525

Gly Val Gly Val Pro Gly Val Gly Val Pro Gly Val Gly Val Pro Gly
        530                 535                 540

Val Gly Val Pro Gly Val Gly Val Pro Gly Val Gly Val Pro Gly Val
545                 550                 555                 560

Gly Val Pro Gly Val Gly Val Pro Gly Val Gly Val Pro Gly Val Gly
                565                 570                 575

Val Pro Gly Val Gly Val Pro Gly Val Gly Val Pro Gly Val Gly Val
                580                 585                 590

Pro Gly Val Gly Val Pro Gly Val Gly Val Pro Gly Val Gly Val Pro
                595                 600                 605

Gly Val Gly Val Pro Gly Val Gly Val Pro Gly Val Gly Val Pro Gly
        610                 615                 620

Val Gly Val Pro Gly Val Gly Val Pro Gly Val Gly Val Pro Gly Val
625                 630                 635                 640

Gly Val Pro Gly Val Gly Tyr
                645

<210> SEQ ID NO 5
<211> LENGTH: 567
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
```

| | |
|---|---|
| tctagaaata attttgttta actttaagaa ggaggagtac atatgggtat ggttaacccg | 60 |
| accgttttct cgacatcgc tgttgacggt gaaccgctgg tcgtgtttc tttcgaactg | 120 |
| ttcgctgaca aagttccgaa aaccgctgaa aacttccgtg ctctgtctac cggtgaaaaa | 180 |
| ggtttcggtt acaaaggttc ttgcttccac cgtatcatcc cgggtttcat gtgccagggt | 240 |
| ggtgacttca cccgtcacaa cggtaccggt ggtaaatcta tctacggtga aaaattcgaa | 300 |
| gacgaaaact tcatcctgaa acacaccggt ccgggtatcc tgtctatggc taacgctggt | 360 |
| ccgaacacca acggttctca gttcttcatc tgcaccgcta aaaccgaatg gctggacggt | 420 |
| aaacacgttg ttttcggtaa agttaaagaa ggtatgaaca tcgttgaagc tatggaacgt | 480 |
| ttcggttctc gtaacggtaa aacctctaaa aaaatcacca tcgctgactg cggtcagctg | 540 |
| gaaggttgat aatgatcttc aggatcc | 567 |

<210> SEQ ID NO 6
<211> LENGTH: 523
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

| | |
|---|---|
| tatgggtatg gttaacccga ccgttttctt cgacatcgct gttgacggtg aaccgctggg | 60 |
| tcgtgtttct ttcgaactgt tcgctgacaa agttccgaaa accgctgaaa acttccgtgc | 120 |
| tctgtctacc ggtgaaaaag gtttcggtta caaaggttct tgcttccacc gtatcatccc | 180 |
| gggtttcatg tgccagggtg gtgacttcac ccgtcacaac ggtaccggtg gtaaatctat | 240 |
| ctacggtgaa aaattcgaag acgaaaactt catcctgaaa cacaccggtc cgggtatcct | 300 |
| gtctatggct aacgctggtc cgaacaccaa cggttctcag ttcttcatct gcaccgctaa | 360 |
| aaccgaatgg ctggacggta aacacgttgt tttcggtaaa gttaaagaag gtatgaacat | 420 |
| cgttgaagct atgaacgtt tcggttctcg taacggtaaa acctctaaaa aaatcaccat | 480 |
| cgctgactgc ggtcagctgg aaggttactg atctcctcgg atc | 523 |

<210> SEQ ID NO 7
<211> LENGTH: 520
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

| | |
|---|---|
| catatggtta acccgaccgt tttcttcgac atcgctgttg acggtgaacc gctgggtcgt | 60 |
| gtttctttcg aactgttcgc tgacaaagtt ccgaaaaccg ctgaaaactt ccgtgctctg | 120 |
| tctaccggtg aaaaaggttt cggttacaaa ggttcttgct tccaccgtat catcccgggt | 180 |
| ttcatgtgcc agggtggtga cttcacccgt cacaacggta ccggtggtaa atctatctac | 240 |
| ggtgaaaaat cgaagacga aaacttcatc ctgaaacaca ccggtccggg tatcctgtct | 300 |
| atggctaacg ctggtccgaa caccaacggt tctcagttct catctgcac cgctaaaacc | 360 |
| gaatggctgg acggtaaaca cgttgttttc ggtaaagtta agaaggtat gaacatcgtt | 420 |
| gaagctatgg aacgtttcgg ttctcgtaac ggtaaaacct ctaaaaaaat caccatcgct | 480 |
| gactgcggtc agctggaagg ttactgatct cctcggatcc | 520 |

```
<210> SEQ ID NO 8
<211> LENGTH: 812
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Met Val Asn Pro Thr Val Phe Phe Asp Ile Ala Val Asp Gly Glu
1               5                   10                  15

Pro Leu Gly Arg Val Ser Phe Glu Leu Phe Ala Asp Lys Val Pro Lys
                20                  25                  30

Thr Ala Glu Asn Phe Arg Ala Leu Ser Thr Gly Glu Lys Gly Phe Gly
            35                  40                  45

Tyr Lys Gly Ser Cys Phe His Arg Ile Ile Pro Gly Phe Met Cys Gln
50                  55                  60

Gly Gly Asp Phe Thr Arg His Asn Gly Thr Gly Lys Ser Ile Tyr
65                  70                  75                  80

Gly Glu Lys Phe Glu Asp Glu Asn Phe Ile Leu Lys His Thr Gly Pro
                85                  90                  95

Gly Ile Leu Ser Met Ala Asn Ala Gly Pro Asn Thr Asn Gly Ser Gln
            100                 105                 110

Phe Phe Ile Cys Thr Ala Lys Thr Glu Trp Leu Asp Gly Lys His Val
        115                 120                 125

Val Phe Gly Lys Val Lys Glu Gly Met Asn Ile Val Glu Ala Met Glu
130                 135                 140

Arg Phe Gly Ser Arg Asn Gly Lys Thr Ser Lys Lys Ile Thr Ile Ala
145                 150                 155                 160

Asp Cys Gly Gln Leu Glu Gly Val Pro Gly Ala Gly Val Pro Gly Ala
                165                 170                 175

Gly Val Pro Gly Ala Gly Val Pro Gly Ala Gly Val Pro Gly Ala Gly
            180                 185                 190

Val Pro Gly Ala Gly Val Pro Gly Ala Gly Val Pro Gly Ala Gly Val
        195                 200                 205

Pro Gly Ala Gly Val Pro Gly Ala Gly Val Pro Gly Ala Gly Val Pro
210                 215                 220

Gly Ala Gly Val Pro Gly Ala Gly Val Pro Gly Ala Gly Val Pro Gly
225                 230                 235                 240

Ala Gly Val Pro Gly Ala Gly Val Pro Gly Ala Gly Val Pro Gly Ala
                245                 250                 255

Gly Val Pro Gly Ala Gly Val Pro Gly Ala Gly Val Pro Gly Ala Gly
            260                 265                 270

Val Pro Gly Ala Gly Val Pro Gly Ala Gly Val Pro Gly Ala Gly Val
        275                 280                 285

Pro Gly Ala Gly Val Pro Gly Ala Gly Val Pro Gly Ala Gly Val Pro
290                 295                 300

Gly Ala Gly Val Pro Gly Ala Gly Val Pro Gly Ala Gly Val Pro Gly
305                 310                 315                 320

Ala Gly Val Pro Gly Ala Gly Val Pro Gly Ala Gly Val Pro Gly Ala
                325                 330                 335

Gly Val Pro Gly Ala Gly Val Pro Gly Ala Gly Val Pro Gly Ala Gly
            340                 345                 350

Val Pro Gly Ala Gly Val Pro Gly Ala Gly Val Pro Gly Ala Gly Val
        355                 360                 365
```

```
Pro Gly Ala Gly Val Pro Gly Ala Gly Val Pro Gly Ala Gly Val Pro
    370                 375                 380
Gly Ala Gly Val Pro Gly Ala Gly Val Pro Gly Ala Gly Val Pro Gly
385                 390                 395                 400
Ala Gly Val Pro Gly Ala Gly Val Pro Gly Ala Gly Val Pro Gly Ala
                405                 410                 415
Gly Val Pro Gly Ala Gly Val Pro Gly Ala Gly Val Pro Gly Ala Gly
            420                 425                 430
Val Pro Gly Ala Gly Val Pro Gly Ala Gly Val Pro Gly Ala Gly Val
        435                 440                 445
Pro Gly Ala Gly Val Pro Gly Ala Gly Val Pro Gly Ala Gly Val Pro
    450                 455                 460
Gly Ala Gly Val Pro Gly Ala Gly Val Pro Gly Ala Gly Val Pro Gly
465                 470                 475                 480
Ala Gly Val Pro Gly Ala Gly Val Pro Gly Ala Gly Val Pro Gly Ala
                485                 490                 495
Gly Val Pro Gly Ala Gly Val Pro Gly Ala Gly Val Pro Gly Ala Gly
            500                 505                 510
Val Pro Gly Ala Gly Val Pro Gly Ala Gly Val Pro Gly Ala Gly Val
        515                 520                 525
Pro Gly Ala Gly Val Pro Gly Ala Gly Val Pro Gly Ala Gly Val Pro
    530                 535                 540
Gly Ala Gly Val Pro Gly Ala Gly Val Pro Gly Ala Gly Val Pro Gly
545                 550                 555                 560
Ala Gly Val Pro Gly Ala Gly Val Pro Gly Ala Gly Val Pro Gly Ala
                565                 570                 575
Gly Val Pro Gly Ala Gly Val Pro Gly Ala Gly Val Pro Gly Ala Gly
            580                 585                 590
Val Pro Gly Ala Gly Val Pro Gly Ala Gly Val Pro Gly Ala Gly Val
        595                 600                 605
Pro Gly Ala Gly Val Pro Gly Ala Gly Val Pro Gly Ala Gly Val Pro
    610                 615                 620
Gly Ala Gly Val Pro Gly Ala Gly Val Pro Gly Ala Gly Val Pro Gly
625                 630                 635                 640
Ala Gly Val Pro Gly Ala Gly Met Val Asn Pro Thr Val Phe Phe Asp
                645                 650                 655
Ile Ala Val Asp Gly Glu Pro Leu Gly Arg Val Ser Phe Glu Leu Phe
                660                 665                 670
Ala Asp Lys Val Pro Lys Thr Ala Glu Asn Phe Arg Ala Leu Ser Thr
                675                 680                 685
Gly Glu Lys Gly Phe Gly Tyr Lys Gly Ser Cys Phe His Arg Ile Ile
            690                 695                 700
Pro Gly Phe Met Cys Gln Gly Gly Asp Phe Thr Arg His Asn Gly Thr
705                 710                 715                 720
Gly Gly Lys Ser Ile Tyr Gly Glu Lys Phe Glu Asp Glu Asn Phe Ile
                725                 730                 735
Leu Lys His Thr Gly Pro Gly Ile Leu Ser Met Ala Asn Ala Gly Pro
            740                 745                 750
Asn Thr Asn Gly Ser Gln Phe Phe Ile Cys Thr Ala Lys Thr Glu Trp
            755                 760                 765
Leu Asp Gly Lys His Val Phe Gly Lys Val Lys Glu Gly Met Asn Ile
        770                 775                 780
Val Glu Ala Met Glu Arg Phe Gly Ser Arg Asn Gly Lys Thr Ser Lys
```

```
                  785             790             795             800

Lys Ile Thr Ile Ala Asp Cys Gly Gln Leu Glu Gly
                805             810

<210> SEQ ID NO 9
<211> LENGTH: 1026
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gly Met Val Asn Pro Thr Val Phe Phe Asp Ile Ala Val Asp Gly
1               5                   10                  15

Glu Pro Leu Gly Arg Val Ser Phe Glu Leu Phe Ala Asp Lys Val Pro
            20                  25                  30

Lys Thr Ala Glu Asn Phe Arg Ala Leu Ser Thr Gly Glu Lys Gly Phe
        35                  40                  45

Gly Tyr Lys Gly Ser Cys Phe His Arg Ile Ile Pro Gly Phe Met Cys
    50                  55                  60

Gln Gly Gly Asp Phe Thr Arg His Asn Gly Thr Gly Lys Ser Ile
65                  70                  75                  80

Tyr Gly Glu Lys Phe Glu Asp Glu Asn Phe Ile Leu Lys His Thr Gly
                85                  90                  95

Pro Gly Ile Leu Ser Met Ala Asn Ala Gly Pro Asn Thr Asn Gly Ser
            100                 105                 110

Gln Phe Phe Ile Cys Thr Ala Lys Thr Glu Trp Leu Asp Gly Lys His
        115                 120                 125

Val Val Phe Gly Lys Val Lys Glu Gly Met Asn Ile Val Glu Ala Met
    130                 135                 140

Glu Arg Phe Gly Ser Arg Asn Gly Lys Thr Ser Lys Lys Ile Thr Ile
145                 150                 155                 160

Ala Asp Cys Gly Gln Leu Glu Gly Val Pro Gly Ala Gly Val Pro Gly
                165                 170                 175

Ala Gly Val Pro Gly Ala Gly Val Pro Gly Ala Gly Val Pro Gly Ala
            180                 185                 190

Gly Val Pro Gly Ala Gly Val Pro Gly Ala Gly Val Pro Gly Ala Gly
        195                 200                 205

Val Pro Gly Ala Gly Val Pro Gly Ala Gly Val Pro Gly Ala Gly Val
    210                 215                 220

Pro Gly Ala Gly Val Pro Gly Ala Gly Val Pro Gly Ala Gly Val Pro
225                 230                 235                 240

Gly Ala Gly Val Pro Gly Ala Gly Val Pro Gly Ala Gly Val Pro Gly
                245                 250                 255

Ala Gly Val Pro Gly Ala Gly Val Pro Gly Ala Gly Val Pro Gly Ala
            260                 265                 270

Gly Val Pro Gly Ala Gly Val Pro Gly Ala Gly Val Pro Gly Ala Gly
        275                 280                 285

Met Val Asn Pro Thr Val Phe Phe Asp Ile Ala Val Asp Gly Glu Pro
    290                 295                 300

Leu Gly Arg Val Ser Phe Glu Leu Phe Ala Asp Lys Val Pro Lys Thr
305                 310                 315                 320

Ala Glu Asn Phe Arg Ala Leu Ser Thr Gly Glu Lys Gly Phe Gly Tyr
                325                 330                 335
```

-continued

```
Lys Gly Ser Cys Phe His Arg Ile Ile Pro Gly Phe Met Cys Gln Gly
                340                 345                 350

Gly Asp Phe Thr Arg His Asn Gly Thr Gly Gly Lys Ser Ile Tyr Gly
            355                 360                 365

Glu Lys Phe Glu Asp Glu Asn Phe Ile Leu Lys His Thr Gly Pro Gly
        370                 375                 380

Ile Leu Ser Met Ala Asn Ala Gly Pro Asn Thr Asn Gly Ser Gln Phe
385                 390                 395                 400

Phe Ile Cys Thr Ala Lys Thr Glu Trp Leu Asp Gly Lys His Val Val
                405                 410                 415

Phe Gly Lys Val Lys Glu Gly Met Asn Ile Val Glu Ala Met Glu Arg
            420                 425                 430

Phe Gly Ser Arg Asn Gly Lys Thr Ser Lys Lys Ile Thr Ile Ala Asp
        435                 440                 445

Cys Gly Gln Leu Glu Gly Val Pro Gly Ala Gly Val Pro Gly Ala Gly
    450                 455                 460

Val Pro Gly Ala Gly Val Pro Gly Ala Gly Val Pro Gly Ala Gly Val
465                 470                 475                 480

Pro Gly Ala Gly Val Pro Gly Ala Gly Val Pro Gly Ala Gly Val Pro
                485                 490                 495

Gly Ala Gly Val Pro Gly Ala Gly Val Pro Gly Ala Gly Val Pro Gly
            500                 505                 510

Ala Gly Val Pro Gly Ala Gly Val Pro Gly Ala Gly Val Pro Gly Ala
        515                 520                 525

Gly Val Pro Gly Ala Gly Val Pro Gly Ala Gly Val Pro Gly Ala Gly
    530                 535                 540

Val Pro Gly Ala Gly Val Pro Gly Ala Gly Val Pro Gly Ala Gly Val
545                 550                 555                 560

Pro Gly Ala Gly Val Pro Gly Ala Gly Val Pro Gly Ala Gly Met Val
                565                 570                 575

Asn Pro Thr Val Phe Phe Asp Ile Ala Val Asp Gly Glu Pro Leu Gly
            580                 585                 590

Arg Val Ser Phe Glu Leu Phe Ala Asp Lys Val Pro Lys Thr Ala Glu
        595                 600                 605

Asn Phe Arg Ala Leu Ser Thr Gly Glu Lys Gly Phe Gly Tyr Lys Gly
    610                 615                 620

Ser Cys Phe His Arg Ile Ile Pro Gly Phe Met Cys Gln Gly Gly Asp
625                 630                 635                 640

Phe Thr Arg His Asn Gly Thr Gly Gly Lys Ser Ile Tyr Gly Glu Lys
                645                 650                 655

Phe Glu Asp Glu Asn Phe Ile Leu Lys His Thr Gly Pro Gly Ile Leu
            660                 665                 670

Ser Met Ala Asn Ala Gly Pro Asn Thr Asn Gly Ser Gln Phe Phe Ile
        675                 680                 685

Cys Thr Ala Lys Thr Glu Trp Leu Asp Gly Lys His Val Val Phe Gly
    690                 695                 700

Lys Val Lys Glu Gly Met Asn Ile Val Glu Ala Met Glu Arg Phe Gly
705                 710                 715                 720

Ser Arg Asn Gly Lys Thr Ser Lys Lys Ile Thr Ile Ala Asp Cys Gly
                725                 730                 735

Gln Leu Glu Gly Val Pro Gly Ala Gly Val Pro Gly Ala Gly Val Pro
            740                 745                 750

Gly Ala Gly Val Pro Gly Ala Gly Val Pro Gly Ala Gly Val Pro Gly
```

```
                        755                 760                 765
Ala Gly Val Pro Gly Ala Gly Val Pro Gly Ala Gly Val Pro Gly Ala
    770                 775                 780

Gly Val Pro Gly Ala Gly Val Pro Gly Ala Gly Val Pro Gly Ala Gly
785                 790                 795                 800

Val Pro Gly Ala Gly Val Pro Gly Ala Gly Val Pro Gly Ala Gly Val
                805                 810                 815

Pro Gly Ala Gly Val Pro Gly Ala Gly Val Pro Gly Ala Gly Val Pro
            820                 825                 830

Gly Ala Gly Val Pro Gly Ala Gly Val Pro Gly Ala Gly Val Pro Gly
        835                 840                 845

Ala Gly Val Pro Gly Ala Gly Val Pro Gly Ala Gly Met Val Asn Pro
    850                 855                 860

Thr Val Phe Phe Asp Ile Ala Val Asp Gly Glu Pro Leu Gly Arg Val
865                 870                 875                 880

Ser Phe Glu Leu Phe Ala Asp Lys Val Pro Lys Thr Ala Glu Asn Phe
                885                 890                 895

Arg Ala Leu Ser Thr Gly Glu Lys Gly Phe Gly Tyr Lys Gly Ser Cys
            900                 905                 910

Phe His Arg Ile Ile Pro Gly Phe Met Cys Gln Gly Gly Asp Phe Thr
        915                 920                 925

Arg His Asn Gly Thr Gly Gly Lys Ser Ile Tyr Gly Glu Lys Phe Glu
    930                 935                 940

Asp Glu Asn Phe Ile Leu Lys His Thr Gly Pro Gly Ile Leu Ser Met
945                 950                 955                 960

Ala Asn Ala Gly Pro Asn Thr Asn Gly Ser Gln Phe Phe Ile Cys Thr
                965                 970                 975

Ala Lys Thr Glu Trp Leu Asp Gly Lys His Val Val Phe Gly Lys Val
            980                 985                 990

Lys Glu Gly Met Asn Ile Val Glu  Ala Met Glu Arg Phe  Gly Ser Arg
        995                 1000                1005

Asn Gly  Lys Thr Ser Lys Lys  Ile Thr Ile Ala Asp  Cys Gly Gln
    1010                1015                1020

Leu Glu  Gly
    1025

<210> SEQ ID NO 10
<211> LENGTH: 1016
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80
```

```
Tyr Ala Tyr Gly Ala Thr Gly His Pro Gly Ile Ile Pro Pro His Ala
                85              90              95
Thr Leu Val Phe Asp Val Glu Leu Leu Lys Leu Glu Val Pro Gly Ala
            100             105             110
Gly Val Pro Gly Ala Gly Val Pro Gly Ala Gly Val Pro Gly Ala Gly
            115             120             125
Val Pro Gly Ala Gly Val Pro Gly Ala Gly Val Pro Gly Ala Gly Val
            130             135             140
Pro Gly Ala Gly Val Pro Gly Ala Gly Val Pro Gly Ala Gly Val Pro
145             150             155             160
Gly Ala Gly Val Pro Gly Ala Gly Val Pro Gly Ala Gly Val Pro Gly
            165             170             175
Ala Gly Val Pro Gly Ala Gly Val Pro Gly Ala Gly Val Pro Gly Ala
            180             185             190
Gly Val Pro Gly Ala Gly Val Pro Gly Ala Gly Val Pro Gly Ala Gly
            195             200             205
Val Pro Gly Ala Gly Val Pro Gly Ala Gly Val Pro Gly Ala Gly Val
            210             215             220
Pro Gly Ala Gly Gly Val Gln Val Glu Thr Ile Ser Pro Gly Asp Gly
225             230             235             240
Arg Thr Phe Pro Lys Arg Gly Gln Thr Cys Val Val His Tyr Thr Gly
            245             250             255
Met Leu Glu Asp Gly Lys Lys Phe Asp Ser Ser Arg Asp Arg Asn Lys
            260             265             270
Pro Phe Lys Phe Met Leu Gly Lys Gln Glu Val Ile Arg Gly Trp Glu
            275             280             285
Glu Gly Val Ala Gln Met Ser Val Gly Gln Arg Ala Lys Leu Thr Ile
            290             295             300
Ser Pro Asp Tyr Ala Tyr Gly Ala Thr Gly His Pro Gly Ile Ile Pro
305             310             315             320
Pro His Ala Thr Leu Val Phe Asp Val Glu Leu Leu Lys Leu Glu Val
            325             330             335
Pro Gly Ala Gly Val Pro Gly Ala Gly Val Pro Gly Ala Gly Val Pro
            340             345             350
Gly Ala Gly Val Pro Gly Ala Gly Val Pro Gly Ala Gly Val Pro Gly
            355             360             365
Ala Gly Val Pro Gly Ala Gly Val Pro Gly Ala Gly Val Pro Gly Ala
            370             375             380
Gly Val Pro Gly Ala Gly Val Pro Gly Ala Gly Val Pro Gly Ala Gly
385             390             395             400
Val Pro Gly Ala Gly Val Pro Gly Ala Gly Val Pro Gly Ala Gly Val
            405             410             415
Pro Gly Ala Gly Val Pro Gly Ala Gly Val Pro Gly Ala Gly Val Pro
            420             425             430
Gly Ala Gly Val Pro Gly Ala Gly Val Pro Gly Ala Gly Val Pro Gly
            435             440             445
Ala Gly Val Pro Gly Ala Gly Val Gln Val Glu Thr Ile Ser Pro
            450             455             460
Gly Asp Gly Arg Thr Phe Pro Lys Arg Gly Gln Thr Cys Val Val His
465             470             475             480
Tyr Thr Gly Met Leu Glu Asp Gly Lys Lys Phe Asp Ser Ser Arg Asp
            485             490             495
Arg Asn Lys Pro Phe Lys Phe Met Leu Gly Lys Gln Glu Val Ile Arg
```

-continued

```
                500                 505                 510
Gly Trp Glu Glu Gly Val Ala Gln Met Ser Val Gly Gln Arg Ala Lys
            515                 520                 525

Leu Thr Ile Ser Pro Asp Tyr Ala Tyr Gly Ala Thr Gly His Pro Gly
            530                 535                 540

Ile Ile Pro Pro His Ala Thr Leu Val Phe Asp Val Glu Leu Leu Lys
545                 550                 555                 560

Leu Glu Val Pro Gly Ala Gly Val Pro Gly Ala Gly Val Pro Gly Ala
                565                 570                 575

Gly Val Pro Gly Ala Gly Val Pro Gly Ala Gly Val Pro Gly Ala Gly
            580                 585                 590

Val Pro Gly Ala Gly Val Pro Gly Ala Gly Val Pro Gly Ala Gly Val
            595                 600                 605

Pro Gly Ala Gly Val Pro Gly Ala Gly Val Pro Gly Ala Gly Val Pro
            610                 615                 620

Gly Ala Gly Val Pro Gly Ala Gly Val Pro Gly Ala Gly Val Pro Gly
625                 630                 635                 640

Ala Gly Val Pro Gly Ala Gly Val Pro Gly Ala Gly Val Pro Gly Ala
                645                 650                 655

Gly Val Pro Gly Ala Gly Val Pro Gly Ala Gly Val Pro Gly Ala Gly
            660                 665                 670

Val Pro Gly Ala Gly Val Pro Gly Ala Gly Gly Val Gln Val Glu Thr
            675                 680                 685

Ile Ser Pro Gly Asp Gly Arg Thr Phe Pro Lys Arg Gly Gln Thr Cys
            690                 695                 700

Val Val His Tyr Thr Gly Met Leu Glu Asp Gly Lys Lys Phe Asp Ser
705                 710                 715                 720

Ser Arg Asp Arg Asn Lys Pro Phe Lys Phe Met Leu Gly Lys Gln Glu
                725                 730                 735

Val Ile Arg Gly Trp Glu Glu Gly Val Ala Gln Met Ser Val Gly Gln
            740                 745                 750

Arg Ala Lys Leu Thr Ile Ser Pro Asp Tyr Ala Tyr Gly Ala Thr Gly
            755                 760                 765

His Pro Gly Ile Ile Pro Pro His Ala Thr Leu Val Phe Asp Val Glu
            770                 775                 780

Leu Leu Lys Leu Glu Val Pro Gly Ala Gly Val Pro Gly Ala Gly Val
785                 790                 795                 800

Pro Gly Ala Gly Val Pro Gly Ala Gly Val Pro Gly Ala Gly Val Pro
                805                 810                 815

Gly Ala Gly Val Pro Gly Ala Gly Val Pro Gly Ala Gly Val Pro Gly
            820                 825                 830

Ala Gly Val Pro Gly Ala Gly Val Pro Gly Ala Gly Val Pro Gly Ala
            835                 840                 845

Gly Val Pro Gly Ala Gly Val Pro Gly Ala Gly Val Pro Gly Ala Gly
            850                 855                 860

Val Pro Gly Ala Gly Val Pro Gly Ala Gly Val Pro Gly Ala Gly Val
865                 870                 875                 880

Pro Gly Ala Gly Val Pro Gly Ala Gly Val Pro Gly Ala Gly Val Pro
                885                 890                 895

Gly Ala Gly Val Pro Gly Ala Gly Val Pro Gly Ala Gly Gly Val Gln
            900                 905                 910

Val Glu Thr Ile Ser Pro Gly Asp Gly Arg Thr Phe Pro Lys Arg Gly
            915                 920                 925
```

```
Gln Thr Cys Val Val His Tyr Thr Gly Met Leu Glu Asp Gly Lys Lys
            930                 935                 940

Phe Asp Ser Ser Arg Asp Arg Asn Lys Pro Phe Lys Phe Met Leu Gly
945                 950                 955                 960

Lys Gln Glu Val Ile Arg Gly Trp Glu Glu Gly Val Ala Gln Met Ser
                965                 970                 975

Val Gly Gln Arg Ala Lys Leu Thr Ile Ser Pro Asp Tyr Ala Tyr Gly
            980                 985                 990

Ala Thr Gly His Pro Gly Ile Ile Pro Pro His Ala Thr Leu Val Phe
        995                1000                1005

Asp Val Glu Leu Leu Lys Leu Glu
       1010                1015

<210> SEQ ID NO 11
<211> LENGTH: 1016
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
                20                  25                  30

Asp Gly Lys Lys Phe Asp Ser Ser Arg Asp Arg Asn Lys Pro Phe Lys
            35                  40                  45

Phe Met Leu Gly Lys Gln Glu Val Ile Arg Gly Trp Glu Glu Gly Val
50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Val Pro Gly Val
            100                 105                 110

Gly Val Pro Gly Val Gly Val Pro Gly Val Gly Val Pro Gly Val Gly
            115                 120                 125

Val Pro Gly Val Gly Val Pro Gly Val Gly Val Pro Gly Val Gly Val
        130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
        195                 200                 205

Val Pro Gly Val Gly Val Pro Gly Val Gly Val Pro Gly Val Gly Val
    210                 215                 220

Pro Gly Val Gly Gly Val Gln Val Glu Thr Ile Ser Pro Gly Asp Gly
225                 230                 235                 240

Arg Thr Phe Pro Lys Arg Gly Gln Thr Cys Val Val His Tyr Thr Gly
                245                 250                 255

Met Leu Glu Asp Gly Lys Lys Phe Asp Ser Ser Arg Asp Arg Asn Lys
```

```
                260                 265                 270
Pro Phe Lys Phe Met Leu Gly Lys Gln Glu Val Ile Arg Gly Trp Glu
            275                 280                 285

Glu Gly Val Ala Gln Met Ser Val Gly Gln Arg Ala Lys Leu Thr Ile
            290                 295                 300

Ser Pro Asp Tyr Ala Tyr Gly Ala Thr Gly His Pro Gly Ile Ile Pro
305                 310                 315                 320

Pro His Ala Thr Leu Val Phe Asp Val Glu Leu Leu Lys Leu Glu Val
                325                 330                 335

Pro Gly Val Gly Val Pro Gly Val Gly Val Pro Gly Val Gly Val Pro
            340                 345                 350

Gly Val Gly Val Pro Gly Val Gly Val Pro Gly Val Gly Val Pro Gly
            355                 360                 365

Val Gly Val Pro Gly Val Gly Val Pro Gly Val Gly Val Pro Gly Val
            370                 375                 380

Gly Val Pro Gly Val Gly Val Pro Gly Val Gly Val Pro Gly Val Gly
385                 390                 395                 400

Val Pro Gly Val Gly Val Pro Gly Val Gly Val Pro Gly Val Gly Val
            405                 410                 415

Pro Gly Val Gly Val Pro Gly Val Gly Val Pro Gly Val Gly Val Pro
            420                 425                 430

Gly Val Gly Val Pro Gly Val Gly Val Pro Gly Val Gly Val Pro Gly
            435                 440                 445

Val Gly Val Pro Gly Val Gly Val Gln Val Glu Thr Ile Ser Pro
            450                 455                 460

Gly Asp Gly Arg Thr Phe Pro Lys Arg Gly Gln Thr Cys Val Val His
465                 470                 475                 480

Tyr Thr Gly Met Leu Glu Asp Gly Lys Lys Phe Asp Ser Ser Arg Asp
                485                 490                 495

Arg Asn Lys Pro Phe Lys Phe Met Leu Gly Lys Gln Glu Val Ile Arg
            500                 505                 510

Gly Trp Glu Glu Gly Val Ala Gln Met Ser Val Gly Gln Arg Ala Lys
            515                 520                 525

Leu Thr Ile Ser Pro Asp Tyr Ala Tyr Gly Ala Thr Gly His Pro Gly
            530                 535                 540

Ile Ile Pro Pro His Ala Thr Leu Val Phe Asp Val Glu Leu Leu Lys
545                 550                 555                 560

Leu Glu Val Pro Gly Val Gly Val Pro Gly Val Gly Val Pro Gly Val
                565                 570                 575

Gly Val Pro Gly Val Gly Val Pro Gly Val Gly Val Pro Gly Val Gly
            580                 585                 590

Val Pro Gly Val Gly Val Pro Gly Val Gly Val Pro Gly Val Gly Val
            595                 600                 605

Pro Gly Val Gly Val Pro Gly Val Gly Val Pro Gly Val Gly Val Pro
            610                 615                 620

Gly Val Gly Val Pro Gly Val Gly Val Pro Gly Val Gly Val Pro Gly
625                 630                 635                 640

Val Gly Val Pro Gly Val Gly Val Pro Gly Val Gly Val Pro Gly Val
                645                 650                 655

Gly Val Pro Gly Val Gly Val Pro Gly Val Gly Val Pro Gly Val Gly
            660                 665                 670

Val Pro Gly Val Gly Val Pro Gly Val Gly Gly Val Gln Val Glu Thr
            675                 680                 685
```

Ile Ser Pro Gly Asp Gly Arg Thr Phe Pro Lys Arg Gly Gln Thr Cys
    690                 695                 700

Val Val His Tyr Thr Gly Met Leu Glu Asp Gly Lys Lys Phe Asp Ser
705                 710                 715                 720

Ser Arg Asp Arg Asn Lys Pro Phe Lys Phe Met Leu Gly Lys Gln Glu
                725                 730                 735

Val Ile Arg Gly Trp Glu Glu Gly Val Ala Gln Met Ser Val Gly Gln
            740                 745                 750

Arg Ala Lys Leu Thr Ile Ser Pro Asp Tyr Ala Tyr Gly Ala Thr Gly
        755                 760                 765

His Pro Gly Ile Ile Pro Pro His Ala Thr Leu Val Phe Asp Val Glu
770                 775                 780

Leu Leu Lys Leu Glu Val Pro Gly Val Gly Val Pro Gly Val Gly Val
785                 790                 795                 800

Pro Gly Val Gly Val Pro Gly Val Gly Val Pro Gly Val Gly Val Pro
                805                 810                 815

Gly Val Gly Val Pro Gly Val Gly Val Pro Gly Val Gly Val Pro Gly
            820                 825                 830

Val Gly Val Pro Gly Val Gly Val Pro Gly Val Gly Val Pro Gly Val
        835                 840                 845

Gly Val Pro Gly Val Gly Val Pro Gly Val Gly Val Pro Gly Val Gly
850                 855                 860

Val Pro Gly Val Gly Val Pro Gly Val Gly Val Pro Gly Val Gly Val
865                 870                 875                 880

Pro Gly Val Gly Val Pro Gly Val Gly Val Pro Gly Val Gly Val Pro
                885                 890                 895

Gly Val Gly Val Pro Gly Val Gly Val Pro Gly Val Gly Val Gly Val Gln
            900                 905                 910

Val Glu Thr Ile Ser Pro Gly Asp Gly Arg Thr Phe Pro Lys Arg Gly
        915                 920                 925

Gln Thr Cys Val Val His Tyr Thr Gly Met Leu Glu Asp Gly Lys Lys
930                 935                 940

Phe Asp Ser Ser Arg Asp Arg Asn Lys Pro Phe Lys Phe Met Leu Gly
945                 950                 955                 960

Lys Gln Glu Val Ile Arg Gly Trp Glu Glu Gly Val Ala Gln Met Ser
                965                 970                 975

Val Gly Gln Arg Ala Lys Leu Thr Ile Ser Pro Asp Tyr Ala Tyr Gly
            980                 985                 990

Ala Thr Gly His Pro Gly Ile Ile Pro Pro His Ala Thr Leu Val Phe
        995                 1000                1005

Asp Val Glu Leu Leu Lys Leu Glu
    1010                1015

<210> SEQ ID NO 12
<211> LENGTH: 273
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atgggtgttc aggttgaaac catctctccg ggtgacggtc gtaccttccc gaaacgtggt      60
cagacctgcg ttgttcacta caccggtatg ctggaagacg gtaaaaaatt cgaccgtggt     120

```
tgggaagaag gtgttgctca gatgtctgtt ggtcagcgtg ctaaactgac catctctccg      180
gactacgctt acggtgctac cggtcacccg ggtatcatcc cgccgcacgc taccctggtt      240
ttcgacgttg aactgctgaa actggaaggt tac                                    273
```

```
<210> SEQ ID NO 13
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gttccgggcg ctggtgtacc aggtgcaggt gtaccgggtg ccggcgtacc tggcgcaggt       60
gtcccgggtg ccggtgttcc gggtgctggt gttccgggcg ctggtgtacc aggtgcaggt      120
gtaccgggtg ccggcgtacc tggcgcaggt gtcccgggtg ccggtgttcc gggtgctggt      180
gttccgggcg ctggtgtacc aggtgcaggt gtaccgggtg ccggcgtacc tggcgcaggt      240
gtcccgggtg ccggtgttcc gggtgctggt gttccgggcg ctggtgtacc aggtgcaggt      300
gtaccgggtg ccggcgtacc tggcgcaggt gtcccgggtg ccggtgttcc gggtgctggt      360
```

```
<210> SEQ ID NO 14
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gttccgggcg tgggtgtacc aggtgtcggt gtaccgggtg tcggcgtacc tggcgtcggt       60
gtcccgggtg ttggtgttcc gggtgtaggt gttccgggcg tgggtgtacc aggtgtcggt      120
gtaccgggtg tcggcgtacc tggcgtcggt gtcccgggtg ttggtgttcc gggtgtaggt      180
gttccgggcg tgggtgtacc aggtgtcggt gtaccgggtg tcggcgtacc tggcgtcggt      240
gtcccgggtg ttggtgttcc gggtgtaggt gttccgggcg tgggtgtacc aggtgtcggt      300
gtaccgggtg tcggcgtacc tggcgtcggt gtcccgggtg ttggtgttcc gggtgtaggt      360
```

```
<210> SEQ ID NO 15
<211> LENGTH: 1009
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15
```

Met Ala Asp Glu Glu Lys Leu Pro Pro Gly Trp Glu Lys Arg Met Ser
1               5                   10                  15

Arg Ser Ser Gly Arg Val Tyr Tyr Phe Asn His Ile Thr Asn Ala Ser
            20                  25                  30

Gln Trp Glu Arg Pro Ser Gly Asn Ser Ser Gly Gly Lys Asn Gly
        35                  40                  45

Gln Gly Glu Pro Ala Arg Val Arg Cys Ser His Leu Leu Val Lys His
    50                  55                  60

Ser Gln Ser Arg Arg Pro Ser Ser Trp Arg Gln Glu Lys Ile Thr Arg
65                  70                  75                  80

Thr Lys Glu Glu Ala Leu Glu Leu Ile Asn Gly Tyr Ile Gln Lys Ile

```
                 85                  90                  95
Lys Ser Gly Glu Glu Asp Phe Glu Ser Leu Ala Ser Gln Phe Ser Asp
                100                 105                 110

Cys Ser Ser Ala Lys Ala Arg Gly Asp Leu Gly Ala Phe Ser Arg Gly
                115                 120                 125

Gln Met Gln Lys Pro Phe Glu Asp Ala Ser Phe Ala Leu Arg Thr Gly
                130                 135                 140

Glu Met Ser Gly Pro Val Phe Thr Asp Ser Gly Ile His Ile Ile Leu
145                 150                 155                 160

Arg Thr Glu Val Pro Gly Ala Gly Val Pro Gly Ala Gly Val Pro Gly
                165                 170                 175

Ala Gly Val Pro Gly Ala Gly Val Pro Gly Ala Gly Val Pro Gly Ala
                180                 185                 190

Gly Val Pro Gly Ala Gly Val Pro Gly Ala Gly Val Pro Gly Ala Gly
                195                 200                 205

Val Pro Gly Ala Gly Val Pro Gly Ala Gly Val Pro Gly Ala Gly Val
                210                 215                 220

Pro Gly Ala Gly Val Pro Gly Ala Gly Val Pro Gly Ala Gly Val Pro
225                 230                 235                 240

Gly Ala Gly Val Pro Gly Ala Gly Val Pro Gly Ala Gly Val Pro Gly
                245                 250                 255

Ala Gly Val Pro Gly Ala Gly Val Pro Gly Ala Gly Val Pro Gly Ala
                260                 265                 270

Gly Val Pro Gly Ala Gly Val Pro Gly Ala Gly Ala Asp Glu Glu Lys
                275                 280                 285

Leu Pro Pro Gly Trp Glu Lys Arg Met Ser Arg Ser Ser Gly Arg Val
290                 295                 300

Tyr Tyr Phe Asn His Ile Thr Asn Ala Ser Gln Trp Glu Arg Pro Ser
305                 310                 315                 320

Gly Asn Ser Ser Ser Gly Gly Lys Asn Gly Gln Gly Glu Pro Ala Arg
                325                 330                 335

Val Arg Cys Ser His Leu Leu Val Lys His Ser Gln Ser Arg Arg Pro
                340                 345                 350

Ser Ser Trp Arg Gln Glu Lys Ile Thr Arg Thr Lys Glu Glu Ala Leu
                355                 360                 365

Glu Leu Ile Asn Gly Tyr Ile Gln Lys Ile Lys Ser Gly Glu Glu Asp
                370                 375                 380

Phe Glu Ser Leu Ala Ser Gln Phe Ser Asp Cys Ser Ser Ala Lys Ala
385                 390                 395                 400

Arg Gly Asp Leu Gly Ala Phe Ser Arg Gly Gln Met Gln Lys Pro Phe
                405                 410                 415

Glu Asp Ala Ser Phe Ala Leu Arg Thr Gly Glu Met Ser Gly Pro Val
                420                 425                 430

Phe Thr Asp Ser Gly Ile His Ile Ile Leu Arg Thr Glu Val Pro Gly
                435                 440                 445

Ala Gly Val Pro Gly Ala Gly Val Pro Gly Ala Gly Val Pro Gly Ala
                450                 455                 460

Gly Val Pro Gly Ala Gly Val Pro Gly Ala Gly Val Pro Gly Ala Gly
465                 470                 475                 480

Val Pro Gly Ala Gly Val Pro Gly Ala Gly Val Pro Gly Ala Gly Val
                485                 490                 495

Pro Gly Ala Gly Val Pro Gly Ala Gly Val Pro Gly Ala Gly Val Pro
                500                 505                 510
```

```
Gly Ala Gly Val Pro Gly Ala Gly Val Pro Gly Ala Gly Val Pro Gly
            515                 520                 525
Ala Gly Val Pro Gly Ala Gly Val Pro Gly Ala Gly Val Pro Gly Ala
        530                 535                 540
Gly Val Pro Gly Ala Gly Val Pro Gly Ala Gly Val Pro Gly Ala Gly
545                 550                 555                 560
Val Pro Gly Ala Gly Ala Asp Glu Glu Lys Leu Pro Pro Gly Trp Glu
                565                 570                 575
Lys Arg Met Ser Arg Ser Ser Gly Arg Val Tyr Tyr Phe Asn His Ile
            580                 585                 590
Thr Asn Ala Ser Gln Trp Glu Arg Pro Ser Gly Asn Ser Ser Ser Gly
        595                 600                 605
Gly Lys Asn Gly Gln Gly Glu Pro Ala Arg Val Arg Cys Ser His Leu
    610                 615                 620
Leu Val Lys His Ser Gln Ser Arg Arg Pro Ser Ser Trp Arg Gln Glu
625                 630                 635                 640
Lys Ile Thr Arg Thr Lys Glu Glu Ala Leu Glu Leu Ile Asn Gly Tyr
                645                 650                 655
Ile Gln Lys Ile Lys Ser Gly Glu Glu Asp Phe Glu Ser Leu Ala Ser
            660                 665                 670
Gln Phe Ser Asp Cys Ser Ser Ala Lys Ala Arg Gly Asp Leu Gly Ala
        675                 680                 685
Phe Ser Arg Gly Gln Met Gln Lys Pro Phe Glu Asp Ala Ser Phe Ala
    690                 695                 700
Leu Arg Thr Gly Glu Met Ser Gly Pro Val Phe Thr Asp Ser Gly Ile
705                 710                 715                 720
His Ile Ile Leu Arg Thr Glu Val Pro Gly Ala Gly Val Pro Gly Ala
                725                 730                 735
Gly Val Pro Gly Ala Gly Val Pro Gly Ala Gly Val Pro Gly Ala Gly
            740                 745                 750
Val Pro Gly Ala Gly Val Pro Gly Ala Gly Val Pro Gly Ala Gly Val
        755                 760                 765
Pro Gly Ala Gly Val Pro Gly Ala Gly Val Pro Gly Ala Gly Val Pro
    770                 775                 780
Gly Ala Gly Val Pro Gly Ala Gly Val Pro Gly Ala Gly Val Pro Gly
785                 790                 795                 800
Ala Gly Val Pro Gly Ala Gly Val Pro Gly Ala Gly Val Pro Gly Ala
                805                 810                 815
Gly Val Pro Gly Ala Gly Val Pro Gly Ala Gly Val Pro Gly Ala Gly
            820                 825                 830
Val Pro Gly Ala Gly Val Pro Gly Ala Gly Val Pro Gly Ala Gly Ala
        835                 840                 845
Asp Glu Glu Lys Leu Pro Pro Gly Trp Glu Lys Arg Met Ser Arg Ser
    850                 855                 860
Ser Gly Arg Val Tyr Tyr Phe Asn His Ile Thr Asn Ala Ser Gln Trp
865                 870                 875                 880
Glu Arg Pro Ser Gly Asn Ser Ser Ser Gly Gly Lys Asn Gly Gln Gly
                885                 890                 895
Glu Pro Ala Arg Val Arg Cys Ser His Leu Leu Val Lys His Ser Gln
            900                 905                 910
Ser Arg Arg Pro Ser Ser Trp Arg Gln Glu Lys Ile Thr Arg Thr Lys
        915                 920                 925
```

Glu Glu Ala Leu Glu Leu Ile Asn Gly Tyr Ile Gln Lys Ile Lys Ser
            930                 935                 940

Gly Glu Glu Asp Phe Glu Ser Leu Ala Ser Gln Phe Ser Asp Cys Ser
945                 950                 955                 960

Ser Ala Lys Ala Arg Gly Asp Leu Gly Ala Phe Ser Arg Gly Gln Met
                965                 970                 975

Gln Lys Pro Phe Glu Asp Ala Ser Phe Ala Leu Arg Thr Gly Glu Met
            980                 985                 990

Ser Gly Pro Val Phe Thr Asp Ser Gly Ile His Ile Ile Leu Arg Thr
                995                1000                1005

Glu

<210> SEQ ID NO 16
<211> LENGTH: 492
<212> TYPE: DNA
<213> ORGANISM: Homo sapiens

<400> SEQUENCE: 16
atgggtgctg acgaagagaa gttacctcca ggctgggaaa aacgtatgtc tcgttcgagc      60
ggcagagtct attacttcaa ccacattacc aacgcatccc agtgggagcg gccctccggg     120
aattcttcta gcggtggcaa aaacggtcag ggtgaaccag ccagagtgcg ctgttcccac     180
ttgttagtta acactctca aagccgtcgc ccctcatctt ggagacagga gaaaattact      240
cggaccaagg aagaggccct tgaacttatc aatggctaca ttcagaagat taagagcggg     300
gaagaggatt tcgaatccct ggcgagtcaa ttctcggatt gttcgagtgc taaagcgcgg     360
ggagatcttg gagcattcag tcgtgggcaa atgcaaaaac cttttgagga cgcttccttt     420
gccttgagaa ctggggaaat gtccggtcca gttttcacag actctggcat ccacatcatc     480
ctgcgtactg ag                                                         492

<210> SEQ ID NO 17
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Gly Gly Gly Ser Gly Gly
        115                 120                 125

Gly Gly Ser Gly Gly Gly Gly Ser Gln Ile Val Leu Ser Gln Ser Pro

```
                    130                 135                 140
Ala Ile Leu Ser Ala Ser Pro Gly Glu Lys Val Thr Met Thr Cys Arg
145                 150                 155                 160

Ala Ser Ser Ser Val Ser Tyr Ile His Trp Phe Gln Gln Lys Pro Gly
                165                 170                 175

Ser Ser Pro Lys Pro Trp Ile Tyr Ala Thr Ser Asn Leu Ala Ser Gly
            180                 185                 190

Val Pro Val Arg Phe Ser Gly Ser Gly Ser Gly Thr Ser Tyr Ser Leu
            195                 200                 205

Thr Ile Ser Arg Val Glu Ala Glu Asp Ala Ala Thr Tyr Tyr Cys Gln
            210                 215                 220

Gln Trp Thr Ser Asn Pro Pro Thr Phe Gly Gly Gly Thr Lys Leu Glu
225                 230                 235                 240

Ile Lys Arg Thr Gly
                245

<210> SEQ ID NO 18
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ala Gly Gly Gly Ser Gly Gly
            115                 120                 125

Gly Gly Ser Gly Gly Gly Gly Ser Gly Gly Gly Gly Ser Gln Ile Val
            130                 135                 140

Leu Ser Gln Ser Pro Ala Ile Leu Ser Ala Ser Pro Gly Glu Lys Val
145                 150                 155                 160

Thr Met Thr Cys Arg Ala Ser Ser Ser Val Ser Tyr Ile His Trp Phe
                165                 170                 175

Gln Gln Lys Pro Gly Ser Ser Pro Lys Pro Trp Ile Tyr Ala Thr Ser
            180                 185                 190

Asn Leu Ala Ser Gly Val Pro Val Arg Phe Ser Gly Ser Gly Ser Gly
            195                 200                 205

Thr Ser Tyr Ser Leu Thr Ile Ser Arg Val Glu Ala Glu Asp Ala Ala
            210                 215                 220

Thr Tyr Tyr Cys Gln Gln Trp Thr Ser Asn Pro Pro Thr Phe Gly Gly
225                 230                 235                 240
```

```
Gly Thr Gly Leu Glu Ile Gly Arg Thr Gly
                245                 250

<210> SEQ ID NO 19
<211> LENGTH: 1208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gly Gln Val Gln Leu Gln Gln Pro Gly Ala Glu Leu Val Lys Pro
1               5                   10                  15

Gly Ala Ser Val Lys Met Ser Cys Lys Ala Ser Gly Tyr Thr Phe Thr
            20                  25                  30

Ser Tyr Asn Met His Trp Val Lys Gln Thr Pro Gly Arg Gly Leu Glu
        35                  40                  45

Trp Ile Gly Ala Ile Tyr Pro Gly Asn Gly Asp Thr Ser Tyr Asn Gln
    50                  55                  60

Lys Phe Lys Gly Lys Ala Thr Leu Thr Ala Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Ser Thr Tyr Tyr Gly Gly Asp Trp Tyr Phe Asn Val
            100                 105                 110

Trp Gly Ala Gly Thr Thr Val Thr Val Ser Ala Gly Gly Gly Gly Ser
        115                 120                 125

Gly Gly Gly Gly Ser Gly Gly Gly Ser Gln Ile Val Leu Ser Gln
    130                 135                 140

Ser Pro Ala Ile Leu Ser Ala Ser Pro Gly Glu Lys Val Thr Met Thr
145                 150                 155                 160

Cys Arg Ala Ser Ser Ser Val Ser Tyr Ile His Trp Phe Gln Gln Lys
                165                 170                 175

Pro Gly Ser Ser Pro Lys Pro Trp Ile Tyr Ala Thr Ser Asn Leu Ala
            180                 185                 190

Ser Gly Val Pro Val Arg Phe Ser Gly Ser Gly Ser Gly Thr Ser Tyr
        195                 200                 205

Ser Leu Thr Ile Ser Arg Val Glu Ala Glu Asp Ala Ala Thr Tyr Tyr
    210                 215                 220

Cys Gln Gln Trp Thr Ser Asn Pro Pro Thr Phe Gly Gly Gly Thr Lys
225                 230                 235                 240

Leu Glu Ile Lys Arg Thr Gly Val Pro Gly Ala Gly Val Pro Gly Ala
                245                 250                 255

Gly Val Pro Gly Ala Gly Val Pro Gly Ala Gly Val Pro Gly Ala Gly
            260                 265                 270

Val Pro Gly Ala Gly Val Pro Gly Ala Gly Val Pro Gly Ala Gly Val
        275                 280                 285

Pro Gly Ala Gly Val Pro Gly Ala Gly Val Pro Gly Ala Gly Val Pro
    290                 295                 300

Gly Ala Gly Val Pro Gly Ala Gly Val Pro Gly Ala Gly Val Pro Gly
305                 310                 315                 320

Ala Gly Val Pro Gly Ala Gly Val Pro Gly Ala Gly Val Pro Gly Ala
                325                 330                 335

Gly Val Pro Gly Ala Gly Val Pro Gly Ala Gly Val Pro Gly Ala Gly
            340                 345                 350
```

```
Val Pro Gly Ala Gly Val Pro Gly Ala Gly Val Pro Gly Ala Gly Val
            355                 360                 365
Pro Gly Ala Gly Val Pro Gly Ala Gly Val Pro Gly Ala Gly Val Pro
        370                 375                 380
Gly Ala Gly Val Pro Gly Ala Gly Val Pro Gly Ala Gly Val Pro Gly
385                 390                 395                 400
Ala Gly Val Pro Gly Ala Gly Val Pro Gly Ala Gly Val Pro Gly Ala
            405                 410                 415
Gly Val Pro Gly Ala Gly Val Pro Gly Ala Gly Val Pro Gly Ala Gly
        420                 425                 430
Val Pro Gly Ala Gly Val Pro Gly Ala Gly Val Pro Gly Ala Gly Val
    435                 440                 445
Pro Gly Ala Gly Val Pro Gly Ala Gly Val Pro Gly Ala Gly Val Pro
        450                 455                 460
Gly Ala Gly Val Pro Gly Ala Gly Val Pro Gly Ala Gly Val Pro Gly
465                 470                 475                 480
Ala Gly Val Pro Gly Ala Gly Val Pro Gly Ala Gly Val Pro Gly Ala
            485                 490                 495
Gly Val Pro Gly Ala Gly Val Pro Gly Ala Gly Val Pro Gly Ala Gly
        500                 505                 510
Val Pro Gly Ala Gly Val Pro Gly Ala Gly Val Pro Gly Ala Gly Val
    515                 520                 525
Pro Gly Ala Gly Val Pro Gly Ala Gly Val Pro Gly Ala Gly Val Pro
        530                 535                 540
Gly Ala Gly Val Pro Gly Ala Gly Val Pro Gly Ala Gly Val Pro Gly
545                 550                 555                 560
Ala Gly Val Pro Gly Ala Gly Val Pro Gly Ala Gly Val Pro Gly Ala
            565                 570                 575
Gly Val Pro Gly Ala Gly Val Pro Gly Ala Gly Val Pro Gly Ala Gly
        580                 585                 590
Val Pro Gly Ala Gly Val Pro Gly Ala Gly Val Pro Gly Ala Gly Val
    595                 600                 605
Pro Gly Ala Gly Val Pro Gly Ala Gly Val Pro Gly Ala Gly Val Pro
        610                 615                 620
Gly Ala Gly Val Pro Gly Ala Gly Val Pro Gly Ala Gly Val Pro Gly
625                 630                 635                 640
Ala Gly Val Pro Gly Ala Gly Val Pro Gly Ala Gly Val Pro Gly Ala
            645                 650                 655
Gly Val Pro Gly Ala Gly Val Pro Gly Ala Gly Val Pro Gly Ala Gly
        660                 665                 670
Val Pro Gly Ala Gly Val Pro Gly Ala Gly Val Pro Gly Ala Gly Val
    675                 680                 685
Pro Gly Ala Gly Val Pro Gly Ala Gly Val Pro Gly Ala Gly Val Pro
        690                 695                 700
Gly Ala Gly Val Pro Gly Ala Gly Val Pro Gly Ala Gly Val Pro Gly
705                 710                 715                 720
Ala Gly Val Pro Gly Ala Gly Val Pro Gly Ile Gly Val Pro Gly Ile
            725                 730                 735
Gly Val Pro Gly Ile Gly Val Pro Gly Ile Gly Val Pro Gly Ile Gly
        740                 745                 750
Val Pro Gly Ile Gly Val Pro Gly Ile Gly Val Pro Gly Ile Gly Val
    755                 760                 765
```

-continued

```
Pro Gly Ile Gly Val Pro Gly Ile Gly Val Pro Gly Ile Gly Val Pro
    770                 775                 780
Gly Ile Gly Val Pro Gly Ile Gly Val Pro Gly Ile Gly Val Pro Gly
785                 790                 795                 800
Ile Gly Val Pro Gly Ile Gly Val Pro Gly Ile Gly Val Pro Gly Ile
                805                 810                 815
Gly Val Pro Gly Ile Gly Val Pro Gly Ile Gly Val Pro Gly Ile Gly
            820                 825                 830
Val Pro Gly Ile Gly Val Pro Gly Ile Gly Val Pro Gly Ile Gly Val
        835                 840                 845
Pro Gly Ile Gly Val Pro Gly Ile Gly Val Pro Gly Ile Gly Val Pro
    850                 855                 860
Gly Ile Gly Val Pro Gly Ile Gly Val Pro Gly Ile Gly Val Pro Gly
865                 870                 875                 880
Ile Gly Val Pro Gly Ile Gly Val Pro Gly Ile Gly Val Pro Gly Ile
                885                 890                 895
Gly Val Pro Gly Ile Gly Val Pro Gly Ile Gly Val Pro Gly Ile Gly
            900                 905                 910
Val Pro Gly Ile Gly Val Pro Gly Ile Gly Val Pro Gly Ile Gly Val
        915                 920                 925
Pro Gly Ile Gly Val Pro Gly Ile Gly Val Pro Gly Ile Gly Val Pro
    930                 935                 940
Gly Ile Gly Val Pro Gly Ile Gly Val Pro Gly Ile Gly Val Pro Gly
945                 950                 955                 960
Ile Gly Val Pro Gly Ile Gly Val Pro Gly Ile Gly Val Pro Gly Ile
                965                 970                 975
Gly Val Pro Gly Ile Gly Val Pro Gly Ile Gly Val Pro Gly Ile Gly
            980                 985                 990
Val Pro Gly Ile Gly Val Pro Gly  Ile Gly Val Pro Gly  Ile Gly Val
        995                 1000                 1005
Pro Gly  Ile Gly Val Pro Gly  Ile Gly Val Pro Gly  Ile Gly Val
    1010                1015                1020
Pro Gly  Ile Gly Val Pro Gly  Ile Gly Val Pro Gly  Ile Gly Val
    1025                1030                1035
Pro Gly  Ile Gly Val Pro Gly  Ile Gly Val Pro Gly  Ile Gly Val
    1040                1045                1050
Pro Gly  Ile Gly Val Pro Gly  Ile Gly Val Pro Gly  Ile Gly Val
    1055                1060                1065
Pro Gly  Ile Gly Val Pro Gly  Ile Gly Val Pro Gly  Ile Gly Val
    1070                1075                1080
Pro Gly  Ile Gly Val Pro Gly  Ile Gly Val Pro Gly  Ile Gly Val
    1085                1090                1095
Pro Gly  Ile Gly Val Pro Gly  Ile Gly Val Pro Gly  Ile Gly Val
    1100                1105                1110
Pro Gly  Ile Gly Val Pro Gly  Ile Gly Val Pro Gly  Ile Gly Val
    1115                1120                1125
Pro Gly  Ile Gly Val Pro Gly  Ile Gly Val Pro Gly  Ile Gly Val
    1130                1135                1140
Pro Gly  Ile Gly Val Pro Gly  Ile Gly Val Pro Gly  Ile Gly Val
    1145                1150                1155
Pro Gly  Ile Gly Val Pro Gly  Ile Gly Val Pro Gly  Ile Gly Val
    1160                1165                1170
Pro Gly  Ile Gly Val Pro Gly  Ile Gly Val Pro Gly  Ile Gly Val
```

-continued

```
            1175                1180                1185

Pro Gly Ile Gly Val Pro Gly Ile Gly Val Pro Gly Ile Gly Val
            1190                1195                1200

Pro Gly Ile Gly Tyr
    1205

<210> SEQ ID NO 20
<211> LENGTH: 1203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Gln Val Gln Leu Gln Gln Pro Gly Ala Glu Leu Val Lys Pro
1               5                   10                  15

Gly Ala Ser Val Lys Met Ser Cys Lys Ala Ser Gly Tyr Thr Phe Thr
            20                  25                  30

Ser Tyr Asn Met His Trp Val Lys Gln Thr Pro Gly Arg Gly Leu Glu
        35                  40                  45

Trp Ile Gly Ala Ile Tyr Pro Gly Asn Gly Asp Thr Ser Tyr Asn Gln
    50                  55                  60

Lys Phe Lys Gly Lys Ala Thr Leu Thr Ala Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Ser Thr Tyr Tyr Gly Gly Asp Trp Tyr Phe Asn Val
            100                 105                 110

Trp Gly Ala Gly Thr Thr Val Thr Val Ser Ala Gly Gly Gly Gly Ser
        115                 120                 125

Gly Gly Gly Gly Ser Gly Gly Gly Ser Gln Ile Val Leu Ser Gln
    130                 135                 140

Ser Pro Ala Ile Leu Ser Ala Ser Pro Gly Glu Lys Val Thr Met Thr
145                 150                 155                 160

Cys Arg Ala Ser Ser Ser Val Ser Tyr Ile His Trp Phe Gln Gln Lys
                165                 170                 175

Pro Gly Ser Ser Pro Lys Pro Trp Ile Tyr Ala Thr Ser Asn Leu Ala
            180                 185                 190

Ser Gly Val Pro Val Arg Phe Ser Gly Ser Gly Ser Gly Thr Ser Tyr
        195                 200                 205

Ser Leu Thr Ile Ser Arg Val Glu Ala Glu Asp Ala Ala Thr Tyr Tyr
    210                 215                 220

Cys Gln Gln Trp Thr Ser Asn Pro Pro Thr Phe Gly Gly Gly Thr Lys
225                 230                 235                 240

Leu Glu Ile Lys Arg Thr Gly Val Pro Gly Ala Gly Val Pro Gly Ala
                245                 250                 255

Gly Val Pro Gly Ala Gly Val Pro Gly Ala Gly Val Pro Gly Ala Gly
            260                 265                 270

Val Pro Gly Ala Gly Val Pro Gly Ala Gly Val Pro Gly Ala Gly Val
        275                 280                 285

Pro Gly Ala Gly Val Pro Gly Ala Gly Val Pro Gly Ala Gly Val Pro
    290                 295                 300

Gly Ala Gly Val Pro Gly Ala Gly Val Pro Gly Ala Gly Val Pro Gly
305                 310                 315                 320
```

Ala Gly Val Pro Gly Ala Gly Val Pro Gly Ala
         325                 330                 335

Gly Val Pro Gly Ala Gly Val Pro Gly Ala Gly
         340                 345                 350

Val Pro Gly Ala Gly Val Pro Gly Ala Gly Val
         355                 360                 365

Pro Gly Ala Gly Val Pro Gly Ala Gly Val Pro
         370                 375                 380

Gly Ala Gly Val Pro Gly Ala Gly Val Pro Gly
385                 390                 395                 400

Ala Gly Val Pro Gly Ala Gly Val Pro Gly Ala
         405                 410                 415

Gly Val Pro Gly Ala Gly Val Pro Gly Ala Gly
         420                 425                 430

Val Pro Gly Ala Gly Val Pro Gly Ala Gly Val
         435                 440                 445

Pro Gly Ala Gly Val Pro Gly Ala Gly Val Pro
         450                 455                 460

Gly Ala Gly Val Pro Gly Ala Gly Val Pro Gly
465                 470                 475                 480

Ala Gly Val Pro Gly Ala Gly Val Pro Gly Ala
         485                 490                 495

Gly Val Pro Gly Ala Gly Val Pro Gly Ala Gly
         500                 505                 510

Val Pro Gly Ala Gly Val Pro Gly Ala Gly Val
         515                 520                 525

Pro Gly Ala Gly Val Pro Gly Ala Gly Val Pro
         530                 535                 540

Gly Ala Gly Val Pro Gly Ala Gly Val Pro Gly
545                 550                 555                 560

Ala Gly Val Pro Gly Ala Gly Val Pro Gly Ala
         565                 570                 575

Gly Val Pro Gly Ala Gly Val Pro Gly Ala Gly
         580                 585                 590

Val Pro Gly Ala Gly Val Pro Gly Ala Gly Val
         595                 600                 605

Pro Gly Ala Gly Val Pro Gly Ala Gly Val Pro
         610                 615                 620

Gly Ala Gly Val Pro Gly Ala Gly Val Pro Gly
625                 630                 635                 640

Ala Gly Val Pro Gly Ala Gly Val Pro Gly Ala
         645                 650                 655

Gly Val Pro Gly Ala Gly Val Pro Gly Ala Gly
         660                 665                 670

Val Pro Gly Ala Gly Val Pro Gly Ala Gly Val
         675                 680                 685

Pro Gly Ala Gly Val Pro Gly Ala Gly Val Pro
         690                 695                 700

Gly Ala Gly Val Pro Gly Ala Gly Val Pro Gly
705                 710                 715                 720

Ala Gly Val Pro Gly Ala Gly Val Pro Gly Ala
         725                 730                 735

Gly Val Pro Gly Ala Gly Val Pro Gly Ala Gly

-continued

```
                740                 745                 750
Val Pro Gly Ala Gly Val Pro Gly Ala Gly Val Pro Gly Ala Gly Val
            755                 760                 765

Pro Gly Ala Gly Val Pro Gly Ala Gly Val Pro Gly Ala Gly Val Pro
        770                 775                 780

Gly Ala Gly Val Pro Gly Ala Gly Val Pro Gly Ala Gly Val Pro Gly
785                 790                 795                 800

Ala Gly Val Pro Gly Ala Gly Val Pro Gly Ala Gly Val Pro Gly Ala
                805                 810                 815

Gly Val Pro Gly Ala Gly Val Pro Gly Ala Gly Val Pro Gly Ala Gly
            820                 825                 830

Val Pro Gly Ala Gly Val Pro Gly Ala Gly Val Pro Gly Ala Gly Val
        835                 840                 845

Pro Gly Ala Gly Val Pro Gly Ala Gly Val Pro Gly Ala Gly Val Pro
    850                 855                 860

Gly Ala Gly Val Pro Gly Ala Gly Val Pro Gly Ala Gly Val Pro Gly
865                 870                 875                 880

Ala Gly Val Pro Gly Ala Gly Val Pro Gly Ala Gly Val Pro Gly Ala
                885                 890                 895

Gly Val Pro Gly Ala Gly Val Pro Gly Ala Gly Val Pro Gly Ala Gly
            900                 905                 910

Val Pro Gly Ala Gly Val Pro Gly Ala Gly Val Pro Gly Ala Gly Val
        915                 920                 925

Pro Gly Ala Gly Val Pro Gly Ala Gly Val Pro Gly Ala Gly Val Pro
    930                 935                 940

Gly Ala Gly Val Pro Gly Ala Gly Val Pro Gly Ala Gly Val Pro Gly
945                 950                 955                 960

Ala Gly Val Pro Gly Ala Gly Val Pro Gly Ala Gly Val Pro Gly Ala
                965                 970                 975

Gly Val Pro Gly Ala Gly Val Pro Gly Ala Gly Val Pro Gly Ala Gly
            980                 985                 990

Val Pro Gly Ala Gly Val Pro Gly  Ala Gly Val Pro Gly  Ala Gly Val
        995                 1000                1005

Pro Gly  Ala Gly Val Pro Gly  Ala Gly Val Pro Gly  Ala Gly Val
    1010                1015                1020

Pro Gly  Ala Gly Val Pro Gly  Ala Gly Val Pro Gly  Ala Gly Val
    1025                1030                1035

Pro Gly  Ala Gly Val Pro Gly  Ala Gly Val Pro Gly  Ala Gly Val
    1040                1045                1050

Pro Gly  Ala Gly Val Pro Gly  Ala Gly Val Pro Gly  Ala Gly Val
    1055                1060                1065

Pro Gly  Ala Gly Val Pro Gly  Ala Gly Val Pro Gly  Ala Gly Val
    1070                1075                1080

Pro Gly  Ala Gly Val Pro Gly  Ala Gly Val Pro Gly  Ala Gly Val
    1085                1090                1095

Pro Gly  Ala Gly Val Pro Gly  Ala Gly Val Pro Gly  Ala Gly Val
    1100                1105                1110

Pro Gly  Ala Gly Val Pro Gly  Ala Gly Val Pro Gly  Ala Gly Val
    1115                1120                1125

Pro Gly  Ala Gly Val Pro Gly  Ala Gly Val Pro Gly  Ala Gly Val
    1130                1135                1140

Pro Gly  Ala Gly Val Pro Gly  Ala Gly Val Pro Gly  Ala Gly Val
    1145                1150                1155
```

```
Pro Gly Ala Gly Val Pro Gly Ala Gly Val Pro Gly Ala Gly Val
        1160                1165                1170

Pro Gly Ala Gly Val Pro Gly Ala Gly Val Pro Gly Ala Gly Val
        1175                1180                1185

Pro Gly Ala Gly Val Pro Gly Ala Gly Val Pro Gly Ala Gly Val
        1190                1195                1200

<210> SEQ ID NO 21
<211> LENGTH: 728
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Gln Val Gln Leu Gln Gln Pro Gly Ala Glu Leu Val Lys Pro
1               5                   10                  15

Gly Ala Ser Val Lys Met Ser Cys Lys Ala Ser Gly Tyr Thr Phe Thr
            20                  25                  30

Ser Tyr Asn Met His Val Lys Gln Thr Pro Gly Arg Gly Leu Glu
        35                  40                  45

Trp Ile Gly Ala Ile Tyr Pro Gly Asn Gly Asp Thr Ser Tyr Asn Gln
    50                  55                  60

Lys Phe Lys Gly Lys Ala Thr Leu Thr Ala Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Ser Thr Tyr Tyr Gly Gly Asp Trp Tyr Phe Asn Val
            100                 105                 110

Trp Gly Ala Gly Thr Thr Val Thr Val Ser Ala Gly Gly Gly Gly Ser
        115                 120                 125

Gly Gly Gly Gly Ser Gly Gly Gly Ser Gln Ile Val Leu Ser Gln
    130                 135                 140

Ser Pro Ala Ile Leu Ser Ala Ser Pro Gly Glu Lys Val Thr Met Thr
145                 150                 155                 160

Cys Arg Ala Ser Ser Ser Val Ser Tyr Ile His Trp Phe Gln Gln Lys
                165                 170                 175

Pro Gly Ser Ser Pro Lys Pro Trp Ile Tyr Ala Thr Ser Asn Leu Ala
            180                 185                 190

Ser Gly Val Pro Val Arg Phe Ser Gly Ser Gly Ser Gly Thr Ser Tyr
        195                 200                 205

Ser Leu Thr Ile Ser Arg Val Glu Ala Glu Asp Ala Ala Thr Tyr Tyr
    210                 215                 220

Cys Gln Gln Trp Thr Ser Asn Pro Pro Thr Phe Gly Gly Gly Thr Lys
225                 230                 235                 240

Leu Glu Ile Lys Arg Thr Gly Val Pro Gly Ser Gly Val Pro Gly Ser
                245                 250                 255

Gly Val Pro Gly Ser Gly Val Pro Gly Ser Gly Val Pro Gly Ser Gly
            260                 265                 270

Val Pro Gly Ser Gly Val Pro Gly Ser Gly Val Pro Gly Ser Gly Val
        275                 280                 285

Pro Gly Ser Gly Val Pro Gly Ser Gly Val Pro Gly Ser Gly Val Pro
    290                 295                 300

Gly Ser Gly Val Pro Gly Ser Gly Val Pro Gly Ser Gly Val Pro Gly
```

-continued

```
            305                 310                 315                 320
        Ser Gly Val Pro Gly Ser Gly Val Pro Gly Ser Gly Val Pro Gly Ser
                        325                 330                 335
        Gly Val Pro Gly Ser Gly Val Pro Gly Ser Gly Val Pro Gly Ser Gly
                        340                 345                 350
        Val Pro Gly Ser Gly Val Pro Gly Ser Gly Val Pro Gly Ser Gly Val
                        355                 360                 365
        Pro Gly Ser Gly Val Pro Gly Ser Gly Val Pro Gly Ser Gly Val Pro
                        370                 375                 380
        Gly Ser Gly Val Pro Gly Ser Gly Val Pro Gly Ser Gly Val Pro Gly
        385                 390                 395                 400
        Ser Gly Val Pro Gly Ser Gly Val Pro Gly Ser Gly Val Pro Gly Ser
                        405                 410                 415
        Gly Val Pro Gly Ser Gly Val Pro Gly Ser Gly Val Pro Gly Ser Gly
                        420                 425                 430
        Val Pro Gly Ser Gly Val Pro Gly Ser Gly Val Pro Gly Ser Gly Val
                        435                 440                 445
        Pro Gly Ser Gly Val Pro Gly Ser Gly Val Pro Gly Ser Gly Val Pro
                        450                 455                 460
        Gly Ser Gly Val Pro Gly Ser Gly Val Pro Gly Ser Gly Val Pro Gly
        465                 470                 475                 480
        Phe Gly Val Pro Gly Ser Gly Val Pro Gly Ile Gly Val Pro Gly Ile
                        485                 490                 495
        Gly Val Pro Gly Ile Gly Val Pro Gly Ile Gly Val Pro Gly Ile Gly
                        500                 505                 510
        Val Pro Gly Ile Gly Val Pro Gly Ile Gly Val Pro Gly Ile Gly Val
                        515                 520                 525
        Pro Gly Ile Gly Val Pro Gly Ile Gly Val Pro Gly Ile Gly Val Pro
                        530                 535                 540
        Gly Ile Gly Val Pro Gly Ile Gly Val Pro Gly Ile Gly Val Pro Gly
        545                 550                 555                 560
        Ile Gly Val Pro Gly Ile Gly Val Pro Gly Ile Gly Val Pro Gly Ile
                        565                 570                 575
        Gly Val Pro Gly Ile Gly Val Pro Gly Ile Gly Val Pro Gly Ile Gly
                        580                 585                 590
        Val Pro Gly Ile Gly Val Pro Gly Ile Gly Val Pro Gly Ile Gly Val
                        595                 600                 605
        Pro Gly Ile Gly Val Pro Gly Ile Gly Val Pro Gly Ile Gly Val Pro
                        610                 615                 620
        Gly Ile Gly Val Pro Gly Ile Gly Val Pro Gly Ile Gly Val Pro Gly
        625                 630                 635                 640
        Ile Gly Val Pro Gly Ile Gly Val Pro Gly Ile Gly Val Pro Gly Ile
                        645                 650                 655
        Gly Val Pro Gly Ile Gly Val Pro Gly Ile Gly Val Pro Gly Ile Gly
                        660                 665                 670
        Val Pro Gly Ile Gly Val Pro Gly Ile Gly Val Pro Gly Ile Gly Val
                        675                 680                 685
        Pro Gly Ile Gly Val Pro Gly Ile Gly Val Pro Gly Ile Gly Val Pro
                        690                 695                 700
        Gly Ile Gly Val Pro Gly Ile Gly Val Pro Gly Ile Gly Val Pro Gly
        705                 710                 715                 720
        Ile Gly Val Pro Gly Ile Gly Tyr
                        725
```

<210> SEQ ID NO 22
<211> LENGTH: 520
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
catatggtta acccgaccgt tttcttcgac atcgctgttg acggtgaacc gctgggtcgt      60
gtttctttcg aactgttcgc tgacaaagtt ccgaaaaccg ctgaaaactt ccgtgctctg     120
tctaccggtg aaaaaggttt cggttacaaa ggttcttgct tccaccgtat catcccgggt    180
ttcatgtgcc aggqtggtga cttcacccgt cacaacggta ccggtggtaa atctatctac    240
ggtgaaaaat cgaagacga aaacttcatc ctgaaacaca ccggtccggg tatcctgtct    300
atggctaacg ctggtccgaa caccaacggt tctcagttct tcatctgcac cgctaaaacc    360
gaatggctgg acggtaaaca cgttgttttc ggtaaagtta agaaggtat gaacatcgtt    420 gaagctatgg aacgtttcgg ttctcgtaac ggtaaaacct ctaaaaaaat caccatcgct    480
gactgcggtc agctggaagg ttactgatct cctcggatcc                         520
```

<210> SEQ ID NO 23
<211> LENGTH: 498
<212> TYPE: DNA
<213> ORGANISM: Homo sapiens

<400> SEQUENCE: 23

```
atggtcaacc ccaccgtgtt cttcgacatt gccgtcgacg gcgagcccct gggccgcgtc      60
tcctttgagc tgtttgcaga caaggtccca agacagcag aaaattttcg tgctctgagc     120
actggagaga aaggatttgg ttataagggt tcctgctttc acagaattat tccagggttt    180
atgtgtcagg gtggtgactt cacacgccat aatggcactg gtggcaagtc catctatggg    240
gagaaatttg aagatgagaa cttcatccta agcatacgg tcctggcat cttgtccatg     300 gcaaatgctg acccaacac aaatggttcc cagttttca tctgcactgc caagactgag     360
tggttggatg gcaagcatgt ggtgtttggc aaagtgaaag aaggcatgaa tattgtggag    420
gccatggagc gctttgggtc caggaatggc aagaccagca gaagatcac cattgctgac    480 tgtggacaac tcgaataa                                                  498
```

<210> SEQ ID NO 24
<211> LENGTH: 107
<212> TYPE: PRT
<213> ORGANISM: Homo sapiens

<400> SEQUENCE: 24

```
Val Gln Val Glu Thr Ile Ser Pro Gly Asp Gly Arg Thr Phe Pro Lys
1               5                   10                  15

Arg Gly Gln Thr Cys Val Val His Tyr Thr Gly Met Leu Glu Asp Gly
            20                  25                  30

Lys Lys Phe Asp Ser Ser Arg Asp Arg Asn Lys Pro Phe Lys Phe Met
        35                  40                  45

Leu Gly Lys Gln Glu Val Ile Arg Gly Trp Glu Glu Gly Val Ala Gln
    50                  55                  60

Met Ser Val Gly Gln Arg Ala Lys Leu Thr Ile Ser Pro Asp Tyr Ala
65                  70                  75                  80
```

```
Tyr Gly Ala Thr Gly His Pro Gly Ile Ile Pro Pro His Ala Thr Leu
                85                  90                  95

Val Phe Asp Val Glu Leu Leu Lys Leu Glu Gly
            100                 105

<210> SEQ ID NO 25
<211> LENGTH: 1176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Phe Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Gly Val Pro Gly
            100                 105                 110

Ala Gly Val Pro Gly Ala Gly Val Pro Gly Ala Gly Val Pro Gly Ala
        115                 120                 125

Gly Val Pro Gly Ala Gly Val Pro Gly Ala Gly Val Pro Gly Ala Gly
    130                 135                 140

Val Pro Gly Ala Gly Val Pro Gly Ala Gly Val Pro Gly Ala Gly Val
145                 150                 155                 160

Pro Gly Ala Gly Val Pro Gly Ala Gly Val Pro Gly Ala Gly Val Pro
                165                 170                 175

Gly Ala Gly Val Pro Gly Ala Gly Val Pro Gly Ala Gly Val Pro Gly
            180                 185                 190

Ala Gly Val Pro Gly Ala Gly Val Pro Gly Ala Gly Val Pro Gly Ala
        195                 200                 205

Gly Val Pro Gly Ala Gly Val Pro Gly Ala Gly Val Pro Gly Ala Gly
    210                 215                 220

Val Pro Gly Ala Gly Val Pro Gly Ala Gly Val Pro Gly Ala Gly Val
225                 230                 235                 240

Pro Gly Ala Gly Val Pro Gly Ala Gly Val Pro Gly Ala Gly Val Pro
                245                 250                 255

Gly Ala Gly Val Pro Gly Ala Gly Val Pro Gly Ala Gly Val Pro Gly
            260                 265                 270

Ala Gly Val Pro Gly Ala Gly Val Pro Gly Ala Gly Val Pro Gly Ala
        275                 280                 285

Gly Val Pro Gly Ala Gly Val Pro Gly Ala Gly Val Pro Gly Ala Gly
    290                 295                 300

Val Pro Gly Ala Gly Val Pro Gly Ala Gly Val Pro Gly Ala Gly Val
305                 310                 315                 320

Pro Gly Ala Gly Val Pro Gly Ala Gly Val Pro Gly Ala Gly Val Pro
                325                 330                 335
```

-continued

Gly Ala Gly Val Pro Gly Ala Gly Val Pro Gly Ala Gly Val Pro Gly
            340                 345                 350
Ala Gly Val Pro Gly Ala Gly Val Pro Gly Ala Gly Val Pro Gly Ala
            355                 360                 365
Gly Val Pro Gly Ala Gly Val Pro Gly Ala Gly Val Pro Gly Ala Gly
            370                 375                 380
Val Pro Gly Ala Gly Val Pro Gly Ala Gly Val Pro Gly Ala Gly Val
385                 390                 395                 400
Pro Gly Ala Gly Val Pro Gly Ala Gly Val Pro Gly Ala Gly Val Pro
            405                 410                 415
Gly Ala Gly Val Pro Gly Ala Gly Val Pro Gly Ala Gly Val Pro Gly
            420                 425                 430
Ala Gly Val Pro Gly Ala Gly Val Pro Gly Ala Gly Val Pro Gly Ala
            435                 440                 445
Gly Val Pro Gly Ala Gly Val Pro Gly Ala Gly Val Pro Gly Ala Gly
            450                 455                 460
Val Pro Gly Ala Gly Val Pro Gly Ala Gly Val Pro Gly Ala Gly Val
465                 470                 475                 480
Pro Gly Ala Gly Val Pro Gly Ala Gly Val Pro Gly Ala Gly Val Pro
            485                 490                 495
Gly Ala Gly Val Pro Gly Ala Gly Val Pro Gly Ala Gly Val Pro Gly
            500                 505                 510
Ala Gly Val Pro Gly Ala Gly Val Pro Gly Ala Gly Val Pro Gly Ala
            515                 520                 525
Gly Val Pro Gly Ala Gly Val Pro Gly Ala Gly Val Pro Gly Ala Gly
            530                 535                 540
Val Pro Gly Ala Gly Val Pro Gly Ala Gly Val Pro Gly Ala Gly Val
545                 550                 555                 560
Pro Gly Ala Gly Val Pro Gly Ala Gly Val Pro Gly Ala Gly Val Pro
            565                 570                 575
Gly Ala Gly Val Pro Gly Ala Gly Val Pro Gly Ala Gly Val Pro Gly
            580                 585                 590
Ala Gly Val Pro Gly Ala Gly Val Pro Gly Ala Gly Val Pro Gly Ala
            595                 600                 605
Gly Val Pro Gly Ala Gly Val Pro Gly Ala Gly Val Pro Gly Ala Gly
            610                 615                 620
Val Pro Gly Ala Gly Val Pro Gly Ala Gly Val Pro Gly Ala Gly Val
625                 630                 635                 640
Pro Gly Ala Gly Val Pro Gly Ala Gly Val Pro Gly Ala Gly Val Pro
            645                 650                 655
Gly Ala Gly Val Pro Gly Ala Gly Val Pro Gly Ala Gly Val Pro Gly
            660                 665                 670
Ala Gly Val Pro Gly Ala Gly Val Pro Gly Ala Gly Val Pro Gly Ala
            675                 680                 685
Gly Val Pro Gly Ala Gly Val Pro Gly Ala Gly Val Pro Gly Ala Gly
            690                 695                 700
Val Pro Gly Ala Gly Val Pro Gly Ala Gly Val Pro Gly Ala Gly Val
705                 710                 715                 720
Pro Gly Ala Gly Val Pro Gly Ala Gly Val Pro Gly Ala Gly Val Pro
            725                 730                 735
Gly Ala Gly Val Pro Gly Ala Gly Val Pro Gly Ala Gly Val Pro Gly
            740                 745                 750

Ala Gly Val Pro Gly Ala Gly Val Pro Gly Ala Gly Val Pro Gly Ala
       755                 760                 765

Gly Val Pro Gly Ala Gly Val Pro Gly Ala Gly Val Pro Gly Ala Gly
       770                 775                 780

Val Pro Gly Ala Gly Val Pro Gly Ala Gly Val Pro Gly Ala Gly Val
785                 790                 795                 800

Pro Gly Ala Gly Val Pro Gly Ala Gly Val Pro Gly Ala Gly Val Pro
       805                 810                 815

Gly Ala Gly Val Pro Gly Ala Gly Val Pro Gly Ala Gly Val Pro Gly
       820                 825                 830

Ala Gly Val Pro Gly Ala Gly Val Pro Gly Ala Gly Val Pro Gly Ala
       835                 840                 845

Gly Val Pro Gly Ala Gly Val Pro Gly Ala Gly Val Pro Gly Ala Gly
       850                 855                 860

Val Pro Gly Ala Gly Val Pro Gly Ala Gly Val Pro Gly Ala Gly Val
865                 870                 875                 880

Pro Gly Ala Gly Val Pro Gly Ala Gly Val Pro Gly Ala Gly Val Pro
       885                 890                 895

Gly Ala Gly Val Pro Gly Ala Gly Val Pro Gly Ala Gly Val Pro Gly
       900                 905                 910

Ala Gly Val Pro Gly Ala Gly Val Pro Gly Ala Gly Val Pro Gly Ala
       915                 920                 925

Gly Val Pro Gly Ala Gly Val Pro Gly Ala Gly Val Pro Gly Ala Gly
       930                 935                 940

Val Pro Gly Ala Gly Val Pro Gly Ala Gly Val Pro Gly Ala Gly Val
945                 950                 955                 960

Pro Gly Ala Gly Val Pro Gly Ala Gly Val Pro Gly Ala Gly Val Pro
       965                 970                 975

Gly Ala Gly Val Pro Gly Ala Gly Val Pro Gly Ala Gly Val Pro Gly
       980                 985                 990

Ala Gly Val Pro Gly Ala Gly Val Pro Gly Ala Gly Val Pro Gly Ala
       995                1000                1005

Gly Val Pro Gly Ala Gly Val Pro Gly Ala Gly Val Pro Gly Ala
      1010                1015                1020

Gly Val Pro Gly Ala Gly Val Pro Gly Ala Gly Val Pro Gly Ala
      1025                1030                1035

Gly Val Pro Gly Ala Gly Val Pro Gly Ala Gly Val Pro Gly Ala
      1040                1045                1050

Gly Val Pro Gly Ala Gly Val Pro Gly Ala Gly Val Pro Gly Ala
      1055                1060                1065

Gly Val Gln Val Glu Thr Ile Ser Pro Gly Asp Gly Arg Thr Phe
      1070                1075                1080

Pro Lys Arg Gly Gln Thr Cys Val Val His Tyr Thr Gly Met Leu
      1085                1090                1095

Glu Asp Gly Lys Lys Phe Asp Ser Ser Arg Asp Arg Asn Lys Pro
      1100                1105                1110

Phe Lys Phe Met Leu Gly Lys Gln Glu Val Ile Arg Gly Trp Glu
      1115                1120                1125

Glu Gly Val Ala Gln Met Ser Val Gly Gln Arg Ala Lys Leu Thr
      1130                1135                1140

Ile Ser Pro Asp Tyr Ala Tyr Gly Ala Thr Gly His Pro Gly Ile
      1145                1150                1155

Ile Pro Pro His Ala Thr Leu Val Phe Asp Val Glu Leu Leu Lys

<210> SEQ ID NO 26
<211> LENGTH: 195
<212> TYPE: PRT
<213> ORGANISM: Human adenovirus 5

<400> SEQUENCE: 26

```
Gly Ala Ile Thr Val Gly Asn Lys Asn Asn Asp Lys Leu Thr Leu Trp
1               5                   10                  15
Thr Thr Pro Ala Pro Ser Pro Asn Cys Arg Leu Asn Ala Glu Lys Asp
            20                  25                  30
Ala Lys Leu Thr Leu Val Leu Thr Lys Cys Gly Ser Gln Ile Leu Ala
        35                  40                  45
Thr Val Ser Val Leu Ala Val Lys Gly Ser Leu Ala Pro Ile Ser Gly
    50                  55                  60
Thr Val Gln Ser Ala His Leu Ile Ile Arg Phe Asp Glu Asn Gly Val
65                  70                  75                  80
Leu Leu Asn Asn Ser Phe Leu Asp Pro Glu Tyr Trp Asn Phe Arg Asn
                85                  90                  95
Gly Asp Leu Thr Glu Gly Thr Ala Tyr Thr Asn Ala Val Gly Phe Met
            100                 105                 110
Pro Asn Leu Ser Ala Tyr Pro Lys Ser His Gly Lys Thr Ala Lys Ser
        115                 120                 125
Asn Ile Val Ser Gln Val Tyr Leu Asn Gly Asp Lys Thr Lys Pro Val
    130                 135                 140
Thr Leu Thr Ile Thr Leu Asn Gly Thr Gln Glu Thr Gly Asp Thr Thr
145                 150                 155                 160
Pro Ser Ala Tyr Ser Met Ser Phe Ser Trp Asp Trp Ser Gly His Asn
                165                 170                 175
Tyr Ile Asn Glu Ile Phe Ala Thr Ser Ser Tyr Thr Phe Ser Tyr Ile
            180                 185                 190
Ala Gln Glu
        195
```

<210> SEQ ID NO 27
<211> LENGTH: 104
<212> TYPE: PRT
<213> ORGANISM: Homo sapiens

<400> SEQUENCE: 27

```
Arg Pro Glu Val His Leu Leu Pro Pro Ser Glu Glu Leu Ala Leu
1               5                   10                  15
Asn Glu Leu Val Thr Leu Thr Cys Leu Ala Arg Gly Phe Ser Pro Lys
            20                  25                  30
Asp Val Leu Val Arg Trp Leu Gln Gly Ser Gln Glu Leu Pro Arg Glu
        35                  40                  45
Lys Tyr Leu Thr Trp Ala Ser Arg Gln Glu Pro Ser Gln Gly Thr Thr
    50                  55                  60
Thr Phe Ala Val Thr Ser Ile Leu Arg Val Ala Ala Glu Asp Trp Lys
65                  70                  75                  80
Lys Gly Asp Thr Phe Ser Cys Met Val Gly His Glu Ala Leu Pro Leu
                85                  90                  95
Ala Phe Thr Gln Lys Thr Ile Asp
```

```
<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Glu Gly Phe Ser Phe Leu Ala Phe Glu Asp Phe Val Ser Ser Ile
1               5                   10                  15

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Trp Cys Glu Tyr Leu Gly Gly Tyr Leu Arg Cys Tyr Ala
1               5                   10

<210> SEQ ID NO 30
<211> LENGTH: 17
<212> TYPE: PRT
<213> ORGANISM: Homo sapiens

<400> SEQUENCE: 30

Asn His Leu Gly Asp Met Thr Ser Glu Glu Val Met Ser Leu Thr Ser
1               5                   10                  15

Ser

<210> SEQ ID NO 31
<211> LENGTH: 163
<212> TYPE: PRT
<213> ORGANISM: Homo sapiens

<400> SEQUENCE: 31

Ala Asp Glu Glu Lys Leu Pro Pro Gly Trp Glu Lys Arg Met Ser Arg
1               5                   10                  15

Ser Ser Gly Arg Val Tyr Tyr Phe Asn His Ile Thr Asn Ala Ser Gln
                20                  25                  30

Trp Glu Arg Pro Ser Gly Asn Ser Ser Gly Gly Lys Asn Gly Gln
            35                  40                  45

Gly Glu Pro Ala Arg Val Arg Cys Ser His Leu Leu Val Lys His Ser
        50                  55                  60

Gln Ser Arg Arg Pro Ser Ser Trp Arg Gln Glu Lys Ile Thr Arg Thr
65                  70                  75                  80

Lys Glu Glu Ala Leu Glu Leu Ile Asn Gly Tyr Ile Gln Lys Ile Lys
                85                  90                  95

Ser Gly Glu Glu Asp Phe Glu Ser Leu Ala Ser Gln Phe Ser Asp Cys
                100                 105                 110

Ser Ser Ala Lys Ala Arg Gly Asp Leu Gly Ala Phe Ser Arg Gly Gln
            115                 120                 125

Met Gln Lys Pro Phe Glu Asp Ala Ser Phe Ala Leu Arg Thr Gly Glu
        130                 135                 140

Met Ser Gly Pro Val Phe Thr Asp Ser Gly Ile His Ile Ile Leu Arg
```

Thr Glu Gly

<210> SEQ ID NO 32
<211> LENGTH: 453
<212> TYPE: PRT
<213> ORGANISM: Homo sapiens

<400> SEQUENCE: 32

```
Gln Thr Ser Val Ser Pro Ser Lys Val Ile Leu Pro Arg Gly Gly Ser
1               5                   10                  15

Val Leu Val Thr Cys Ser Thr Ser Cys Asp Gln Pro Lys Leu Leu Gly
            20                  25                  30

Ile Glu Thr Pro Leu Pro Lys Lys Glu Leu Leu Leu Pro Gly Asn Asn
        35                  40                  45

Arg Lys Val Tyr Glu Leu Ser Asn Val Gln Glu Asp Ser Gln Pro Met
    50                  55                  60

Cys Tyr Ser Asn Cys Pro Asp Gly Gln Ser Thr Ala Lys Thr Phe Leu
65                  70                  75                  80

Thr Val Tyr Trp Thr Pro Glu Arg Val Glu Leu Ala Pro Leu Pro Ser
                85                  90                  95

Trp Gln Pro Val Gly Lys Asn Leu Thr Leu Arg Cys Gln Val Glu Gly
            100                 105                 110

Gly Ala Pro Arg Ala Asn Leu Thr Val Val Leu Leu Arg Gly Glu Lys
        115                 120                 125

Glu Leu Lys Arg Glu Pro Ala Val Gly Glu Pro Ala Glu Val Thr Thr
    130                 135                 140

Thr Val Leu Val Arg Arg Asp His His Gly Ala Asn Phe Ser Cys Arg
145                 150                 155                 160

Thr Glu Leu Asp Leu Arg Pro Gln Gly Leu Glu Leu Phe Glu Asn Thr
                165                 170                 175

Ser Ala Pro Tyr Gln Leu Gln Thr Phe Val Leu Pro Ala Thr Pro Pro
            180                 185                 190

Gln Leu Val Ser Pro Arg Val Leu Glu Val Asp Thr Gln Gly Thr Val
        195                 200                 205

Val Cys Ser Leu Asp Gly Leu Phe Pro Val Ser Glu Ala Gln Val His
    210                 215                 220

Leu Ala Leu Gly Asp Gln Arg Leu Asn Pro Thr Val Thr Tyr Gly Asn
225                 230                 235                 240

Asp Ser Phe Ser Ala Lys Ala Ser Val Ser Val Thr Ala Glu Asp Glu
                245                 250                 255

Gly Thr Gln Arg Leu Thr Cys Ala Val Ile Leu Gly Asn Gln Ser Gln
            260                 265                 270

Glu Thr Leu Gln Thr Val Thr Ile Tyr Ser Phe Pro Ala Pro Asn Val
        275                 280                 285

Ile Leu Thr Lys Pro Glu Val Ser Glu Gly Thr Glu Val Thr Val Lys
    290                 295                 300

Cys Glu Ala His Pro Arg Ala Lys Val Thr Leu Asn Gly Val Pro Ala
305                 310                 315                 320

Gln Pro Leu Gly Pro Arg Ala Gln Leu Leu Lys Ala Thr Pro Glu
                325                 330                 335

Asp Asn Gly Arg Ser Phe Ser Cys Ser Ala Thr Leu Glu Val Ala Gly
            340                 345                 350

Gln Leu Ile His Lys Asn Gln Thr Arg Glu Leu Arg Val Leu Tyr Gly
```

```
                355                 360                 365
Pro Arg Leu Asp Glu Arg Asp Cys Pro Gly Asn Trp Thr Trp Pro Glu
    370                 375                 380

Asn Ser Gln Gln Thr Pro Met Cys Gln Ala Trp Gly Asn Pro Leu Pro
385                 390                 395                 400

Glu Leu Lys Cys Leu Lys Asp Gly Thr Phe Pro Leu Pro Ile Gly Glu
                405                 410                 415

Ser Val Thr Val Thr Arg Asp Leu Glu Gly Thr Tyr Leu Cys Arg Ala
            420                 425                 430

Arg Ser Thr Gln Gly Glu Val Thr Arg Lys Val Thr Val Asn Val Leu
        435                 440                 445

Ser Pro Arg Tyr Glu
    450

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Ala Ala Ala Lys
1               5

<210> SEQ ID NO 34
<211> LENGTH: 960
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Val Pro Gly Ala Gly Val Pro Gly Ala Gly Val Pro Gly Ala Gly Val
1               5                   10                  15

Pro Gly Ala Gly Val Pro Gly Ala Gly Val Pro Gly Ala Gly Val Pro
            20                  25                  30

Gly Ala Gly Val Pro Gly Ala Gly Val Pro Gly Ala Gly Val Pro Gly
        35                  40                  45

Ala Gly Val Pro Gly Ala Gly Val Pro Gly Ala Gly Val Pro Gly Ala
    50                  55                  60

Gly Val Pro Gly Ala Gly Val Pro Gly Ala Gly Val Pro Gly Ala Gly
65                  70                  75                  80

Val Pro Gly Ala Gly Val Pro Gly Ala Gly Val Pro Gly Ala Gly Val
                85                  90                  95

Pro Gly Ala Gly Val Pro Gly Ala Gly Val Pro Gly Ala Gly Val Pro
            100                 105                 110

Gly Ala Gly Val Pro Gly Ala Gly Val Pro Gly Ala Gly Val Pro Gly
        115                 120                 125

Ala Gly Val Pro Gly Ala Gly Val Pro Gly Ala Gly Val Pro Gly Ala
    130                 135                 140

Gly Val Pro Gly Ala Gly Val Pro Gly Ala Gly Val Pro Gly Ala Gly
145                 150                 155                 160

Val Pro Gly Ala Gly Val Pro Gly Ala Gly Val Pro Gly Ala Gly Val
                165                 170                 175

Pro Gly Ala Gly Val Pro Gly Ala Gly Val Pro Gly Ala Gly Val Pro
```

-continued

```
                180                 185                 190
Gly Ala Gly Val Pro Gly Ala Gly Val Pro Gly Ala Gly Val Pro Gly
            195                 200                 205
Ala Gly Val Pro Gly Ala Gly Val Pro Gly Ala Gly Val Pro Gly Ala
            210                 215                 220
Gly Val Pro Gly Ala Gly Val Pro Gly Ala Gly Val Pro Gly Ala Gly
225                 230                 235                 240
Val Pro Gly Ala Gly Val Pro Gly Ala Gly Val Pro Gly Ala Gly Val
                245                 250                 255
Pro Gly Ala Gly Val Pro Gly Ala Gly Val Pro Gly Ala Gly Val Pro
            260                 265                 270
Gly Ala Gly Val Pro Gly Ala Gly Val Pro Gly Ala Gly Val Pro Gly
            275                 280                 285
Ala Gly Val Pro Gly Ala Gly Val Pro Gly Ala Gly Val Pro Gly Ala
            290                 295                 300
Gly Val Pro Gly Ala Gly Val Pro Gly Ala Gly Val Pro Gly Ala Gly
305                 310                 315                 320
Val Pro Gly Ala Gly Val Pro Gly Ala Gly Val Pro Gly Ala Gly Val
                325                 330                 335
Pro Gly Ala Gly Val Pro Gly Ala Gly Val Pro Gly Ala Gly Val Pro
            340                 345                 350
Gly Ala Gly Val Pro Gly Ala Gly Val Pro Gly Ala Gly Val Pro Gly
            355                 360                 365
Ala Gly Val Pro Gly Ala Gly Val Pro Gly Ala Gly Val Pro Gly Ala
            370                 375                 380
Gly Val Pro Gly Ala Gly Val Pro Gly Ala Gly Val Pro Gly Ala Gly
385                 390                 395                 400
Val Pro Gly Ala Gly Val Pro Gly Ala Gly Val Pro Gly Ala Gly Val
                405                 410                 415
Pro Gly Ala Gly Val Pro Gly Ala Gly Val Pro Gly Ala Gly Val Pro
            420                 425                 430
Gly Ala Gly Val Pro Gly Ala Gly Val Pro Gly Ala Gly Val Pro Gly
            435                 440                 445
Ala Gly Val Pro Gly Ala Gly Val Pro Gly Ala Gly Val Pro Gly Ala
            450                 455                 460
Gly Val Pro Gly Ala Gly Val Pro Gly Ala Gly Val Pro Gly Ala Gly
465                 470                 475                 480
Val Pro Gly Ala Gly Val Pro Gly Ala Gly Val Pro Gly Ala Gly Val
                485                 490                 495
Pro Gly Ala Gly Val Pro Gly Ala Gly Val Pro Gly Ala Gly Val Pro
            500                 505                 510
Gly Ala Gly Val Pro Gly Ala Gly Val Pro Gly Ala Gly Val Pro Gly
            515                 520                 525
Ala Gly Val Pro Gly Ala Gly Val Pro Gly Ala Gly Val Pro Gly Ala
            530                 535                 540
Gly Val Pro Gly Ala Gly Val Pro Gly Ala Gly Val Pro Gly Ala Gly
545                 550                 555                 560
Val Pro Gly Ala Gly Val Pro Gly Ala Gly Val Pro Gly Ala Gly Val
                565                 570                 575
Pro Gly Ala Gly Val Pro Gly Ala Gly Val Pro Gly Ala Gly Val Pro
            580                 585                 590
Gly Ala Gly Val Pro Gly Ala Gly Val Pro Gly Ala Gly Val Pro Gly
            595                 600                 605
```

```
Ala Gly Val Pro Gly Ala Gly Val Pro Gly Ala Gly Val Pro Gly Ala
    610                 615                 620
Gly Val Pro Gly Ala Gly Val Pro Gly Ala Gly Val Pro Gly Ala Gly
625                 630                 635                 640
Val Pro Gly Ala Gly Val Pro Gly Ala Gly Val Pro Gly Ala Gly Val
                645                 650                 655
Pro Gly Ala Gly Val Pro Gly Ala Gly Val Pro Gly Ala Gly Val Pro
            660                 665                 670
Gly Ala Gly Val Pro Gly Ala Gly Val Pro Gly Ala Gly Val Pro Gly
        675                 680                 685
Ala Gly Val Pro Gly Ala Gly Val Pro Gly Ala Gly Val Pro Gly Ala
    690                 695                 700
Gly Val Pro Gly Ala Gly Val Pro Gly Ala Gly Val Pro Gly Ala Gly
705                 710                 715                 720
Val Pro Gly Ala Gly Val Pro Gly Ala Gly Val Pro Gly Ala Gly Val
                725                 730                 735
Pro Gly Ala Gly Val Pro Gly Ala Gly Val Pro Gly Ala Gly Val Pro
            740                 745                 750
Gly Ala Gly Val Pro Gly Ala Gly Val Pro Gly Ala Gly Val Pro Gly
        755                 760                 765
Ala Gly Val Pro Gly Ala Gly Val Pro Gly Ala Gly Val Pro Gly Ala
    770                 775                 780
Gly Val Pro Gly Ala Gly Val Pro Gly Ala Gly Val Pro Gly Ala Gly
785                 790                 795                 800
Val Pro Gly Ala Gly Val Pro Gly Ala Gly Val Pro Gly Ala Gly Val
                805                 810                 815
Pro Gly Ala Gly Val Pro Gly Ala Gly Val Pro Gly Ala Gly Val Pro
            820                 825                 830
Gly Ala Gly Val Pro Gly Ala Gly Val Pro Gly Ala Gly Val Pro Gly
        835                 840                 845
Ala Gly Val Pro Gly Ala Gly Val Pro Gly Ala Gly Val Pro Gly Ala
    850                 855                 860
Gly Val Pro Gly Ala Gly Val Pro Gly Ala Gly Val Pro Gly Ala Gly
865                 870                 875                 880
Val Pro Gly Ala Gly Val Pro Gly Ala Gly Val Pro Gly Ala Gly Val
                885                 890                 895
Pro Gly Ala Gly Val Pro Gly Ala Gly Val Pro Gly Ala Gly Val Pro
            900                 905                 910
Gly Ala Gly Val Pro Gly Ala Gly Val Pro Gly Ala Gly Val Pro Gly
        915                 920                 925
Ala Gly Val Pro Gly Ala Gly Val Pro Gly Ala Gly Val Pro Gly Ala
    930                 935                 940
Gly Val Pro Gly Ala Gly Val Pro Gly Ala Gly Val Pro Gly Ala Gly
945                 950                 955                 960

<210> SEQ ID NO 35
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Val Pro Gly Ala Gly Val Pro Gly Ala Gly Val Pro Gly Ala Gly Val
```

-continued

```
1               5                   10                  15
Pro Gly Ala Gly Val Pro Gly Ala Gly Val Pro Gly Ala Gly Val Pro
                20                  25                  30
Gly Ala Gly Val Pro Gly Ala Gly Val Pro Gly Ala Gly Val Pro Gly
                35                  40                  45
Ala Gly Val Pro Gly Ala Gly Val Pro Gly Ala Gly Val Pro Gly Ala
                50                  55                  60
Gly Val Pro Gly Ala Gly Val Pro Gly Ala Gly Val Pro Gly Ala Gly
 65                 70                  75                  80
Val Pro Gly Ala Gly Val Pro Gly Ala Gly Val Pro Gly Ala Gly Val
                85                  90                  95
Pro Gly Ala Gly Val Pro Gly Ala Gly Val Pro Gly Ala Gly Val Pro
                100                 105                 110
Gly Ala Gly Val Pro Gly Ala Gly Val Pro Gly Ala Gly Val Pro Gly
                115                 120                 125
Ala Gly Val Pro Gly Ala Gly Val Pro Gly Ala Gly Val Pro Gly Ala
                130                 135                 140
Gly Val Pro Gly Ala Gly Val Pro Gly Ala Gly Val Pro Gly Ala Gly
145                 150                 155                 160
Val Pro Gly Ala Gly Val Pro Gly Ala Gly Val Pro Gly Ala Gly Val
                165                 170                 175
Pro Gly Ala Gly Val Pro Gly Ala Gly Val Pro Gly Ala Gly Val Pro
                180                 185                 190
Gly Ala Gly Val Pro Gly Ala Gly Val Pro Gly Ala Gly Val Pro Gly
                195                 200                 205
Ala Gly Val Pro Gly Ala Gly Val Pro Gly Ala Gly Val Pro Gly Ala
                210                 215                 220
Gly Val Pro Gly Ala Gly Val Pro Gly Ala Gly Val Pro Gly Ala Gly
225                 230                 235                 240
Val Pro Gly Ala Gly Val Pro Gly Ala Gly Val Pro Gly Ala Gly Val
                245                 250                 255
Pro Gly Ala Gly Val Pro Gly Ala Gly Val Pro Gly Ala Gly Val Pro
                260                 265                 270
Gly Ala Gly Val Pro Gly Ala Gly Val Pro Gly Ala Gly Val Pro Gly
                275                 280                 285
Ala Gly Val Pro Gly Ala Gly Val Pro Gly Ala Gly Val Pro Gly Ala
                290                 295                 300
Gly Val Pro Gly Ala Gly Val Pro Gly Ala Gly Val Pro Gly Ala Gly
305                 310                 315                 320
Val Pro Gly Ala Gly Val Pro Gly Ala Gly Val Pro Gly Ala Gly Val
                325                 330                 335
Pro Gly Ala Gly Val Pro Gly Ala Gly Val Pro Gly Ala Gly Val Pro
                340                 345                 350
Gly Ala Gly Val Pro Gly Ala Gly Val Pro Gly Ala Gly Val Pro Gly
                355                 360                 365
Ala Gly Val Pro Gly Ala Gly Val Pro Gly Ala Gly Val Pro Gly Ala
                370                 375                 380
Gly Val Pro Gly Ala Gly Val Pro Gly Ala Gly Val Pro Gly Ala Gly
385                 390                 395                 400
Val Pro Gly Ala Gly Val Pro Gly Ala Gly Val Pro Gly Ala Gly Val
                405                 410                 415
Pro Gly Ala Gly Val Pro Gly Ala Gly Val Pro Gly Ala Gly Val Pro
                420                 425                 430
```

```
Gly Ala Gly Val Pro Gly Ala Gly Val Pro Gly Ala Gly Val Pro Gly
        435                 440                 445

Ala Gly Val Pro Gly Ala Gly Val Pro Gly Ala Gly Val Pro Gly Ala
    450                 455                 460

Gly Val Pro Gly Ala Gly Val Pro Gly Ala Gly Val Pro Gly Ala Gly
465                 470                 475                 480

<210> SEQ ID NO 36
<211> LENGTH: 960
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Val Pro Gly Ala Gly Val Pro Gly Ala Gly Val Pro Gly Ala Gly Val
1               5                   10                  15

Pro Gly Ala Gly Val Pro Gly Ala Gly Val Pro Gly Ala Gly Val Pro
            20                  25                  30

Gly Ala Gly Val Pro Gly Ala Gly Val Pro Gly Ala Gly Val Pro Gly
        35                  40                  45

Ala Gly Val Pro Gly Ala Gly Val Pro Gly Ala Gly Val Pro Gly Ala
    50                  55                  60

Gly Val Pro Gly Ala Gly Val Pro Gly Ala Gly Val Pro Gly Ala Gly
65                  70                  75                  80

Val Pro Gly Ala Gly Val Pro Gly Ala Gly Val Pro Gly Ala Gly Val
                85                  90                  95

Pro Gly Ala Gly Val Pro Gly Ala Gly Val Pro Gly Ala Gly Val Pro
            100                 105                 110

Gly Ala Gly Val Pro Gly Ala Gly Val Pro Gly Ala Gly Val Pro Gly
        115                 120                 125

Ala Gly Val Pro Gly Ala Gly Val Pro Gly Ala Gly Val Pro Gly Ala
    130                 135                 140

Gly Val Pro Gly Ala Gly Val Pro Gly Ala Gly Val Pro Gly Ala Gly
145                 150                 155                 160

Val Pro Gly Ala Gly Val Pro Gly Ala Gly Val Pro Gly Ala Gly Val
                165                 170                 175

Pro Gly Ala Gly Val Pro Gly Ala Gly Val Pro Gly Ala Gly Val Pro
            180                 185                 190

Gly Ala Gly Val Pro Gly Ala Gly Val Pro Gly Ala Gly Val Pro Gly
        195                 200                 205

Ala Gly Val Pro Gly Ala Gly Val Pro Gly Ala Gly Val Pro Gly Ala
    210                 215                 220

Gly Val Pro Gly Ala Gly Val Pro Gly Ala Gly Val Pro Gly Ala Gly
225                 230                 235                 240

Val Pro Gly Ala Gly Val Pro Gly Ala Gly Val Pro Gly Ala Gly Val
                245                 250                 255

Pro Gly Ala Gly Val Pro Gly Ala Gly Val Pro Gly Ala Gly Val Pro
            260                 265                 270

Gly Ala Gly Val Pro Gly Ala Gly Val Pro Gly Ala Gly Val Pro Gly
        275                 280                 285

Ala Gly Val Pro Gly Ala Gly Val Pro Gly Ala Gly Val Pro Gly Ala
    290                 295                 300

Gly Val Pro Gly Ala Gly Val Pro Gly Ala Gly Val Pro Gly Ala Gly
```

-continued

```
            305                 310                 315                 320
Val Pro Gly Ala Gly Val Pro Gly Ala Gly Val Pro Gly Ala Gly Val
                    325                 330                 335
Pro Gly Ala Gly Val Pro Gly Ala Gly Val Pro Gly Ala Gly Val Pro
                    340                 345                 350
Gly Ala Gly Val Pro Gly Ala Gly Val Pro Gly Ala Gly Val Pro Gly
                    355                 360                 365
Ala Gly Val Pro Gly Ala Gly Val Pro Gly Ala Gly Val Pro Gly Ala
                    370                 375                 380
Gly Val Pro Gly Ala Gly Val Pro Gly Ala Gly Val Pro Gly Ala Gly
385                 390                 395                 400
Val Pro Gly Ala Gly Val Pro Gly Ala Gly Val Pro Gly Ala Gly Val
                    405                 410                 415
Pro Gly Ala Gly Val Pro Gly Ala Gly Val Pro Gly Ala Gly Val Pro
                    420                 425                 430
Gly Ala Gly Val Pro Gly Ala Gly Val Pro Gly Ala Gly Val Pro Gly
                    435                 440                 445
Ala Gly Val Pro Gly Ala Gly Val Pro Gly Ala Gly Val Pro Gly Ala
                    450                 455                 460
Gly Val Pro Gly Ala Gly Val Pro Gly Ala Gly Val Pro Gly Ala Gly
465                 470                 475                 480
Val Pro Gly Ile Gly Val Pro Gly Ile Gly Val Pro Gly Ile Gly Val
                    485                 490                 495
Pro Gly Ile Gly Val Pro Gly Ile Gly Val Pro Gly Ile Gly Val Pro
                    500                 505                 510
Gly Ile Gly Val Pro Gly Ile Gly Val Pro Gly Ile Gly Val Pro Gly
                    515                 520                 525
Ile Gly Val Pro Gly Ile Gly Val Pro Gly Ile Gly Val Pro Gly Ile
                    530                 535                 540
Gly Val Pro Gly Ile Gly Val Pro Gly Ile Gly Val Pro Gly Ile Gly
545                 550                 555                 560
Val Pro Gly Ile Gly Val Pro Gly Ile Gly Val Pro Gly Ile Gly Val
                    565                 570                 575
Pro Gly Ile Gly Val Pro Gly Ile Gly Val Pro Gly Ile Gly Val Pro
                    580                 585                 590
Gly Ile Gly Val Pro Gly Ile Gly Val Pro Gly Ile Gly Val Pro Gly
                    595                 600                 605
Ile Gly Val Pro Gly Ile Gly Val Pro Gly Ile Gly Val Pro Gly Ile
                    610                 615                 620
Gly Val Pro Gly Ile Gly Val Pro Gly Ile Gly Val Pro Gly Ile Gly
625                 630                 635                 640
Val Pro Gly Ile Gly Val Pro Gly Ile Gly Val Pro Gly Ile Gly Val
                    645                 650                 655
Pro Gly Ile Gly Val Pro Gly Ile Gly Val Pro Gly Ile Gly Val Pro
                    660                 665                 670
Gly Ile Gly Val Pro Gly Ile Gly Val Pro Gly Ile Gly Val Pro Gly
                    675                 680                 685
Ile Gly Val Pro Gly Ile Gly Val Pro Gly Ile Gly Val Pro Gly Ile
                    690                 695                 700
Gly Val Pro Gly Ile Gly Val Pro Gly Ile Gly Val Pro Gly Ile Gly
705                 710                 715                 720
Val Pro Gly Ile Gly Val Pro Gly Ile Gly Val Pro Gly Ile Gly Val
                    725                 730                 735
```

```
Pro Gly Ile Gly Val Pro Gly Ile Gly Val Pro Gly Ile Gly Val Pro
            740                 745                 750

Gly Ile Gly Val Pro Gly Ile Gly Val Pro Gly Ile Gly Val Pro Gly
            755                 760                 765

Ile Gly Val Pro Gly Ile Gly Val Pro Gly Ile Gly Val Pro Gly Ile
            770                 775                 780

Gly Val Pro Gly Ile Gly Val Pro Gly Ile Gly Val Pro Gly Ile Gly
785                 790                 795                 800

Val Pro Gly Ile Gly Val Pro Gly Ile Gly Val Pro Gly Ile Gly Val
                805                 810                 815

Pro Gly Ile Gly Val Pro Gly Ile Gly Val Pro Gly Ile Gly Val Pro
            820                 825                 830

Gly Ile Gly Val Pro Gly Ile Gly Val Pro Gly Ile Gly Val Pro Gly
            835                 840                 845

Ile Gly Val Pro Gly Ile Gly Val Pro Gly Ile Gly Val Pro Gly Ile
            850                 855                 860

Gly Val Pro Gly Ile Gly Val Pro Gly Ile Gly Val Pro Gly Ile Gly
865                 870                 875                 880

Val Pro Gly Ile Gly Val Pro Gly Ile Gly Val Pro Gly Ile Gly Val
                885                 890                 895

Pro Gly Ile Gly Val Pro Gly Ile Gly Val Pro Gly Ile Gly Val Pro
            900                 905                 910

Gly Ile Gly Val Pro Gly Ile Gly Val Pro Gly Ile Gly Val Pro Gly
            915                 920                 925

Ile Gly Val Pro Gly Ile Gly Val Pro Gly Ile Gly Val Pro Gly Ile
            930                 935                 940

Gly Val Pro Gly Ile Gly Val Pro Gly Ile Gly Val Pro Gly Ile Gly
945                 950                 955                 960

<210> SEQ ID NO 37
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Val Pro Gly Ala Gly Val Pro Gly Ala Gly Val Pro Gly Ala Gly Val
1               5                   10                  15

Pro Gly Ala Gly Val Pro Gly Ala Gly Val Pro Gly Ala Gly Val Pro
            20                  25                  30

Gly Ala Gly Val Pro Gly Ala Gly Val Pro Gly Ala Gly Val Pro Gly
            35                  40                  45

Ala Gly Val Pro Gly Ala Gly Val Pro Gly Ala Gly Val Pro Gly Ala
    50                  55                  60

Gly Val Pro Gly Ala Gly Val Pro Gly Ala Gly Val Pro Gly Ala Gly
65                  70                  75                  80

Val Pro Gly Ala Gly Val Pro Gly Ala Gly Val Pro Gly Ala Gly Val
                85                  90                  95

Pro Gly Ala Gly Val Pro Gly Ala Gly Val Pro Gly Ala Gly Val Pro
            100                 105                 110

Gly Ala Gly Val Pro Gly Ala Gly
        115                 120
```

-continued

```
<210> SEQ ID NO 38
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Val Pro Gly Val Gly Val Pro Gly Val Gly Val Pro Gly Val Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
            100                 105                 110

Pro Gly Val Gly Val Pro Gly Val Gly
        115                 120

<210> SEQ ID NO 39
<211> LENGTH: 11
<212> TYPE: PRT
<213> ORGANISM: Unknown
<220> FEATURE:
<223> OTHER INFORMATION: Description of Unknown:
      Cyclosporin A peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (6)..(6)
<223> OTHER INFORMATION: Abu
<220> FEATURE:
<221> NAME/KEY: MOD_RES
<222> LOCATION: (7)..(7)
<223> OTHER INFORMATION: Sar
<220> FEATURE:
<223> OTHER INFORMATION: See specification as filed for detailed
      description of substitutions and preferred embodiments

<400> SEQUENCE: 39

Ala Leu Leu Val Thr Xaa Xaa Leu Val Leu Ala
1               5                   10

<210> SEQ ID NO 40
<211> LENGTH: 365
<212> TYPE: PRT
<213> ORGANISM: Homo sapiens

<400> SEQUENCE: 40

Met Ala Leu Leu Leu Cys Phe Val Leu Leu Cys Gly Val Val Asp Phe
1               5                   10                  15

Ala Arg Ser Leu Ser Ile Thr Thr Pro Glu Glu Met Ile Glu Lys Ala
            20                  25                  30

Lys Gly Glu Thr Ala Tyr Leu Pro Cys Lys Phe Thr Leu Ser Pro Glu
        35                  40                  45
```

```
Asp Gln Gly Pro Leu Asp Ile Glu Trp Leu Ile Ser Pro Ala Asp Asn
        50                  55                  60

Gln Lys Val Asp Gln Val Ile Ile Leu Tyr Ser Gly Asp Lys Ile Tyr
 65                  70                  75                  80

Asp Asp Tyr Tyr Pro Asp Leu Lys Gly Arg Val His Phe Thr Ser Asn
                85                  90                  95

Asp Leu Lys Ser Gly Asp Ala Ser Ile Asn Val Thr Asn Leu Gln Leu
                100                 105                 110

Ser Asp Ile Gly Thr Tyr Gln Cys Lys Val Lys Ala Pro Gly Val
        115                 120                 125

Ala Asn Lys Lys Ile His Leu Val Val Leu Val Lys Pro Ser Gly Ala
    130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Trp Leu Ala Glu Met
                180                 185                 190

Thr Ser Ser Val Ile Ser Val Lys Asn Ala Ser Ser Glu Tyr Ser Gly
        195                 200                 205

Thr Tyr Ser Cys Thr Val Arg Asn Arg Val Gly Ser Asp Gln Cys Leu
    210                 215                 220

Leu Arg Leu Asn Val Val Pro Pro Ser Asn Lys Ala Gly Leu Ile Ala
225                 230                 235                 240

Gly Ala Ile Ile Gly Thr Leu Leu Ala Leu Ala Leu Ile Gly Leu Ile
                245                 250                 255

Ile Phe Cys Cys Arg Lys Lys Arg Arg Glu Glu Lys Tyr Glu Lys Glu
                260                 265                 270

Val His His Asp Ile Arg Glu Asp Val Pro Pro Lys Ser Arg Thr
        275                 280                 285

Ser Thr Ala Arg Ser Tyr Ile Gly Ser Asn His Ser Ser Leu Gly Ser
    290                 295                 300

Met Ser Pro Ser Asn Met Glu Gly Tyr Ser Lys Thr Gln Tyr Asn Gln
305                 310                 315                 320

Val Pro Ser Glu Asp Phe Glu Arg Thr Pro Gln Ser Pro Thr Leu Pro
                325                 330                 335

Pro Ala Lys Val Ala Ala Pro Asn Leu Ser Arg Met Gly Ala Ile Pro
                340                 345                 350

Val Met Ile Pro Ala Gln Ser Lys Asp Gly Ser Ile Val
                355                 360                 365

<210> SEQ ID NO 41
<211> LENGTH: 344
<212> TYPE: PRT
<213> ORGANISM: Homo sapiens

<400> SEQUENCE: 41

Met Ala Leu Leu Leu Cys Phe Val Leu Leu Cys Gly Val Val Asp Phe
 1               5                   10                  15

Ala Arg Ser Leu Ser Ile Thr Thr Pro Glu Glu Met Ile Glu Lys Ala
                20                  25                  30

Lys Gly Glu Thr Ala Tyr Leu Pro Cys Lys Phe Thr Leu Ser Pro Glu
            35                  40                  45

Asp Gln Gly Pro Leu Asp Ile Glu Trp Leu Ile Ser Pro Ala Asp Asn
```

```
              50                  55                  60
Gln Lys Val Asp Gln Val Ile Ile Leu Tyr Ser Gly Asp Lys Ile Tyr
 65                  70                  75                  80

Asp Asp Tyr Tyr Pro Asp Leu Lys Gly Arg Val His Phe Thr Ser Asn
                 85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
            115                 120                 125

Ala Asn Lys Lys Ile His Leu Val Val Leu Val Lys Pro Ser Gly Ala
            130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Trp Leu Ala Glu Met
            180                 185                 190

Thr Ser Ser Val Ile Ser Val Lys Asn Ala Ser Ser Glu Tyr Ser Gly
            195                 200                 205

Thr Tyr Ser Cys Thr Val Arg Asn Arg Val Gly Ser Asp Gln Cys Leu
            210                 215                 220

Leu Arg Leu Asn Val Val Pro Pro Ser Asn Lys Ala Gly Leu Ile Ala
225                 230                 235                 240

Gly Ala Ile Ile Gly Thr Leu Leu Ala Leu Ala Leu Ile Gly Leu Ile
                245                 250                 255

Ile Phe Cys Cys Arg Lys Lys Arg Arg Glu Glu Lys Tyr Glu Lys Glu
                260                 265                 270

Val His His Asp Ile Arg Glu Asp Val Pro Pro Lys Ser Arg Thr
                275                 280                 285

Ser Thr Ala Arg Ser Tyr Ile Gly Ser Asn His Ser Ser Leu Gly Ser
            290                 295                 300

Met Ser Pro Ser Asn Met Glu Gly Tyr Ser Lys Thr Gln Tyr Asn Gln
305                 310                 315                 320

Val Pro Ser Glu Asp Phe Glu Arg Thr Pro Gln Ser Pro Thr Leu Pro
                325                 330                 335

Pro Ala Lys Phe Lys Tyr Pro Tyr
            340

<210> SEQ ID NO 42
<211> LENGTH: 89
<212> TYPE: PRT
<213> ORGANISM: Homo sapiens

<400> SEQUENCE: 42

Met Ala Leu Leu Leu Cys Phe Val Leu Leu Cys Gly Val Val Asp Phe
 1               5                  10                  15

Ala Arg Ser Leu Ser Ile Thr Thr Pro Glu Glu Met Ile Glu Lys Ala
                20                  25                  30

Lys Gly Glu Thr Ala Tyr Leu Pro Cys Lys Phe Thr Leu Ser Pro Glu
            35                  40                  45

Asp Gln Gly Pro Leu Asp Ile Glu Trp Leu Ile Ser Pro Ala Asp Asn
            50                  55                  60

Gln Lys Val Asp Gln Val Gly Arg Cys Ala Thr Ser Lys Glu Pro Tyr
 65                  70                  75                  80
```

Val His Cys Gln Lys Leu His Arg Gln
            85

<210> SEQ ID NO 43
<211> LENGTH: 200
<212> TYPE: PRT
<213> ORGANISM: Homo sapiens

<400> SEQUENCE: 43

Met Ala Leu Leu Leu Cys Phe Val Leu Leu Cys Gly Val Val Asp Phe
1               5                   10                  15

Ala Arg Ser Leu Ser Ile Thr Thr Pro Glu Glu Met Ile Glu Lys Ala
            20                  25                  30

Lys Gly Glu Thr Ala Tyr Leu Pro Cys Lys Phe Thr Leu Ser Pro Glu
        35                  40                  45

Asp Gln Gly Pro Leu Asp Ile Glu Trp Leu Ile Ser Pro Ala Asp Asn
    50                  55                  60

Gln Lys Val Asp Gln Val Ile Ile Leu Tyr Ser Gly Asp Lys Ile Tyr
65                  70                  75                  80

Asp Asp Tyr Tyr Pro Asp Leu Lys Gly Arg Val His Phe Thr Ser Asn
                85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Ala Pro Gly Val
        115                 120                 125

Ala Asn Lys Lys Ile His Leu Val Val Leu Gly Lys Met Cys His Leu
    130                 135                 140

Gln Arg Ala Val Arg Pro Leu Pro Glu Ala Thr Ser Ala Val Ile Ile
145                 150                 155                 160

His Pro Trp Gly Pro Cys Leu Leu Pro Thr Trp Lys Asp Ile Pro Arg
                165                 170                 175

Leu Ser Ile Thr Lys Tyr Gln Val Lys Thr Leu Asn Ala Leu Leu Arg
            180                 185                 190

Val Arg Leu Ser His Leu Leu Arg
        195                 200

<210> SEQ ID NO 44
<211> LENGTH: 250
<212> TYPE: PRT
<213> ORGANISM: Homo sapiens

<400> SEQUENCE: 44

Met Ala Leu Leu Leu Cys Phe Val Leu Leu Cys Gly Val Val Asp Phe
1               5                   10                  15

Ala Arg Ser Leu Ser Ile Thr Thr Pro Glu Glu Met Ile Glu Lys Ala
            20                  25                  30

Lys Gly Glu Thr Ala Tyr Leu Pro Cys Lys Phe Thr Leu Ser Pro Glu
        35                  40                  45

Asp Gln Gly Pro Leu Asp Ile Glu Trp Leu Ile Ser Pro Ala Asp Asn
    50                  55                  60

Gln Lys Val Asp Gln Val Ile Ile Leu Tyr Ser Gly Asp Lys Ile Tyr
65                  70                  75                  80

Asp Asp Tyr Tyr Pro Asp Leu Lys Gly Arg Val His Phe Thr Ser Asn
                85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
            115                 120                 125

Ala Asn Lys Lys Ile His Leu Val Val Leu Val Lys Pro Ser Gly Ala
        130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Trp Leu Ala Gly Lys
            180                 185                 190

Met Cys His Leu Gln Arg Ala Val Arg Pro Leu Pro Glu Ala Thr Ser
        195                 200                 205

Ala Val Ile Ile His Pro Trp Gly Pro Cys Leu Leu Pro Thr Trp Lys
    210                 215                 220

Asp Ile Pro Arg Leu Ser Ile Thr Lys Tyr Gln Val Lys Thr Leu Asn
225                 230                 235                 240

Ala Leu Leu Arg Val Arg Leu Ser His Leu
            245                 250

<210> SEQ ID NO 45
<211> LENGTH: 350
<212> TYPE: PRT
<213> ORGANISM: Homo sapiens

<400> SEQUENCE: 45

Met Ala Leu Leu Leu Cys Phe Val Leu Leu Cys Gly Val Val Asp Phe
1               5                   10                  15

Ala Arg Ser Leu Ser Ile Thr Thr Pro Glu Glu Met Ile Glu Lys Ala
            20                  25                  30

Lys Gly Glu Thr Ala Tyr Leu Pro Cys Lys Phe Thr Leu Ser Pro Glu
        35                  40                  45

Asp Gln Gly Pro Leu Asp Ile Glu Trp Leu Ile Ser Pro Ala Asp Asn
    50                  55                  60

Gln Lys Val Asp Gln Val Ile Leu Tyr Ser Gly Asp Lys Ile Tyr
65                  70                  75                  80

Asp Asp Tyr Tyr Pro Asp Leu Lys Gly Arg Val His Phe Thr Ser Asn
                85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Ile His Leu Val Val Leu Val Lys Pro Ser Gly Ala
    130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Trp Leu Ala Glu Met
            180                 185                 190

Thr Ser Ser Val Ile Ser Val Lys Asn Ala Ser Ser Glu Tyr Ser Gly
        195                 200                 205

Thr Tyr Ser Cys Thr Val Arg Asn Arg Val Gly Ser Asp Gln Cys Leu
    210                 215                 220

Leu Arg Leu Asn Val Val Pro Pro Ser Asn Lys Ala Gly Leu Ile Ala
225                 230                 235                 240

```
Gly Ala Ile Ile Gly Thr Leu Leu Ala Leu Ala Leu Ile Gly Leu Ile
                245                 250                 255

Ile Phe Cys Cys Arg Lys Lys Arg Glu Glu Lys Tyr Glu Lys Glu
            260                 265                 270

Val His His Asp Ile Arg Glu Asp Val Pro Pro Lys Ser Arg Thr
        275                 280                 285

Ser Thr Ala Arg Ser Tyr Ile Gly Ser Asn His Ser Ser Leu Gly Ser
290                 295                 300

Met Ser Pro Ser Asn Met Glu Gly Tyr Ser Lys Thr Gln Tyr Asn Gln
305                 310                 315                 320

Val Pro Ser Glu Asp Phe Glu Arg Thr Pro Gln Ser Pro Thr Leu Pro
                325                 330                 335

Pro Ala Lys Phe Lys Tyr Pro Tyr Lys Thr Asp Gly Ile Thr
                340                 345                 350

<210> SEQ ID NO 46
<211> LENGTH: 324
<212> TYPE: PRT
<213> ORGANISM: Homo sapiens

<400> SEQUENCE: 46

Met Ala Leu Leu Leu Cys Phe Val Leu Leu Cys Gly Val Val Asp Phe
1               5                   10                  15

Ala Arg Ser Leu Ser Ile Thr Thr Pro Glu Glu Met Ile Glu Lys Ala
                20                  25                  30

Lys Gly Glu Thr Ala Tyr Leu Pro Cys Lys Phe Thr Leu Ser Pro Glu
            35                  40                  45

Asp Gln Gly Pro Leu Asp Ile Glu Trp Leu Ile Ser Pro Ala Asp Asn
        50                  55                  60

Gln Lys Val Asp Gln Val Ile Ile Leu Tyr Ser Gly Asp Lys Ile Tyr
65                  70                  75                  80

Asp Asp Tyr Tyr Pro Asp Leu Lys Gly Arg Val His Phe Thr Ser Asn
                85                  90                  95

Asp Leu Lys Ser Gly Asp Ala Ser Ile Asn Val Thr Asn Leu Gln Leu
            100                 105                 110

Ser Asp Ile Gly Thr Tyr Gln Cys Lys Val Lys Lys Ala Pro Gly Val
        115                 120                 125

Ala Asn Lys Lys Ile His Leu Val Val Leu Val Lys Pro Ser Gly Ala
130                 135                 140

Arg Cys Tyr Val Asp Gly Ser Glu Glu Ile Gly Ser Asp Phe Lys Ile
145                 150                 155                 160

Lys Cys Glu Pro Lys Glu Gly Ser Leu Pro Leu Gln Tyr Glu Trp Gln
                165                 170                 175

Lys Leu Ser Asp Ser Gln Lys Met Pro Thr Ser Trp Leu Ala Ala Ser
            180                 185                 190

Asn Lys Ala Gly Leu Ile Ala Gly Ala Ile Gly Thr Leu Leu Ala
        195                 200                 205

Leu Ala Leu Ile Gly Leu Ile Ile Phe Cys Cys Arg Lys Lys Arg Arg
        210                 215                 220

Glu Glu Lys Tyr Glu Lys Glu Val His His Asp Ile Arg Glu Asp Val
225                 230                 235                 240

Pro Pro Pro Lys Ser Arg Thr Ser Thr Ala Arg Ser Tyr Ile Gly Ser
                245                 250                 255

Asn His Ser Ser Leu Gly Ser Met Ser Pro Ser Asn Met Glu Gly Tyr
```

```
                    260                 265                 270
Ser Lys Thr Gln Tyr Asn Gln Val Pro Ser Glu Asp Phe Glu Arg Thr
                275                 280                 285

Pro Gln Ser Pro Thr Leu Pro Pro Ala Lys Val Ala Ala Pro Asn Leu
            290                 295                 300

Ser Arg Met Gly Ala Ile Pro Val Met Ile Pro Ala Gln Ser Lys Asp
305                 310                 315                 320

Gly Ser Ile Val

<210> SEQ ID NO 47
<211> LENGTH: 764
<212> TYPE: PRT
<213> ORGANISM: Homo sapiens

<400> SEQUENCE: 47

Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Ser Lys Tyr Ala Gly
65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
    210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Val Asn Thr Leu Gly Lys
        275                 280                 285

Arg Ala Pro Ala Phe Glu Gly Arg Ile Leu Leu Asn Pro Gln Asp Lys
    290                 295                 300

Asp Gly Ser Phe Ser Val Val Ile Thr Gly Leu Arg Lys Glu Asp Ala
```

```
                305                 310                 315                 320
Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
                340                 345                 350

Pro Arg Ser Pro Thr Val Val Lys Gly Val Ala Gly Gly Ser Val Ala
                355                 360                 365

Val Leu Cys Pro Tyr Asn Arg Lys Glu Ser Lys Ser Ile Lys Tyr Trp
            370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415

Glu Glu Pro Gly Asn Gly Thr Phe Thr Val Ile Leu Asn Gln Leu Thr
                420                 425                 430

Ser Arg Asp Ala Gly Phe Tyr Trp Cys Leu Thr Asn Gly Asp Thr Leu
                435                 440                 445

Trp Arg Thr Thr Val Glu Ile Lys Ile Ile Glu Gly Glu Pro Asn Leu
        450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
                500                 505                 510

Pro Ser Lys Ala Phe Val Asn Cys Asp Glu Asn Ser Arg Leu Val Ser
            515                 520                 525

Leu Thr Leu Asn Leu Val Thr Arg Ala Asp Glu Gly Trp Tyr Trp Cys
        530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
                565                 570                 575

Lys Ala Asp Ala Ala Pro Asp Glu Lys Val Leu Asp Ser Gly Phe Arg
                580                 585                 590

Glu Ile Glu Asn Lys Ala Ile Gln Asp Pro Arg Leu Phe Ala Glu Glu
            595                 600                 605

Lys Ala Val Ala Asp Thr Arg Asp Gln Ala Asp Gly Ser Arg Ala Ser
            610                 615                 620

Val Asp Ser Gly Ser Ser Glu Glu Gln Gly Gly Ser Ser Arg Ala Leu
625                 630                 635                 640

Val Ser Thr Leu Val Pro Leu Gly Leu Val Leu Ala Val Gly Ala Val
                645                 650                 655

Ala Val Gly Val Ala Arg Ala Arg His Arg Lys Asn Val Asp Arg Val
                660                 665                 670

Ser Ile Arg Ser Tyr Arg Thr Asp Ile Ser Met Ser Asp Phe Glu Asn
        675                 680                 685

Ser Arg Glu Phe Gly Ala Asn Asp Asn Met Gly Ala Ser Ser Ile Thr
        690                 695                 700

Gln Glu Thr Ser Leu Gly Gly Lys Glu Glu Phe Val Ala Thr Thr Glu
705                 710                 715                 720

Ser Thr Thr Glu Thr Lys Glu Pro Lys Lys Ala Lys Arg Ser Ser Lys
                725                 730                 735
```

```
Glu Glu Ala Glu Met Ala Tyr Lys Asp Phe Leu Leu Gln Ser Ser Thr
                740                 745                 750

Val Ala Ala Glu Ala Gln Asp Gly Pro Gln Glu Ala
        755                 760

<210> SEQ ID NO 48
<211> LENGTH: 19
<212> TYPE: PRT
<213> ORGANISM: Homo sapiens

<400> SEQUENCE: 48

Thr Trp Ala Ser Arg Gln Glu Pro Ser Gln Gly Thr Thr Thr Phe Ala
1               5                   10                  15

Val Thr Ser

<210> SEQ ID NO 49
<211> LENGTH: 19
<212> TYPE: PRT
<213> ORGANISM: Homo sapiens

<400> SEQUENCE: 49

Thr Trp Ala Ser Arg Gln Glu Pro Ser Gln Gly Thr Thr Thr Phe Ala
1               5                   10                  15

Val Thr Ser

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Gly Gly Gly Ser
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<223> OTHER INFORMATION: See specification as filed for detailed
      description of substitutions and preferred embodiments

<400> SEQUENCE: 51

Val Pro Gly Xaa Gly
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
```

```
<223> OTHER INFORMATION: Any amino acid
<220> FEATURE:
<221> NAME/KEY: MOD_RES
<222> LOCATION: (6)..(6)
<223> OTHER INFORMATION: Glu or Gln
<220> FEATURE:
<223> OTHER INFORMATION: See specification as filed for detailed
      description of substitutions and preferred embodiments

<400> SEQUENCE: 52

Gly Val Pro Gly Xaa Xaa
1               5

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Pro Gly Ala Gly Val Pro Gly Ile Gly
1               5                   10

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Val Pro Gly Ala Gly
1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Pro Gly Val Gly
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His His His His His His
1               5

<210> SEQ ID NO 57
<211> LENGTH: 854
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 57

Met Gly Met Val Asn Pro Thr Val Phe Phe Asp Ile Ala Val Asp Gly
1               5                   10                  15

Glu Pro Leu Gly Arg Val Ser Phe Glu Leu Phe Ala Asp Lys Val Pro
            20                  25                  30

Lys Thr Ala Glu Asn Phe Arg Ala Leu Ser Thr Gly Glu Lys Gly Phe
        35                  40                  45

Gly Tyr Lys Gly Ser Cys Phe His Arg Ile Ile Pro Gly Phe Met Cys
    50                  55                  60

Gln Gly Gly Asp Phe Thr Arg His Asn Gly Thr Gly Gly Lys Ser Ile
65                  70                  75                  80

Tyr Gly Glu Lys Phe Glu Asp Glu Asn Phe Ile Leu Lys His Thr Gly
                85                  90                  95

Pro Gly Ile Leu Ser Met Ala Asn Ala Gly Pro Asn Thr Asn Gly Ser
            100                 105                 110

Gln Phe Phe Ile Cys Thr Ala Lys Thr Glu Trp Leu Lys His Val Val
        115                 120                 125

Phe Gly Lys Val Lys Glu Gly Met Asn Ile Val Glu Ala Met Glu Arg
130                 135                 140

Phe Gly Ser Arg Asn Gly Lys Thr Ser Lys Lys Ile Thr Ile Ala Asp
145                 150                 155                 160

Cys Gly Gln Leu Glu Gly Val Pro Gly Ala Gly Val Pro Gly Ala Gly
                165                 170                 175

Val Pro Gly Ala Gly Val Pro Gly Ala Gly Val Pro Gly Ala Gly Val
            180                 185                 190

Pro Gly Ala Gly Val Pro Gly Ala Gly Val Pro Gly Ala Gly Val Pro
        195                 200                 205

Gly Ala Gly Val Pro Gly Ala Gly Val Pro Gly Ala Gly Val Pro Gly
    210                 215                 220

Ala Gly Val Pro Gly Ala Gly Val Pro Gly Ala Gly Val Pro Gly Ala
225                 230                 235                 240

Gly Val Pro Gly Ala Gly Val Pro Gly Ala Gly Val Pro Gly Ala Gly
                245                 250                 255

Val Pro Gly Ala Gly Val Pro Gly Ala Gly Val Pro Gly Ala Gly Val
            260                 265                 270

Pro Gly Ala Gly Val Pro Gly Ala Gly Val Pro Gly Ala Gly Met Val
        275                 280                 285

Asn Pro Thr Val Phe Phe Asp Ile Ala Val Asp Gly Glu Pro Leu Gly
    290                 295                 300

Arg Val Ser Phe Glu Leu Phe Ala Asp Lys Val Pro Lys Thr Ala Glu
305                 310                 315                 320

Asn Phe Arg Ala Leu Ser Thr Gly Glu Lys Gly Phe Gly Tyr Lys Gly
                325                 330                 335

Ser Cys Phe His Arg Ile Ile Pro Gly Phe Met Cys Gln Gly Gly Asp
            340                 345                 350

Phe Thr Arg His Asn Gly Thr Gly Gly Lys Ser Ile Tyr Gly Glu Lys
        355                 360                 365

Phe Glu Asp Glu Asn Phe Ile Leu Lys His Thr Gly Pro Gly Ile Leu
    370                 375                 380

Ser Met Ala Asn Ala Gly Pro Asn Thr Asn Gly Ser Gln Phe Phe Ile
385                 390                 395                 400

Cys Thr Ala Lys Thr Glu Trp Leu Lys His Val Val Phe Gly Lys Val
                405                 410                 415
```

```
Lys Glu Gly Met Asn Ile Val Glu Ala Met Glu Arg Phe Gly Ser Arg
                420                 425                 430

Asn Gly Lys Thr Ser Lys Lys Ile Thr Ile Ala Asp Cys Gly Gln Leu
            435                 440                 445

Glu Gly Val Pro Gly Ala Gly Val Pro Gly Ala Gly Val Pro Gly Ala
        450                 455                 460

Gly Val Pro Gly Ala Gly Val Pro Gly Ala Gly Val Pro Gly Ala Gly
465                 470                 475                 480

Val Pro Gly Ala Gly Val Pro Gly Ala Gly Val Pro Gly Ala Gly Val
                485                 490                 495

Pro Gly Ala Gly Val Pro Gly Ala Gly Val Pro Gly Ala Gly Val Pro
            500                 505                 510

Gly Ala Gly Val Pro Gly Ala Gly Val Pro Gly Ala Gly Val Pro Gly
        515                 520                 525

Ala Gly Val Pro Gly Ala Gly Val Pro Gly Ala Gly Val Pro Gly Ala
    530                 535                 540

Gly Val Pro Gly Ala Gly Val Pro Gly Ala Gly Val Pro Gly Ala Gly
545                 550                 555                 560

Val Pro Gly Ala Gly Val Pro Gly Ala Gly Met Val Asn Pro Thr Val
                565                 570                 575

Phe Phe Asp Ile Ala Val Asp Gly Glu Pro Leu Gly Arg Val Ser Phe
            580                 585                 590

Glu Leu Phe Ala Asp Lys Val Pro Lys Thr Ala Glu Asn Phe Arg Ala
        595                 600                 605

Leu Ser Thr Gly Glu Lys Gly Phe Gly Tyr Lys Gly Ser Cys Phe His
    610                 615                 620

Arg Ile Ile Pro Gly Phe Met Cys Gln Gly Gly Asp Phe Thr Arg His
625                 630                 635                 640

Asn Gly Thr Gly Gly Lys Ser Ile Tyr Gly Glu Lys Phe Glu Asp Glu
                645                 650                 655

Asn Phe Ile Leu Lys His Thr Gly Pro Gly Ile Leu Ser Met Ala Asn
            660                 665                 670

Ala Gly Pro Asn Thr Asn Gly Ser Gln Phe Phe Ile Cys Thr Ala Lys
        675                 680                 685

Thr Glu Trp Leu Lys His Val Val Phe Gly Lys Val Lys Glu Gly Met
    690                 695                 700

Asn Ile Val Glu Ala Met Glu Arg Phe Gly Ser Arg Asn Gly Lys Thr
705                 710                 715                 720

Ser Lys Lys Ile Thr Ile Ala Asp Cys Gly Gln Leu Glu Gly Val Pro
                725                 730                 735

Gly Ala Gly Val Pro Gly Ala Gly Val Pro Gly Ala Gly Val Pro Gly
            740                 745                 750

Ala Gly Val Pro Gly Ala Gly Val Pro Gly Ala Gly Val Pro Gly Ala
        755                 760                 765

Gly Val Pro Gly Ala Gly Val Pro Gly Ala Gly Val Pro Gly Ala Gly
    770                 775                 780

Val Pro Gly Ala Gly Val Pro Gly Ala Gly Val Pro Gly Ala Gly Val
785                 790                 795                 800

Pro Gly Ala Gly Val Pro Gly Ala Gly Val Pro Gly Ala Gly Val Pro
                805                 810                 815

Gly Ala Gly Val Pro Gly Ala Gly Val Pro Gly Ala Gly Val Pro Gly
            820                 825                 830
```

```
Ala Gly Val Pro Gly Ala Gly Val Pro Gly Ala Gly Val Pro Gly Ala
        835                 840                 845

Gly Val Pro Gly Ala Gly
    850
```

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<223> OTHER INFORMATION: See specification as filed for detailed
      description of substitutions and preferred embodiments

<400> SEQUENCE: 58

```
Gly Val Pro Gly Xaa Gly
1               5
```

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<223> OTHER INFORMATION: See specification as filed for detailed
      description of substitutions and preferred embodiments

<400> SEQUENCE: 59

```
Gly Val Pro Gly Xaa Gly Tyr
1               5
```

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Val Pro Gly Ser Gly
1               5
```

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Val Pro Gly Ala Gly
1               5
```

<210> SEQ ID NO 62
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Val Pro Gly Val Gly
1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Val Pro Gly Ile Gly
1               5

<210> SEQ ID NO 64
<211> LENGTH: 520
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
catatggtta acccgaccgt tttcttcgac atcgctgttg acggtgaacc gctgggtcgt      60
gtttctttcg aactgttcgc tgacaaagtt ccgaaaaccg ctgaaaactt ccgtgctctg     120
tctaccggta aaaaggtttt cggttacaaa ggttcttgct tccaccgtat catcccgggt     180
ttcatgtgcc agggtggtga cttcacccgt cacaacggta ccggtggtaa atctatctac     240
ggtgaaaaat tcgaagacga aaacttcatc ctgaaacaca ccggtccggg tatcctgtct     300
atggctaacg ctggtccgaa caccaacggt tctcagttct tcatctgcac cgctaaaacc     360
gaatggctgg acggtaaaca cgttgttttc ggtaaagtta agaaggtat gaacatcgtt     420 gaagctatgg aacgtttcgg ttctcgtaac ggtaaaacct ctaaaaaaat caccatcgct     480
gactgcggtc agctggaagg ttactgatct cctcggatcc                          520

<210> SEQ ID NO 65
<211> LENGTH: 962
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gly Val Pro Gly Ala Gly Val Pro Gly Ala Gly Val Pro Gly Ala Gly
1               5                   10                  15

Val Pro Gly Ala Gly Val Pro Gly Ala Gly Val Pro Gly Ala Gly Val
                20                  25                  30

Pro Gly Ala Gly Val Pro Gly Ala Gly Val Pro Gly Ala Gly Val Pro
            35                  40                  45

Gly Ala Gly Val Pro Gly Ala Gly Val Pro Gly Ala Gly Val Pro Gly
        50                  55                  60

Ala Gly Val Pro Gly Ala Gly Val Pro Gly Ala Gly Val Pro Gly Ala
65                  70                  75                  80
```

```
Gly Val Pro Gly Ala Gly Val Pro Gly Ala Gly Val Pro Gly Ala Gly
            85                  90                  95
Val Pro Gly Ala Gly Val Pro Gly Ala Gly Val Pro Gly Ala Gly Val
            100                 105                 110
Pro Gly Ala Gly Val Pro Gly Ala Gly Val Pro Gly Ala Gly Val Pro
            115                 120                 125
Gly Ala Gly Val Pro Gly Ala Gly Val Pro Gly Ala Gly Val Pro Gly
            130                 135                 140
Ala Gly Val Pro Gly Ala Gly Val Pro Gly Ala Gly Val Pro Gly Ala
145                 150                 155                 160
Gly Val Pro Gly Ala Gly Val Pro Gly Ala Gly Val Pro Gly Ala Gly
            165                 170                 175
Val Pro Gly Ala Gly Val Pro Gly Ala Gly Val Pro Gly Ala Gly Val
            180                 185                 190
Pro Gly Ala Gly Val Pro Gly Ala Gly Val Pro Gly Ala Gly Val Pro
            195                 200                 205
Gly Ala Gly Val Pro Gly Ala Gly Val Pro Gly Ala Gly Val Pro Gly
            210                 215                 220
Ala Gly Val Pro Gly Ala Gly Val Pro Gly Ala Gly Val Pro Gly Ala
225                 230                 235                 240
Gly Val Pro Gly Ala Gly Val Pro Gly Ala Gly Val Pro Gly Ala Gly
            245                 250                 255
Val Pro Gly Ala Gly Val Pro Gly Ala Gly Val Pro Gly Ala Gly Val
            260                 265                 270
Pro Gly Ala Gly Val Pro Gly Ala Gly Val Pro Gly Ala Gly Val Pro
            275                 280                 285
Gly Ala Gly Val Pro Gly Ala Gly Val Pro Gly Ala Gly Val Pro Gly
            290                 295                 300
Ala Gly Val Pro Gly Ala Gly Val Pro Gly Ala Gly Val Pro Gly Ala
305                 310                 315                 320
Gly Val Pro Gly Ala Gly Val Pro Gly Ala Gly Val Pro Gly Ala Gly
            325                 330                 335
Val Pro Gly Ala Gly Val Pro Gly Ala Gly Val Pro Gly Ala Gly Val
            340                 345                 350
Pro Gly Ala Gly Val Pro Gly Ala Gly Val Pro Gly Ala Gly Val Pro
            355                 360                 365
Gly Ala Gly Val Pro Gly Ala Gly Val Pro Gly Ala Gly Val Pro Gly
            370                 375                 380
Ala Gly Val Pro Gly Ala Gly Val Pro Gly Ala Gly Val Pro Gly Ala
385                 390                 395                 400
Gly Val Pro Gly Ala Gly Val Pro Gly Ala Gly Val Pro Gly Ala Gly
            405                 410                 415
Val Pro Gly Ala Gly Val Pro Gly Ala Gly Val Pro Gly Ala Gly Val
            420                 425                 430
Pro Gly Ala Gly Val Pro Gly Ala Gly Val Pro Gly Ala Gly Val Pro
            435                 440                 445
Gly Ala Gly Val Pro Gly Ala Gly Val Pro Gly Ala Gly Val Pro Gly
            450                 455                 460
Ala Gly Val Pro Gly Ala Gly Val Pro Gly Ala Gly Val Pro Gly Ala
465                 470                 475                 480
Gly Val Pro Gly Ala Gly Val Pro Gly Ala Gly Val Pro Gly Ala Gly
            485                 490                 495
```

```
Val Pro Gly Ala Gly Val Pro Gly Ala Gly Val Pro Gly Ala Gly Val
            500                 505                 510
Pro Gly Ala Gly Val Pro Gly Ala Gly Val Pro Gly Ala Gly Val Pro
        515                 520                 525
Gly Ala Gly Val Pro Gly Ala Gly Val Pro Gly Ala Gly Val Pro Gly
    530                 535                 540
Ala Gly Val Pro Gly Ala Gly Val Pro Gly Ala Gly Val Pro Gly Ala
545                 550                 555                 560
Gly Val Pro Gly Ala Gly Val Pro Gly Ala Gly Val Pro Gly Ala Gly
            565                 570                 575
Val Pro Gly Ala Gly Val Pro Gly Ala Gly Val Pro Gly Ala Gly Val
        580                 585                 590
Pro Gly Ala Gly Val Pro Gly Ala Gly Val Pro Gly Ala Gly Val Pro
        595                 600                 605
Gly Ala Gly Val Pro Gly Ala Gly Val Pro Gly Ala Gly Val Pro Gly
    610                 615                 620
Ala Gly Val Pro Gly Ala Gly Val Pro Gly Ala Gly Val Pro Gly Ala
625                 630                 635                 640
Gly Val Pro Gly Ala Gly Val Pro Gly Ala Gly Val Pro Gly Ala Gly
            645                 650                 655
Val Pro Gly Ala Gly Val Pro Gly Ala Gly Val Pro Gly Ala Gly Val
        660                 665                 670
Pro Gly Ala Gly Val Pro Gly Ala Gly Val Pro Gly Ala Gly Val Pro
        675                 680                 685
Gly Ala Gly Val Pro Gly Ala Gly Val Pro Gly Ala Gly Val Pro Gly
    690                 695                 700
Ala Gly Val Pro Gly Ala Gly Val Pro Gly Ala Gly Val Pro Gly Ala
705                 710                 715                 720
Gly Val Pro Gly Ala Gly Val Pro Gly Ala Gly Val Pro Gly Ala Gly
            725                 730                 735
Val Pro Gly Ala Gly Val Pro Gly Ala Gly Val Pro Gly Ala Gly Val
        740                 745                 750
Pro Gly Ala Gly Val Pro Gly Ala Gly Val Pro Gly Ala Gly Val Pro
        755                 760                 765
Gly Ala Gly Val Pro Gly Ala Gly Val Pro Gly Ala Gly Val Pro Gly
    770                 775                 780
Ala Gly Val Pro Gly Ala Gly Val Pro Gly Ala Gly Val Pro Gly Ala
785                 790                 795                 800
Gly Val Pro Gly Ala Gly Val Pro Gly Ala Gly Val Pro Gly Ala Gly
            805                 810                 815
Val Pro Gly Ala Gly Val Pro Gly Ala Gly Val Pro Gly Ala Gly Val
        820                 825                 830
Pro Gly Ala Gly Val Pro Gly Ala Gly Val Pro Gly Ala Gly Val Pro
        835                 840                 845
Gly Ala Gly Val Pro Gly Ala Gly Val Pro Gly Ala Gly Val Pro Gly
    850                 855                 860
Ala Gly Val Pro Gly Ala Gly Val Pro Gly Ala Gly Val Pro Gly Ala
865                 870                 875                 880
Gly Val Pro Gly Ala Gly Val Pro Gly Ala Gly Val Pro Gly Ala Gly
            885                 890                 895
Val Pro Gly Ala Gly Val Pro Gly Ala Gly Val Pro Gly Ala Gly Val
        900                 905                 910
Pro Gly Ala Gly Val Pro Gly Ala Gly Val Pro Gly Ala Gly Val Pro
```

```
                915                 920                 925

Gly Ala Gly Val Pro Gly Ala Gly Val Pro Gly Ala Gly Val Pro Gly
            930                 935                 940

Ala Gly Val Pro Gly Ala Gly Val Pro Gly Ala Gly Val Pro Gly Ala
945                 950                 955                 960

Gly Tyr

<210> SEQ ID NO 66
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gly Val Pro Gly Val Gly Val Pro Gly Val Gly Val Pro Gly Val Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
                85                  90                  95

Val Pro Gly Val Gly Val Pro Gly Val Gly Val Pro Gly Val Gly Val
            100                 105                 110

Pro Gly Val Gly Val Pro Gly Val Gly Val Pro Gly Val Gly Val Pro
        115                 120                 125

Gly Val Gly Val Pro Gly Val Gly Val Pro Gly Val Gly Val Pro Gly
    130                 135                 140

Val Gly Val Pro Gly Val Gly Val Pro Gly Val Gly Val Pro Gly Val
145                 150                 155                 160

Gly Val Pro Gly Val Gly Val Pro Gly Val Gly Val Pro Gly Val Gly
                165                 170                 175

Val Pro Gly Val Gly Val Pro Gly Val Gly Val Pro Gly Val Gly Val
            180                 185                 190

Pro Gly Val Gly Val Pro Gly Val Gly Val Pro Gly Val Gly Val Pro
        195                 200                 205

Gly Val Gly Val Pro Gly Val Gly Val Pro Gly Val Gly Val Pro Gly
    210                 215                 220

Val Gly Val Pro Gly Val Gly Val Pro Gly Val Gly Val Pro Gly Val
225                 230                 235                 240

Gly Val Pro Gly Val Gly Val Pro Gly Val Gly Val Pro Gly Val Gly
                245                 250                 255

Val Pro Gly Val Gly Val Pro Gly Val Gly Val Pro Gly Val Gly Val
            260                 265                 270

Pro Gly Val Gly Val Pro Gly Val Gly Val Pro Gly Val Gly Val Pro
        275                 280                 285

Gly Val Gly Val Pro Gly Val Gly Val Pro Gly Val Gly Val Pro Gly
    290                 295                 300

Val Gly Val Pro Gly Val Gly Val Pro Gly Val Gly Val Pro Gly Val
```

```
                305                 310                 315                 320
Gly Val Pro Gly Val Gly Val Pro Gly Val Gly Val Pro Gly Val Gly
                    325                 330                 335
Val Pro Gly Val Gly Val Pro Gly Val Gly Val Pro Gly Val Gly Val
                    340                 345                 350
Pro Gly Val Gly Val Pro Gly Val Gly Val Pro Gly Val Gly Val Pro
                    355                 360                 365
Gly Val Gly Val Pro Gly Val Gly Val Pro Gly Val Gly Val Pro Gly
        370                 375                 380
Val Gly Val Pro Gly Val Gly Val Pro Gly Val Gly Val Pro Gly Val
385                 390                 395                 400
Gly Val Pro Gly Val Gly Val Pro Gly Val Gly Val Pro Gly Val Gly
                    405                 410                 415
Val Pro Gly Val Gly Val Pro Gly Val Gly Val Pro Gly Val Gly Val
                    420                 425                 430
Pro Gly Val Gly Val Pro Gly Val Gly Val Pro Gly Val Gly Val Pro
                    435                 440                 445
Gly Val Gly Val Pro Gly Val Gly Val Pro Gly Val Gly Val Pro Gly
        450                 455                 460
Val Gly Val Pro Gly Val Gly Val Pro Gly Val Gly Val Pro Gly Val
465                 470                 475                 480
Gly Tyr

<210> SEQ ID NO 67
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Val Pro Gly Val Gly Val Pro Gly Val Gly Val Pro Gly Val Gly Val
1               5                   10                  15
Pro Gly Val Gly Val Pro Gly Val Gly Val Pro Gly Val Gly Val Pro
                20                  25                  30
Gly Val Gly Val Pro Gly Val Gly Val Pro Gly Val Gly Val Pro Gly
        35                  40                  45
Val Gly Val Pro Gly Val Gly Val Pro Gly Val Gly Val Pro Gly Val
    50                  55                  60
Gly Val Pro Gly Val Gly Val Pro Gly Val Gly Val Pro Gly Val Gly
65                  70                  75                  80
Val Pro Gly Val Gly Val Pro Gly Val Gly Val Pro Gly Val Gly Val
                85                  90                  95
Pro Gly Val Gly Val Pro Gly Val Gly Val Pro Gly Val Gly Val Pro
                100                 105                 110
Gly Val Gly Val Pro Gly Val Gly
        115                 120
```